US009850242B2

(12) United States Patent
Boivin et al.

(10) Patent No.: US 9,850,242 B2
(45) Date of Patent: Dec. 26, 2017

(54) TETRAHYDROPYRAZOLOPYRIMIDINE COMPOUNDS

(71) Applicant: EISAI R&D MANAGEMENT CO., LTD., Tokyo (JP)

(72) Inventors: Roch Boivin, North Chelmsford, MA (US); Eric Carlson, Merrimack, NH (US); Atsushi Endo, Andover, MA (US); Hans Hansen, Somerville, MA (US); Lynn D. Hawkins, Concord, MA (US); Sally Ishizaka, Weston, MA (US); Matthew Mackey, Melrose, MA (US); Sridhar Narayan, Belmont, MA (US); Takashi Satoh, Andover, MA (US); Shawn Schiller, Haverhill, MA (US)

(73) Assignee: Eisai R&D Management Co., Ltd, Tokyo (JP)

(*) Notice: Subject to any disclaimer, the term of this patent is extended or adjusted under 35 U.S.C. 154(b) by 0 days.

(21) Appl. No.: 15/233,520

(22) Filed: Aug. 10, 2016

(65) Prior Publication Data

US 2016/0339032 A1    Nov. 24, 2016

Related U.S. Application Data

(62) Division of application No. 14/806,174, filed on Jul. 22, 2015, now Pat. No. 9,446,046, which is a division of application No. 13/907,202, filed on May 31, 2013, now Pat. No. 9,126,999.

(60) Provisional application No. 61/654,023, filed on May 31, 2012.

(51) Int. Cl.
| | |
|---|---|
| A01N 43/90 | (2006.01) |
| A61K 31/519 | (2006.01) |
| C07D 471/04 | (2006.01) |
| C07D 487/04 | (2006.01) |
| A61K 31/55 | (2006.01) |

(52) U.S. Cl.
CPC .......... *C07D 471/04* (2013.01); *A61K 31/519* (2013.01); *A61K 31/55* (2013.01); *C07D 487/04* (2013.01)

(58) Field of Classification Search
None
See application file for complete search history.

(56) References Cited

U.S. PATENT DOCUMENTS

| 5,032,594 A | 7/1991 | Takehiko et al. |
| 5,356,897 A | 10/1994 | Oku et al. |
| 6,174,884 B1 | 1/2001 | Haning et al. |
| 6,472,416 B1 | 10/2002 | Kolasa et al. |
| 9,126,999 B2 * | 9/2015 | Boivin ............. C07D 471/04 |
| 9,446,046 B2 * | 9/2016 | Boivin ............. C07D 471/04 |

| 2002/0010183 A1 | 1/2002 | Sui et al. |
| 2002/0050013 A1 | 5/2002 | Vidal et al. |
| 2002/0173656 A1 | 11/2002 | Peyman et al. |
| 2003/0225056 A1 | 12/2003 | Freeman-Cook et al. |
| 2004/0006079 A1 | 1/2004 | Jiang et al. |
| 2004/0127508 A1 | 7/2004 | Gerlach et al. |
| 2005/0004114 A1 | 1/2005 | Whitehouse et al. |
| 2005/0009817 A1 | 1/2005 | Savoy et al. |
| 2005/0085531 A1 | 4/2005 | Hodge et al. |
| 2005/0096256 A1 | 5/2005 | Sinclair et al. |
| 2005/0136537 A1 | 6/2005 | Sinclair et al. |
| 2005/0164030 A1 | 7/2005 | Knowles et al. |
| 2006/0025337 A1 | 2/2006 | Sinclair et al. |
| 2006/0052380 A1 | 3/2006 | Cooper et al. |
| 2006/0079536 A1 | 4/2006 | Yasuma et al. |
| 2006/0122222 A1 | 6/2006 | Whitehouse et al. |
| 2006/0122278 A1 | 6/2006 | Olsson et al. |
| 2006/0135594 A1 | 6/2006 | Fraley et al. |
| 2006/0142348 A1 | 6/2006 | Singh et al. |
| 2006/0229265 A1 | 10/2006 | Milburn et al. |
| 2006/0276416 A1 | 12/2006 | Sinclair et al. |
| 2007/0149466 A1 | 6/2007 | Milburn et al. |
| 2007/0155749 A1 | 7/2007 | Galli et al. |
| 2007/0203236 A1 | 8/2007 | Smith et al. |
| 2007/0219205 A1 | 9/2007 | Brenchley et al. |
| 2008/0004263 A1 | 1/2008 | Santora et al. |
| 2008/0045505 A1 | 2/2008 | Bruton et al. |
| 2008/0045570 A1 | 2/2008 | Brenchley et al. |
| 2008/0051418 A1 | 2/2008 | Maekawa et al. |
| 2008/0070965 A1 | 3/2008 | Brenchley et al. |
| 2008/0167338 A1 | 7/2008 | Spevak et al. |
| 2008/0176832 A1 | 7/2008 | Bamford et al. |
| 2008/0176883 A1 | 7/2008 | George et al. |

(Continued)

FOREIGN PATENT DOCUMENTS

| CN | 102048738 A | 5/2011 |
| EP | 2371219 A1 | 10/2011 |

(Continued)

OTHER PUBLICATIONS

Kono et al., "How Dying Cells Alert the Immune System to Danger", Nature Reviews Immunology 8, 279-289 (Apr. 2008).
Kirou et al., "Activation of the Interferon-alpha Pathway Identifies a Subgroup of Systemic Lupus Erythematosus Patients with Distinct Serologic Features and Active Disease", Arthritis Rheum. May 2005; 52(5): 1491-503.
Means et al., "Human Lupus Autoantibody-DNA Complexes Activate DCs through Cooperation of CD32 and TLR9", J. Clin. Invest. Feb. 2005; 115(2): 407-417.
Vollmer et al., "Immune Stimulation Mediated by Autoantigen Binding Sites within Small Nuclear RNAs involves Toll-Like Receptors 7 and 8", J. Exp. Med. Dec. 5, 2005; 202(11): 1575-1585.
Savarese et al., "U1 Small Nuclear Ribonucleoprotein Immune Complexes Induce Type I Interferon in Plasmacytoid Dendritic Cells through TLR7", Blood, Apr. 15, 2006; 107(8): 3229-3234, Epub. Dec. 20, 2005.

(Continued)

*Primary Examiner* — Jeffrey H Murray
(74) *Attorney, Agent, or Firm* — Buchanan Ingersoll & Rooney PC

(57) ABSTRACT

Embodiments of the disclosure relate to tetrahydropyrazolopyrimidine compounds that act as antagonists or inhibitors for Toll-like receptors 7 and/or 8, and their use in pharmaceutical compositions effective for treatment of systemic lupus erythematosus (SLE) and lupus nephritis.

12 Claims, 80 Drawing Sheets

(56) References Cited

U.S. PATENT DOCUMENTS

| | | |
|---|---|---|
| 2008/0194803 A1 | 8/2008 | Sinclair et al. |
| 2009/0042856 A1 | 2/2009 | Yamazaki et al. |
| 2009/0069305 A1 | 3/2009 | Gaul et al. |
| 2009/0124602 A1 | 5/2009 | Maltais et al. |
| 2009/0124610 A1 | 5/2009 | Saxty et al. |
| 2009/0163545 A1 | 6/2009 | Goldfarb et al. |
| 2009/0170907 A1 | 7/2009 | Turnbull et al. |
| 2009/0181941 A1 | 7/2009 | Leblanc et al. |
| 2009/0209539 A1 | 8/2009 | Leblanc et al. |
| 2009/0270402 A1 | 10/2009 | Calderwood et al. |
| 2009/0304821 A1 | 12/2009 | Notoya et al. |
| 2009/0325985 A1 | 12/2009 | Regueiro-Ren et al. |
| 2010/0004324 A1 | 1/2010 | Skaar et al. |
| 2010/0022543 A1 | 1/2010 | Melvin, Jr. et al. |
| 2010/0120778 A1 | 5/2010 | Hu et al. |
| 2010/0173888 A1 | 7/2010 | Thorarensen et al. |
| 2010/0183743 A1 | 7/2010 | Przytulinska et al. |
| 2010/0196357 A1 | 8/2010 | Huang et al. |
| 2010/0286110 A1 | 11/2010 | Fyfe et al. |
| 2010/0286142 A1 | 11/2010 | Ibrahim et al. |
| 2010/0298337 A1 | 11/2010 | Hunt et al. |
| 2010/0324029 A1 | 12/2010 | Fischer et al. |
| 2011/0003849 A1 | 1/2011 | Shen et al. |
| 2011/0021531 A1 | 1/2011 | Chobanian et al. |
| 2011/0077237 A1 | 3/2011 | Jimenez et al. |
| 2011/0098325 A1 | 4/2011 | Raynham et al. |
| 2011/0136800 A1 | 6/2011 | Eckhardt et al. |
| 2011/0144056 A1 | 6/2011 | Lin et al. |
| 2011/0144119 A1 | 6/2011 | Chobanian et al. |
| 2011/0152282 A1 | 6/2011 | Cheng et al. |
| 2011/0165220 A1 | 7/2011 | Lambert et al. |
| 2011/0173726 A1 | 7/2011 | Groβ et al. |
| 2011/0190266 A1 | 8/2011 | Chu et al. |
| 2011/0212971 A1 | 9/2011 | Wang et al. |
| 2011/0218182 A1 | 9/2011 | Dakin et al. |
| 2011/0251172 A1 | 10/2011 | Rivkin et al. |
| 2011/0262397 A1 | 10/2011 | Slomczynska et al. |
| 2011/0269746 A1 | 11/2011 | Kanno et al. |
| 2011/0269769 A1 | 11/2011 | Lin et al. |
| 2011/0306597 A1 | 12/2011 | Crawforth et al. |
| 2012/0010177 A1 | 1/2012 | Huang et al. |
| 2012/0046250 A1 | 2/2012 | Orton |

FOREIGN PATENT DOCUMENTS

| | | |
|---|---|---|
| EP | 2401915 A1 | 1/2012 |
| JP | 4133055 A | 5/1992 |
| JP | 2003332786 A | 11/2003 |
| JP | 2006522744 | 10/2006 |
| JP | 2006522744 A | 10/2006 |
| JP | 2013159564 | 8/2013 |
| JP | 2013159564 A | 8/2013 |
| WO | 2004037159 A2 | 5/2004 |
| WO | 2005108337 A2 | 11/2005 |
| WO | 2006129583 A1 | 12/2006 |
| WO | 2006129587 A1 | 12/2006 |
| WO | 2007005453 A2 | 1/2007 |
| WO | 2007008541 A2 | 1/2007 |
| WO | 2007146838 A2 | 12/2007 |
| WO | 2008033894 A2 | 3/2008 |
| WO | 2008155745 A2 | 12/2008 |
| WO | 2009064274 A1 | 5/2009 |
| WO | 2009076512 A1 | 6/2009 |
| WO | 2010096115 | 8/2010 |
| WO | 2010096115 A1 | 8/2010 |
| WO | 2010101964 A2 | 9/2010 |
| WO | 2010141696 A1 | 12/2010 |
| WO | 2011025706 A2 | 3/2011 |
| WO | 2011045415 A2 | 4/2011 |
| WO | 2011062253 | 5/2011 |
| WO | 2011062253 A1 | 5/2011 |
| WO | 2011070298 A1 | 6/2011 |
| WO | 2011072064 A1 | 6/2011 |
| WO | 2011079000 A1 | 6/2011 |
| WO | 2011088192 A1 | 7/2011 |
| WO | 2011094209 A1 | 8/2011 |
| WO | 2011117381 A1 | 9/2011 |
| WO | 2011117382 A1 | 9/2011 |
| WO | 2011127070 A2 | 10/2011 |
| WO | 2011133447 A1 | 10/2011 |
| WO | 2011133727 A2 | 10/2011 |
| WO | 2013019548 A1 | 2/2013 |
| WO | 2013019561 A1 | 2/2013 |
| WO | 2013122823 A1 | 8/2013 |
| WO | 2013178362 A1 | 12/2013 |

OTHER PUBLICATIONS

Banchereau et al., "Type I Interferon in Systemic Lupus Erythematosus and Other Autoimmune Diseases", Immunity, Sep. 2006; 25(3): 383-392.

Shen et al., "Sex-Specific Association of X-linked Toll-Like Receptor 7 (TLR7) with Male Systemic Lupus Erythematosus", Proc. Natl. Acad. Sci. USA, Sep. 7, 2010; 107(36): 15838-15843, Epub. Aug. 23, 2010.

Gorden et al., "Synthetic TLR Agonists Reveal Functional Differences between Human TLR7 and TLR8", The Journal of Immunology, Feb. 1, 2005, vol. 174, No. 3, 1259-1268.

Nickerson et al., "TLR9 Regulates TLR7- and MyD88-Dependent Autoantibody Production and Disease in a Murine Model of Lupus", J. Immunol. Feb. 15, 2010; 184(4): 1840-1849, Epub. Jan. 20, 2010.

Fairhurst et al., "Yaa Autoimmune Phenotypes are Conferred by Overexpression of TLR7", Eur. J. Immunol., Jul. 2008; 38(7): 1971-1978.

Deane et al., "Control of Toll-Like Receptor 7 Expression is Essential to Restrict Autoimmunity and Dendritic Cell Proliferation", Immunity, Nov. 2007; 27(5): 801-810, Epub. Nov. 8, 2007.

Barrat et al., "Treatment of Lupus-Prone Mice with a Dual Inhibitor of TLR7 and TLR9 Leads to Reduction of Autoantibody Production and Amelioration of Disease Symptoms", Eur. J. Immunol., Dec. 2007; 37(12): 3582-3586.

Savarese et al., "Requirement of Toll-Like Receptor 7 for Pristane-Induced Production of Autoantibodies and Development of Murine Lupus Nephritis", Arthritis Rheum., Apr. 2008; 58(4): 1107-1115.

Lafyatis et al., "Antimalarial Agents: Closing the Gate on Toll-Like Receptors?", Arthritis Rheum., Oct. 2006; 54(10): 3068-3070.

Costedoat-Chalumeau et al., "Low Blood Concentration of Hydroxychloroquine is a Marker for and Predictor of Disease Exacerbations in Patients with Systemic Lupus Erythematosus", Arthritis Rheum., Oct. 2006; 54(10): 3284-3290.

Casanova et al., "Human TLRs and IL-1Rs in Host Defense: Natural Insights from Evolutionary, Epidemiological, and Clinical Genetics", Annu. Rev. of Immunol., 2011; 29: 447-491.

Zhu et al., "IMO-8400, A Novel TLR7, TLR8 and TLR9 Antagonist, Inhibits Disease Development in Lupus-Prone NZBW/F1 Mice", The Journal of Immunology, 2012, 188: 119.12 (Abstract).

Maddry et al., "Antituberculosis Activity of the Molecular Libraries Screening Center Network Library", Tuberculosis, vol. 89, Issue 5, pp. 354-363, Sep. 2009.

Dalinger et al., "Liquid-Phase Synthesis of Combinatorial Libraries based on 7-Trifluoromethyl-Substituted Pyrazolo [1,5-a]Pyrimidine Scaffold", J. Comb. Chem., Mar.-Apr. 2005; 7(2): 236-245.

Muravyova et al., "Switchable Selectivity in Multicomponent Heterocyclizations of Acetoacetamides, Aldehydes, and 3-Amino-1,2,4-Triazoles/5-Aminopyrazoles", Tetrahedron, 2011, 67(48), 9389-9400.

Yoshida et al., "Novel and Potent Calcium-Sensing Receptor Antagonists: Discovery of (5R)-N-[1-ethyl-1-(4-ethylphenyl)propyl]-2,7,7-trimethyl-5-phenyl-4,5,6,7-tetrahydropyrazolo[1,5-a]pyrimidine-3-carboxamide monotosylate (TAK-075) as an Orally Active Bone Anabolic Agent", Bioorg. Med. Chem. Mar. 15, 2011; 19(6): 1881-1894, Epub. Feb. 24, 2011.

Hammouda et al., "Ethyl Alpha-Phenylthiocarbamylglyoxate in the Synthesis of Heterocyclic Compounds with Bridgehead Nitrogen and Related Compounds", Journal of the Serbian Chemical Society, (1992), 57(3), 165-170.

(56) References Cited

OTHER PUBLICATIONS

El-Agamey et al., "Alpha-Beta-Unsaturated Nitriles in Heterocyclic Synthesis: Synthesis of Some New Pyrazolo[1,5-a] Pyrimidine Derivatives", Monatshefte fuer Chemie (1984), 115(12), 1413-1419.

International Search Report and Written Opinion for PCT/US2013/043679 dated Feb. 4, 2014.

Japanese Office Action dated Mar. 8, 2017 for Japanese Patent Application No. 2015-515255 filed May 31, 2013.

Dalinger, I. L., et al.; Liquid-Phase Synthesis of Combinatorial Libraries Based on 7-Trifluoromethyl-Substituted Pyrazolo[1,5-a]Pyrimidine Scaffold; J. Comb. Chem 2005; vol. 7; pp. 236-245; American Chemical Society.

Japanese Patent Office, Office Action for Application No. 2015-515255, dated Mar. 8, 2017.

\* cited by examiner

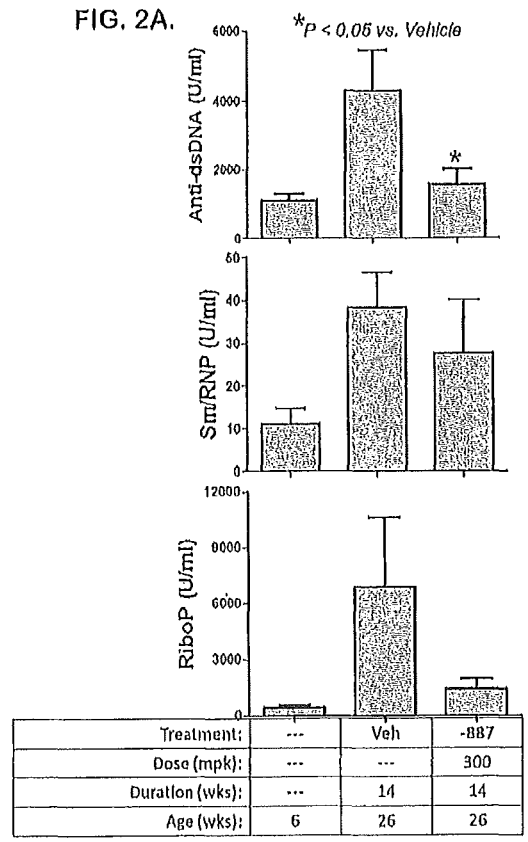

| Treatment: | Veh | -887 | Veh | -887 |
|---|---|---|---|---|
| Dose (mpk): | --- | 300 | --- | 300 |
| Duration (wks): | --- | --- | 13 | 13 |
| Age (wks): | 12 | 12 | 25 | 25 |

| Glomerulonephritis (GN) Evaluation in BXSB-Yaa Strain | | Vehicle | ER-892887 (300mpk) |
|---|---|---|---|
| | Total Mice Examined: | 10 | 7 |
| | GN Score: | | |
| | 0/1 | 1 | 2 |
| | 2 | 1 | 5 |
| | 3 | 6 | 0 |
| | 4 | 2 | 0 |
| Percent combined Incidence of Grade 3 and 4 | | 80% | 0% |

Grade 0/1: within normal limits; Grade 2: MILD; Grade 3: MODERATE; Grade 4: MARKED

| BXSB-Yaa Study Treatment: | Vehicle | ER-892887 |
|---|---|---|
| Mortality (# deaths/total group #): | 3/13 | 6/13 |
| Dosing duration at death (days): | 24, 31, 56 | 4, 10, 14, 32, 47, >81d |

FIG. 3C.

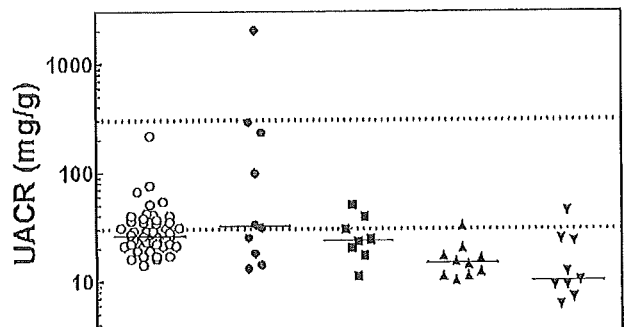

| Treatment: | | Veh | -887 | -887 | -887 |
|---|---|---|---|---|---|
| Dose (mpk): | --- | --- | 33 | 100 | 300 |
| Duration (wks): | --- | 22 | 22 | 22 | 22 |
| Age (wks): | 6 | 45 | 45 | 45 | 45 |

FIG. 3D.

| Treatment: | Vehicle | ER-892887 | | |
|---|---|---|---|---|
| Dose (mpk): | | 33 | 100 | 300 |
| Mortality (# deaths/total group #): | 1/12 | 0/11 | 1/12 | 2/12 |
| Dosing duration at death (days): | 54 | | 85 | 17, 53 |

FIG. 3E.

| Glomerulonephritis (GN) Evaluation In NZB/W – Experiment #1 | | | | |
|---|---|---|---|---|
| | Vehicle | ER-892887 | | |
| Dose: | --- | 33mpk | 100mpk | 300mpk |
| Total Mice Examined: | 10 | 12 | 10 | 9 |
| GN Score: | | | | |
| 0/1+ | 4 | 8 | 9 | 5 |
| 2+ | 1 | 4 | 1 | 4 |
| 3+ | 1 | 0 | 0 | 0 |
| 4+ | 4 | 0 | 0 | 0 |
| Percent combined Incidence of Grade 3 and 4 | 50% | 0% | 0% | 0% |
| Grade 0/1: within normal limits; Grade 2: MILD; Grade 3: MODERATE; Grade 4: MARKED | | | | |

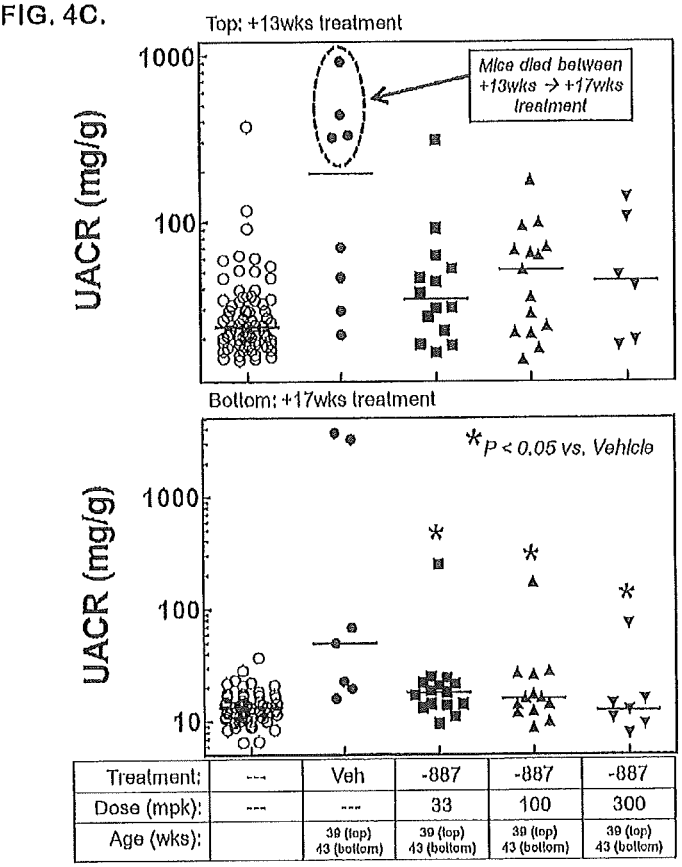

FIG. 4F.

| Treatment: | Vehicle | ER-892887 | | |
|---|---|---|---|---|
| Dose (mpk): | | 33 | 100 | 300 |
| Mortality: (# deaths/total group #) | 9/16 | 0/16 | 1/16 | 9/16 |
| Dosing duration at death (days): | 67, 67, 82, 84, 90, 102, 104, 104, 113 | | 83 | 8, 19, 26, 28, 29, 80, 82, 82, 96 . |

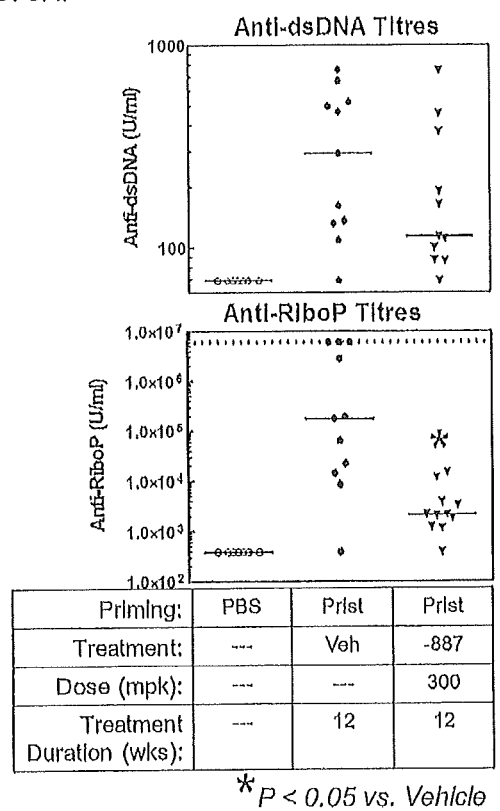

FIG. 5D.

| Gene #: | Gene Name: |
|---|---|
| 1 | Mx1 * |
| 2 | Ifi44 * |
| 3 | Irf7 |
| 4 | Ifit1 |
| 5 | Isg15 |
| 6 | Usp18 |
| 7 | Ifi204 |
| 8 | Oas3 |
| 9 | Fcgr1 |
| 10 | Oasl2 |
| 11 | Xaf1 |
| 12 | Mmp8 |
| 13 | Ifi202b |
| 14 | Mmp9 |
| 15 | Fpr1 |
| 16 | C3 |
| 17 | Ms4a6c |
| 18 | Stat1 |
| 19 | Epsti1 |
| 20 | Ifi35 |
| 21 | Bst2 |

Twenty-one (21) genes significantly upregulated between Vehicle + Pristane vs. PBS control

*Significantly reduced by ER-892887 (2 genes)

| Priming: | PBS | Prist | Prist | Prist | Prist |
|---|---|---|---|---|---|
| Treatment: | --- | Veh | -887 | -887 | -887 |
| Dose (mpk): | --- | --- | 33 | 100 | 300 |
| Treatment Duration (wks): | --- | 12 | 12 | 12 | 12 |

| Treatment: | Vehicle | ER-892887 | | |
|---|---|---|---|---|
| Dose (mpk): | | 33 | 100 | 300 |
| Mortality: (# deaths/total group #) | 0/12 | 1/12 | 0/12 | 1/12 |
| Dosing duration at death (days): | | 1 | | 51 |

FIG. 6G.

| Gene #: | Gene Name: |
|---|---|
| 1 | Bst2 * |
| 2 | Herc6 * |
| 3 | Ifi204 * |
| 4 | Ifi44 * |
| 5 | Irf7 |
| 6 | Ifi27l2a |
| 7 | Oas3 |
| 8 | Oasl2 |
| 9 | Usp18 |
| 10 | Mmp8 |
| 11 | Fcgr1 |
| 12 | Ifit3 |
| 13 | Isg15 |
| 14 | Xaf1 |
| 15 | Ifit1 |
| 16 | Ifih1 |
| 17 | Tnfsf13b |
| 18 | Cmpk2 |
| 19 | Ms4a6c |
| 20 | Ccr2 |
| 21 | Fpr1 |
| 22 | Mmp9 |

Twenty-one (22) genes significantly upregulated between Vehicle + Pristane vs. PBS control

*Significantly reduced by ER-892887 (4 genes)

| Treatment: | Veh | -454 | -454 |
|---|---|---|---|
| Dose (mpk): | --- | 100 | 300 |
| Duration (wks): | 15 | 15 | 15 |
| Age (wks): | 24 | 24 | 24 |

| Glomerulonephritis (GN) Evaluation in BXSB-Yaa Strain | | | | |
|---|---|---|---|---|
| | | Vehicle | ER-885454 (100mpk) | ER-885454 (300mpk) |
| Total Mice Examined: | | 6 | 12 | 13 |
| | GN Score: | | | |
| | 0/1 | 2 | 11 | 10 |
| | 2 | 1 | 1 | 3 |
| | 3 | 2 | 0 | 0 |
| | 4 | 1 | 0 | 0 |
| Percent combined incidence of Grade 3 and 4 | | 50% | 0% | 0% |
| Grade 0/1: within normal limits; Grade 2: MILD; Grade 3: MODERATE; Grade 4: MARKED | | | | |

FIG. 8D.

| Glomerulonephritis (GN) Evaluation in BXSB-Yaa Strain | | | |
|---|---|---|---|
| | | Vehicle | ER-886464 (300mpk) |
| | Total Mice Examined: | 7 | 10 |
| | GN Score: | | |
| | 0/1 | 2 | 10 |
| | 2 | 0 | 0 |
| | 3 | 3 | 0 |
| | 4 | 2 | 0 |
| Percent combined incidence of Grade 3 and 4 | | 71% | 0% |
| Grade 0/1: within normal limits; Grade 2: MILD; Grade 3: MODERATE; Grade 4: MARKED | | | |

| Treatment: | --- | Veh | -454 |
|---|---|---|---|
| Dose (mpk): | --- | --- | 300 |
| Duration (wks): | --- | 23 | 23 |
| Age (wks): | 6 | 47 | 47 |

| Glomerulonephritis (GN) Evaluation in NZBxNZW Strain | | Vehicle | ER-885454 (300mpk) |
|---|---|---|---|
| Total Mice Examined: | | 17 | 21 |
| | GN Score: | | |
| | 0 | 12/17 | 21 |
| | 1 | 4/17 | 0 |
| | 2 | 0 | 0 |
| | 3 | 1/17 | 0 |
| | 4 | 0 | 0 |
| Percent combined incidence of Grade 3 and 4 | | 6% | 0% |
| Grade 0/1: within normal limits; Grade 2: MILD; Grade 3: MODERATE; Grade 4: MARKED | | | |

FIG. 11A

| ER-Number | Structure | Chemical Name | HEK/TLR7 IC50 (µM) | HEK/TLR9 IC50 (µM) | 1H NMR | MS |
|---|---|---|---|---|---|---|
| ER-885454 | $C_{20}H_{19}F_3N_4O_2$ | (5S,7R)-5-(3,4-dimethoxyphenyl)-2-(pyridin-4-yl)-7-(trifluoromethyl)-4,5,6,7-tetrahydropyrazolo[1,5-a]pyrimidine | 0.050 | >10 | 1H NMR (400 MHz, CHLOROFORM-d) δ ppm 2.29 - 2.46 (m, 2 H) 2.47 - 2.60 (m, 2 H) 3.91 (s, 3 H) 3.93 (s, 3 H) 4.36 (s, 1 H) 4.45 (d, J=9.96 Hz, 1 H) 4.93 (dt, J=11.28, 5.79 Hz, 2 H) 5.85 (s, 1 H) 6.85 - 6.93 (m, 1 H) 6.93 - 7.04 (m, 2 H) 7.59 - 7.70 (m, 2 H) 8.56 - 8.66 (m, 2 H) | 405.2 |
| ER-885690 | $C_{22}H_{19}F_3N_4O_2$ | 4-((5S,7R)-5-(3,4-dimethoxyphenyl)-7-(trifluoromethyl)-4,5,6,7-tetrahydropyrazolo[1,5-a]pyrimidin-2-yl)benzonitrile | 0.050 | >10 | see ER-885484 | |
| ER-886434 | $C_{21}H_{21}F_3N_4O_3$ | 5-(3,4-dimethoxyphenyl)-2-(2-methoxypyridin-4-yl)-7-(trifluoromethyl)-4,5,6,7-tetrahydropyrazolo[1,5-a]pyrimidine | 0.090 | >10 | 1H NMR (400 MHz, CHLOROFORM-d) δ ppm 2.36 - 2.47 (m, 1 H) 2.54 (d, J=6.14 Hz, 3 H) 3.94 (s, 3 H) 3.96 (s, 3 H) 4.00 (s, 3 H) 4.34 (s, 1 H) 4.47 (dd, J=11.73, 2.08 Hz, 1 H) 4.89 - 5.01 (m, 1 H) 5.84 (s, 1 H) 6.89 - 6.95 (m, 1 H) 6.99 - 7.04 (m, 2 H) 7.09 - 7.13 (m, 1 H) 7.35 (dd, J=5.36, 1.39 Hz, 1 H) 8.20 (dd, J=5.36, 0.51 Hz, 1 H) | 435.6 |
| ER-886622 | $C_{21}H_{21}F_3N_4O_3$ | (5S,7R)-5-(3,4-dimethoxyphenyl)-2-(2-methoxypyridin-4-yl)-7-(trifluoromethyl)-4,5,6,7-tetrahydropyrazolo[1,5-a]pyrimidine | 0.020 | >10 | see ER-886434 | |
| ER-887238 | $C_{22}H_{19}F_3N_4O_2$ | 3-(5-(3,4-dimethoxyphenyl)-7-(trifluoromethyl)-4,5,6,7-tetrahydropyrazolo[1,5-a]pyrimidin-2-yl)benzonitrile | 0.070 | >10 | | |

FIG. 11B

| ER-Number | Structure | Chemical Name | HEK/TLR7 IC50 (µM) | HEK/TLR9 IC50 (µM) | 1H NMR | MS |
|---|---|---|---|---|---|---|
| ER-887734 | C22H23F3N4O3 | N-(3-((5S,7R)-5-(3,4-dimethoxyphenyl)-7-(trifluoromethyl)-4,5,6,7-tetrahydropyrazolo[1,5-a]pyrimidin-2-yl)phenyl)acetamide | 0.100 | >10 | | 461.3 |
| ER-887738 | C23H21F3N4O2 | (5S,7R)-5-(3,4-dimethoxyphenyl)-2-(1H-indol-6-yl)-7-(trifluoromethyl)-4,5,6,7-tetrahydropyrazolo[1,5-a]pyrimidine | 0.090 | >10 | | 443 |
| ER-889862 | C21H19F3N6 | 5-(5-(1,3-dimethyl-1H-pyrazol-4-yl)-7-(trifluoromethyl)-4,5,6,7-tetrahydropyrazolo[1,5-a]pyrimidin-2-yl)isoquinoline | 0.040 | >10 | | 413 |
| ER-889871 | C22H21F3N4O3 | 4-(5-(3,4-dimethoxyphenyl)-7-(trifluoromethyl)-4,5,6,7-tetrahydropyrazolo[1,5-a]pyrimidin-2-yl)benzamide | 0.020 | >10 | | 447.5 |
| ER-889874 | C22H22F3N3O3 | (4-(5-(3,4-dimethoxyphenyl)-7-(trifluoromethyl)-4,5,6,7-tetrahydropyrazolo[1,5-a]pyrimidin-2-yl)phenyl)methanol | 0.060 | >10 | | 434 |

FIG. 11C

| ER-Number | Structure | Chemical Name | HEK/TLR7 IC50 (µM) | HEK/TLR9 IC50 (µM) | 1H NMR | MS |
|---|---|---|---|---|---|---|
| ER-889925 | C24H21F3N4O2 | 5-(5-(3,4-dimethoxyphenyl)-7-(trifluoromethyl)-4,5,6,7-tetrahydropyrazolo[1,5-a]pyrimidin-2-yl)isoquinoline | 0.030 | > 10 | | 455.1 |
| ER-890007 | C22H21F3N5 | 5-(5-(1,3-dimethyl-1H-pyrazol-4-yl)-7-(trifluoromethyl)-4,5,6,7-tetrahydropyrazolo[1,5-a]pyrimidin-2-yl)-8-methylquinoline | 0.050 | > 10 | | 427 |
| ER-890017 | C22H20F4N4O3 | 4-(5-(3,4-dimethoxyphenyl)-7-(trifluoromethyl)-4,5,6,7-tetrahydropyrazolo[1,5-a]pyrimidin-2-yl)-3-fluorobenzamide | 0.070 | > 10 | see ER-892892 | 465 |
| ER-890019 | C22H20F4N4O3 | 4-(5-(3,4-dimethoxyphenyl)-7-(trifluoromethyl)-4,5,6,7-tetrahydropyrazolo[1,5-a]pyrimidin-2-yl)-2-fluorobenzamide | 0.020 | > 10 | | 465 |
| ER-890020 | C22H20ClF3N4O3 | 2-chloro-4-(5-(3,4-dimethoxyphenyl)-7-(trifluoromethyl)-4,5,6,7-tetrahydropyrazolo[1,5-a]pyrimidin-2-yl)benzamide | 0.030 | > 10 | | 481 |

FIG. 11D

| ER-Number | Structure | Chemical Name | HEK/ TLR7 IC50 (µM) | HEK/ TLR9 IC50 (µM) | 1H NMR | MS |
|---|---|---|---|---|---|---|
| ER-890024 | 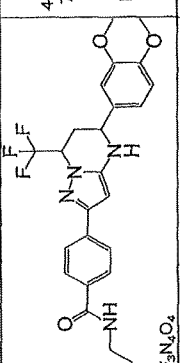 $C_{25}H_{27}F_3N_4O_4$ | 4-(5-(3,4-dimethoxyphenyl)-7-(trifluoromethyl)-4,5,6,7-tetrahydropyrazolo[1,5-a]pyrimidin-2-yl)-N-(3-hydroxypropyl)benzamide | 0.050 | > 10 | see ER-892893 | 505 |
| ER-890027 | 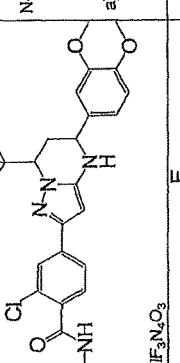 $C_{29}H_{26}ClF_3N_4O_3$ | N-benzyl-2-chloro-4-(5-(3,4-dimethoxyphenyl)-7-(trifluoromethyl)-4,5,6,7-tetrahydropyrazolo[1,5-a]pyrimidin-2-yl)benzamide | 0.030 | > 10 | | 571 |
| ER-890028 | 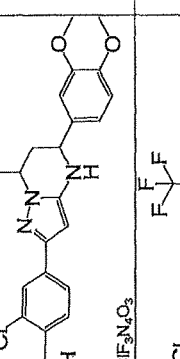 $C_{25}H_{26}ClF_3N_4O_3$ | 2-chloro-4-(5-(3,4-dimethoxyphenyl)-7-(trifluoromethyl)-4,5,6,7-tetrahydropyrazolo[1,5-a]pyrimidin-2-yl)-N-isopropylbenzamide | 0.030 | > 10 | | 523 |
| ER-890029 | 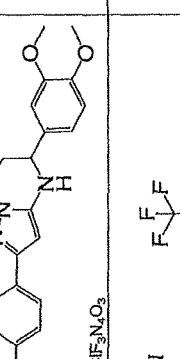 $C_{23}H_{22}ClF_3N_4O_3$ | 2-chloro-4-(5-(3,4-dimethoxyphenyl)-7-(trifluoromethyl)-4,5,6,7-tetrahydropyrazolo[1,5-a]pyrimidin-2-yl)-N-methylbenzamide | 0.030 | > 10 | see ER-892889 | 495 |
| ER-890035 | 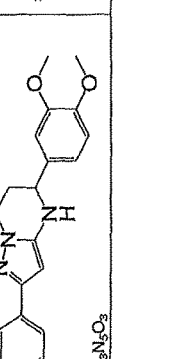 $C_{24}H_{22}F_3N_5O_3$ | 3-(5-(3,4-dimethoxyphenyl)-7-(trifluoromethyl)-4,5,6,7-tetrahydropyrazolo[1,5-a]pyrimidin-2-yl)phenyl)-5-methyl-1,2,4-oxadiazole | 0.002 | > 10 | | 486 |

FIG. 11E

| ER-Number | Structure | Chemical Name | HEK/ TLR7 IC50 (µM) | HEK/ TLR9 IC50 (µM) | 1H NMR | MS |
|---|---|---|---|---|---|---|
| ER-890043 | C22H20F3N5O3 | 5-(5-(3,4-dimethoxyphenyl)-7-(trifluoromethyl)-4,5,6,7-tetrahydropyrazolo[1,5-a]pyrimidin-2-yl)-1H-benzo[d]imidazol-2(3H)-one | 0.010 | >10 | | 460 |
| ER-890044 | C25H26F3N5O3 | (4-(5-(3,4-dimethoxyphenyl)-7-(trifluoromethyl)-4,5,6,7-tetrahydropyrazolo[1,5-a]pyrimidin-2-yl)phenyl)(piperazin-1-yl)methanone | 0.005 | >10 | 1H NMR (400 MHz, METHANOL-d4) δ ppm 2.23 (dt, J=13.30, 11.35 Hz, 1 H) 2.54 (ddd, J=13.38, 6.28, 2.46 Hz, 1 H) 2.82 (br. s, 2 H) 2.90 (br. s, 2 H) 3.66 - 3.79 (m, 1 H) 3.85 (s, 3 H) 3.88 (s, 3 H) 4.46 (dd, J=11.70, 2.30 Hz, 1 H) 5.01 - 5.16 (m, 1 H) 5.86 (s, 1 H) 6.99 (d, J=8.33 Hz, 1 H) 7.06 (dd, J=8.33, 1.92 Hz, 1 H) 7.12 (d, J=1.92 Hz, 1 H) 7.39 - 7.49 (m, 2 H) 7.80 - 7.90 (m, 2 H) | 516.6 |
| ER-890050 | C24H22F3N5O2 | 2-(3-(1H-pyrazol-1-yl)phenyl)-5-(3,4-dimethoxyphenyl)-7-(trifluoromethyl)-4,5,6,7-tetrahydropyrazolo[1,5-a]pyrimidine | 0.005 | >10 | | 470 |
| ER-890978 | C20H18ClF3N4O2 | 2-(2-chloropyridin-4-yl)-5-(3,4-dimethoxyphenyl)-7-(trifluoromethyl)-4,5,6,7-tetrahydropyrazolo[1,5-a]pyrimidine | 0.040 | >10 | 1H NMR (400 MHz, METHANOL-d4) δ ppm 2.23 (dt, J=13.32, 11.42 Hz, 1 H) 2.53 (ddd, J=13.36, 6.04, 2.31 Hz, 1 H) 3.84 (s, 3 H) 3.87 (s, 4 H) 4.47 (dd, J=11.60, 2.21 Hz, 1 H) 5.07 - 5.17 (m, 1 H) 5.96 (s, 1 H) 6.96 - 7.00 (m, 1 H) 7.03 - 7.07 (m, 1 H) 7.10 (d, J=1.87 Hz, 1 H) 7.70 (dd, J=5.26, 1.41 Hz, 1 H) 7.75 - 7.80 (m, 1 H) 8.33 (dd, J=5.25, 0.55 Hz, 1 H) | 439.5 |
| ER-891029 | C22H22F3N5O3 | 5-(5-(3,4-dimethoxyphenyl)-7-(trifluoromethyl)-4,5,6,7-tetrahydropyrazolo[1,5-a]pyrimidin-2-yl)-N-methylpicolinamide | 0.050 | >10 | | 462 |

FIG. 11F

| Structure | ER-Number | Chemical Name | HEK/ TLR7 IC50 (μM) | HEK/ TLR9 IC50 (μM) | 1H NMR | MS |
|---|---|---|---|---|---|---|
| 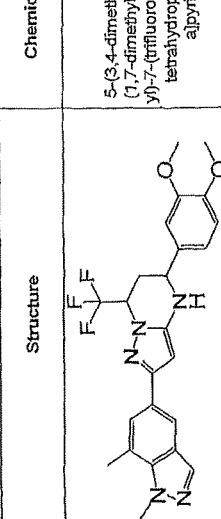 C24H24F3N5O2 | ER-891043 | 5-(3,4-dimethoxyphenyl)-2-(1,7-dimethyl-1H-indazol-5-yl)-7-(trifluoromethyl)-4,5,6,7-tetrahydropyrazolo[1,5-a]pyrimidine | 0.004 | > 10 | | 472 |
| 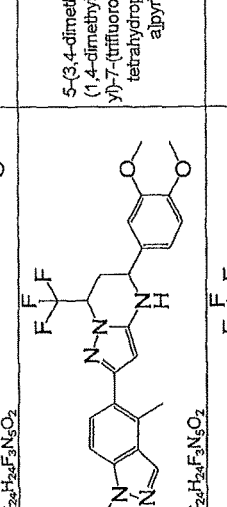 C24H24F3N5O2 | ER-891044 | 5-(3,4-dimethoxyphenyl)-2-(1,4-dimethyl-1H-indazol-5-yl)-7-(trifluoromethyl)-4,5,6,7-tetrahydropyrazolo[1,5-a]pyrimidine | 0.010 | > 10 | | 472 |
| 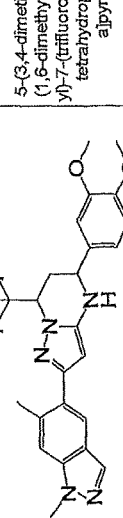 C24H24F3N5O2 | ER-891047 | 5-(3,4-dimethoxyphenyl)-2-(1,6-dimethyl-1H-indazol-5-yl)-7-(trifluoromethyl)-4,5,6,7-tetrahydropyrazolo[1,5-a]pyrimidine | 0.008 | > 10 | | 472 |
| 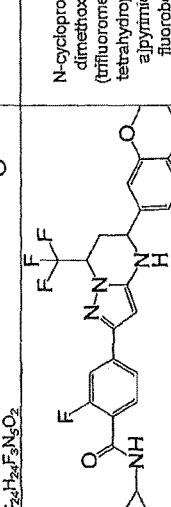 C25H24F4N4O3 | ER-891058 | N-cyclopropyl-4-(5-(3,4-dimethoxyphenyl)-7-(trifluoromethyl)-4,5,6,7-tetrahydropyrazolo[1,5-a]pyrimidin-2-yl)-2-fluorobenzamide | 0.050 | > 10 | | 505 |
| 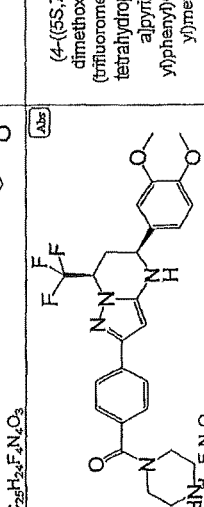 C26H29F3N5O3 | ER-892887 | (4-((5S,7R)-5-(3,4-dimethoxyphenyl)-7-(trifluoromethyl)-4,5,6,7-tetrahydropyrazolo[1,5-a]pyrimidin-2-yl)phenyl)(piperazin-1-yl)methanone | 0.006 | 6.02 | 1H NMR (400 MHz, METHANOL-d4) δ ppm 1.15 (d, J=6.15 Hz, 1 H) 2.23 (dt, J=13.27, 11.34 Hz, 1 H) 2.54 (ddd, J=13.38, 6.28, 2.49 Hz, 1 H) 3.85 (s, 3 H) 3.87 (s, 4 H) 4.46 (dd, J=11.57, 2.16 Hz, 1 H) 5.09 (dd, J=10.93, 6.06 Hz, 1 H) 5.88 (s, 1 H) 6.96-7.01 (m, 1 H) 7.03-7.08 (m, 1 H) 7.11 (d, J=1.94 Hz, 1 H) 7.47-7.56 (m, 2 H) 7.81-7.95 (m, 2 H) | 516.6 |

FIG. 11G

| ER-Number | Structure | Chemical Name | HEK/ TLR7 IC50 (µM) | HEK/ TLR9 IC50 (µM) | 1H NMR | MS |
|---|---|---|---|---|---|---|
| ER-892887 | C26H29ClF3N5O3 | 4-(4-((5S,7R)-5-(3,4-dimethoxyphenyl)-7-(trifluoromethyl)-4,5,6,7-tetrahydropyrazolo[1,5-a]pyrimidin-2-yl)benzoyl)piperazin-1-ium chloride | 0.010 | > 10 | see ER-890044 | 516.6 |
| ER-892889 | C23H22ClF3N4O3 | 2-chloro-4-((5S,7R)-5-(3,4-dimethoxyphenyl)-7-(trifluoromethyl)-4,5,6,7-tetrahydropyrazolo[1,5-a]pyrimidin-2-yl)-N-methylbenzamide | 0.020 | > 10 | 1H NMR (400 MHz, METHANOL-d4) δ ppm 2.23 (dt, J=13.29, 11.38 Hz, 1 H) 2.53 (ddd, J=13.34, 6.19, 2.44 Hz, 1 H) 2.86 - 2.96 (m, 3 H) 3.84 (s, 3 H) 3.87 (s, 3 H) 4.45 (dd, J=11.62, 2.23 Hz, 1 H) 5.03 - 5.16 (m, 1 H) 5.86 (s, 1 H) 6.98 (d, J=8.28 Hz, 1 H) 7.05 (dd, J=8.34, 1.93 Hz, 1 H) 7.11 (d, J=1.91 Hz, 1 H) 7.46 (d, J=7.97 Hz, 1 H) 7.72 (dd, J=7.97, 1.56 Hz, 1 H) 7.83 (d, J=1.45 Hz, 1 H) | 496 |
| ER-892890 | C22H20ClF3N4O3 | 2-chloro-4-((5S,7R)-5-(3,4-dimethoxyphenyl)-7-(trifluoromethyl)-4,5,6,7-tetrahydropyrazolo[1,5-a]pyrimidin-2-yl)benzamide | 0.040 | > 10 | 1H NMR (400 MHz, METHANOL-d4) δ ppm 2.20 - 2.29 (m, 1 H) 2.50 - 2.58 (m, 1 H) 3.83 - 3.86 (m, 3 H) 3.86 - 3.90 (m, 3 H) 4.46 (dd, J=11.65, 2.12 Hz, 1 H) 5.10 - 5.11 (m, 1 H) 5.87 (s, 1 H) 6.99 (d, J=8.28 Hz, 1 H) 7.06 (dd, J=8.32, 2.02 Hz, 1 H) 7.11 (d, J=1.91 Hz, 1 H) 7.51 - 7.55 (m, 1 H) 7.70 - 7.75 (m, 1 H) 7.84 (d, J=1.49 Hz, 1 H) | 482.2 |
| ER-892892 | C22H20F4N4O3 | 4-((5S,7R)-5-(3,4-dimethoxyphenyl)-7-(trifluoromethyl)-4,5,6,7-tetrahydropyrazolo[1,5-a]pyrimidin-2-yl)-3-fluorobenzamide | 0.040 | > 10 | 1H NMR (400 MHz, METHANOL-d4) δ ppm 2.20 (dt, J=13.26, 11.41 Hz, 1 H) 2.50 (ddd, J=13.36, 6.20, 2.45 Hz, 1 H) 3.27 (dt, J=3.31, 1.64 Hz, 1 H) 3.80 (s, 4 H) 3.83 (s, 3 H) 4.42 (dd, J=11.57, 2.20 Hz, 1 H) 5.02 - 5.12 (m, 1 H) 5.92 (d, J=4.21 Hz, 1 H) 6.94 (d, J=8.35 Hz, 1 H) 7.02 (dd, J=8.39, 1.90 Hz, 1 H) 7.08 (d, J=1.98 Hz, 1 H) 7.58 - 7.72 (m, 2 H) 8.00 (t, J=7.84 Hz, 1 H) | 465.5 |
| ER-892900 | C21H22F3N7 | 2-(1,4-dimethyl-1H-indazol-5-yl)-5-((5S,7R)-5-(1,3-dimethyl-1H-pyrazol-4-yl)-7-(trifluoromethyl)-4,5,6,7-tetrahydropyrazolo[1,5-a]pyrimidine | 0.100 | > 10 | | 430.1 |

FIG. 11H

| ER-Number | Structure | Chemical Name | HEK/TLR7 IC50 (μM) | HEK/TLR9 IC50 (μM) | 1H NMR | MS |
|---|---|---|---|---|---|---|
| ER-892908 | C26H28F4N4O3 | N-(tert-butyl)-4-(5-(3,4-dimethoxyphenyl)-7-(trifluoromethyl)-4,5,6,7-tetrahydropyrazolo[1,5-a]pyrimidin-2-yl)-2-fluorobenzamide | 0.050 | > 10 | | 521 |
| ER-892930 | C25H27F3N4O5 | N-(2,3-dihydroxypropyl)-4-(5-(3,4-dimethoxyphenyl)-7-(trifluoromethyl)-4,5,6,7-tetrahydropyrazolo[1,5-a]pyrimidin-2-yl)benzamide | 0.030 | > 10 | | |
| ER-892931 | C19H20F3N5O | 5-(3,4-dimethoxyphenyl)-2-(1H-indazol-4-yl)-7-(trifluoromethyl)-4,5,6,7-tetrahydropyrazolo[1,5-a]pyrimidine | 0.040 | > 10 | | 444 |
| ER-893888 | C22H23F3N6O2 | 1-(4-(5-(1,3-dimethyl-1H-pyrazol-4-yl)-7-(trifluoromethyl)-4,5,6,7-tetrahydropyrazolo[1,5-a]pyrimidin-2-yl)phenyl)urea | 0.020 | > 10 | δ 2.04, (m, 1H), 2.12, (s, 3H), 2.36, (m, 1H), 3.69, (s, 3H), 4.35, (m, 1H), 5.24, (m, 1H), 5.56, (s, 1H), 5.79, (s, 2H), 6.44, (s, 1H), 7.31, (d, 2H), 7.49, (d, 2H), 7.65, (s, 1H), 8.52, (s, 1H) | |
| ER-893961 | C24H24F3N5O2 | (5S,7R)-5-(3,4-dimethoxyphenyl)-2-(1,6-dimethyl-1H-indazol-5-yl)-7-(trifluoromethyl)-4,5,6,7-tetrahydropyrazolo[1,5-a]pyrimidine | 0.040 | > 10 | 1H NMR (400 MHz, METHANOL-d4) δ ppm 2.24 (dt, J=13.17, 11.38 Hz, 2 H) 2.48 - 2.55 (m, 1 H) 2.56 (s, 4 H) 3.84 (s, 3 H) 3.87 (s, 3 H) 4.05 (s, 3 H) 4.47 (dd, J=11.58, 2.08 Hz, 1 H) 5.02 - 5.16 (m, 1 H) 5.62 (s, 1 H) 6.98 (d, J=8.28 Hz, 1 H) 7.03 - 7.10 (m, 1 H) 7.12 (d, J=1.87 Hz, 1 H) 7.41 (s, 1 H) 7.78 (s, 1 H) 7.91 - 7.99 (m, 1 H) | 472.5 |

FIG. 11I

| ER-Number | Structure | Chemical Name | HEK/ TLR7 IC50 (μM) | HEK/ TLR9 IC50 (μM) | 1H NMR | MS |
|---|---|---|---|---|---|---|
| ER-893969 | C22H20F3N5O3 | 5-((5S,7R)-5-(3,4-dimethoxyphenyl)-7-(trifluoromethyl)-4,5,6,7-tetrahydropyrazolo[1,5-a]pyrimidin-2-yl)-1H-benzo[d]imidazol-2(3H)-one | 0.020 | > 10 | 1H NMR (400 MHz, METHANOL-d4) δ ppm 2.15 - 2.28 (m, 1 H) 2.47 - 2.56 (m, 1 H) 3.84 (s, 3 H) 3.87 (s, 3 H) 4.44 (dd, J=11.52, 2.12 Hz, 1 H) 5.04 (dd, J=11.37, 5.46 Hz, 1 H) 5.77 (s, 1 H) 6.95 - 7.01 (m, 1 H) 7.02 - 7.08 (m, 1 H) 7.09 - 7.14 (m, 1 H) 7.40 - 7.49 (m, 1 H) 7.52 - 7.60 (m, 2 H) 7.60 - 7.70 (m, 2 H) | 460.5 |
| ER-893972 | C24H24F3N5O2 | (5S,7R)-5-(3,4-dimethoxyphenyl)-2-(1,4-dimethyl-1H-indazol-5-yl)-7-(trifluoromethyl)-4,5,6,7-tetrahydropyrazolo[1,5-a]pyrimidine | 0.010 | > 10 | 1H NMR (400 MHz, METHANOL-d4) δ ppm 2.21 (dt, J=13.06, 11.42 Hz, 1 H) 2.47 - 2.55 (m, 1 H) 2.65 (s, 3 H) 3.78 - 3.82 (overlapping signals, 5 H) 3.83 (s, 4 H) 3.87 - 3.91 (m, 1 H) 4.03 (s, 3 H) 4.45 (dd, J=11.63, 2.22 Hz, 1 H) 5.07 (m, J=4.70 Hz, 1 H) 5.61 (s, 1 H) 6.95 (d, J=8.35 Hz, 1 H) 7.04 (dd, J=8.37, 1.81 Hz, 1 H) 7.10 (d, J=1.98 Hz, 1 H) 7.35 (d, J=8.61 Hz, 1 H) 7.52 (d, J=8.68 Hz, 1 H) 8.06 (d, J=0.88 Hz, 1 H) | 472.3 |
| ER-893987 | C21H22F3N7 | (5R,7S)-2-(1,4-dimethyl-1H-indazol-5-yl)-5-(1,3-dimethyl-1H-pyrazol-4-yl)-7-(trifluoromethyl)-4,5,6,7-tetrahydropyrazolo[1,5-a]pyrimidine | 0.090 | > 10 | δ 2.05, (m, 1H), 2.14, (s, 3H), 2.36, (m, 1H), 2.62, (s, 3H), 3.70, (s, 3H), 3.97, (s, 3H), 4.38, (m, 1H), 5.22, (m, 1H), 5.51, (s, 1H), 6.44, (s, 1H), 7.38, (d, 1H), 7.49, (d, 1H), 7.63, (s, 1H), 8.08, (s, 1H) | |
| ER-893990 | C20H20F3N7 | (5S,7R)-5-(1,3-dimethyl-1H-pyrazol-4-yl)-2-(2-methyl-2H-indazol-5-yl)-7-(trifluoromethyl)-4,5,6,7-tetrahydropyrazolo[1,5-a]pyrimidine | 0.080 | > 10 | δ 2.03, (m, 1H), 2.11, (s, 3H), 2.33, (m, 1H), 3.69, (s, 3H), 4.09, (s, 3H), 4.33, (m, 1H), 5.19, (m, 1H), 5.67, (s, 1H), 6.48, (s, 1H), 7.50, (d, 1H), 7.62, (d, 1H), 7.65, (s, 1H), 7.91, (s, 1H), 8.26, (s, 1H) | |
| ER-894462 | C25H25F3N4O4 | (4-(5-(3,4-dimethoxyphenyl)-7-(trifluoromethyl)-4,5,6,7-tetrahydropyrazolo[1,5-a]pyrimidin-2-yl)phenyl)(3-hydroxyazetidin-1-yl)methanone | 0.060 | > 10 | | 503 |

FIG. 11J

| ER-Number | Structure | Chemical Name | HEK/ TLR7 IC50 (μM) | HEK/ TLR9 IC50 (μM) | 1H NMR | MS |
|---|---|---|---|---|---|---|
| ER-894463 | C25H29ClF3N5O3 | 4-(5-(3,4-dimethoxyphenyl)-7-(trifluoromethyl)-4,5,6,7-tetrahydropyrazolo[1,5-a]pyrimidin-2-yl)-N-(pyrrolidin-3-yl)benzamide hydrochloride | 0.050 | 6.09 | | |
| ER-894464 | C25H29ClF3N5O3 | (3-aminopyrrolidin-1-yl)(4-(5-(3,4-dimethoxyphenyl)-7-(trifluoromethyl)-4,5,6,7-tetrahydropyrazolo[1,5-a]pyrimidin-2-yl)phenyl)methanone hydrochloride | 0.006 | > 10 | 1H NMR (400 MHz, METHANOL-d4) δ ppm 1.82 (dd, 1 H) 2.17 - 2.32 (m, 2 H) 2.54 (dd, 1 H) 3.38 (m, 1H) 3.47 - 3.60 (m,1 H) 3.60 - 3.74 (m, 2 H) 3.74 - 3.83 (m, 1 H) 3.85 (m, 3 H) 3.87(m, 3 H) 4.46 (d, 1 H) 5.00 - 5.14 (m, 1 H) 6.91 - 7.02(m, 2 H) 7.02 - 7.16 (m, 2 H) 7.57 (t, 2 H) 7.84 (d, 2 H) | 516.6 |
| ER-894465 | C25H27F3N4O4 | (4-(5-(3,4-dimethoxyphenyl)-7-(trifluoromethyl)-4,5,6,7-tetrahydropyrazolo[1,5-a]pyrimidin-2-yl)phenyl)(3-hydroxypyrrolidin-1-yl)methanone | 0.009 | > 10 | 1H NMR (400 MHz, METHANOL-d4) δ ppm 1.89 - 2.16 (m,overlapping signals, 3 H) 2.23 (dt, 1 H) 2.52 (ddd, 1 H) 3.39 (d,1 H) 3.46 - 3.62 (m, 1 H) 3.62 - 3.81 (m, 2 H) 3.84 (s, 3 H) 3.87 (s, 3 H) 4.28 - 4.54 (m, 2 H) 4.98 - 5.17 (m, 1 H) 6.91 - 7.20 (m, 4 H) 7.48 - 7.65 (m, 2 H) 7.77 - 7.94 (m, 2 H) | 518.6 |
| ER-894466 | C25H29F3N5O3 | (4-(7-(difluoromethyl)-5-(3,4-dimethoxyphenyl)-4,5,6,7-tetrahydropyrazolo[1,5-a]pyrimidin-2-yl)phenyl)(piperazin-1-yl)methanone | 0.010 | 10.00 | 1H NMR (400 MHz, METHANOL-d4) δ ppm 2.21 - 2.37 (m, 1 H) 2.89-2.92(M,4h) 2.99-3.02(m,overlapping signals, 1h)3.46-3.50(m, 2H) 3.67-3.75(m, 2h) 3.85(s, 3 H) 3.87 (s, 3 H) 4.47(dd, 1 H) 4.65 - 4.80 (m, 1 H) 6.49(d), 6.63(t, 1H)7.05 (m, 4 H) 7.36 - 7.49 (m, 2 H) 7.79 - 7.89 (m, 2 H) | 498.6 |
| ER-894595 | C19H20F3N7O | 1-(4-(4-((5S,7R)-5-(1,3-dimethyl-1H-pyrazol-4-yl)-7-(trifluoromethyl)-4,5,6,7-tetrahydropyrazolo[1,5-a]pyrimidin-2-yl)phenyl)urea | 0.060 | > 10 | δ 2.04, (m, 1H), 2.12, (s, 3H), 2.36, (m, 1H), 3.69, (s, 3H), 4.35, (s, 1H), 5.24, (m, 1H), 5.56, (s, 1H), 5.79, (s, 2H), 6.44, (s, 1H), 7.31, (d, 2H), 7.49, (d, 2H), 7.65, (s, 1H), 8.52, (s, 1H) | |

FIG. 11K

| ER-Number | Structure | Chemical Name | HEK/ TLR7 IC50 (μM) | HEK/ TLR9 IC50 (μM) | 1H NMR | MS |
|---|---|---|---|---|---|---|
| ER-894646 | C₂₃H₂₂F₃N₅O₂ | (5S,7R)-5-(3,4-dimethoxyphenyl)-2-(6-methyl-1H-indazol-5-yl)-7-(trifluoromethyl)-4,5,6,7-tetrahydropyrazolo[1,5-a]pyrimidine | 0.030 | > 10 | 1H NMR (400 MHz, CHLOROFORM-d) δ ppm 2.33 - 2.45 (m, 1 H) 2.50 (m, 1 H) 2.56 (s, 3 H, overlapping signals) 3.91 (s, 3 H) 3.93 (s, 3 H) 4.34 (s, 1 H) 4.41 - 4.50 (m, 1 H) 4.94 (dt, J=11.27, 5.77 Hz, 1 H) 5.63 (s, 1 H) 6.89 (d, J=8.20 Hz, 1 H) 6.96 - 7.06 (m, 2 H) 7.30 (s, 1 H) 7.85 (s, 1 H) 8.01 (s, 1 H) | 458.3 |
| ER-894647 | C₂₃H₂₂F₃N₅O₂ | (5S,7R)-5-(3,4-dimethoxyphenyl)-2-(5-methyl-1H-indazol-6-yl)-7-(trifluoromethyl)-4,5,6,7-tetrahydropyrazolo[1,5-a]pyrimidine | 0.050 | > 10 | 1H NMR (400 MHz, CHLOROFORM-d) δ ppm 2.36 - 2.49 (m, 1 H) 2.49 - 2.55 (m, 1 H) 2.55 (s, 3 H, overlapping signals) 3.91 (s, 3 H) 3.93 (s, 3 H) 4.32 (s, 1 H) 4.48 (d, J=9.92 Hz, 1 H) 4.95 (dt, J=11.37, 5.76 Hz, 1 H) 5.67 (s, 1 H) 6.85 - 6.94 (m, 1 H) 6.95 - 7.05 (m, 2 H) 7.59 (s, 1 H) 7.63 - 7.68 (m, 2 H) | |
| ER-894680 | C₂₃H₂₂F₃N₅O₂ | (5S,7R)-5-(3,4-dimethoxyphenyl)-2-(4-methyl-1H-indazol-5-yl)-7-(trifluoromethyl)-4,5,6,7-tetrahydropyrazolo[1,5-a]pyrimidine | 0.040 | > 10 | 1H NMR (400 MHz, METHANOL-d4) δ ppm 2.18 - 2.29 (m, 2 H) 2.47 - 2.55 (m, 1 H) 2.66 (s, 2 H) 3.81 (s, 3 H) 3.84 (s, 3 H) 4.45 (dd, J=11.55, 2.18 Hz, 1 H) 5.61 (s, 1 H) 6.89 - 6.98 (m, 2 H) 7.01 - 7.06 (m, 1 H) 7.10 (d, J=1.94 Hz, 1 H) 7.34 (d, J=8.64 Hz, 1 H) 7.48 (d, J=8.64 Hz, 1 H) 8.05 - 8.15 (m, 1 H) | 458.6 |
| ER-895077 | C₂₅H₂₇ClF₃N₅O₃ | N-(azetidin-3-yl)-4-(5-(3,4-dimethoxyphenyl)-7-(trifluoromethyl)-4,5,6,7-tetrahydropyrazolo[1,5-a]pyrimidin-2-yl)benzamide hydrochloride | 0.050 | > 10 | 1H NMR (400 MHz, METHANOL-d4) δ ppm 2.12 - 2.33 (m, 1 H) 2.54 (td, 1 H) 2.95-3.12(m, 1H) 3.85 (s, 3 H) 3.86 - 3.92 (m,3 H) 3.92 - 4.00 (m,2 H) 4.00 - 4.08 (m, 2 H) 4.46 (d, 2 H) 5.04 - 5.15 (m, 1 H) 6.94 - 7.17 (m, 4 H) 7.78 - 7.91 (m, 4 H) | 502.5 |
| ER-895078 | C₂₅H₂₇ClF₃N₅O₃ | (3-aminoazetidin-1-yl)(4-(5-(3,4-dimethoxyphenyl)-7-(trifluoromethyl)-4,5,6,7-tetrahydropyrazolo[1,5-a]pyrimidin-2-yl)phenyl)methanone hydrochloride | 0.020 | > 10 | | 502 |

FIG. 11L

| ER-Number | Structure | Chemical Name | HEK/ TLR7 IC50 (µM) | HEK/ TLR9 IC50 (µM) | 1H NMR | MS |
|---|---|---|---|---|---|---|
| ER-895080 | C29H31F6N5O5 | (4-(5-(3,4-dimethoxyphenyl)-7-(trifluoromethyl)-4,5,6,7-tetrahydropyrazolo[1,5-a]pyrimidin-2-yl)phenyl)(2,6-diazaspiro[3.4]octan-2-yl)methanone 2,2,2-trifluoroacetate | 0.050 | > 10 | 1H NMR (400 MHz, METHANOL-d4) δ ppm 1.77 - 1.97 (m, 1 H) 2.06 - 2.18 (m, 1 H) 2.18 - 2.31 (m, 1 H) 2.89 (d, 2 H) 2.96 - 3.09 (m,2 H) 3.11 - 3.21 (m, 2 H)3.85 (s, 3 H) 3.87(s, 3 H) 4.14 (br. s, 2 H) 4.37 (br. s., 2 H) 4.46 (d, 1 H) 6.90 -7.17 (m, 4 H) 7.59 - 7.76 (m, 2 H) 7.80 - 7.90 (m, 2 H) | 542.6 |
| ER-895081 | C31H33F6N5O5 | N-(6-aminospiro[3.3]heptan-2-yl)-4-(5-(3,4-dimethoxyphenyl)-7-(trifluoromethyl)-4,5,6,7-tetrahydropyrazolo[1,5-a]pyrimidin-2-yl)benzamide 2,2,2-trifluoroacetate | 0.050 | > 10 |  | 556 |
| ER-895082 | C31H33F6N5O5 | (4-(5-(3,4-dimethoxyphenyl)-7-(trifluoromethyl)-4,5,6,7-tetrahydropyrazolo[1,5-a]pyrimidin-2-yl)phenyl)(2,7-diazaspiro[4.4]nonan-2-yl)methanone 2,2,2-trifluoroacetate | 0.070 | > 10 | 1H NMR (400 MHz, METHANOL-d4) δ ppm 1.94 - 2.19 (m, 3 H) 2.21 - 2.26 (m,overlapping signals, 1 H) 2.54 (ddd, 1 H) 3.06 - 3.19 (m, 2 H) 3.24 (d, 1 H) 3.39 (t, 1 H) 3.59 (d,1 H) 3.62 - 3.78 (m, overlapping sigan/s, 4 H) 3.85 (s, 3 H) 3.87 (s, 3 H) 4.46 (dd,1 H) 5.00 - 5.15 (m, 1 H) 6.93 -7.15 (m, 4 H) 7.51 - 7.65 (m, 2 H) 7.79 -7.91 (m, 2 H) | 556.6 |
| ER-895083 | C29H31F6N5O5 | (4-(5-(3,4-dimethoxyphenyl)-7-(trifluoromethyl)-4,5,6,7-tetrahydropyrazolo[1,5-a]pyrimidin-2-yl)phenyl)(3-((methylamino)methyl)azetidin-1-yl)methanone 2,2,2-trifluoroacetate | 0.070 | > 10 | 1H NMR (400 MHz, METHANOL-d4) δ ppm 1.23 - 1.38 (m, 1 H) 2.17 - 2.33 (m, 1 H) 2.37 - 2.45 (m, 2 H) 2.53 (ddd, 1 H)2.77 (q, 1 H) 2.82 - 2.92 (m, 3 H) 3.84 (s, 3 H) 3.87 (m, 3 H) 4.10 (dd, 1 H) 4.28 (t, 1 H) 4.42 - 4.54(m, 2 H) 5.00 - 5.14 (m, 1 H) 6.96 -7.20 (m, 4 H) 7.61 - 7.73 (m, 2 H) 7.76 -7.91 (m, 2 H) | 530.6 |

FIG. 11M

| ER-Number | Structure | Chemical Name | HEK/ TLR7 IC50 (μM) | HEK/ TLR9 IC50 (μM) | 1H NMR | MS |
|---|---|---|---|---|---|---|
| ER-895088 | C27H32ClF2N5O3 · H-Cl | (4-(7-(difluoromethyl)-5-(3,4-dimethoxyphenyl)-4,5,6,7-tetrahydropyrazolo[1,5-a]pyrimidin-2-yl)phenyl)((S)-2-methylpiperazin-1-yl)methanone hydrochloride | 0.020 | 8.99 | 1H NMR (400 MHz, METHANOL-d4) δ ppm 1.18 - 1.30 (m, 1 H) 1.36 (d, 3 H) 2.21 - 2.41 (m, 2 H) 2.63 - 2.77 (m, 2 H) 2.84 (m, 2H) 2.93 (dd, 2 H) 3.85 (s, 3 H) 3.87 (s, 3 H) 4.47 (dd, 1 H) 6.93 - 7.02 (m, 1 H) 7.02 - 7.18 (m, 2 H) 7.41 (d, 2H) 7.76 - 7.89 (m, 4H) | 512.7 |
| ER-895089 | C26H30ClF2N5O3 · H-Cl | ((S)-3-aminopyrrolidin-1-yl)(4-(7-(difluoromethyl)-5-(3,4-dimethoxyphenyl)-4,5,6,7-tetrahydropyrazolo[1,5-a]pyrimidin-2-yl)phenyl)methanone hydrochloride | 0.020 | 7.73 | | 498 |
| ER-895090 | C27H30ClF2N5O3 · H-Cl | (1S,4S)-2,5-diazabicyclo[2.2.1]heptan-2-yl)(4-(7-(difluoromethyl)-5-(3,4-dimethoxyphenyl)-4,5,6,7-tetrahydropyrazolo[1,5-a]pyrimidin-2-yl)phenyl)methanone hydrochloride | 0.010 | 4.57 | 1H NMR (400 MHz, METHANOL-d4) δ ppm 2.20 - 2.40 (m, 1 H) 2.98 - 3.09 (m, 7 H) 3.10 - 3.20 (m, 1 H) 3.61 - 3.73 (m, 1 H) 3.85 (s, 3 H) 3.87 (s, 3 H) 4.38 - 4.52 (m, 2 H) 6.93 - 7.02 (m, 1 H) 7.02 - 7.17 (m, 2 H) 7.48 - 7.62 (m, 2 H) 7.77 - 7.90 (m, 2 H) | 510.6 |
| ER-895091 | C26H29ClF3N5O3 · H-Cl | (4-(7-(difluoromethyl)-5-(3,4-dimethoxyphenyl)-4,5,6,7-tetrahydropyrazolo[1,5-a]pyrimidin-2-yl)-2-fluorophenyl)(piperazin-1-yl)methanone hydrochloride | 0.080 | 8.40 | | 516 |
| ER-895092 | C27H31ClF3N5O3 · H-Cl | 4-(7-(difluoromethyl)-5-(3,4-dimethoxyphenyl)-4,5,6,7-tetrahydropyrazolo[1,5-a]pyrimidin-2-yl)-2-fluoro-N-(piperidin-4-yl)benzamide hydrochloride | 0.010 | 4.34 | | 530 |

FIG. 11N

| ER-Number | Structure | Chemical Name | HEK/ TLR7 IC50 (µM) | HEK/ TLR9 IC50 (µM) | 1H NMR | MS |
|---|---|---|---|---|---|---|
| ER-895093 | C27H31ClF3N5O3 | 4-(7-(difluoromethyl)-5-(3,4-dimethoxyphenyl)-4,5,6,7-tetrahydropyrazolo[1,5-a]pyrimidin-2-yl)-2-fluoro-N-((S)-piperidin-3-yl)benzamide hydrochloride | 0.040 | 10.00 | | 530 |
| ER-895094 | C27H31ClF3N5O3 | 4-(7-(difluoromethyl)-5-(3,4-dimethoxyphenyl)-4,5,6,7-tetrahydropyrazolo[1,5-a]pyrimidin-2-yl)-2-fluoro-N-((R)-piperidin-3-yl)benzamide hydrochloride | 0.030 | 8.46 | | 530 |
| ER-895096 | C28H33ClF3N5O3 | (4-(7-(difluoromethyl)-5-(3,4-dimethoxyphenyl)-4,5,6,7-tetrahydropyrazolo[1,5-a]pyrimidin-2-yl)((2R,5S)-2,5-dimethylpiperazin-1-yl)methanone hydrochloride | 0.030 | 9.35 | 1H NMR (400 MHz, METHANOL-d4) δ ppm 1.12 - 1.38 (br. m., 6 H) 2.31 (m, 2 H) 2.59 (m, 1 H) 2.74 (m, 1 H) 2.94 (m, 1 H) 3.12 (m, 1 H) 3.22 (m, 2 H) 3.83 (s, 3 H) 3.86 (s, 3 H) 4.46 (d, 1 H) 4.74 (m, 1 H) 6.62 (t, 1 H) 6.95 - 7.11 (m, 4 H) 7.32 - 7.38 (m, 1 H) 7.53 - 7.67 (m, 2 H) | 544 |
| ER-895097 | C26H29ClF3N5O3 | 4-(7-(difluoromethyl)-5-(3,4-dimethoxyphenyl)-4,5,6,7-tetrahydropyrazolo[1,5-a]pyrimidin-2-yl)-2-fluoro-N-((R)-pyrrolidin-3-yl)benzamide hydrochloride | 0.050 | 4.27 | | 516 |
| ER-895098 | C26H29ClF3N5O3 | 4-(7-(difluoromethyl)-5-(3,4-dimethoxyphenyl)-4,5,6,7-tetrahydropyrazolo[1,5-a]pyrimidin-2-yl)-2-fluoro-N-((S)-pyrrolidin-3-yl)benzamide hydrochloride | 0.020 | 4.03 | 1H NMR (400 MHz, METHANOL-d4) δ ppm 1.76 - 1.96 (m, 1 H) 2.12 - 2.39 (m, 2 H) 3.34 (br. s., 2 H) 3.53 - 3.81 (m, overlapping signals, 2 H) 3.85 (s, 3 H) 3.87 (s, 3 H) 3.93 (br. s., 1 H) 4.47 (dd, 1 H) 4.63 - 4.83 (m, 1 H) 6.63 (t, 1 H) 6.92 - 7.02 (m, 1 H) 7.02 - 7.18 (m, 3H) 7.51 - 7.65 (m, 2 H) 7.74 - 7.90 (m, 2 H) | 498.6 |

FIG. 110

| ER-Number | Structure | Chemical Name | HEK/ TLR7 IC50 (µM) | HEK/ TLR9 IC50 (µM) | 1H NMR | MS |
|---|---|---|---|---|---|---|
| ER-895099 | C27H27F6N5O5 | N-(azetidin-3-yl)-4-(7-(difluoromethyl)-5-(3,4-dimethoxyphenyl)-4,5,6,7-tetrahydropyrazolo[1,5-a]pyrimidin-2-yl)-2-fluorobenzamide 2,2,2-trifluoroacetate | 0.030 | 4.48 | 1H NMR (400 MHz, METHANOL-d4) δ ppm 2.31 (m, 2 H) 3.83 (s, 3 H) 3.86 (s, 3 H) 3.93 (m, 3 H) 4.04 (m, 2 H) 4.46 (d, 1 H) 4.72 (m, 1 H) 6.63 (t, 1 H) 6.93 - 7.12 (m, 4 H) 7.53 - 7.68 (m, 2 H) 7.74 (t, 1 H) | 502 |
| ER-895101 | C27H29F6N5O3 | (1S,4S)-2,5-diazabicyclo[2.2.1]heptan-2-yl(4-(7-(difluoromethyl)-5-(3,4-dimethoxyphenyl)-4,5,6,7-tetrahydropyrazolo[1,5-a]pyrimidin-2-yl)-2-fluorophenyl)methanone hydrochloride | 0.030 | 10.00 | 1H NMR (400 MHz, METHANOL-d4) δ ppm 1.80 (dd, 2 H) 2.20 - 2.39 (m, 2 H) 2.91 (m, 1 H) 3.04 (m, 1 H) 3.23 (m, 1 H) 3.47 (m, 1 H) 3.61 (m, 1 H) 3.77 (m, 1 H) 3.83 (s, 3 H) 3.86 (s, 3 H) 4.46 (d, 1 H) 4.72 (m, 1 H) 6.63 (t, 1 H) 6.95 - 7.12 (m, 4 H) 7.39 - 7.49 (m, 2 H) 7.55 - 7.69 (m, 1 H) | 528 |
| ER-895102 | C25H29ClF3N5O3 | (4-(7-(difluoromethyl)-5-(3,4-dimethoxyphenyl)-4,5,6,7-tetrahydropyrazolo[1,5-a]pyrimidin-2-yl)-3-fluorophenyl)(piperazin-1-yl)methanone hydrochloride | 0.080 | 10.00 | | 516 |
| ER-895104 | C27H31ClF3N5O3 | 4-(7-(difluoromethyl)-5-(3,4-dimethoxyphenyl)-4,5,6,7-tetrahydropyrazolo[1,5-a]pyrimidin-2-yl)-3-fluoro-N-((S)-piperidin-3-yl)benzamide hydrochloride | 0.090 | 10.00 | | 530 |
| ER-895105 | C27H31ClF3N5O3 | 4-(7-(difluoromethyl)-5-(3,4-dimethoxyphenyl)-4,5,6,7-tetrahydropyrazolo[1,5-a]pyrimidin-2-yl)-3-fluoro-N-((R)-piperidin-3-yl)benzamide hydrochloride | 0.080 | 10.00 | | 530 |

FIG. 11P

| ER-Number | Structure | Chemical Name | HEK/ TLR7 IC50 (µM) | HEK/ TLR9 IC50 (µM) | 1H NMR | MS |
|---|---|---|---|---|---|---|
| ER-895106 | C27H31ClF3N5O3 | (4-(7-(difluoromethyl)-5-(3,4-dimethoxyphenyl)-4,5,6,7-tetrahydropyrazolo[1,5-a]pyrimidin-2-yl)-3-fluorophenyl)((S)-2-methylpiperazin-1-yl)methanone hydrochloride | 0.060 | 10.00 | | 530 |
| ER-895107 | C28H33ClF3N5O3 | (4-(7-(difluoromethyl)-5-(3,4-dimethoxyphenyl)-4,5,6,7-tetrahydropyrazolo[1,5-a]pyrimidin-2-yl)-3-fluorophenyl)((2R,5S)-2,5-dimethylpiperazin-1-yl)methanone hydrochloride | 0.020 | 10.00 | | 544 |
| ER-895109 | C26H29ClF3N5O3 | 4-(7-(difluoromethyl)-5-(3,4-dimethoxyphenyl)-4,5,6,7-tetrahydropyrazolo[1,5-a]pyrimidin-2-yl)-3-fluoro-N-((S)-pyrrolidin-3-yl)benzamide hydrochloride | 0.100 | 10.00 | | 516 |
| ER-895111 | C29H29F6N5O5 | (4-(7-(difluoromethyl)-5-(3,4-dimethoxyphenyl)-4,5,6,7-tetrahydropyrazolo[1,5-a]pyrimidin-2-yl)-3-fluorophenyl)(2,6-diazaspiro[3.3]heptan-2-yl)methanone 2,2,2-trifluoroacetate | 0.090 | 10.00 | | 528 |
| ER-895112 | C27H29ClF3N5O3 | (1S,4S)-2,5-diazabicyclo[2.2.1]heptan-2-yl)(4-(7-(difluoromethyl)-5-(3,4-dimethoxyphenyl)-4,5,6,7-tetrahydropyrazolo[1,5-a]pyrimidin-2-yl)-3-fluorophenyl)methanone hydrochloride | 0.050 | 10.00 | | 528 |

FIG. 11Q

| ER-Number | Structure | Chemical Name | HEK/ TLR7 IC50 (µM) | HEK/ TLR9 IC50 (µM) | 1H NMR | MS |
|---|---|---|---|---|---|---|
| ER-895115 | C26H30ClF2N5O3 | 4-(7-(difluoromethyl)-5-(3,4-dimethoxyphenyl)-4,5,6,7-tetrahydropyrazolo[1,5-a]pyrimidin-2-yl)-N-((S)-pyrrolidin-3-yl)benzamide hydrochloride | 0.050 | 10.00 | 1H NMR (400 MHz, METHANOL-d4) δ ppm 2.15 - 2.24 (m, 1 H) 2.27 (d, 1 H) 2.29 - 2.46 (m, 1 H) 3.11 - 3.25 (m, 3 H) 3.33 - 3.43 (m, 1 H) 3.43 - 3.65 (m, 2 H) 3.85 (s, 3 H) 3.87 (s, 3 H) 4.42 - 4.53 (m, 1 H) 4.55 - 4.66 (m, 1 H) 6.63 (s, 1 H) 6.90 - 7.18 (m, 4 H) 7.79 - 7.93 (m, 2H) 8.53 (s, 1 H) | 498.6 |
| ER-895116 | C26H30ClF2N5O3 | ((R)-3-aminopyrrolidin-1-yl)(4-(7-(difluoromethyl)-5-(3,4-dimethoxyphenyl)-4,5,6,7-tetrahydropyrazolo[1,5-a]pyrimidin-2-yl)phenyl)methanone hydrochloride | 0.030 | 10.00 | 1H NMR (400 MHz, METHANOL-d4) δ ppm 1.67 - 1.92 (m, 1 H) 2.07 - 2.17 (m, 1 H) 2.17 - 2.42 (m, 1 H) 3.40 (dd, 1 H) 3.44 - 3.59 (m, 1 H) 3.62 - 3.75 (m, 2 H) 3.75 - 3.82 (m, 1 H) 3.85 (s, 3 H) 3.87 (s, 3 H) 4.47 (dd, 1 H) 4.62 - 4.80 (m, 1H) 6.63 (t, 1 H) 6.94 - 7.02 (m, 1 H) 7.02 - 7.18 (m, 3 H) 7.57 (t, 2 H) 7.79 - 7.89 (m, 2 H) | 498.7 |
| ER-895302 | C26H29F2N5O3 | (4-((5S,7R)-7-(difluoromethyl)-5-(3,4-dimethoxyphenyl)-4,5,6,7-tetrahydropyrazolo[1,5-a]pyrimidin-2-yl)phenyl)(piperazin-1-yl)methanone | 0.020 | 10.00 | | |
| ER-895303 | C26H29F2N5O3 | (4-((5R,7S)-7-(difluoromethyl)-5-(3,4-dimethoxyphenyl)-4,5,6,7-tetrahydropyrazolo[1,5-a]pyrimidin-2-yl)phenyl)(piperazin-1-yl)methanone | 0.030 | 6.39 | | |
| ER-895396 | C26H29ClF3N5O3 | 1-(4-((5S,7R)-5-(3,4-dimethoxyphenyl)-7-(trifluoromethyl)-4,5,6,7-tetrahydropyrazolo[1,5-a]pyrimidin-2-yl)benzoyl)pyrrolidin-3-aminium chloride | 0.020 | > 10 | | |

FIG. 11R

| ER-Number | Structure | Chemical Name | HEK/ TLR7 IC50 (μM) | HEK/ TLR9 IC50 (μM) | 1H NMR | MS |
|---|---|---|---|---|---|---|
| ER-895436 | H-Cl / HN piperazine structure / C27H32ClF2N5O3 | 2-(4-(7-(difluoromethyl)-5-(3,4-dimethoxyphenyl)-4,5,6,7-tetrahydropyrazolo[1,5-a]pyrimidin-2-yl)phenyl)-1-(piperazin-1-yl)ethanone hydrochloride | 0.020 | 10.00 | (DMSO-d6) δ 2.03, (m, 1H), 2.18, (m, 1H), 2.98, (m, 4H), 3.52, (s, 2H), 3.65, (m, 4H), 3.68, (s, 3H), 3.72, (s, 3H), 4.21, (m, 1H), 4.75, (m, 1H), 5.66, (s, 1H), 6.62, (s, 1H), 6.64, (br t, 1H), 6.92, (dd, 2H), 7.00, (s, 1H), 7.18, (d, 2H), 7.62, (d, 2H), 8.97, (s, 1H) | |
| ER-895437 | HN-azetidine structure / H-Cl / C26H30ClF2N5O3 | N-(azetidin-3-yl)-2-(4-(7-(difluoromethyl)-5-(3,4-dimethoxyphenyl)-4,5,6,7-tetrahydropyrazolo[1,5-a]pyrimidin-2-yl)phenyl)acetamide hydrochloride | 0.080 | 10.00 | (DMSO-d6) δ 2.03, (m, 1H), 2.18, (m, 1H), 3.40, (s, 2H), 3.68, (s, 3H), 3.72, (s, 3H), 4.01 (m, 5H), 4.40, (m, 1H), 4.75, (m, 1H), 5.65, (s, 1H), 6.62, (s, 1H), 6.64, (br t, 1H), 6.92, (m, 2H), 7.00, (s, 1H), 7.18, (d, 2H), 7.62, (d, 2H), 8.22, (br s, 1H) | |
| ER-895438 | H-Cl / H2N-azetidine structure / C26H30ClF2N5O3 | 1-(3-aminoazetidin-1-yl)-2-(4-(7-(difluoromethyl)-5-(3,4-dimethoxyphenyl)-4,5,6,7-tetrahydropyrazolo[1,5-a]pyrimidin-2-yl)phenyl)ethanone hydrochloride | 0.070 | 10.00 | (DMSO-d6) δ 2.03, (m, 1H), 2.18, (m, 1H), 3.40, (s, 2H), 3.68, (s, 3H), 3.72, (s, 3H), 3.86, (m, 2H), 4.03, (m, 2H), 3.91, (m, 1H), 4.40, (m, 1H), 4.75, (m, 1H), 5.65, (s, 1H), 6.62, (s, 1H), 6.64, (br t, 1H), 6.92, (m, 2H), 7.00, (s, 1H), 7.18, (d, 2H), 7.62, (d, 2H), 8.84, (d, 2H) | |
| ER-895496 | Abs / azetidine structure / +H3N Cl- / C25H27ClF3N5O3 | 1-(4-((5S,7R)-5-(3,4-dimethoxyphenyl)-7-(trifluoromethyl)-4,5,6,7-tetrahydropyrazolo[1,5-a]pyrimidin-2-yl)benzoyl)azetidin-3-aminium chloride | 0.030 | > 10 | NMR for racemate reported | |
| ER-895498 | Abs / azetidine structure / +H3N Cl- / C25H27ClF3N5O3 | 3-(4-((5S,7R)-5-(3,4-dimethoxyphenyl)-7-(trifluoromethyl)-4,5,6,7-tetrahydropyrazolo[1,5-a]pyrimidin-2-yl)benzamido)azetidin-1-ium chloride | 0.020 | > 10 | | |

FIG. 11S

| ER-Number | Structure | Chemical Name | HEK/ TLR7 IC50 (µM) | HEK/ TLR9 IC50 (µM) | 1H NMR | MS |
|---|---|---|---|---|---|---|
| ER-895548 | C28H34ClF2N5O3 | (4-(7-(difluoromethyl)-5-(3,4-dimethoxyphenyl)-4,5,6,7-tetrahydropyrazolo[1,5-a]pyrimidin-2-yl)phenyl)((2R,5S)-2,5-dimethylpiperazin-1-yl)methanone hydrochloride | 0.008 | 10.00 | | |
| ER-895550 | C27H32ClF2N5O3 | 4-(7-(difluoromethyl)-5-(3,4-dimethoxyphenyl)-4,5,6,7-tetrahydropyrazolo[1,5-a]pyrimidin-2-yl)-N-(R)-piperidin-3-yl)benzamide hydrochloride | 0.030 | 5.97 | | |
| ER-895577 | C27H32ClF2N5O3 | 4-(7-(difluoromethyl)-5-(3,4-dimethoxyphenyl)-4,5,6,7-tetrahydropyrazolo[1,5-a]pyrimidin-2-yl)-N-((S)-piperidin-3-yl)benzamide hydrochloride | 0.020 | 7.82 | | |
| ER-895676 | C26H29ClF3N5O3 | (R)-3-(4-((5S,7R)-5-(3,4-dimethoxyphenyl)-7-(trifluoromethyl)-4,5,6,7-tetrahydropyrazolo[1,5-a]pyrimidin-2-yl)benzamido)pyrrolidin-1-ium chloride | 0.030 | 7.20 | NMR for racemate reported | |
| ER-895678 | C26H29ClF3N5O3 | (S)-3-(4-((5S,7R)-5-(3,4-dimethoxyphenyl)-7-(trifluoromethyl)-4,5,6,7-tetrahydropyrazolo[1,5-a]pyrimidin-2-yl)benzamido)pyrrolidin-1-ium chloride | 0.020 | 8.60 | NMR for racemate preferable | |

FIG. 11T

| ER-Number | Structure | Chemical Name | HEK/ TLR7 IC50 (µM) | HEK/ TLR9 IC50 (µM) | 1H NMR | MS |
|---|---|---|---|---|---|---|
| ER-895718 | C28H34ClF2N5O3 · H-Cl | 4-(7-(difluoromethyl)-5-(3,4-dimethoxyphenyl)-4,5,6,7-tetrahydropyrazolo[1,5-a]pyrimidin-2-yl)-3-methyl-N-(piperidin-4-yl)benzamide hydrochloride | 0.040 | 10.00 | | 526 |
| ER-895719 | C28H34ClF2N5O3 · H-Cl | 4-(7-(difluoromethyl)-5-(3,4-dimethoxyphenyl)-4,5,6,7-tetrahydropyrazolo[1,5-a]pyrimidin-2-yl)-3-methyl-N-((S)-piperidin-3-yl)benzamide hydrochloride | 0.030 | 5.24 | | 526 |
| ER-895720 | C28H34ClF2N5O3 · H-Cl | 4-(7-(difluoromethyl)-5-(3,4-dimethoxyphenyl)-4,5,6,7-tetrahydropyrazolo[1,5-a]pyrimidin-2-yl)-3-methyl-N-((R)-piperidin-3-yl)benzamide hydrochloride | 0.030 | 4.96 | | 526 |
| ER-895721 | C28H34ClF2N5O3 · H-Cl | (4-(7-(difluoromethyl)-5-(3,4-dimethoxyphenyl)-4,5,6,7-tetrahydropyrazolo[1,5-a]pyrimidin-2-yl)-3-methylphenyl)((S)-2-methylpiperazin-1-yl)methanone hydrochloride | 0.050 | 10.00 | | 526 |
| ER-895722 | C28H34ClF2N5O3 · H-Cl | (4-(7-(difluoromethyl)-5-(3,4-dimethoxyphenyl)-4,5,6,7-tetrahydropyrazolo[1,5-a]pyrimidin-2-yl)-3-methylphenyl)((R)-2-methylpiperazin-1-yl)methanone hydrochloride | 0.070 | 10.00 | | 526 |

FIG. 11U

| ER-Number | Structure | Chemical Name | HEK/ TLR7 IC50 (µM) | HEK/ TLR9 IC50 (µM) | 1H NMR | MS |
|---|---|---|---|---|---|---|
| ER-895723 | C29H35ClF2N5O3 | (4-(7-(difluoromethyl)-5-(3,4-dimethoxyphenyl)-4,5,6,7-tetrahydropyrazolo[1,5-a]pyrimidin-2-yl)((2R,5S)-2,5-dimethylpiperazin-1-yl)methanone hydrochloride | 0.030 | 10.00 | | 540 |
| ER-895725 | C27H32ClF2N5O3 | 4-(7-(difluoromethyl)-5-(3,4-dimethoxyphenyl)-4,5,6,7-tetrahydropyrazolo[1,5-a]pyrimidin-2-yl)-3-methyl-N-((S)-pyrrolidin-3-yl)benzamide hydrochloride | 0.030 | 2.91 | | 512 |
| ER-895726 | C27H32ClF2N5O3 | 4-(7-(difluoromethyl)-5-(3,4-dimethoxyphenyl)-4,5,6,7-tetrahydropyrazolo[1,5-a]pyrimidin-2-yl)-3-methyl-N-((R)-pyrrolidin-3-yl)benzamide hydrochloride | 0.030 | 1.29 | | 512 |
| ER-895727 | C28H30F5N5O5 | N-(azetidin-3-yl)-4-(7-(difluoromethyl)-5-(3,4-dimethoxyphenyl)-4,5,6,7-tetrahydropyrazolo[1,5-a]pyrimidin-2-yl)-3-methylbenzamide 2,2,2-trifluoroacetate | 0.030 | 5.50 | | 498 |
| ER-895729 | C28H32ClF2N5O3 | (1S,4S)-2,5-diazabicyclo[2.2.1]heptan-2-yl(4-(7-(difluoromethyl)-5-(3,4-dimethoxyphenyl)-4,5,6,7-tetrahydropyrazolo[1,5-a]pyrimidin-2-yl)-3-methylphenyl)methanone hydrochloride | 0.040 | 10.00 | | 524 |

FIG. 11V

| ER-Number | Structure | Chemical Name | HEK/ TLR7 IC50 (μM) | HEK/ TLR9 IC50 (μM) | 1H NMR | MS |
|---|---|---|---|---|---|---|
| ER-895730 | C29H30ClF2N5O3 | (4-(7-(difluoromethyl)-5-(3,4-dimethoxyphenyl)-4,5,6,7-tetrahydropyrazolo[1,5-a]pyrimidin-2-yl)-3-methylphenyl)(hexahydropyrrolo[3,4-c]pyrrol-2(1H)-yl)methanone hydrochloride | 0.020 | 8.54 | 1H NMR (400 MHz, METHANOL-d4) ppm 2.46 (s, 3 H), 2.57 (m, 1 H) 2.72 (m, 1 H) 2.87 (m, 3 H) 2.99 (m, 2 H) 3.08 (m, 2 H) 3.54 (m, 2 H) 3.71 (m, 2 H) 3.81 (s, 3 H) 3.84 (s, 3 H) 4.45 (d, 1 H) 4.70 (m, 1 H) 6.54 (t, 1 H) 6.95 (d, 1 H) 7.03 (d, 1 H) 7.09 (s, 1 H) 7.35 (m, 2 H) 7.52 (d, 1 H) | 538 |
| ER-895731 | C25H30ClF2N5O3 | (3-(7-(difluoromethyl)-5-(3,4-dimethoxyphenyl)-4,5,6,7-tetrahydropyrazolo[1,5-a]pyrimidin-2-yl)phenyl)(piperazin-1-yl)methanone hydrochloride | 0.060 | 10.00 | 1H NMR (400 MHz, METHANOL-d4) δ ppm 2.31 (m, 2 H) 2.79 (br.m., 4 H) 3.46 (br. m., 4 H) 3.83 (s, 3 H) 3.86 (s, 3 H) 4.46 (d, 1 H) 4.72 (br. m, 1 H) 6.61 (t, 1 H) 6.96 - 7.11 (m, 4 H) 7.32 (d, 1 H) 7.47 (t, 1 H) 7.75 - 7.85 (m, 2 H) | 498 |
| ER-895732 | C27H32ClF2N5O3 | 3-(7-(difluoromethyl)-5-(3,4-dimethoxyphenyl)-4,5,6,7-tetrahydropyrazolo[1,5-a]pyrimidin-2-yl)-N-(piperidin-4-yl)benzamide hydrochloride | 0.020 | 10.00 | 1H NMR (400 MHz, METHANOL-d4) δ ppm 1.51 - 1.66 (m, 2 H) 1.98 (d, 2 H) 2.23 - 2.40 (m, 2 H) 2.69 - 2.80 (m, 2 H) 3.13 (d, 2 H) 3.83 (s, 3 H) 3.86 (s, 3 H) 4.47 (d, 1 H) 4.72 (br. m, 1 H) 6.63 (t, 1 H) 6.94 - 7.11 (m, 4 H) 7.46 (t, 1 H) 7.73 (d, 1 H) 7.89 (d, 1 H) 8.17 (s, 1 H) | 512 |
| ER-895733 | C27H32ClF2N5O3 | 3-(7-(difluoromethyl)-5-(3,4-dimethoxyphenyl)-4,5,6,7-tetrahydropyrazolo[1,5-a]pyrimidin-2-yl)-N-(S)-piperidin-3-yl)benzamide hydrochloride | 0.010 | 10.00 | | 512 |
| ER-895734 | C27H32ClF2N5O3 | 3-(7-(difluoromethyl)-5-(3,4-dimethoxyphenyl)-4,5,6,7-tetrahydropyrazolo[1,5-a]pyrimidin-2-yl)-N-(R)-piperidin-3-yl)benzamide hydrochloride | 0.009 | 10.00 | | 512 |

FIG. 11W

| ER-Number | Structure | Chemical Name | HEK/ TLR7 IC50 (µM) | HEK/ TLR9 IC50 (µM) | 1H NMR | MS |
|---|---|---|---|---|---|---|
| ER-895739 | 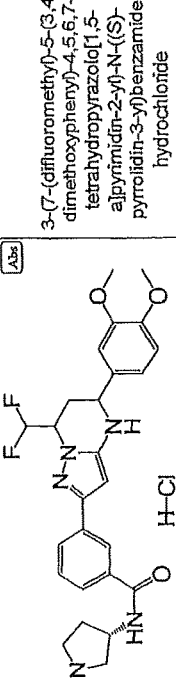 C26H30ClF2N5O3 | 3-(7-(difluoromethyl)-5-(3,4-dimethoxyphenyl)-4,5,6,7-tetrahydropyrazolo[1,5-a]pyrimidin-2-yl)-N-((S)-pyrrolidin-3-yl)benzamide hydrochloride | 0.010 | 0.31 | | 498 |
| ER-895740 | 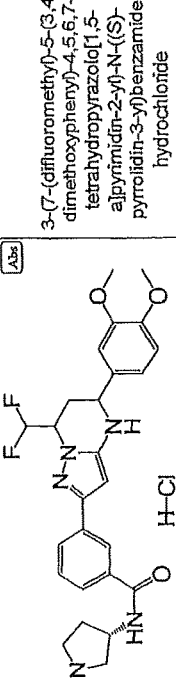 C26H30ClF2N5O3 | 3-(7-(difluoromethyl)-5-(3,4-dimethoxyphenyl)-4,5,6,7-tetrahydropyrazolo[1,5-a]pyrimidin-2-yl)-N-((R)-pyrrolidin-3-yl)benzamide hydrochloride | 0.020 | 1.38 | | 498 |
| ER-895741 | 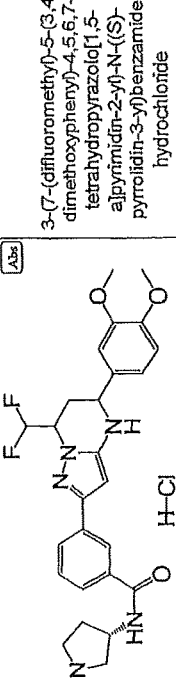 C27H28F5N5O5 | N-(azetidin-3-yl)-3-(7-(difluoromethyl)-5-(3,4-dimethoxyphenyl)-4,5,6,7-tetrahydropyrazolo[1,5-a]pyrimidin-2-yl)benzamide 2,2,2-trifluoroacetate | 0.070 | 7.95 | | 484 |
| ER-895744 | 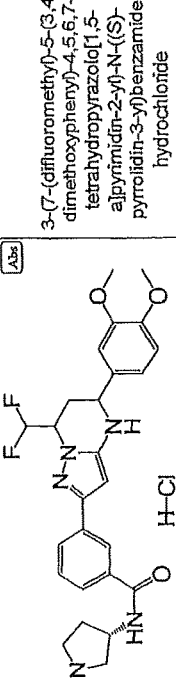 C26H32ClF2N5O3 | (3-(7-(difluoromethyl)-5-(3,4-dimethoxyphenyl)-4,5,6,7-tetrahydropyrazolo[1,5-a]pyrimidin-2-yl)phenyl)(hexahydropyrrolo[3,4-c]pyrrol-2(1H)-yl)methanone hydrochloride | 0.040 | 0.15 | 1H NMR (400 MHz, METHANOL-d4) δ ppm 2.20 - 2.44 (m, 1 H) 2.70 (br. s., 1) 2.83 (d, 1 H) 2.95 (br. s., 1 H) 3.03 - 3.14 (m, 1 H) 3.18 (dd, 1 H) 3.33 - 3.36 (m, 1 H) 3.41 (d, 1 H) 3.60 (d, 1 H) 3.70 - 3.81 (m, 1 H) 3.85 (s, 3 H) 3.87 (s, 3 H) 4.47 (dd, 1 H) 4.66 - 4.80 (m, 1 H) 6.63 (t, 1 H) 6.92 - 7.02 (m, 1 H) 7.02 - 7.17 (m, 3 H) 7.49 -7.61 (m, 2 H) 7.76 - 7.89 (m, 2 H) | 524.7 |

FIG. 11X

| ER-Number | Structure | Chemical Name | HEK/TLR7 IC50 (µM) | HEK/TLR9 IC50 (µM) | 1H NMR | MS |
|---|---|---|---|---|---|---|
| ER-895745 | C28H32ClF2N5O3 | (4-(7-(difluoromethyl)-5-(3,4-dimethoxyphenyl)-4,5,6,7-tetrahydropyrazolo[1,5-a]pyrimidin-2-yl)phenyl)(hexahydropyrrolo[3,4-c]pyrrol-2(1H)-yl)methanone hydrochloride | 0.080 | 3.86 | | 524 |
| ER-895746 | C28H31ClF3N5O3 | (4-(5-(3,4-dimethoxyphenyl)-7-(trifluoromethyl)-4,5,6,7-tetrahydropyrazolo[1,5-a]pyrimidin-2-yl)phenyl)(hexahydropyrrolo[3,4-c]pyrrol-2(1H)-yl)methanone hydrochloride | 0.020 | 3.51 | | 542 |
| ER-895748 | C27H31ClF3N5O3 | 4-(5-(3,4-dimethoxyphenyl)-7-(trifluoromethyl)-4,5,6,7-tetrahydropyrazolo[1,5-a]pyrimidin-2-yl)-N-(S)-piperidin-3-yl)benzamide hydrochloride | 0.030 | > 10 | 1H NMR (400 MHz, METHANOL-d4) δ ppm 1.57 - 1.72 (m, 2 H) 1.77 - 1.89 (m, 1 H) 2.04 (d, 1 H) 2.23 (dt, 1 H) 2.48 - 2.71 (m, 3 H) 3.00 (d, 1 H) 3.21 (dd, 1 H) 3.84 (s, 3 H) 3.87 (m, 3 H) 3.99 - 4.13 (m, 1 H) 4.46 (dd, 1 H) 5.02 - 5.16 (m, 1 H) 6.91 - 7.16 (m, 4 H) 7.78 - 7.92 (m, 4 H) | 530.7 |
| ER-895749 | C27H31ClF3N5O3 | 4-(5-(3,4-dimethoxyphenyl)-7-(trifluoromethyl)-4,5,6,7-tetrahydropyrazolo[1,5-a]pyrimidin-2-yl)-N-((R)-piperidin-3-yl)benzamide hydrochloride | 0.030 | > 10 | 1H NMR (400 MHz, METHANOL-d4) δ ppm 1.56 - 1.71 (m, 2 H) 1.82 (d, 1 H) 2.05 (br. s., 1 H) 2.23 (dt, 1 H) 2.54 (ddd, 1 H) 2.58 - 2.70 (m, 2 H) 3.00 (d, 1 H) 3.21 (dd, 1 H) 3.85 (s, 3 H) 3.87 (s, 3 H) 4.01 - 4.11 (m, 1 H) 4.46 (dd, 1 H) 5.03 - 5.14 (m, 1 H) 6.99 (d, 1 H) 7.06 (dd, 1 H) 7.12 (d 2H) 7.79 - 7.90 (m, 4 H) | 530.6 |

FIG. 11Y

| ER-Number | Structure | Chemical Name | HEK/TLR7 IC50 (μM) | HEK/TLR9 IC50 (μM) | 1H NMR | MS |
|---|---|---|---|---|---|---|
| ER-895750 | $C_{27}H_{31}ClF_3N_5O_3$ · HCl | (4-(5-(3,4-dimethoxyphenyl)-7-(trifluoromethyl)-4,5,6,7-tetrahydropyrazolo[1,5-a]pyrimidin-2-yl)phenyl)((S)-2-methylpiperazin-1-yl)methanone hydrochloride | 0.040 | > 10 | | 530 |
| ER-895751 | $C_{27}H_{31}ClF_3N_5O_3$ · HCl | (4-(5-(3,4-dimethoxyphenyl)-7-(trifluoromethyl)-4,5,6,7-tetrahydropyrazolo[1,5-a]pyrimidin-2-yl)phenyl)((R)-2-methylpiperazin-1-yl)methanone hydrochloride | 0.030 | > 10 | 1H NMR (400 MHz, METHANOL-d4) δ ppm 2.12 - 2.31 (m, 2H) 2.54 (ddd, 2 H) 2.63 - 2.78 (m, 2 H) 2.78 - 2.88 (m, 2 H) 2.94 (dd, 2 H) 3.85 (s, 3 H) 3.87 (s, 3 H) 4.46 (dd, 1 H) 5.09 (dt, 1 H) 6.90 - 7.02 (m, 1 H) 7.02 - 7.16 (m, 3 H) 7.42 (d, 2 H) 7.85 (d, 4 H) | 530.7 |
| ER-895752 | $C_{28}H_{33}ClF_3N_5O_3$ · HCl | (4-(5-(3,4-dimethoxyphenyl)-7-(trifluoromethyl)-4,5,6,7-tetrahydropyrazolo[1,5-a]pyrimidin-2-yl)phenyl)((2R,5S)-2,5-dimethylpiperazin-1-yl)methanone hydrochloride | 0.009 | > 10 | 1H NMR (400 MHz, METHANOL-d4) δ ppm 1.20(m, 3H) 1.35 (d, 3 H) 2.09 - 2.31 (m, 1 H) 2.45 - 2.62 (m, 2 H) 2.94 (m, 1H) 3.15 (br. s., 1 H) 3.22 (dd, 1 H) 3.43 (dd, 1 H) 3.85 (s, 3 H) 3.87 (s, 3 H) 4.46 (dd, 1 H) 5.09 (dt, 1 H) 6.92 - 7.02 (m, 2 H) 7.02 - 7.16 (m, 2 H) 7.40 (d, 2 H) 7.85 (d, 2 H) | 544.6 |
| ER-895753 | $C_{28}H_{33}ClF_3N_5O_3$ · HCl | (4-(5-(3,4-dimethoxyphenyl)-7-(trifluoromethyl)-4,5,6,7-tetrahydropyrazolo[1,5-a]pyrimidin-2-yl)phenyl)((2R,5R)-2,5-dimethylpiperazin-1-yl)methanone hydrochloride | 0.070 | > 10 | 1H NMR (400 MHz, METHANOL-d4) δ ppm 1.00 (br. s., 1 H) 1.09 - 1.26 (m, 4 H) 1.26 - 1.42 (m, 3 H) 2.23 (dt, 1 H) 2.54 (dtd, 1 H) 2.95 (br. s., 1 H) 3.20 (m, 1H) 3.24(dd, 1H) 3.39 - 3.51 (m, 1 H) 3.85 (s, 3 H) 3.87 (m, 3 H) 4.46 (dd, 1 H)4.99 - 5.17 (m, 1 H) 6.93 - 7.02 (m, 1 H) 7.18 (m, 3 H) 7.40 (d, 2 H) 7.85 (d, 2 H) | 544.6 |

FIG. 11Z

| ER-Number | Structure | Chemical Name | HEK/TLR7 IC50 (µM) | HEK/TLR9 IC50 (µM) | 1H NMR | MS |
|---|---|---|---|---|---|---|
| ER-895754 | 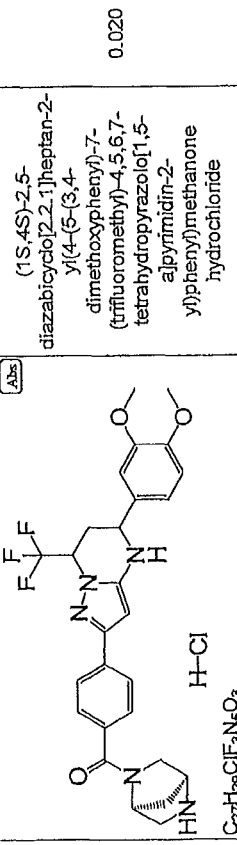 C27H29ClF3N5O3 | (1S,4S)-2,5-diazabicyclo[2.2.1]heptan-2-yl)(4-(5-(3,4-dimethoxyphenyl)-7-(trifluoromethyl)-4,5,6,7-tetrahydropyrazolo[1,5-a]pyrimidin-2-yl)phenyl)methanone hydrochloride | 0.020 | 5.95 | | 528 |
| ER-895755 | 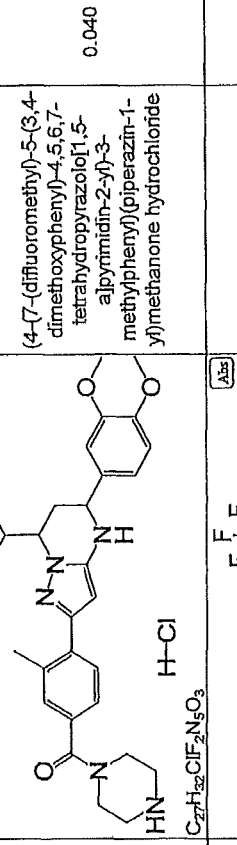 C27H28ClF2N5O3 | (4-(7-(difluoromethyl)-5-(3,4-dimethoxyphenyl)-4,5,6,7-tetrahydropyrazolo[1,5-a]pyrimidin-2-yl)-3-methylphenyl)(piperazin-1-yl)methanone hydrochloride | 0.040 | 10.00 | | 512 |
| ER-895809 | 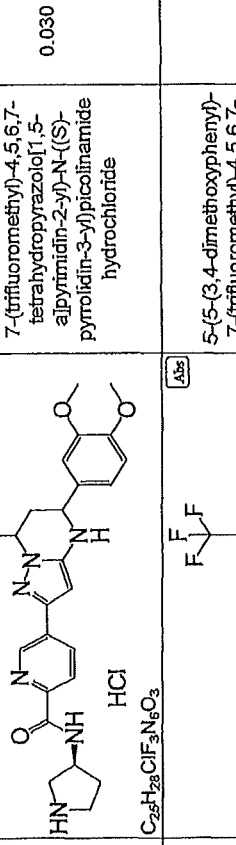 C25H28ClF3N6O3 | 5-(5-(3,4-dimethoxyphenyl)-7-(trifluoromethyl)-4,5,6,7-tetrahydropyrazolo[1,5-a]pyrimidin-2-yl)-N-((S)-pyrrolidin-3-yl)picolinamide hydrochloride | 0.030 | 3.83 | | 517.5 |
| ER-895810 | 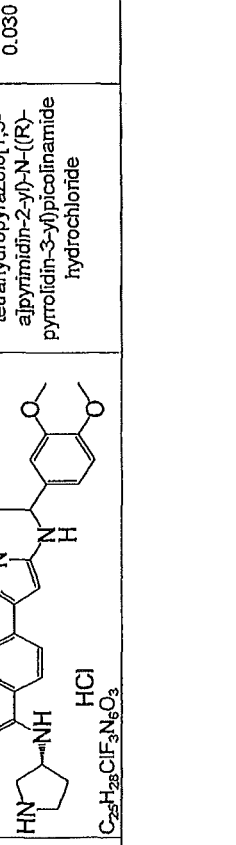 C25H28ClF3N6O3 | 5-(5-(3,4-dimethoxyphenyl)-7-(trifluoromethyl)-4,5,6,7-tetrahydropyrazolo[1,5-a]pyrimidin-2-yl)-N-((R)-pyrrolidin-3-yl)picolinamide hydrochloride | 0.030 | 2.83 | | 517.5 |

FIG. 11AA

| ER-Number | Structure | Chemical Name | HEK/ TLR7 IC50 (μM) | HEK/ TLR9 IC50 (μM) | 1H NMR | MS |
|---|---|---|---|---|---|---|
| ER-895811 |  C25H29ClF3N5O3 | 3-(5-(3,4-dimethoxyphenyl)-7-(trifluoromethyl)-4,5,6,7-tetrahydropyrazolo[1,5-a]pyrimidin-2-yl)-N-((S)-pyrrolidin-3-yl)benzamide hydrochloride | 0.040 | 5.31 | 1H NMR (400 MHz, DMSO-d6) δ ppm: 2.04 (m, 1H), 2.12 (dd, 1H), 2.20-2.33 (m, 1H), 2.44 (m, 1H), 3.17-3.27 (m, 2H), 3.33-3.43 (m, 2H), 3.76 and 3.79 (2s, 6H), 4.46 (d, 1H), 4.53 (m, 1H), 5.27-5.28 (m, 1H), 5.84 (s, 1H), 6.82 (s, 1H), 6.96-7.01 (m, 2H), 7.08 (s, 1H), 7.49 (t, 1H), 7.79 (d, 1H), 7.89 (d, 1H), 8.17 (s, 1H), 8.81 (s, 1H). | 516.5 |
| ER-896059 |  C28H34ClF2N5O3 | 2-(4-(7-(difluoromethyl)-5-(3,4-dimethoxyphenyl)-4,5,6,7-tetrahydropyrazolo[1,5-a]pyrimidin-2-yl)phenyl)-N-(piperidin-4-yl)acetamide hydrochloride | 0.090 | 0.19 | | 526 |
| ER-896060 |  C28H34ClF2N5O3 | 2-(4-(7-(difluoromethyl)-5-(3,4-dimethoxyphenyl)-4,5,6,7-tetrahydropyrazolo[1,5-a]pyrimidin-2-yl)phenyl)-N-((S)-piperidin-3-yl)acetamide hydrochloride | 0.030 | 10.00 | | 526 |
| ER-896061 |  C28H34ClF2N5O3 | 2-(4-(7-(difluoromethyl)-5-(3,4-dimethoxyphenyl)-4,5,6,7-tetrahydropyrazolo[1,5-a]pyrimidin-2-yl)phenyl)-N-((R)-piperidin-3-yl)acetamide hydrochloride | 0.030 | 9.41 | | 526 |

FIG. 11BB

| ER-Number | Structure | Chemical Name | HEK/ TLR7 IC50 (µM) | HEK/ TLR9 IC50 (µM) | 1H NMR | MS |
|---|---|---|---|---|---|---|
| ER-896062 | C28H34ClF2N5O3 | 2-(4-(7-(difluoromethyl)-5-(3,4-dimethoxyphenyl)-4,5,6,7-tetrahydropyrazolo[1,5-a]pyrimidin-2-yl)phenyl)-1-((S)-2-methylpiperazin-1-yl)ethanone hydrochloride | 0.030 | 6.93 | | 526 |
| ER-896063 | C28H34ClF2N5O3 | 2-(4-(7-(difluoromethyl)-5-(3,4-dimethoxyphenyl)-4,5,6,7-tetrahydropyrazolo[1,5-a]pyrimidin-2-yl)phenyl)-1-((R)-2-methylpiperazin-1-yl)ethanone hydrochloride | 0.070 | 9.62 | | 526 |
| ER-896064 | C29H36ClF2N5O3 | 2-(4-(7-(difluoromethyl)-5-(3,4-dimethoxyphenyl)-4,5,6,7-tetrahydropyrazolo[1,5-a]pyrimidin-2-yl)phenyl)-1-((2R,5S)-2,5-dimethylpiperazin-1-yl)ethanone hydrochloride | 0.050 | 6.95 | | 540 |
| ER-896067 | C28H32ClF2N5O3 | 1-((1S,4S)-2,5-diazabicyclo[2.2.1]heptan-2-yl)-2-(4-(7-(difluoromethyl)-5-(3,4-dimethoxyphenyl)-4,5,6,7-tetrahydropyrazolo[1,5-a]pyrimidin-2-yl)phenyl)ethanone hydrochloride | 0.040 | 9.64 | | 524 |
| ER-896068 | C29H34ClF2N5O3 | 2-(4-(7-(difluoromethyl)-5-(3,4-dimethoxyphenyl)-4,5,6,7-tetrahydropyrazolo[1,5-a]pyrimidin-2-yl)phenyl)-1-(hexahydropyrrolo[3,4-c]pyrrol-2(1H)-yl)ethanone hydrochloride | 0.040 | 7.80 | | 538 |

FIG. 11CC

| ER-Number | Structure | Chemical Name | HEK/TLR7 IC50 (µM) | HEK/TLR9 IC50 (µM) | 1H NMR | MS |
|---|---|---|---|---|---|---|
| ER-896071 | C28H30F7N5O5 | N-(azetidin-3-ylmethyl)-3-(7-(difluoromethyl)-5-(3,4-dimethoxyphenyl)-4,5,6,7-tetrahydropyrazolo[1,5-a]pyrimidin-2-yl))benzamide 2,2,2-trifluoroacetate | 0.090 | 10.00 | | 498 |
| ER-896072 | C26H32Cl2F3N5O2 | 5-(3,4-dimethoxyphenyl)-2-(3-(piperazin-1-ylmethyl)phenyl)-7-(trifluoromethyl)-4,5,6,7-tetrahydropyrazolo[1,5-a]pyrimidine dihydrochloride | 0.090 | > 10 | | |
| ER-896073 | C27H34Cl2F3N5O2 | 5-(3,4-dimethoxyphenyl)-2-(4-((4-methylpiperazin-1-yl)methyl)phenyl)-7-(trifluoromethyl)-4,5,6,7-tetrahydropyrazolo[1,5-a]pyrimidine dihydrochloride | 0.050 | 8.64 | | |
| ER-896133 | C25H29Cl2F3N6O3 | (5-(5-(3,4-dimethoxyphenyl)-7-(trifluoromethyl)-4,5,6,7-tetrahydropyrazolo[1,5-a]pyrimidin-2-yl)pyridin-2-yl)(piperazin-1-yl)methanone dihydrochloride | 0.020 | > 10 | 1H NMR (400 MHz, Methanol-d4) δ ppm: 2.25 (dd, 1H), 2.53-2.58 (m, 1H), 3.35 (m, 4H), 3.85 and 3.88 (2s, 6H), 3.91-4.03 (m, 4H), 4.49 (dd, 1H), 5.11-5.17 (m, 1H), 6.99 (d, 1H), 7.00 (s, 1H), 7.06 (dd, 1H), 7.11 (d, 1H), 7.81 (d, 1H), 8.33 (dd, 1H), 9.01 (d, 1H). | 517.5 |
| ER-896134 | C26H31Cl2F3N6O3 | 5-(5-(3,4-dimethoxyphenyl)-7-(trifluoromethyl)-4,5,6,7-tetrahydropyrazolo[1,5-a]pyrimidin-2-yl)-N-(piperidin-4-yl)picolinamide dihydrochloride | 0.020 | > 10 | 1H NMR (400 MHz, Methanol-d4) δ ppm: 1.57-1.63 (m, 2H), 1.89-2.03 (m, 2H), 2.23 (dd, 1H), 2.56-2.58 (m, 1H), 2.74 (t, 2H), 3.12 (d, 2H), 3.85 and 3.88 (2s, 6H), 4.03-4.07 (m, 1H), 4.48 (d, 1H), 5.10-5.16 (m, 1H), 6.00 (s, 1H), 7.00 (d, 1H), 7.08 (dd, 1H), 7.11 (d, 1H), 8.10 (d, 1H), 8.27 (d, 1H), 9.03 (s, 1H). | 531.5 |

FIG. 11DD

| ER-Number | Structure | Chemical Name | HEK/TLR7 IC50 (µM) | HEK/TLR9 IC50 (µM) | 1H NMR | MS |
|---|---|---|---|---|---|---|
| ER-896135 | [structure] C26H31Cl2F3N6O3 | 5-(5-(3,4-dimethoxyphenyl)-7-(trifluoromethyl)-4,5,6,7-tetrahydropyrazolo[1,5-a]pyrimidin-2-yl)-N-((S)-piperidin-3-yl)picolinamide dihydrochloride | 0.030 | 7.94 | 1H NMR (400 MHz, Methanol-d4) δ ppm: 1.84-1.89 (m, 2H), 2.08-2.10 (m, 2H), 2.24 (dd, 1H), 2.52-2.57 (m, 1H), 3.01-3.13 (m, 2H), 3.34-3.50 (m, 2H), 3.85 and 3.87 (2s, 6H), 4.30 (m, 1H), 4.48 (d, 1H), 5.10-5.16 (m, 1H), 5.94 (s, 1H), 6.99 (d, 1H), 7.06 (dd, 1H), 7.11 (d, 1H), 8.11 (d, 1H), 8.27 (d, 1H), 9.03 (s, 1H). | 531.5 |
| ER-896136 | [structure] C26H31Cl2F3N6O3 | 5-(5-(3,4-dimethoxyphenyl)-7-(trifluoromethyl)-4,5,6,7-tetrahydropyrazolo[1,5-a]pyrimidin-2-yl)-N-((R)-piperidin-3-yl)picolinamide dihydrochloride | 0.030 | 6.38 | 1H NMR (400 MHz, Methanol-d4) δ ppm: 1.84-1.89 (m, 2H), 2.08-2.10 (m, 2H), 2.24 (dd, 1H), 2.52-2.57 (m, 1H), 3.01-3.14 (m, 2H), 3.34-3.52 (m, 2H), 3.85 and 3.88 (2s, 6H), 4.28-4.31 (m, 1H), 4.48 (d, 1H), 5.10-5.15 (m, 1H), 5.96 (s, 1H), 6.99 (d, 1H), 7.06 (dd, 1H), 7.11 (d, 1H), 8.11 (d, 1H), 8.27 (d, 1H), 9.03 (s, 1H). | 531.5 |
| ER-896386 | [structure] C28H31ClF3N5O3 | (3-((5S,7R)-5-(3,4-dimethoxyphenyl)-7-(trifluoromethyl)-4,5,6,7-tetrahydropyrazolo[1,5-a]pyrimidin-2-yl)phenyl)(hexahydropyrrolo[3,4-c]pyrrol-2(1H)-yl)methanone hydrochloride | 0.030 | 0.36 | 1H NMR (400 MHz, DMSO-d6) δ ppm: 1.23-1.28 (m, 2H), 2.07-2.16 (dd, 1H), 2.42-2.46 (m, 1H), 3.00-4.00 (m, 8H), 3.76 and 3.79 (2s, 6H), 4.45 (dd, 1H), 5.24-5.30 (m, 1H), 5.81 (s, 1H), 6.81 (s, 1H), 6.96-7.01 (m, 2H), 7.07 (d, 1H), 7.41-7.47 (m, 2H), 7.79-7.82 (m, 2H). | 542.4 |
| ER-896387 | [structure] C28H31ClF3N5O3 | (3-((5R,7S)-5-(3,4-dimethoxyphenyl)-7-(trifluoromethyl)-4,5,6,7-tetrahydropyrazolo[1,5-a]pyrimidin-2-yl)phenyl)(hexahydropyrrolo[3,4-c]pyrrol-2(1H)-yl)methanone hydrochloride | 0.080 | 0.39 | 1H NMR (400 MHz, DMSO-d6) δ ppm: 1.23-1.28 (m, 2H), 2.07-2.16 (dd, 1H), 2.42-2.46 (m, 1H), 3.00-4.00 (m, 8H), 3.76 and 3.79 (2s, 6H), 4.45 (dd, 1H), 5.24-5.30 (m, 1H), 5.81 (s, 1H), 6.81 (s, 1H), 6.96-7.01 (m, 2H), 7.07 (d, 1H), 7.41-7.47 (m, 2H), 7.79-7.82 (m, 2H). | 542.4 |

FIG. 11EE

| ER-Number | Structure | Chemical Name | HEK/ TLR7 IC50 (µM) | HEK/ TLR9 IC50 (µM) | 1H NMR | MS |
|---|---|---|---|---|---|---|
| ER-896388 | C26H29ClF3N5O3 | (3-(5-(3,4-dimethoxyphenyl)-7-(trifluoromethyl)-4,5,6,7-tetrahydropyrazolo[1,5-a]pyrimidin-2-yl)phenyl)(piperazin-1-yl)methanone hydrochloride | 0.030 | > 10 | | 515.2 |
| ER-896389 | C28H33ClF3N5O3 | ((3R,5S)-3-amino-5-methylpiperidin-1-yl)(3-(5-(3,4-dimethoxyphenyl)-7-(trifluoromethyl)-4,5,6,7-tetrahydropyrazolo[1,5-a]pyrimidin-2-yl)phenyl)methanone hydrochloride | 0.090 | 13.37 | | 544.4 |
| ER-896452 | C20H25ClF3N5O3 | (5-(3,4-dimethoxyphenyl)-7-(trifluoromethyl)-4,5,6,7-tetrahydropyrazolo[1,5-a]pyrimidin-2-yl)(piperazin-1-yl)methanone hydrochloride | 0.185 | 10.00 | 1H NMR (400 MHz, DMSO-d6) δ ppm: 2.10 (dd, 1H), 2.42-2.47 (m, 1H), 3.15-3.23 (m, 4H), 3.67-3.86 (m, 2H), 3.76 and 3.78 (2s, 6H), 4.12-4.26 (m, 2H), 4.45 (d, 1H), 5.26-5.33 (m, 1H), 5.65 (s, 1H), 6.91 (s, 1H), 6.97 (s, 2H), 7.05 (s, 1H), 9.13 (br, 2H). | 440.3 |
| ER-896453 | C21H26F3N5O3 | 5-(3,4-dimethoxyphenyl)-N-((S)-piperidin-3-yl)-7-(trifluoromethyl)-4,5,6,7-tetrahydropyrazolo[1,5-a]pyrimidine-2-carboxamide | 0.224 | 10.00 | 1H NMR (400 MHz, DMSO-d6) δ ppm: 1.62-1.71 (m, 2H), 1.84-187 (m, 2H), 2.11 (dd, 1H), 2.42-2.47 (m, 1H), 2.72 (m, 1H), 2.89-2.91 (m, 1H), 3.17-3.22 (m, 2H), 3.75 and 3.78 (2s, 6H), 4.14-4.16 (m, 1H), 4.40 (dd, 1H), 5.29 (m, 1H), 5.74 (s, 1H), 6.88 (s, 1H), 6.97 (s, 2H), 7.05 (s, 1H), 7.86 (t, 1H), 8.84 (br, 1H), 9.05 (br, 2H). | 454.3 |

FIG. 11FF

| ER-Number | Structure | Chemical Name | HEK/ TLR7 IC50 (µM) | HEK/ TLR9 IC50 (µM) | 1H NMR | MS |
|---|---|---|---|---|---|---|
| ER-896993 | $C_{21}H_{25}ClF_3N_4O_2$ | 5-(3,4-dimethoxyphenyl)-2-(6-methyl-1,2,3,6-tetrahydropyridin-4-yl)-7-(trifluoromethyl)-4,5,6,7-tetrahydropyrazolo[1,5-a]pyrimidine hydrochloride | 0.065 | 10.00 | | |
| ER-896997 | $C_{26}H_{28}ClF_3N_4O_2$ | 5-(3,4-dimethoxyphenyl)-2-(6-phenyl-1,2,3,6-tetrahydropyridin-4-yl)-7-(trifluoromethyl)-4,5,6,7-tetrahydropyrazolo[1,5-a]pyrimidine hydrochloride | 0.130 | 7.60 | | |
| ER-897034 | $C_{25}H_{29}Cl_2F_3N_6O_3$ | (4-(5-(3,4-dimethoxyphenyl)-7-(trifluoromethyl)-4,5,6,7-tetrahydropyrazolo[1,5-a]pyrimidin-2-yl)pyridin-2-yl)(piperazin-1-yl)methanone dihydrochloride | 0.110 | > 10 | 1H NMR (400 MHz, Methanol-d4) δ ppm: 2.25 (dd, 1H), 2.53-2.58 (m, 1H), 3.31 (m, 4H), 3.85 and 3.87 (2s, 6H), 3.80-4.20 (m, 4H), 4.49 (dd, 1H), 5.14-5.20 (m, 1H), 6.99 (d, 1H), 7.05 (d, 1H), 7.10 (s, 1H), 8.02 (d, 1H), 8.19 (s, 1H), 8.66 (d, 1H). | 517.4 |
| ER-897036 | $C_{26}H_{31}Cl_2F_3N_6O_3$ | 4-(5-(3,4-dimethoxyphenyl)-7-(trifluoromethyl)-4,5,6,7-tetrahydropyrazolo[1,5-a]pyrimidin-2-yl)-N-((S)-piperidin-3-yl)picolinamide dihydrochloride | 0.010 | 5.06 | 1H NMR (400 MHz, Methanol-d4) δ ppm 1.83-1.90 (m, 2H), 2.09-2.12 (m, 2H), 2.25 (dd, 1H), 2.53-2.59 (m, 1H), 3.01-3.12 (m, 2H), 3.30-3.54 (m, 2H), 3.85 and 3.88 (2s, 6H), 4.31-4.36 (m, 1H), 4.50 (d, 1H), 5.14-5.20 (m, 1H), 6.99 (d, 1H), 7.05 (dd, 1H), 7.11 (d, 1H), 8.05 (d, 1H), 8.58 (s, 1H), 8.67 (d, 1H). | 531.4 |

FIG. 11GG

| ER-Number | Structure | Chemical Name | HEK/ TLR7 IC50 (μM) | HEK/ TLR9 IC50 (μM) | 1H NMR | MS |
|---|---|---|---|---|---|---|
| ER-897037 | $C_{28}H_{31}Cl_2F_3N_6O_3$ | 4-(5-(3,4-dimethoxyphenyl)-7-(trifluoromethyl)-4,5,6,7-tetrahydropyrazolo[1,5-a]pyrimidin-2-yl)-N-(piperidin-4-yl)picolinamide dihydrochloride | 0.010 | 6.17 | 1H NMR (400 MHz, Methanol-d4) δ ppm: 1.90-2.00 (m, 2H), 2.21-2.30 (m, 3H), 2.53-2.59 (m, 1H), 3.13-3.21 (m, 2H), 3.49-3.52 (m, 2H), 3.85 and 3.87 (2s, 6H), 4.21-4.27 (m, 1H), 4.50 (d, 1H), 5.15-5.21 (m, 1H), 6.99 (d, 1H), 7.06 (dd, 1H), 7.11 (d, 1H), 8.10 (d, 1H), 8.62 (s, 1H), 8.67 (d, 1H). | 531.5 |
| ER-897077 | $C_{26}H_{31}F_2N_5O_3$ | (3-((5S,7R)-7-(difluoromethyl)-5-(3,4-dimethoxyphenyl)-4,5,6,7-tetrahydropyrazolo[1,5-a]pyrimidin-2-yl)phenyl)(hexahydropyrrolo[3,4-c]pyrrol-2(1H)-yl)methanone | 0.090 | > 10 | | |
| ER-897090 | $C_{21}H_{25}F_3N_4O_2$ | 5-(3,4-dimethoxyphenyl)-2-(2,3,6,7-tetrahydro-1H-azepin-4-yl)-7-(trifluoromethyl)-4,5,6,7-tetrahydropyrazolo[1,5-a]pyrimidine | 0.030 | 10.00 | NMR of each isomer available | 423.06 |
| ER-897097 | $C_{20}H_{23}F_3N_4O_2$ | 5-(3,4-dimethoxyphenyl)-2-(1,2,3,6-tetrahydropyridin-4-yl)-7-(trifluoromethyl)-4,5,6,7-tetrahydropyrazolo[1,5-a]pyrimidine | 0.058 | 10.00 | NMR of each isomer available | 409.08 |

FIG. 11HH

| ER-Number | Structure | Chemical Name | HEK/ TLR7 IC50 (μM) | HEK/ TLR9 IC50 (μM) | 1H NMR | MS |
|---|---|---|---|---|---|---|
| ER-897105 | $C_{23}H_{27}F_3N_6O_2$ | 5-(3,4-dimethoxyphenyl)-2-(1-(piperidin-4-yl)-1H-pyrazol-4-yl)-7-(trifluoromethyl)-4,5,6,7-tetrahydropyrazolo[1,5-a]pyrimidine | 0.010 | 3.25 | NMR of each isomer available | 477.09 |
| ER-897130 | $C_{19}H_{21}F_3N_4O_2$ | 2-(2,5-dihydro-1H-pyrrol-3-yl)-5-(3,4-dimethoxyphenyl)-7-(trifluoromethyl)-4,5,6,7-tetrahydropyrazolo[1,5-a]pyrimidine | 0.059 | 10.00 | 1H NMR (400 MHz, METHANOL-d4) δ ppm 2.08 - 2.26 (m, 1 H) 2.50 (ddd, 1 H) 3.76 - 3.91 (m, 8 H) 4.00 (d, 2 H) 4.36 - 4.44 (m, 1 H) 4.94 - 5.05 (m, 1 H) 5.61 (s, 1 H) 6.16 (t, 1 H) 6.90 - 7.14 (m, 3 H). | 395.03 |
| ER-897142 | $C_{21}H_{25}F_3N_4O_2$ | 4-(5-(3,4-dimethoxyphenyl)-7-(trifluoromethyl)-4,5,6,7-tetrahydropyrazolo[1,5-a]pyrimidin-2-yl)cyclohex-3-enamine | 0.009 | 10.00 | NMR of each isomer available | 423.06 |
| ER-897178 | $C_{23}H_{30}ClF_3N_4O_2$ | 5-(3,4-dimethoxyphenyl)-2-(2-isopropyl-1,2,3,6-tetrahydropyridin-4-yl)-7-(trifluoromethyl)-4,5,6,7-tetrahydropyrazolo[1,5-a]pyrimidine hydrochloride | 0.060 | 6.87 | | |
| ER-897212 | $C_{21}H_{25}F_3N_4O_2$ | (5S,7R)-5-(3,4-dimethoxyphenyl)-2-(2,3,6,7-tetrahydro-1H-azepin-4-yl)-7-(trifluoromethyl)-4,5,6,7-tetrahydropyrazolo[1,5-a]pyrimidine | 0.030 | 6.29 | (400 MHz, METHANOL-d4) δ ppm 1.67 - 1.81 (m, 2 H) 2.07 - 2.19 (m, 1 H) 2.43 (ddd, 1 H) 2.71 - 2.80 (m, 2 H) 2.99 - 3.09 (m, 2 H) 3.40 (d, 2 H) 3.77 - 3.84 (m, 6 H) 4.26 - 4.38 (m, 1 H) 4.87 - 4.96 (m, 1 H) 5.50 (s, 1 H) 6.29 (t, 1 H) 6.86 - 7.08 (m, 3 H). | 423.44 |

FIG. 11I

| ER-Number | Structure | Chemical Name | HEK/ TLR7 IC50 (μM) | HEK/ TLR9 IC50 (μM) | 1H NMR | MS |
|---|---|---|---|---|---|---|
| ER-897214 | $C_{23}H_{27}F_3N_6O_2$ | (5S,7R)-5-(3,4-dimethoxyphenyl)-2-(1-(piperidin-4-yl)-1H-pyrazol-4-yl)-7-(trifluoromethyl)-4,5,6,7-tetrahydropyrazolo[1,5-a]pyrimidine | 0.009 | 6.21 | 1H-NMR (400 MHz, METHANOL-d4) δ ppm 1.83 - 2.01 (m, 2 H) 2.05 - 2.29 (m, 3 H) 2.46 - 2.56 (m, 1 H) 2.67 - 2.82 (m, 2 H) 3.17 (d, 2 H) 3.82 - 3.95 (m, 6 H) 4.21 - 4.35 (m, 1 H) 4.36 - 4.50 (m, 1 H) 4.95 - 5.10 (m, 1 H) 5.59 - 5.71 (m, 1 H) 6.89 - 7.19 (m, 3 H) 7.70 - 7.85 (m, 1 H) 7.93 - 8.07 (m, 1 H), | 477.44 |
| ER-897215 | $C_{23}H_{27}F_3N_6O_2$ | (5R,7S)-5-(3,4-dimethoxyphenyl)-2-(1-(piperidin-4-yl)-1H-pyrazol-4-yl)-7-(trifluoromethyl)-4,5,6,7-tetrahydropyrazolo[1,5-a]pyrimidine | 0.060 | 3.50 | 1H NMR (400 MHz, METHANOL-d4) δ ppm 1.82 - 2.01 (m, 2 H) 2.03 - 2.29 (m, 3 H) 2.40 - 2.58 (m, 1 H) 2.67 - 2.83 (m, 2 H) 3.17 (d, 2 H) 3.84 (s, 3 H) 3.86 (s, 3 H) 4.29 (ddd, 1 H) 4.41 (d, 1 H) 4.94 - 5.09 (m, 1 H) 5.60 - 5.68 (m, 1 H) 6.90 - 7.15 (m, 3 H) 7.70 - 7.81 (m, 1 H) 7.93 - 8.03 (m, 1 H) | 477.44 |
| ER-897269 | $C_{20}H_{23}F_3N_4O_2$ | (5S,7R)-5-(3,4-dimethoxyphenyl)-2-(1,2,3,6-tetrahydropyridin-4-yl)-7-(trifluoromethyl)-4,5,6,7-tetrahydropyrazolo[1,5-a]pyrimidine | 0.030 | > 10 | 1H-NMR (400 MHz, METHANOL-d4) δ ppm 2.04 - 2.20 (m, 1 H) 2.37 - 2.49 (m, 3 H) 2.89 - 3.02 (m, 2 H) 3.31 (s, 1 H) 3.35 - 3.43 (m, 2 H) 3.76 - 3.90 (m, 8 H) 4.26 - 4.38 (m, 1 H) 4.88 - 4.97 (m, 1 H) 5.50 (s, 1 H) 6.15 (br. s., 1 H) 6.86 - 7.11 (m, 1 H) | 408.39 |
| ER-897364 | $C_{21}H_{25}F_3N_4O_2$ | 4-((5S,7R)-5-(3,4-dimethoxyphenyl)-7-(trifluoromethyl)-4,5,6,7-tetrahydropyrazolo[1,5-a]pyrimidin-2-yl)cyclohex-3-enamine | 0.040 | > 10 | 1H NMR (400 MHz, METHANOL-d4) δ ppm 1.29 (br. s., 1 H) 1.49 - 1.66 (m, 1 H) 1.92 - 2.08 (m, 2 H) 2.33 - 2.53 (m, 3 H) 2.62 (d, 1 H) 3.04 (br. s., 1 H) 3.82 - 3.88 (m, 6 H) 4.37 (d, 1 H) 4.92 - 5.00 (m, 1 H) 5.53 (d, 1 H) 6.13 (br. s., 1 H) 6.90 - 7.12 (m, 3 H), | 424.44 |

FIG. 11JJ

| ER-Number | Structure | Chemical Name | HEK/TLR7 IC50 (µM) | HEK/TLR9 IC50 (µM) | 1H NMR | MS |
|---|---|---|---|---|---|---|
| ER-897365 | C21H25F3N4O2 | 4-((5R,7S)-5-(3,4-dimethoxyphenyl)-7-(trifluoromethyl)-4,5,6,7-tetrahydropyrazolo[1,5-a]pyrimidin-2-yl)cyclohex-3-enamine | 0.040 | > 10 | 1H NMR (400 MHz, METHANOL-d4) δ ppm 1.29 (br. s., 1 H) 1.48 - 1.64 (m, 1 H) 1.90 - 2.05 (m, 2 H) 2.33 - 2.53 (m, 3 H) 2.61 (d, 1 H) 3.02 (d, 1 H) 3.84 (d, 6 H) 4.36 (d, 1 H) 4.92 - 5.00 (m, 1 H) 5.49 - 5.56 (m, 1 H) 6.13 (br. s., 1 H) 6.92 - 7.12 (m, 3 H), | 424.44 |
| ER-897381 | C23H26F3N7O2 | 5-(3,4-dimethoxyphenyl)-2-(2-(piperazin-1-yl)pyrimidin-5-yl)-7-(trifluoromethyl)-4,5,6,7-tetrahydropyrazolo[1,5-a]pyrimidine | 0.030 | 4.73 | NMR of each isomer available | 490.07 |
| ER-897405 | C24H27F3N6O2 | 5-(3,4-dimethoxyphenyl)-2-(6-(piperazin-1-yl)pyridin-3-yl)-7-(trifluoromethyl)-4,5,6,7-tetrahydropyrazolo[1,5-a]pyrimidine | 0.050 | 2.02 | NMR of each isomer available | 489.04 |
| ER-897547 | C21H25F3N4O2 | 5-(3,4-dimethoxyphenyl)-2-(3-methyl-1,2,3,6-tetrahydropyridin-4-yl)-7-(trifluoromethyl)-4,5,6,7-tetrahydropyrazolo[1,5-a]pyrimidine | 0.070 | 8.78 | 1H NMR (400 MHz, METHANOL-d4) δ ppm 1.12 - 1.21 (m, 3 H) 2.08 - 2.27 (m, 1 H) 2.42 - 2.55 (m, 1 H) 2.68 - 2.86 (m, 2 H) 3.01 (dt, 1 H) 3.35 - 3.43 (m, 2 H) 3.84 (s, 3 H) 3.86 (s, 3 H) 4.39 (d, 1 H) 4.98 (dd, 1 H) 5.46 - 5.53 (m, 1 H) 6.04 - 6.15 (m, 1 H) 6.91 - 7.15 (m, 3 H), | 423.1 |
| ER-897560 | C25H29Cl2F3N6O3 · H-Cl · H-Cl | (5-((5S,7R)-5-(3,4-dimethoxyphenyl)-7-(trifluoromethyl)-4,5,6,7-tetrahydropyrazolo[1,5-a]pyrimidin-2-yl)pyridin-2-yl)(piperazin-1-yl)methanone dihydrochloride | 0.050 | > 10 | 1H NMR (400 MHz, METHANOL-d4) δ ppm 2.25 (1 H), 2.32 (1 H), 2.56 (1 H), 3.38 (4 H), 3.66 (1 H), 3.86 (6 H), 3.99 (4 H), 4.50 (1 H), 5.15 (1 H), 7.05 (4 H), 7.85 (1 H), 8.40 (1H), 9.04 (1H) | 518.52 |

FIG. 11KK

| ER-Number | Structure | Chemical Name | HEK/ TLR7 IC50 (μM) | HEK/ TLR9 IC50 (μM) | 1H NMR | MS |
|---|---|---|---|---|---|---|
| ER-897597 | [structure] $C_{25}H_{29}F_3N_4O_2$ | 5-(3,4-dimethoxyphenyl)-2-(4-(piperidin-4-yl)phenyl)-7-(trifluoromethyl)-4,5,6,7-tetrahydropyrazolo[1,5-a]pyrimidine | 0.020 | 2.07 | NMR of each isomer available | 486.95 |
| ER-897714 | [structure] $C_{23}H_{26}F_3N_7O_2$ | (5S,7R)-5-(3,4-dimethoxyphenyl)-2-(2-(piperazin-1-yl)pyrimidin-5-yl)-7-(trifluoromethyl)-4,5,6,7-tetrahydropyrazolo[1,5-a]pyrimidine | 0.020 | 2.20 | 1H-NHR (400 MHz, METHANOL-d4) δ ppm 2.13 - 2.29 (m, 1 H) 2.52 (ddd, 1 H) 2.82 - 2.95 (m, 4 H) 3.76 - 3.94 (m, 10 H) 4.37 - 4.48 (m, 1 H) 4.99 - 5.12 (m, 1 H) 5.74 (s, 1 H) 6.91 - 7.18 (m, 3 H) 8.56 - 8.73 (m, 2 H) | 490.22 |
| ER-897715 | [structure] $C_{23}H_{26}F_3N_7O_2$ | (5R,7S)-5-(3,4-dimethoxyphenyl)-2-(2-(piperazin-1-yl)pyrimidin-5-yl)-7-(trifluoromethyl)-4,5,6,7-tetrahydropyrazolo[1,5-a]pyrimidine | 0.070 | 2.41 | 1H NMR (400 MHz, METHANOL-d4) δ ppm 2.15 - 2.28 (m, 1 H) 2.44 - 2.59 (m, 1 H) 2.81 - 2.98 (m, 4 H) 3.74 - 4.06 (m, 10 H) 4.36 - 4.50 (m, 1 H) 5.05 (dt, 1 H) 5.74 (s, 1 H) 6.91 - 7.28 (m, 3 H) 8.65 (s, 2 H) | 490.26 |
| ER-897716 | [structure] $C_{24}H_{27}F_3N_6O_2$ | (5S,7R)-5-(3,4-dimethoxyphenyl)-2-(6-(piperazin-1-yl)pyridin-3-yl)-7-(trifluoromethyl)-4,5,6,7-tetrahydropyrazolo[1,5-a]pyrimidine | 0.008 | 4.47 | 1H NMR (400 MHz, METHANOL-d4) δ ppm 2.14 - 2.30 (m, 1 H) 2.52 (ddd, 1 H) 2.88 - 3.02 (m, 4 H) 3.50 - 3.59 (m, 4 H) 3.84 (s, 3 H) 3.87 (s, 3 H) 4.35 - 4.51 (m, 1 H) 4.95 - 5.13 (m, 1 H) 5.74 (s, 1 H) 6.85 (d, 1 H) 6.94 - 7.17 (m, 3 H) 7.92 (dd, 1 H) 8.45 (d, 1 H), | 489.25 |

FIG. 11LL

| ER-Number | Structure | Chemical Name | HEK/ TLR7 IC50 (μM) | HEK/ TLR9 IC50 (μM) | 1H NMR | MS |
|---|---|---|---|---|---|---|
| ER-897717 | $C_{24}H_{27}F_3N_6O_2$ | (5R,7S)-5-(3,4-dimethoxyphenyl)-2-(6-(piperazin-1-yl)pyridin-3-yl)-7-(trifluoromethyl)-4,5,6,7-tetrahydropyrazolo[1,5-a]pyrimidine | 0.070 | 0.87 | 1H NMR (400 MHz, METHANOL-d4) δ ppm 2.14 - 2.30 (m, 1 H) 2.52 (ddd, 1 H) 2.90 - 3.02 (m, 4 H) 3.49 - 3.61 (m, 4 H) 3.84 (s, 3 H) 3.87 (s, 3 H) 4.38 - 4.48 (m, 1 H) 4.97 - 5.11 (m, 1 H) 5.74 (s, 1 H) 6.86 (d, 1 H) 6.95 - 7.17 (m, 3 H) 7.93 (dd, 1 H) 8.45 (d, 1 H). | 489.29 |
| ER-897728 | $C_{25}H_{31}F_3N_4O_2$ | 5-(3,4-dimethoxyphenyl)-2-(3-azaspiro[5.5]undec-8-en-9-yl)-7-(trifluoromethyl)-4,5,6,7-tetrahydropyrazolo[1,5-a]pyrimidine | 0.010 | 5.46 | NMR of each isomer available | 477.13 |
| ER-897765 | $C_{25}H_{29}F_3N_6O_2$ | 1-(5-(5-(3,4-dimethoxyphenyl)-7-(trifluoromethyl)-4,5,6,7-tetrahydropyrazolo[1,5-a]pyrimidin-2-yl)pyridin-2-yl)piperidin-4-amine | 0.080 | 2.13 | 1H NMR (400 MHz, METHANOL-d4) δ ppm 1.45 (qd, 2 H) 1.96 (d, 2 H) 2.14 - 2.30 (m, 1 H) 2.52 (ddd, 1 H) 2.86 - 3.10 (m, 3 H) 3.82 - 3.95 (m, 7 H) 4.29 - 4.47 (m, 3 H) 4.99 - 5.09 (m, 1 H) 5.73 (s, 1 H) 6.82 - 7.14 (m, 4 H) 7.90 (dd, 1 H) 8.43 (d, 1 H). | 503.04 |
| ER-897777 | $C_{25}H_{29}Cl_2F_3N_6O_3$ | (4-((5S,7R)-5-(3,4-dimethoxyphenyl)-7-(trifluoromethyl)-4,5,6,7-tetrahydropyrazolo[1,5-a]pyrimidin-2-yl)pyridin-2-yl)(piperazin-1-yl)methanone dihydrochloride | 0.100 | 10.00 | | |

FIG. 11MM

| ER-Number | Structure | Chemical Name | HEK/ TLR7 IC50 (μM) | HEK/ TLR9 IC50 (μM) | 1H NMR | MS |
|---|---|---|---|---|---|---|
| ER-897789 | 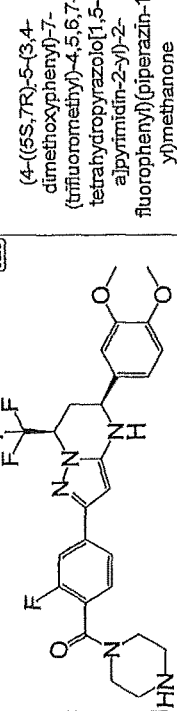 C26H29Cl2F4N5O3 | (4-((5S,7R)-5-(3,4-dimethoxyphenyl)-7-(trifluoromethyl)-4,5,6,7-tetrahydropyrazolo[1,5-a]pyrimidin-2-yl)-2-fluorophenyl)(piperazin-1-yl)methanone dihydrochloride | 0.050 | 10.00 | | |
| ER-897791 | 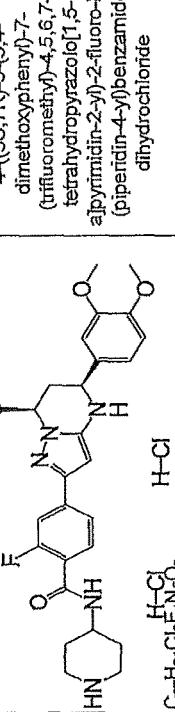 C27H31Cl2F4N5O3 | 4-((5S,7R)-5-(3,4-dimethoxyphenyl)-7-(trifluoromethyl)-4,5,6,7-tetrahydropyrazolo[1,5-a]pyrimidin-2-yl)-2-fluoro-N-(piperidin-4-yl)benzamide dihydrochloride | 0.040 | 5.99 | | |
| ER-897814 | 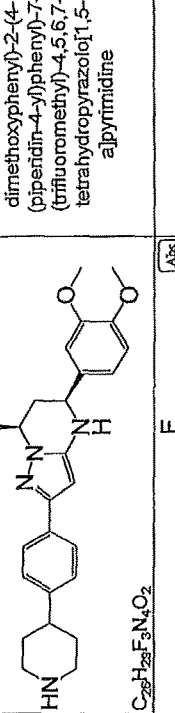 C26H29F3N4O2 | (5S,7R)-5-(3,4-dimethoxyphenyl)-2-(4-(piperidin-4-yl)phenyl)-7-(trifluoromethyl)-4,5,6,7-tetrahydropyrazolo[1,5-a]pyrimidine | 0.030 | 1.37 | 1H NMR (400 MHz, METHANOL-d4) δ ppm 1.61 - 1.79 (m, 2 H) 1.81 - 1.95 (m, 2 H) 2.13 - 2.31 (m, 1 H) 2.53 (ddd, 1 H) 2.64 - 2.85 (m, 3 H) 3.18 (d, 2 H) 3.84 (s, 3 H) 3.87 (s, 3 H) 4.38 - 4.49 (m, 1 H) 5.00 - 5.11 (m, 1 H) 5.76 - 5.82 (m, 1 H) 6.94 - 7.14 (m, 3 H) 7.23 - 7.30 (m, 2 H) 7.63 - 7.72 (m, 2 H), | |
| ER-897815 | 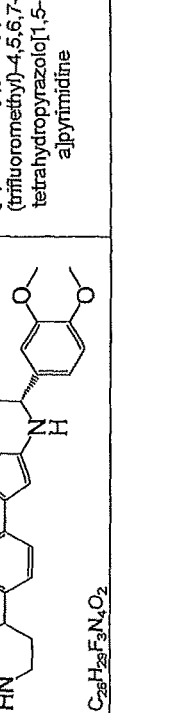 C26H29F3N4O2 | (5R,7S)-5-(3,4-dimethoxyphenyl)-2-(4-(piperidin-4-yl)phenyl)-7-(trifluoromethyl)-4,5,6,7-tetrahydropyrazolo[1,5-a]pyrimidine | 0.100 | 2.00 | 1H NMR (400 MHz, METHANOL-d4) δ ppm 1.63 - 1.77 (m, 2 H) 1.79 - 1.94 (m, 2 H) 2.09 - 2.31 (m, 1 H) 2.53 (ddd, 1 H) 2.63 - 2.84 (m, 3 H) 3.17 (d, 2 H) 3.84 (s, 3 H) 3.87 (s, 3 H) 4.38 - 4.49 (m, 1 H) 4.99 - 5.12 (m, 1 H) 5.79 (s, 1 H) 6.94 - 7.14 (m, 3 H) 7.26 (d, 2 H) 7.64 - 7.71 (m, 2 H), | |

FIG. 11NN

| ER-Number | Structure | Chemical Name | HEK/ TLR7 IC50 (µM) | HEK/ TLR9 IC50 (µM) | 1H NMR | MS |
|---|---|---|---|---|---|---|
| ER-897851 | [Structure shown] Abs; C₂₅H₃₁F₃N₄O₂ | (5S,7R)-5-(3,4-dimethoxyphenyl)-2-(3-azaspiro[5.5]undec-8-en-9-yl)-7-(trifluoromethyl)-4,5,6,7-tetrahydropyrazolo[1,5-a]pyrimidine | 0.041 | 8.63 | 1H NMR (400 MHz, METHANOL-d4) δ ppm 1.36 - 1.48 (m, 4 H) 1.52 - 1.65 (m, 2 H) 1.97 - 2.20 (m, 3 H) 2.27 - 2.51 (m, 3 H) 2.68 - 2.89 (m, 4 H) 3.74 - 3.84 (m, 6 H) 4.24 - 4.37 (m, 1 H) 4.90 (dd, 1 H) 5.44 - 5.50 (m, 1 H) 6.02 - 6.14 (m, 1 H) 6.86 - 7.09 (m, 3 H). | 477.3 |

FIG. 13C.

| Gene #: | Gene Name |
|---|---|
| 1 | Ccl2 |
| 2 | Ifit1* |
| 3 | Ifit3 |
| 4 | Ifi44* |
| 5 | Oasl2* |
| 6 | Isg15 |
| 7 | Mmp8 |
| 8 | Fcgr1* |
| 9 | Ifi27l2a* |
| 10 | Oas3* |
| 11 | Usp18* |
| 12 | C1qa* |
| 13 | Irf7 |
| 14 | Ddx60* |
| 15 | Cmpk2* |
| 16 | Xaf1 |
| 17 | Fpr1 |
| 18 | Ifi204* |
| 19 | Cxcl10 |
| 20 | Siglec1* |
| 21 | Mx1* |
| 22 | Herc6* |
| 23 | Ms4a6c |
| 24 | Ifi202b |
| 25 | Il6 |
| 26 | Cd40 |
| 27 | Prf1 |
| 28 | Cd38 |
| 29 | Irf5 |
| 30 | Lta |
| 31 | Il6ra |
| 32 | Trex1 |

TETRAHYDROPYRAZOLOPYRIMIDINE COMPOUNDS

CROSS-REFERENCE TO RELATED APPLICATIONS

This application claims the benefit of priority as a divisional of U.S. patent application Ser. No. 14/806,174, filed on Jul. 22, 2015, now U.S. Pat. No. 9,446,046, issued on Sep. 20, 2016, which was a divisional of U.S. patent application Ser. No. 13/907,202, filed May 31, 2013, and now U.S. Pat. No. 9,126,999, issued on Sep. 8, 2015, which claimed the benefit of U.S. Provisional Patent Application No. 61/654,023, filed on May 31, 2012. Those applications are incorporated by reference herein.

BACKGROUND

Field of the Disclosure

Embodiments of the disclosure relate to tetrahydropyrazolopyrimidine ("THPP") compounds and pharmaceutical agents comprising one or more of those compounds as active ingredient(s). More particularly, embodiments of the disclosure relate to a THPP compound that acts as an antagonist or inhibitor for Toll-like receptors (TLR) 7 and 8, and its use in a pharmaceutical composition effective for treatment of systemic lupus erythematosus (SLE) and lupus nephritis.

Description of Related Art

Systemic lupus erythematosus (SLE) and lupus nephritis are autoimmune diseases characterized by inflammation and tissue damage. For example, SLE may cause damage to the skin, liver, kidneys, joints, lungs, and central nervous system. SLE sufferers may experience general symptoms such as extreme fatigue, painful and swollen joints, unexplained fever, skin rash, and kidney dysfunction. Because organ involvement differs amongst patients, symptoms may vary. SLE is predominantly a disease of younger women, with peak onset between 15-40 years of age and an approximate 10-fold higher prevalence in women vs. men.

Current treatments for SLE typically involve immunomodulatory drugs such as hydroxychloroquine, prednisone, and cyclophosphamide. All of these drugs may have dose-limiting side effects.

BRIEF SUMMARY OF THE DISCLOSURE

Embodiments of the disclosure provide compounds and methods of use for preventing or treating diseases or conditions characterized by Toll-like receptor 7 or 8 activation in patients. One embodiment features a compound of formula (I):

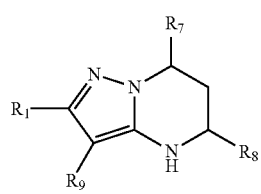

Formula (I)

or a pharmaceutically acceptable salt thereof, or a stereoisomer thereof or mixture of stereoisomers thereof, wherein
$R_1$ is optionally substituted piperidinyl, optionally substituted pyridyl, optionally substituted pyrrolyl, optionally substituted pyrroldinyl, optionally substituted thiazolyl, 1,4-dimethylthiazolyl, 2-ethyl-4-methylthiazolyl, 2-isopropylthiazol-5-yl, thiazolyl, 3-ethylthiazol-5-yl, 1-methylsulfonylpiperidin-4-yl, or
$R_1$ is —C(O)Z, where Z is optionally substituted piperazinyl, optionally substituted pyridyl, optionally substituted pyrrolyl, (S)-2-(3-ethylpiperazin-1-yl), optionally substituted pyrrolopyrrolyl, piperidin-3-ylamino, or,
$R_1$ is

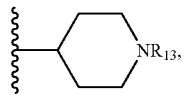

where $R_{13}$ is H, optionally substituted pyrazolyl, optionally substituted imidazolyl, benzyl, 3-hydroxybutyl, 3-(dimethylamino)-2,2-dimethylpropyl, amide, methylamide, ethylamide, optionally substituted pyridyl, methylsulfonyl, (1-methylimidazol-2-yl)methyl, (1,5-dimethylimidazol-4-yl)methyl, (1-methylpyrrol-2-yl)methyl, or where $R_{13}$ is C(O)W, where W is —N(CH$_3$)$_2$, optionally substituted piperidinyl, optionally substituted piperazinyl, optionally substituted pyrazolyl, optionally substituted pyrrolyl, or optionally substituted morpholinyl, or,
$R_1$ is

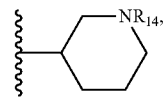

where $R_{14}$ is —C(O)CH$_3$, H, or (1-methylpyrrol-2-yl)methyl, or,
$R_1$ is

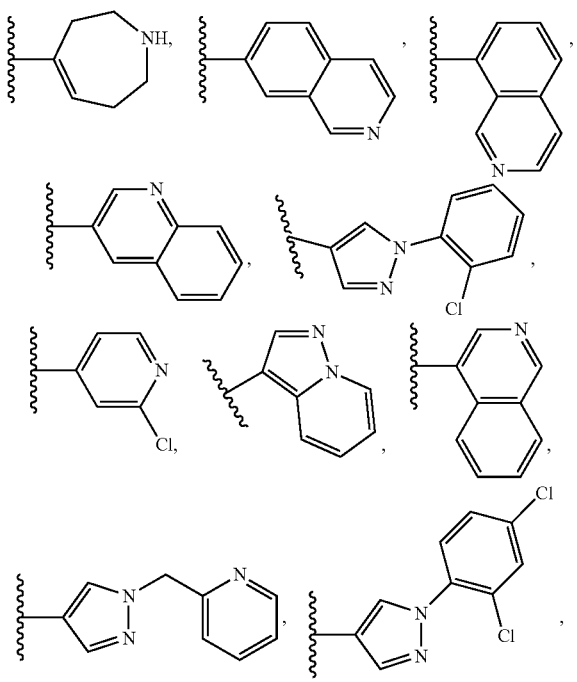

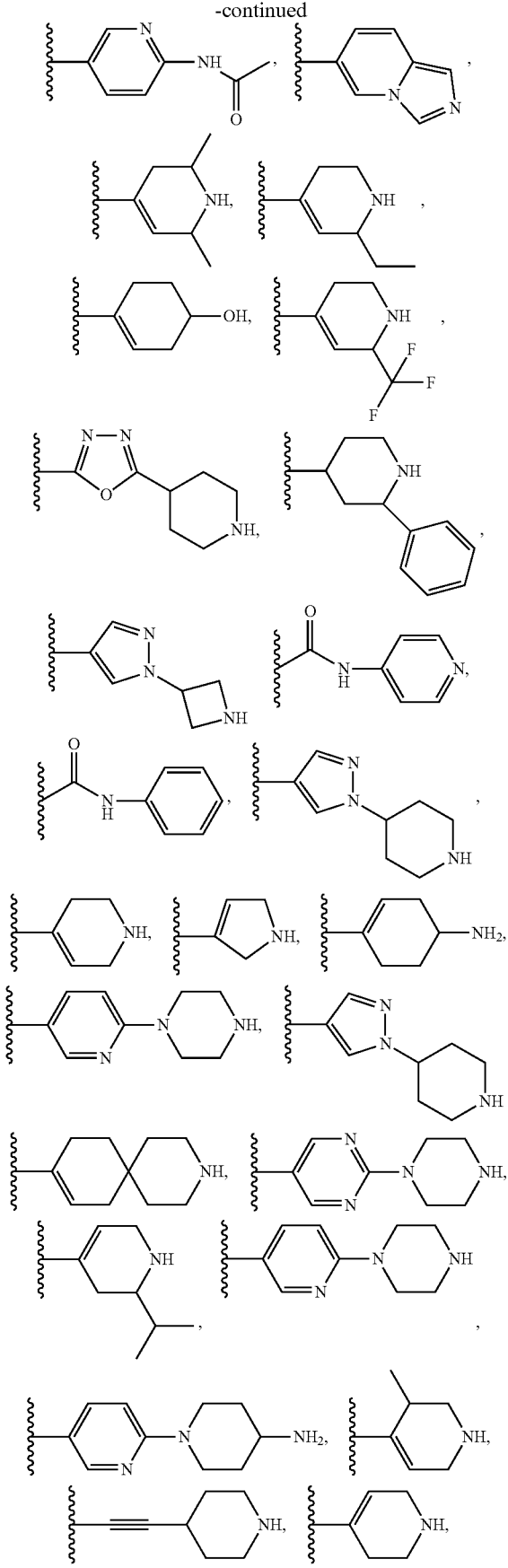

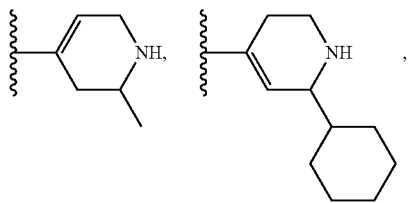

optionally substituted piperidinyl, optionally substituted piperazinyl, optionally substituted pyrazolyl, optionally substituted pyrrolyl, or R₁ is

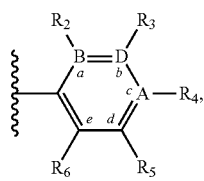

where A, B, and D may all be carbon, or where two of A, B, and D are carbon and the other is nitrogen, or where one of A, B, and D is carbon and the remaining two are nitrogen; and when A is nitrogen R₄ is absent, when B is nitrogen R₂ is absent, and when D is nitrogen R₃ is absent; and wherein R₂ is H, —CH₃, or F, or, with R₃ and the atoms at positions a and b, forms an optionally substituted pyridine or a pyrazole; and wherein R₃ is H, F, Cl, —CN, —CH₃, —OCH₃, —OH, —NH₂, methylsulfonyl,

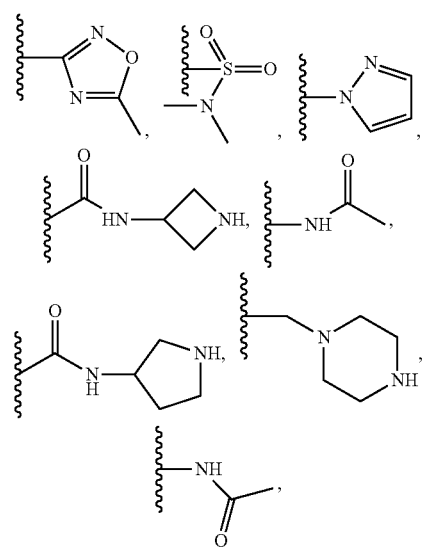

or, with R₄ and the atoms at b and c, forms an optionally substituted benzene, optionally substituted imidazole, optionally substituted pyrazole, optionally substituted pyrazolidine, optionally substituted imidazolidine, optionally substituted isothiazole,

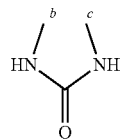

or, with $R_2$ and the atoms at a and b, forms an optionally substituted pyridine or optionally substituted pyrazole; and wherein
$R_4$ is F, —CN, —OCH$_3$, —OEt, H, Cl, Br, —NH—C(O)—CH—(CH$_3$)$_2$, —N(CH$_3$)$_2$, —CH$_3$, —CH$_2$OH,

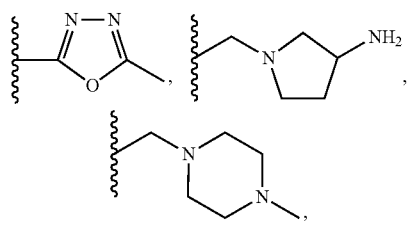

optionally substituted piperazinyl, optionally substituted piperidinyl, optionally substituted pyrazolyl, optionally substituted pyrrolyl, 4-hydroxypiperizin-1-yl, optionally substituted piperidinyl not attached to a phenyl group through a nitrogen, or, with $R_3$ and the atoms at b and c, forms an optionally substituted pyrazole ring or

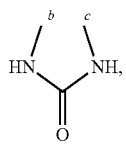

or, with $R_5$ and the atoms at c and d, forms an optionally substituted pyrazole or an optionally substituted pyrrole, or,
$R_4$ is -(q)-C(O)X, where q is a single bond, is —NH—, or is —CH$_2$—, and
where X is —NR$_{11}$R$_{12}$,
where R$_{11}$ and R$_{12}$ are both H, both —CH$_2$CH$_3$, or both —CH$_3$, or where one of R$_{11}$ and R$_{12}$ is H and the other is 1,1-dimethylethyl, cyclobutyl, cyclopropyl, lower alkyl, methyl alcohol, ethyl alcohol, propyl alcohol, cyclobutylmethyl; 2,3-dihydroxypropyl, benzyl, azetidinyl, optionally substituted piperidinyl, optionally substituted piperazinyl, optionally substituted pyrazolyl, optionally substituted pyrrolyl, optionally substituted azetidinyl, —CH$_2$—NH—CH$_3$, alcohol, —OCH$_3$, or

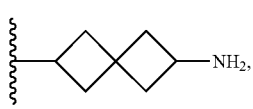 [SMILES: *C1CC2(C1)CC(N)C2]

or
where X is optionally substituted pyrrolidinyl, optionally substituted piperidinyl, optionally substituted pyrrolidinyl, optionally substituted piperazinyl, or optionally substituted morpholinyl,

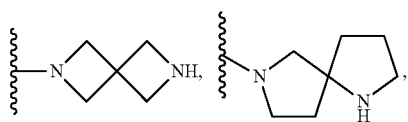

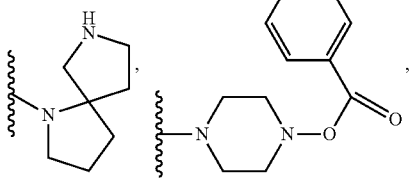

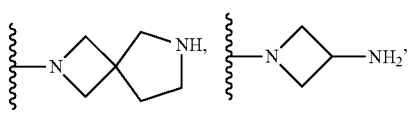

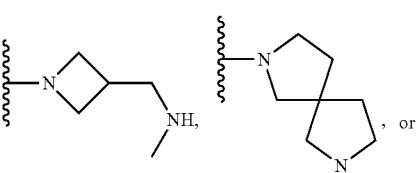

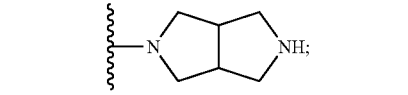

and wherein
$R_5$ is H, F, Cl, —CH$_3$, —OCH$_3$, pyrrolyl, —CH$_2$OH, —NH$_2$, —OH,

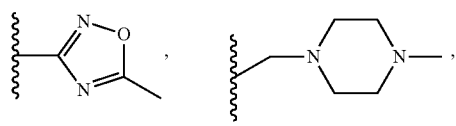

or, with $R_4$ and the atoms at c and d, forms an optionally substituted benzene, an optionally substituted pyrazole, an optionally substituted piperidinyl, an optionally substituted piperazinyl, or an optionally substituted pyrrole, or, with $R_6$ and the atoms at d and e, forms an optionally substituted pyridine, or $R_5$ is C(O)Y, where Y is —NH$_2$, —N(CH$_3$)$_2$, optionally substituted piperazinyl, optionally substituted piperidinyl, optionally substituted piperidinyl, optionally substituted piperazinyl, optionally substituted pyrazolyl, optionally substituted pyrrolyl,

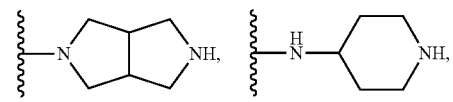

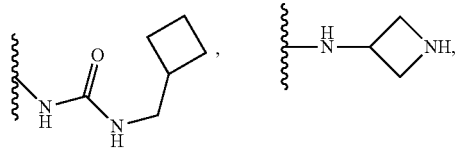

-continued

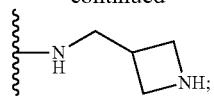

and wherein
R₆ is H, F, —CH₃, —CF₃, or, with R₅ and the atoms at c and d, forms an optionally substituted benzene or an optionally substituted pyrazole; and wherein
R₇ is H, —CF₃, —CHF₂, —CF₂CH₃, —CH₃, or —C(CH₃)₃; and wherein
R₈ is

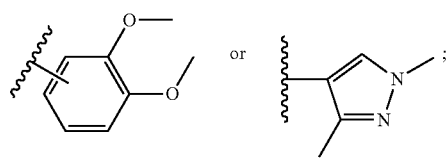

and wherein
R₉ is Br, Cl, F, I, or H.

In some embodiments of the disclosure one or more provisos are applied. These provisos typically exclude one or more compounds that might otherwise be included within a stated genus. When reviewing the provisos below, it will be understood that the converse is also true. For example, if a proviso states that when R₄ is F: then R₂ is not CH₃ or F, then it is also true that when R₂ is selected to be —CH₃ or F, then R₄ is not F. It will also be noted that when a proviso is presented as a series of statements, the later statements are not related unless directly presented as provisos elsewhere in the document. For example, if a proviso states that when R₄ is F: R₂ is not —CH₃ or F; and R₃ is not —CH₃, then the implication should not be made from that statement alone that when R₃ is —CH₃, then R₂ is not —CH₃ or F.

One or more of the following provisos may be applied in various embodiments presented herein:
  when R₄ is F: R₂ is not —CH₃ or F; R₃ is not —CH₃, —CN, F, Cl, or —OCH₃; R₅ is not —CH₃, F, Cl, or —OCH₃; and R₆ is not —CH₃ or F;
  when R₄ is Cl: R₂ is not F; R₃ is not F or —CN; R₅ is not F, —CN, or —C(O)N(CH₃)₂; R₆ is not —CF₃ or F; D is not nitrogen; and either R₅ is —C(O)NH₂ or one of R₂, R₃, R₅, and R₆ is —CH₃;
  when R₄ is —CH₃: R₃ is not F; R₅ is not F; and R₅ and R₆ do not form a pyrimidine together with the atoms at d and e;
  when R₄ is —OCH₃: R₂ is not F; R₃ is not Cl or —OCH₃, R₅ is not Cl or —OCH₃; and R₆ is not F or —CF₃;
  when R₄ is —CN: R₂ is not F; R₃ is not Cl, F, or —OCH₃, R₅ is not Cl, F, or —OCH₃; and R₆ is not F;
  when R₄ is —OCH₂CH₃: R₃ is not Cl or F; R₅ is not Cl or F; and R₆ is not —CF₃;
  when R₄ is

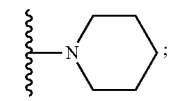

R₃ is not H or F; and R₅ is not H or F;

when R₄ is

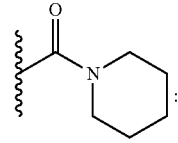 [SMILES: *C(=O)N1CCCCC1]

at least one of R₂, R₃, R₅, and R₆ is not H;
when R₄ is

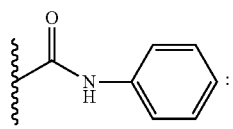

R₃ is not F; and R₅ is not F;
when R₂ is F: R₃ is not —OCH₃ or F; R₅ is not —CN; and at least one of R₃, R₄, R₅, and R₆ is not H;
when R₂ is Cl: R₃ is not F;
when R₂ is —CH₃: R₃ is not Cl; at least one of R₃, R₄, R₅, and R₆ is not —CH₃; and R₄ and R₅ do not form a pyrazolyl with the atoms at c and d;
when R₃ is —OCH₃: R₂ is not F; and R₆ is not F;
when R₃ is F: R₂ is not —OCH₃; and X is not

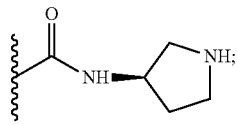 [SMILES: *C(=O)N[C@@H]1CCNC1]

when R₃ is Cl: R₅ is not Cl; R₁₁ is not benzyl; and R₁₂ is not benzyl;
when R₅ is Cl, R₆ is not —CH₃; R₁₁ is not benzyl; and R₁₂ is not benzyl;
when R₅ is F or —OCH₃: R₆ is not F;
when R₆ is F: at least one of R₂, R₃, R₄, and R₅ is not H;
when R₃ and R₅ are H: R₁₁ is not cyclopropyl; and R₁₂ is not cyclopropyl;
when R₉ is Cl, R₁ is not an amide group;
when B is nitrogen and A and D are carbon: R₄ may not be —CN or

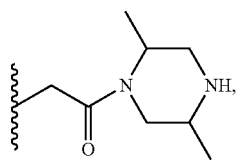 [SMILES: *CC(=O)N1CC(C)NCC1C]

when R₇ is —CHF₂ and R₄ is then R₄ does not have the absolute stereochemistry

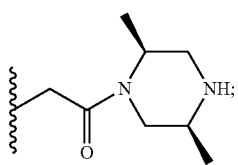 [SMILES: *CC(=O)N1C[C@H](C)NC[C@@H]1C]

and
wherein, when R₈ is

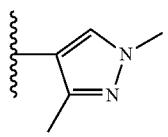

then the following provisos are in effect:
when R₄ is F: at least one of R₂, R₃, R₅, and R₆ is not H; R₃ is not C(O)N(CH₃)₂; and R₅ is not C(O)N(CH₃)₂;
when R₄ is Cl: at least one of R₂, R₃, R₅, and R₆ is not H;
when R₃ is F: R₄ is not C(O)NHCH₂CH₂CH₂CH₃, C(O)N(CH₃)₂, C(O)NHCH₂CH₂CH₃, or C(O)NHC(CH₃)₃;
R₄ is not C(O)NHCH₂CH₂OH, C(O)NHCH(CH₃)₂, —CN, or

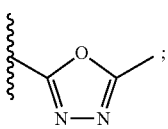 [SMILES: *c1nnc(C)o1]

R₁ is not

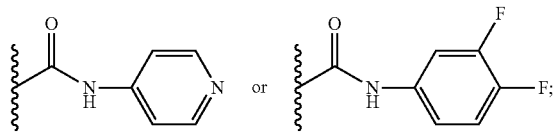 [SMILES: *C(=O)Nc1ccncc1 ; *C(=O)Nc1ccc(F)c(F)c1]

R₅ is not

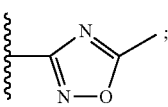 [SMILES: *c1noc(C)n1]

R₃ is not

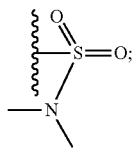 [SMILES: *S(=O)(=O)N(C)C]

when R₂ is F: R₅ is not —C(O)NH₂;
when R₂ is —CH₃, R₄ and R₅ do not form a pyrazole with atoms at c and d; and
when B is nitrogen, R₃ and R₄ do not form an optionally substituted imidazole with the atoms at b and c; and wherein, when R₈ is

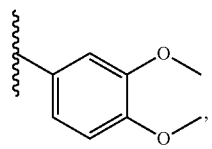 [SMILES: *c1ccc(OC)c(OC)c1]

then following provisos are in effect:
R₄ is not —CH₃, —C(O)NHCH₂CH₂OH, —NHC(O)CH(CH₃)₂, or

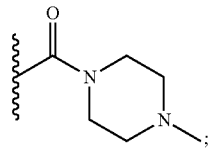 [SMILES: *C(=O)N1CCN(C)CC1]

when R₄ is C(O)NHCH₃, at least one of R₂, R₃, R₅, and R₆ is not H;
when R₄ is —OCH₃: R₃ is not F or —CH₃; and R₅ is not F or —CH₃;
when R₄ is

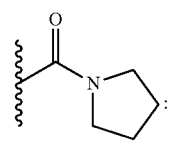 [SMILES: *C(=O)N1CCCC1]

R₃ is not Cl; and R₅ is not Cl;
when R₄ is —C(O)NHCH(CH₃)₂ or —C(O)N(CH₂CH₃)₂: at least one of R₃ and R₅ is not H;
R₅ is not —C(O)NH₂; and
R₆ is not —CF₃.

In a further embodiment the compound of formula (I) has the absolute stereochemistry set forth in formula (II):

Formula (II)

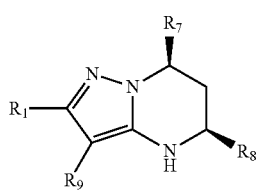

with the proviso that, when R₈ is

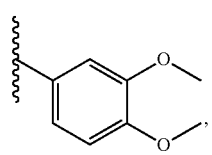 [SMILES: *c1ccc(OC)c(OC)c1]

the following provisos are in effect:
  when $R_3$ is F, $R_4$ is not

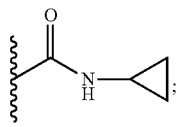 [SMILES: *C(=O)NC1CC1]

when $R_5$ is F, $R_4$ is not

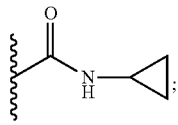 [SMILES: *C(=O)NC1CC1]

when $R_5$ is —$CH_3$, $R_3$ and $R_4$, with atoms at b and c, do not form

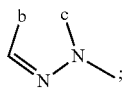

and
  when $R_3$ is —$CH_3$, $R_4$ and $R_5$, with the atoms at c and d, do not form

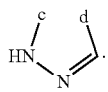

In a further embodiment the compound of formula (I) has the absolute stereochemistry set forth in formula (III):

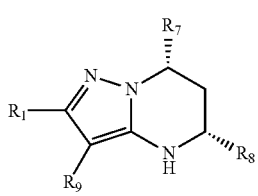

Formula (III)

with the proviso that when $R_8$ is

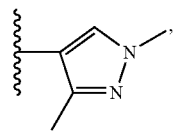 [SMILES: *c1cn(C)nc1C]

R4 is not

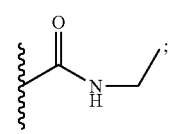 [SMILES: *C(=O)NCC]

and
with the proviso that when $R_8$ is

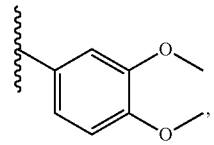 [SMILES: *c1ccc(OC)c(OC)c1]

the following provisos are in effect:
  when $R_2$ is —$CH_3$: $R_3$ and $R_4$ do not form an optionally substituted pyrazolyl with the atoms at b and c;
  when $R_2$ is —$CH_3$: $R_4$ and $R_5$ do not form an optionally substituted pyrazolyl with the atoms at c and d;
  when $R_2$ is F: $R_4$ is not $C(O)NH_2$;
  $R_3$ and $R_4$, with the atoms at b and c, do not form

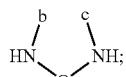

when $R_3$ is Cl: $R_4$ is not —$C(O)NHCH_3$ or —$C(O)NH_2$;
  $R_3$ is not pyrazolyl;
  when $R_3$ is F: $R_4$ is not

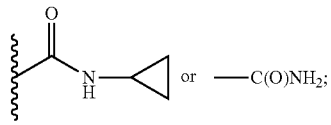

when $R_3$ is —$CH_3$: $R_4$ and $R_5$ do not form an optionally substituted pyrazolyl with the atoms at c and d;
  $R_4$ is not —$C(O)NHCH_2CH_2CH_2OH$;
  $R_4$ is not —CN or

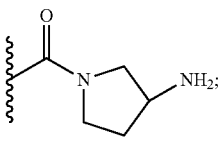 [SMILES: *C(=O)N1CCC(N)C1]

when $R_5$ is —$CH_3$, $R_3$ and $R_4$ do not form an optionally substituted pyrazolyl with the atoms at b and c;
  when $R_5$ is Cl: $R_4$ is not —$C(O)NH_2$;
  when $R_5$ is F: $R_4$ is not $C(O)NH_2$;
  $R_5$ is not pyrazolyl;
  when $R_6$ is —$CH_3$: $R_4$ and $R_5$ do not form an optionally substituted pyrazolyl with the atoms at c and d; and
  when B is nitrogen, $R_4$ is not —$C(O)NHCH_3$.

In one embodiment, $R_1$ is piperidinyl or pyridyl; $R_7$ is —$CF_3$; $R_8$ is

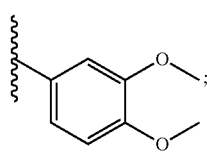 [SMILES: *c1ccc(OC)c(OC)c1]

and R$_9$ is F, Cl, Br, or I.

In another embodiment, R$_1$ is —C(O)Z, where Z is piperazinyl, piperidinyl, pyrrolopyrrolyl, or piperidinyl propyl; R$_7$ is —CF$_3$; R$_8$ is

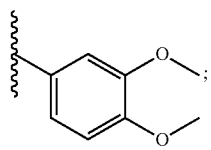 [SMILES: *c1ccc(OC)c(OC)c1]

and R$_9$ is H.

In another embodiment, R$_1$ is

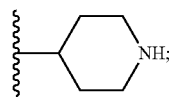 [SMILES: *C1CCNCC1]

R$_7$ is —CF$_3$, R$_8$ is

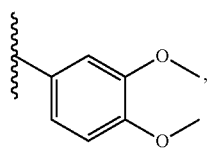 [SMILES: *c1ccc(OC)c(OC)c1]

and R$_9$ is H.

In another embodiment, R$_1$ is

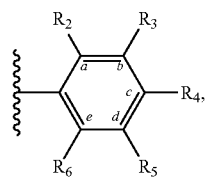

R$_2$ is H, —CH$_3$, or, with R$_3$, forms

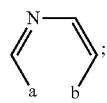

R$_3$ is H or, with R$_2$, forms

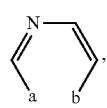

or, with R$_4$, forms

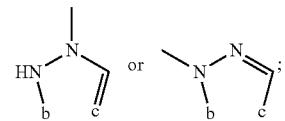

R$_4$ is H, —CH$_3$, —NHC(O)NH$_2$, or, with R$_3$, forms

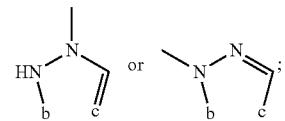

R$_5$ is H; R$_6$ is H; R$_7$ is —CF$_3$; R$_8$ is

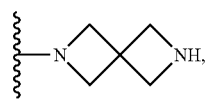

and R$_9$ is H.

In another embodiment R$_1$ is

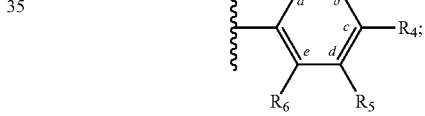

R$_2$ is H, F, or —CH$_3$, R$_3$ is H or F; R$_4$ is -(q)-C(O)X, where q is a bond or —CH$_2$—, and X is piperazinyl attached through a nitrogen to the carbonyl group of R$_4$, pyrrolidinyl attached through a nitrogen to the carbonyl group of R$_4$, pyrrolopyrrolyl attached through a nitrogen to the carbonyl group of R$_4$, azetidinyl attached through a nitrogen to the carbonyl group of R$_4$, or

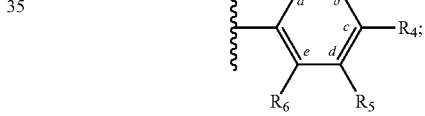

or X is —NR$_{11}$R$_{12}$, where one of R$_{11}$ and R$_{12}$ is H and the other is optionally substituted pyrrolidinyl, optionally substituted piperidinyl, optionally substituted piperazinyl, or optionally substituted azetidinyl; R$_5$ is H or C(O)Y, where Y is, —NH(CH$_3$)$_2$, optionally substituted piperazinyl, optionally substituted piperidinyl,

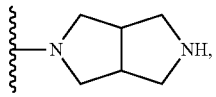 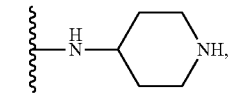

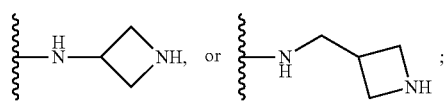

$R_6$ is H, $R_7$ is —CHF$_2$, $R_8$ is

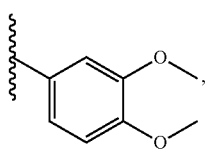 [SMILES: *c1ccc(OC)c(OC)c1]

and $R_9$ is H.

In a further embodiment, $R_1$ is

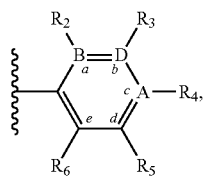

where A, B, and D may all be carbon, or where two of A, B, and D are carbon and the other is nitrogen, and when A is nitrogen $R_4$ is absent, when B is nitrogen $R_2$ is absent, and when D is nitrogen $R_3$ is absent; $R_2$ is H; $R_3$ is H or —CH$_3$; $R_4$ is —C(O)X, where X is optionally substituted piperazinyl, or X is —NR$_{11}$R$_{12}$, where R$_{11}$ and R$_{12}$ are H, or where one of R$_{11}$ or R$_{12}$ is H, and the other is piperidinyl, pyrrolidinyl, or —CH$_3$; $R_5$ is —OCH$_3$, H, or Cl; $R_6$ is H, $R_7$ is —CF$_3$, $R_8$ is

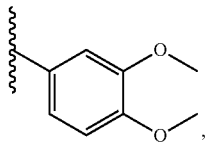 [SMILES: *c1ccc(OC)c(OC)c1]

and $R_9$ is H.

In a further embodiment, $R_1$ is

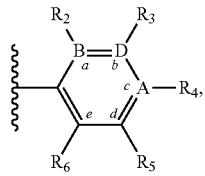

where A, B, and D are carbon;

$R_2$ is H, —CH$_3$, or F, or, with $R_3$ and the atoms at positions a and b, forms an optionally substituted pyrazole;

$R_3$ is H, F, Cl, —CN, —CH$_3$,

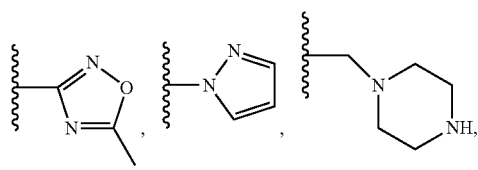

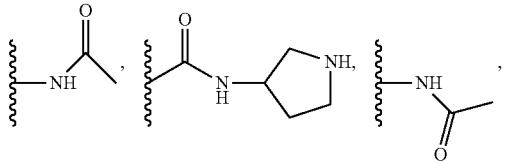

or, with $R_4$ and the atoms at b and c, forms optionally substituted pyrazole or

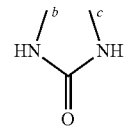

or, with $R_2$ and the atoms at a and b, forms an optionally substituted pyrazole;

$R_4$ is —CN, —CH$_2$OH, H,

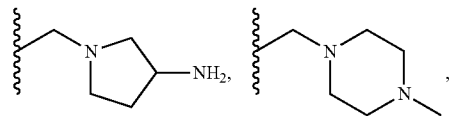

optionally substituted piperazinyl, or, with $R_3$ and the atoms at b and c, forms an optionally substituted pyrazole ring or

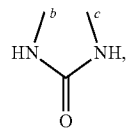

or, with $R_5$ and the atoms at c and d, forms an optionally substituted pyrazole ring, or $R_4$ is -(q)-C(O)X, where q is a bond, and where X is —NR$_{11}$R$_{12}$, where R$_{11}$ and R$_{12}$ are both H, or where one of R$_{11}$ and R$_{12}$ is H and the other is 1,1-dimethylethyl, cyclobutyl, cyclopropyl, lower alkyl, C$_{1-3}$ alcohol, cyclobutylmethyl; 2,3-dihydroxypropyl, benzyl, azetidinyl, pyrrolidinyl, piperidinyl, methylazetidinyl, pyrazolyl, piperazinyl, alcohol, —OCH$_3$, or

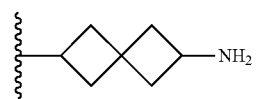 [SMILES: *C1CC2(C1)CC(N)C2]

or where X is an optionally substituted piperidinyl attached through a nitrogen to the carbonyl group of $R_4$, optionally substituted piperazinyl attached through a nitrogen to the carbonyl group of $R_4$, optionally substituted pyrrolidinyl attached through a nitrogen to the carbonyl group of $R_4$, or optionally substituted azetidinyl attached through a nitrogen to the carbonyl group of $R_4$,

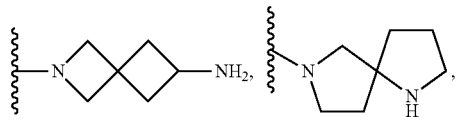

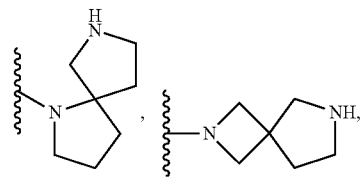

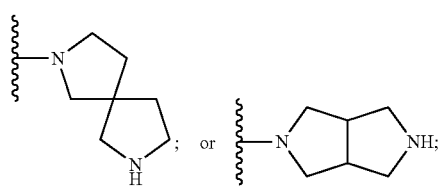

and $R_5$ is H, or, with $R_4$ and the atoms at c and d, forms an optionally substituted benzene, an optionally substituted pyrazole, or, with $R_6$ and the atoms at d and e, forms an optionally substituted pyridine, or $R_5$ is C(O)Y, where Y is —$NH_2$, —$NH(CH_3)_2$, optionally substituted piperazinyl attached through a nitrogen to the carbonyl group of $R_5$, optionally substituted piperidinyl attached through a nitrogen to the carbonyl group of $R_5$,

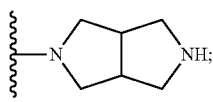

and $R_6$ is H, F, —$CH_3$, or, with $R_5$ and the atoms at c and d, forms an optionally substituted pyrazole;

$R_7$ is —$CF_3$;

$R_8$ is

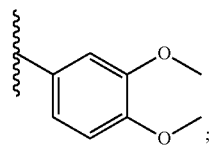 [SMILES: *c1ccc(OC)c(OC)c1]

and $R_9$ is H.

Another embodiment includes a compound of formula (IV)

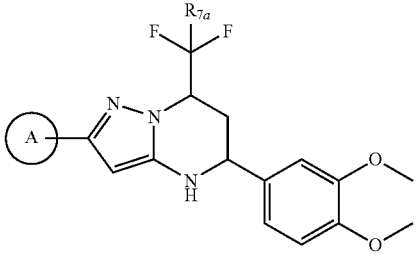

Formula (IV)

or a pharmaceutically acceptable salt thereof, or a stereoisomer thereof or mixture of stereoisomers thereof, wherein: $R_{7a}$ is H or F; and wherein Ring A is:

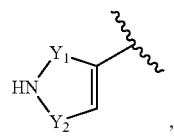

wherein $Y_1$ and $Y_2$ are independently selected from the group consisting of —$CH_2$— and —$CH_2CH_2$—, and wherein each of $Y_1$ and $Y_2$ is optionally substituted by $C_{1-3}$ alkyl;

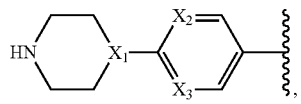

wherein $X_1$, $X_2$, and $X_3$ are independently selected from the group consisting of —CH— and N;

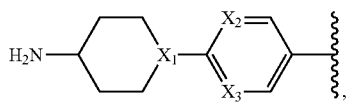

wherein $X_1$, $X_2$, and $X_3$ are independently selected from the group consisting of —CH— and N;

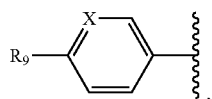

wherein X is N or —CH— optionally substituted by —$CH_3$, F, or Cl, and wherein $R_9$ is —C(O)Z, wherein Z is 2,3-dihydroxypropylamine; a five to seven member cyclic diamine that is optionally bridged or optionally substituted at a carbon atom with a lower alkyl; a seven to ten member bicyclodiamine; a seven to eleven member spirodiamine; —NH substituted with a four to seven member cyclic amine optionally substituted with —NH$_2$; —OH; —CH$_2$NHR, wherein R is H or lower alkyl; —NH substituted with a seven to eleven member spiroalkane optionally substituted with —NH$_2$; or R$_9$ is CH$_3$NHC(O)—, and a carbon atom on the aryl ring to which R$_9$ is attached is substituted with one of —CH$_3$, F, or Cl; R$_9$ is (CH$_3$)$_2$CHNHC(O)—, and a carbon atom on the aryl ring to which R$_9$ is attached is substituted with one of —CH$_3$, F, or Cl; or R$_9$ is (CH$_3$)$_3$CNHC(O)— and a carbon atom on the aryl ring to which R$_9$ is attached is substituted with one of —CH$_3$, F, or Cl; or R$_9$ is

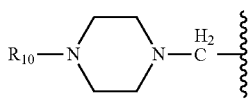

wherein the piperazine is optionally bridged or substituted with lower alkyl and R$_{10}$ is H or —CH$_3$; or R$_9$ is

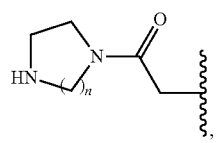

wherein n is 1-3 and the cyclic diamine is optionally bridged or substituted with lower alkyl; or R$_9$ is

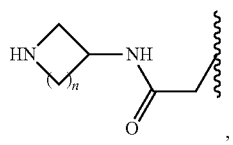

wherein n is 1-4; or

R$_9$ is —NHC(O)NH$_2$, —CH$_2$C(O)NH— wherein the nitrogen is substituted with a four to seven member cyclic amine; —CH$_2$—C(O)— wherein the carbonyl is substituted with a seven to ten member bicyclodiamine; and a four to seven member cyclic amine substituted with —CH$_2$C(O)NH$_2$; or

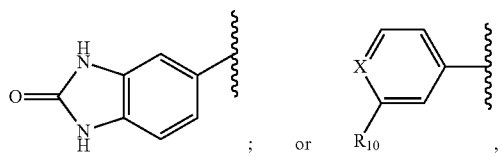

wherein X is N or —CH— wherein the C is optionally substituted by —CH$_3$, F, or Cl, and wherein R$_{10}$ is —C(O)NH— wherein the nitrogen is substituted by a four to seven member cyclic amine; —C(O)— substituted by a seven to ten member bicyclodiamine; —C(O)— substituted by a seven to eleven member spirodiamine; pyrazole; [1,2,4]oxadiazole optionally substituted by —CH$_3$ on a carbon atom of the oxadiazole; —NHC(O)CH$_3$; —CH$_2$— substituted by a piperazine; —CH$_2$— substituted by a piperazine including a methyl substituent; —C(O)— substituted by a five to seven member cyclic diamine; —C(O)NHCH$_2$— wherein the —CH$_2$— is substituted by azetidine; or —C(O)— substituted with a five to seven member cyclic amine wherein the amine includes an —NH$_2$ substituent; or cyanophenyl; isoquinoline; cyclohexene substituted with —NH$_2$ at the 4' position; 1,4-dimethylindazole-5-yl; 1,6-dimethylindazole-5-yl; cyclohexene substituted with spiropiperidine at the 4' position; 1-piperidinopyrazole; or o-methoxypyridine.

In a further embodiment, a compound or pharmaceutically effective salt of the preceding paragraph of this disclosure has an IC50 less than or equal to 100 nM against human TLR7 receptors expressed in a HEK-293 cell line. In a further embodiment C50 against human TLR7 receptors expressed in a HEK-293 cell line is measured by (1) plating cells of the HEK-293 cell line stably expressing TLR7 in Dulbecco's modified Eagle's medium containing 10% fetal bovine serum at a density of 2.22×105 cells/ml into a 384-well plate and incubating for 2 days at 37° C., 5% CO2; (2) adding the compound or pharmaceutically acceptable salt thereof and incubating the cells for 30 minutes; (3) adding CLO97 (InvivoGen) at 3 ug/ml and incubating the cells for approximately 20 hours; and (4) quantifying NF-kappaB dependent reporter activation by measuring luminescence.

A further embodiment includes a compound of formula IV, or pharmaceutically effective salt thereof, wherein Ring A is:

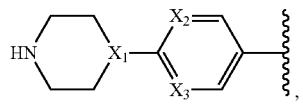

wherein X$_1$, X$_2$, and X$_3$ are independently selected from the group consisting of —CH— and N;

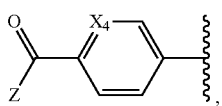

wherein X$_4$ is —CH— or N; and wherein Z is piperazine, optionally bridged or substituted on a carbon by —CH$_3$; hexahydropyrrolo[3,4]pyrrole; a four to seven member cyclic amine substituted with —OH or —NH$_2$; or —NH— substituted with a four to seven member cyclic amine;

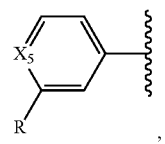

wherein X$_5$ is —CH— or N; and wherein R is pyrazole; [1,2,4]oxadiazole optionally substituted by a —CH$_3$ on a carbon of the oxadiazole; or —C(O)NH— substituted on its nitrogen by a four to seven member cyclic amine;

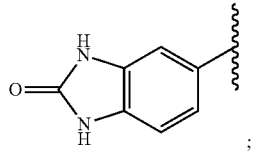

1,4-dimethylindazole-5-yl; 1,6-dimethylindazole-5-yl; 1-piperidinopyrazole; cyclohexene substituted with —NH$_2$ at the 4' position; cyclohexene substituted with spiropiperidine at the 4' position; or 2-methoxypyridine-4-yl.

In a further embodiment the compound or pharmaceutically effective salt thereof of the preceding paragraph of this disclosure has an IC50 less than or equal to 20 nM against human TLR7 receptors expressed in a HEK-293 cell line. In a further embodiment the compound or pharmaceutically effective salt thereof of the preceding paragraph of this disclosure has an IC50 less than or equal to 100 nM against human TLR7 receptors expressed in a HEK-293 cell line. In a further embodiment the IC50 against human TLR7 receptors expressed in a HEK-293 cell line is measured by (1) plating cells of the HEK-293 cell line stably expressing TLR7 in Dulbecco's modified Eagle's medium containing 10% fetal bovine serum at a density of 2.22×105 cells/ml into a 384-well plate and incubating for 2 days at 37° C., 5% CO2; (2) adding the compound or pharmaceutically acceptable salt thereof and incubating the cells for 30 minutes; (3) adding CLO97 (InvivoGen) at 3 ug/ml and incubating the cells for approximately 20 hours; and (4) quantifying NF-kappaB dependent reporter activation by measuring luminescence.

A further embodiment includes a compound having the absolute stereochemistry set forth in formula (V):

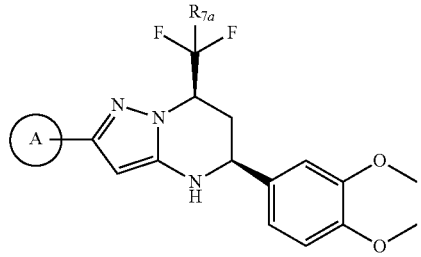

or pharmaceutically acceptable salt thereof, wherein: $R_{7a}$ is H or F; wherein Ring A is:

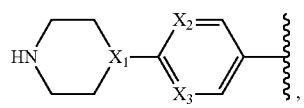

wherein $X_1$, $X_2$, and $X_3$ are independently selected from the group consisting of —CH— and N;

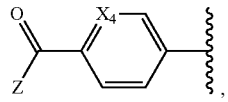

wherein $X_4$ is —CH— or N; and wherein Z is piperazine, optionally bridged or substituted on a carbon by —CH$_3$; hexahydropyrrolo[3,4]pyrrole; a four to seven member cyclic amine substituted with —OH or —NH$_2$; or —NH— substituted with a four to seven member cyclic amine;

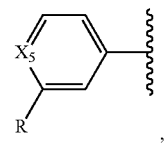

wherein $X_5$ is —CH— or N; and wherein R is pyrazole; [1,2,4]oxadiazole optionally substituted by a —CH$_3$ on a carbon of the oxadiazole; or —C(O)NH— substituted on its nitrogen by a four to seven member cyclic amine;
1,4-dimethylindazole-5-yl; 1,6-dimethylindazole-5-yl;

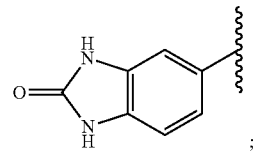 [SMILES: *c1ccc2[nH]c(=O)[nH]c2c1]

1-piperidinopyrazole; cyclohexene substituted with —NH$_2$ at the 4' position; cyclohexene substituted with spiropiperidine at the 4' position; or 2-methoxypyridine-4-yl.

In a further embodiment the compound or pharmaceutically effective salt thereof of the preceding paragraph has an IC50 less than or equal to 20 nM against human TLR7 receptors expressed in a HEK-293 cell line. In a further embodiment the compound or pharmaceutically effective salt thereof of the preceding paragraph of this disclosure has an IC50 less than or equal to 100 nM against human TLR7 receptors expressed in a HEK-293 cell line. In a further embodiment the IC50 against human TLR7 receptors expressed in a HEK-293 cell line is measured by (1) plating cells of the HEK-293 cell line stably expressing TLR7 in Dulbecco's modified Eagle's medium containing 10% fetal bovine serum at a density of 2.22×105 cells/ml into a 384-well plate and incubating for 2 days at 37° C., 5% CO2; (2) adding the compound or pharmaceutically acceptable salt thereof and incubating the cells for 30 minutes; (3) adding CLO97 (InvivoGen) at 3 ug/ml and incubating the cells for approximately 20 hours; and (4) quantifying NF-kappaB dependent reporter activation by measuring luminescence.

In further embodiments of the disclosure, compounds have an IC50 against human TLR7 receptors expressed in a HEK-293 cell line less than or equal to 200 nM, less than or equal to 180 nM, less than or equal to 160 nM, less than or equal to 140 nM, less than or equal to 120 nM, less than or equal to 100 nM, less than or equal to 80 nM, less than or equal to 60 nM, less than or equal to 40 nM, or less than or equal to 20 nM. In further embodiments of the disclosure, compounds have an IC50 against human TLR7 receptors expressed in a HEK-293 cell line from 10 nM to 30 nM, from 10 nM to 50 nM, from 10 nM to 100 nM, from 30 nM to 50 nM, from 30 nM to 100 nM, or from 50 nM to 100 nM. In further embodiments the IC50 against human TLR7 receptors expressed in a HEK-293 cell line is measured by (1) plating cells of the HEK-293 cell line stably expressing TLR7 in Dulbecco's modified Eagle's medium containing 10% fetal bovine serum at a density of 2.22×105 cells/ml into a 384-well plate and incubating for 2 days at 37° C., 5% CO2; (2) adding the compound or pharmaceutically acceptable salt thereof and incubating the cells for 30 minutes; (3) adding CLO97 (InvivoGen) at 3 ug/ml and incubating the cells for approximately 20 hours; and (4) quantifying NF-kappaB dependent reporter activation by measuring luminescence.

Further embodiments provide methods for treatment of a systematic lupus erythematosus or lupus including administering a pharmaceutically effective amount of a compound or pharmaceutically acceptable salt of the disclosure.

Further embodiments provide methods for antagonizing TLR7, including administering a pharmaceutically effective amount of a compound or pharmaceutically acceptable salt of the disclosure.

Further embodiments provide methods for antagonizing TLR8, including administering a pharmaceutically effective amount of a compound or pharmaceutically acceptable salt of the disclosure.

Further embodiments provide pharmaceutical compositions comprising at least one compound or pharmaceutically acceptable salt of the disclosure and at least one pharmaceutically acceptable carrier.

Further embodiments provide methods for treatment of a systematic lupus erythematosus or lupus, including administering a pharmaceutically effective amount of a compound or pharmaceutically acceptable salt of the disclosure.

Further embodiments provide methods for antagonizing TLR7, including administering a pharmaceutically effective amount of a compound or pharmaceutically acceptable salt of the disclosure.

Further embodiments provide methods for antagonizing TLR8, including administering a pharmaceutically effective amount of a compound or pharmaceutically acceptable salt of the disclosure.

Further embodiments provide pharmaceutical compositions comprising at least one compound or pharmaceutically acceptable salt of the disclosure and at least one pharmaceutically acceptable carrier.

The term "optionally substituted," as used herein, means that the subject structure may include, but is not required to include, one or more substituents independently selected from lower alkyl, methoxy-, —OH, —NH$_2$, —CH$_2$—NH—CH$_2$, —OCH$_2$CH$_2$CH$_3$, or —OCH(CH$_3$)$_2$. If the optionally substituted moiety is cyclic, then the optional substitution may be a methyl bridge between two atoms in the ring.

The symbol "C(O)" as used herein refers to a carbonyl group having the formula C=O.

Unless otherwise specified, "a" and "an" as used in this disclosure, including the claims, mean "one or more."

As used herein, "lower alkyl" refers to straight, or, in the case of three- and four-carbon groups, straight, branched, or cyclic saturated hydrocarbons having between one and four carbon atoms.

As used herein, the term "attached through a nitrogen" when referring to a heterocyclic moiety including nitrogen, means that a point of attachment of the moiety to another structure is through a nitrogen that is part of the heterocycle.

As used herein, the term "TLR7/8" means "TLR7 and TLR8" or "TLR7 or TLR8" or "TLR7 and/or TLR8." The particular meaning can be understood by a person skilled in the art based upon the context in which "TLR7/8" appears.

Heterocyclic moieties recited herein include azetidinyl, pyrrolidinyl, piperidinyl, methylazetidinyl, pyrazolyl, piperazinyl, morpholinyl, thiazolyl, pyrrolopyrrolyl, imidazolidinyl, and isothiazolyl. Where a heterocyclic group is mentioned, unless otherwise indicated it will be understood that the heterocyclic atom(s) in the group may be at any position in the group. It will further be understood that imidazolyl, pyrazolyl, thiazolyl, and pyrrolyl may be unsaturated or partially unsaturated. An embodiment of the disclosure may include a pharmaceutical composition that includes one or more compounds of the disclosure with a pharmaceutically acceptable excipient. These pharmaceutical compositions may be used to treat or prevent a disease or condition characterized by TLR7/8 activation in a patient, typically a human patient, who has or is predisposed to have such a condition or disease. Examples of diseases or conditions characterized by TLR7/8 activation include systemic lupus erythematosus (SLE) and lupus nephritis.

As used herein, "effective amount" of a compound of an embodiment of the disclosure is effective amount of the above-identified compounds in an amount sufficient to treat or prevent SLE and lupus nephritis.

Embodiments presented herein may include asymmetric or chiral centers. Embodiments include the various stereoisomers and mixtures thereof. Individual stereoisomers of compounds of embodiments of the disclosure may be prepared synthetically from commercially available starting materials that contain asymmetric or chiral centers, or by preparation of mixtures of enantiomeric compounds followed by resolution of those compounds. Suitable methods of resolution include attachment of a racemic mixture of enantiomers, designated (+/−), to a chiral auxiliary, separation of the resulting diastereomer by chromatography or recrystallization and separation of the optically pure product from the auxiliary; or direct separation of the mixture of optical enantiomers on chiral chromatographic columns.

Embodiments of the disclosure also include a pharmaceutical composition including any compound of the disclosure as well as a pharmaceutically acceptable excipient. The pharmaceutical compositions can be used to treat or prevent SLE and lupus nephritis. Therefore, embodiments of the disclosure may also feature a method for treating or preventing SLE or lupus nephritis in a human patient having or predisposed to having lupus nephritis or SLE.

Embodiments of the disclosure include pharmaceutically acceptable salts of the compounds presented herein. The term "pharmaceutically acceptable salt" refers to those salts that are, within the scope of sound medical judgment, suitable for use in contact with the tissues of humans and animals without undue toxicity, irritation, or allergic response. Pharmaceutically acceptable salts are well known in the art. For example, S. M. Berge, et al., describes pharmaceutically acceptable salts in detail in J. Pharmaceutical Sciences 66:1-19, 1977. Salts can be prepared in situ during final isolation and purification of a compound or separately by reacting a free base group with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, monomaleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, trifluoroacetate, undecanoate, valerate salts, and the like. Representative alkali or alkaline earth metal salts include sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The term "pharmaceutically acceptable ester," as used herein, represents esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic, and alkanedioic acids, in which each alkyl or alkenyl group typically has not more than 6 carbon atoms. Examples of particular esters include formates, acetates, propionates, butyates, acrylates, and ethylsuccinates.

In this application enantiomers are designated by the symbols "R" or "S" or are drawn by conventional means with a bolded line defining a substituent above the plane of the page in three-dimensional space and a hashed or dashed line defining a substituent beneath the plane of the printed page in three-dimensional space. If no stereochemical designation is made, then the structure definition includes both stereochemical options.

BRIEF SUMMARY OF THE FIGURES

FIG. 2A through FIG. 2D shows results of testing compound ER-892887 in the BXSB-Yaa strain lupus disease model. Figure Legend: Twelve week old BXSB-Yaa mice were randomized into groups with equivalent median anti-dsDNA titers and treated once-a-day orally with Vehicle (Veh; 0.5% methyl-cellulose) alone or 300 mg/kg ER-892887 for 14 weeks total. (FIG. 2A) All mice were sacrificed at 26 weeks of age and final anti-dsDNA, anti-Sm/nRNP, and anti-RiboP titers were evaluated by ELISA as compared to titers observed in 6 wk old pre-diseased mice. (FIG. 2B) Approximately one week prior to sacrifice (25 weeks of age, 13 weeks of treatment), mice were housed 1-2 per cage in metabolic cages for 18 hours to collect urine, and the Urinary Albumin Creatinine Ratio (UACR, proteinuria) was determined for each animal as an indirect measure of kidney function. (FIG. 2C) At the time of sacrifice, kidneys were collected from individual mice, fixed in 10% formalin for 24 hours, embedded in paraffin, and H&E stained sections were generated for histopathology assessment in a blinded fashion. (FIG. 2D) Summary of mortality observed in the SLE-8 study. Statistical significance was determined by Mann-Whitney test for (A).

FIG. 3A through FIG. 3E show results of testing compound ER-892887 in the NZBΔNZW strain lupus disease model. Figure Legend: Female NZBWF1/J mice were received at 6 weeks of age, baseline bleeds were performed, and mice were monitored for disease progression by following anti-dsDNA titers. At 20 weeks of age, mice were randomized into groups with equivalent median anti-dsDNA titers and treated at 23 weeks of age with Vehicle (Veh; 0.5% methyl-cellulose) alone or 33, 100, or 300 mg/kg ER-892887 once-a-day orally (QD PO). All mice were sacrificed at 45 weeks of age (22 weeks total treatment) and blood plasma anti-dsDNA titers were determined by ELISA. (FIG. 3A) Impact of ER-892887 treatment over time on anti-dsDNA titers. (FIG. 3B) Bar graph of +22 weeks treatment data for ER-892887 derived from data shown in (A). (FIG. 3C) Just prior to termination at 45 weeks of age (following 22 weeks of treatment), urine was collected from individual mice, and the Urinary Albumin Creatinine Ratio (UACR, proteinuria) was determined for each animal as an indirect measure of kidney function. (FIG. 3D) Summary of mortality observed in this study. (FIG. 3E) At the time of sacrifice, kidneys were collected from individual mice, fixed in 10% formalin for 24 hours, embedded in paraffin, and H&E stained sections were generated for histopathology assessment in a blinded fashion. Statistical significance was determined by Mann-Whitney test for (C).

FIG. 4A through FIG. 4F show results of additional testing of compound ER-892887 in the NZBΔNZW strain lupus disease model. Figure Legend. Female NZBWF1/J mice were received at 8 weeks of age, baseline bleeds were performed, and mice were monitored for disease progression by following anti-dsDNA titers. At 24 weeks of age, mice were randomized into groups with equivalent median anti-dsDNA titers and treated at 25 weeks of age QD PO with Vehicle (Veh; 0.5% methyl-cellulose) alone or 33, 100, or 300 mg/kg ER-892887. Anti-dsDNA titers were determined by ELISA on blood plasma samples at the time points indicated. (FIG. 4A) Impact of compound treatment on median anti-dsDNA titers over time up to +17 weeks of treatment. (FIG. 4B) Impact of compound treatment on median anti-dsDNA at the +13 weeks of treatment time point only from data shown in (A). (FIG. 4C) After 13 weeks (top graph) or 17 weeks (bottom graph) of compound treatment, urine was collected from individual mice, and the Urinary Albumin Creatinine Ratio (UACR, proteinuria) was determined for each animal as an indirect measure of kidney function. Mice indicated within the circle with high UACR were those animals that died between the +13 wks and +17 wks of treatment (statistical significance was determined by Mann-Whitney test). (FIG. 4D) Blood urea nitrogen (BUN) measured in the plasma from select groups after 13 weeks of treatment. (FIG. 4E) Mortality curves for Vehicle versus compound treated mice up to 17 weeks of treatment. Mortality curve analysis out to +17 wks treatment indicated that 33 mg/kg and 100 mg/kg ER-892887 treatment afforded statistically significant survival benefit vs. Vehicle as determined by Log-rank (Mantel-Cox) test. (FIG. 4F) Summary of mortality observed in this study.

FIG. 5A through FIG. 5D show results of testing compound ER-892887 in the Pristane: DBA/1 strain lupus disease model. Figure Legend: Female DBA/1 mice at 10-11 weeks of age were given an intraperitoneal injection of 0.5 ml pristane or PBS. Once-a-day oral dosing with Vehicle (Veh; 0.5% methyl-cellulose) or 300 mg/kg ER-892887 was begun 3.5 months after pristane injection for a total of 3 months treatment. (FIG. 5A) Mice were euthanized after 3 months of compound treatment, and anti-dsDNA and anti-RiboP titers were measured in blood plasma samples by ELISA (statistical significance determined by Mann-Whitney test). (FIG. 5B) Arthritis development was assessed monthly by visual scoring. (FIG. 5C) The expression of IFN-regulated genes in whole blood was measured by a qPCR panel after 3 months of treatment, and an IFN gene signature score was calculated (see Pharmacology Materials and Methods section for details regarding IFN score calculation). (FIG. 5D) Full list of 21 genes significantly upregulated by pristane treatment vs. PBS controls and individual genes which were significantly reduced by ER-892887 (Student's t-test).

FIG. 6A through FIG. 6G show results of additional testing of compound ER-892887 in the Pristane: DBA/1 strain lupus disease model. Figure Legend: Female DBA/1 mice at 11-12 weeks of age were given an intraperitoneal injection of 0.5 ml of pristane or PBS. Once-a-day oral dosing with Vehicle (Veh; 0.5% methyl-cellulose) or 33, 100, or 300 mg/kg ER-892887 was begun 2 months after pristane injection for a total of 3 months treatment. Mice were euthanized after 3 months of compound treatment, and anti-dsDNA (FIG. 6A), -RiboP (FIG. 6B), -Sm/nRNP (FIG. 6C), and -Histone (FIG. 6D) titers were measured in blood plasma samples by ELISA (statistical significance determined by Mann-Whitney test). (FIG. 6E) Summary of mortality observed in the study during 3 months of compound treatment. (FIG. 6F) The expression of IFN-regulated genes in whole blood was measured by a qPCR panel at the last time point for Vehicle and 300 mg/kg ER-892887 treated mice, and an IFN gene signature score was calculated (see Pharmacology Materials and Methods section for details regarding IFN score calculation). (FIG. 6G) Full list of 22 genes significantly upregulated by pristane treatment vs. PBS controls and individual genes which were significantly reduced by ER-892887 (Student's t-test).

(FIG. 7C) Approximately one week prior to sacrifice, mice were housed 1-2 per cage in metabolic cages for 18 hours to collect urine, and the Urinary Albumin Creatinine Ratio (UACR, proteinuria) was determined for each animal as an indirect measure of kidney function. (FIG. 7D) At the time of sacrifice, kidneys were collected from individual mice, fixed in 10% formalin for 24 hours, embedded in paraffin, and H&E stained sections were generated for histopathology assessment in a blinded fashion. Statistical significance was determined by Mann-Whitney test for (A), (B), and (C) above.

FIG. 8A through FIG. 8D show results of additional testing of compound ER-885454 in the BXSB-Yaa strain lupus disease model. Figure Legend: Seventeen week old BXSB-Yaa mice were randomized into two groups with equivalent median anti-dsDNA titers and treated once-a-day orally with Vehicle (Veh; 0.5% methyl-cellulose) alone or 300 mg/kg ER-885454 for 13 weeks total. All mice were sacrificed at 30 weeks of age and final anti-dsDNA (FIG. 8A) and anti-Sm/RNP (FIG. 8B) titers were evaluated by ELISA as compared to titers observed in 7 wk old pre-diseased mice. (FIG. 8C) Approximately one week prior to sacrifice, mice were housed 1-2 per cage in metabolic cages for 18 hours to collect urine, and the Urinary Albumin Creatinine Ratio (UACR, proteinuria) was determined for each animal as an indirect measure of kidney function. (FIG. 8D) At the time of sacrifice, kidneys were collected from individual mice, fixed in 10% formalin for 24 hours, embedded in paraffin, and H&E stained sections were generated for histopathology assessment in a blinded fashion. Statistical significance was determined by Mann-Whitney test for (A), (B), and (C) above.

(FIG. 9B) Just prior to termination at 47 weeks of age, urine was collected from individual mice, and Urinary Albumin Creatinine Ratio (UACR, proteinuria) was determined for each animal as an indirect measure of kidney function. (FIG. 9C) At the time of sacrifice, kidneys were collected from individual mice, fixed in 10% formalin for 24 hours, embedded in paraffin, and H&E stained sections were generated for histopathology assessment in a blinded fashion. Statistical significance was determined by Mann-Whitney test for (A) above.

FIG. 11A through FIG. 11NN show structures and corresponding chemical names according to various embodiments presented herein. "ER-Number" is a reference number assigned to each compound. Where available, activity against a HEK cell line stably expressing human TLR7, activity against a HEK cell line stably expressing human TLR9, 1H NMR data, and mass spectrometry data are also included.

(FIG. 12A) Impact of ER-892887 treatment on anti-dsDNA titers at termination. (FIG. 12B) At 41 weeks of age (following 15 weeks of treatment), urine was collected from individual mice, and the Urinary Albumin Creatinine Ratio (UACR, proteinuria) was determined for each animal as an indirect measure of kidney function. (FIG. 12C) Urine was later collected from individual mice just prior to termination at 45 weeks of age, following 19 weeks of treatment, and the Urinary Albumin Creatinine Ratio (UACR, proteinuria) was determined for each animal. (FIG. 12D, FIG. 12E, FIG. 12F) Survival curves observed in this study during treatment with E6887, each standard treatment comparator (FIG. 12D, hydroxychloroquine; FIG. 12E, 0.1 mg/kg prednisolone; FIG. 12F, 0.5 mg/kg prednisolone), or the combination of E6887 and one of the comparators. Treated groups tested versus vehicle by Mantel-Cox.

FIG. 13A through FIG. 13E show results of testing compound ER-892887 and three commonly used human lupus treatments in the Pristane: DBA/1 strain lupus disease model. Figure Legend: Female DBA/1 mice at 11 weeks of age were given an intraperitoneal injection of 0.5 ml pristane or PBS. Once-a-day oral dosing with Vehicle (Veh; 0.5% methyl-cellulose) or 300 mg/kg ER-892887, 100 mg/kg hydroxychloroquine, 1 mg/kg prednisolone or 100 mg/kg mycophenolate was begun 2 months after pristane injection and continued for 3 months of treatment. (FIG. 13A) At the end of the 3 month treatment arthritis development was assessed by visual scoring of swelling and inflammation. (FIG. 13B) Mice were euthanized after 3 months of compound treatment, and anti-dsDNA, anti-histone, anti-Sm/RNP and anti-RiboP titers were measured in blood plasma samples by ELISA (statistical significance determined by Mann-Whitney test). ELISA values falling above or below the range of the standard curve were assigned a value equal to the highest or lowest valid measurement, as appropriate. (FIG. 13C, FIG. 13D, and FIG. 13E, with FIG. 13D being a continuation of FIG. 13C) The expression of IFN-regulated genes in whole blood was measured by a qPCR panel after 3 months of treatment. The full list of interferon-regulated genes significantly upregulated by pristane treatment vs. PBS controls is shown, and individual genes that were significantly reduced by ER-892887 (Student's t-test) are marked in bold with an asterisk.

(FIG. 14A) Top—Arthritis scores were calculated monthly in vehicle and compound dosed-groups. (FIG. 14A) Bottom—X-ray scores were calculated after three months of treatment. (FIG. 14B and FIG. 14C) Autoantibody titers were measured in terminal blood plasma samples by ELISA (statistical significance determined by Mann-Whitney test).

DETAILED DESCRIPTION OF THE DISCLOSURE

Figure 1:
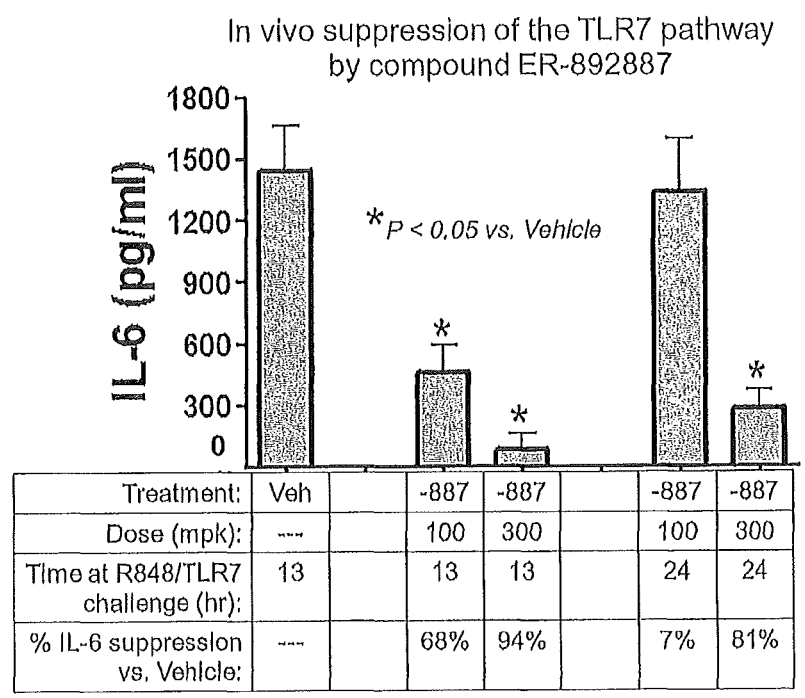
FIG. 1 shows short-term in vivo potency against the TLR7 pathway in mouse for compound ER-892887 (which has the chemical name (4-((5S,7R)-5-(3,4-dimethoxyphenyl)-7-(trifluoromethyl)-4,5,6,7-tetrahydropyrazolo[1,5-a]pyrimidin-2-yl)phenyl)(piperazin-1-yl)methanone). Figure Legend: Female BALB/c mice were dosed by oral gavage with Vehicle alone (0.5% aqueous methyl-cellulose) or compound ER-892887 formulated in Vehicle at 100 mg/kg or 300 mg/kg. At 13 or 24 hours following oral dosing, mice were injected subcutaneously with 15 ug R848 to stimulate TLR7. Blood plasma was collected by cardiac puncture, and the IL-6 level at 1.5 hours after TLR7 stimulation was then assessed by standard ELISA procedure. Percent suppression indicated is relative to IL-6 induction following Vehicle control dosing. Statistical significance was determined by Mann-Whitney test.
Figures 2B, 2C, 2D:
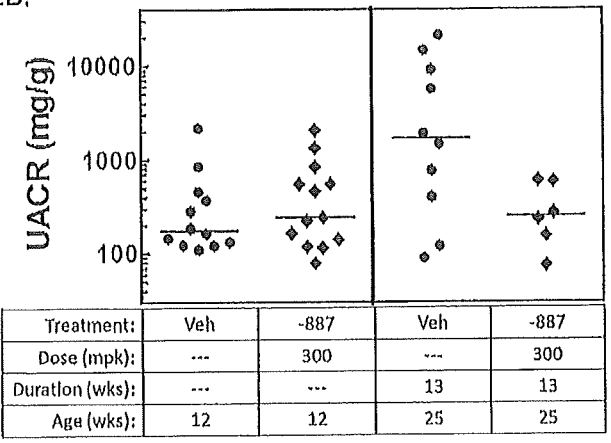
Figure 3A:
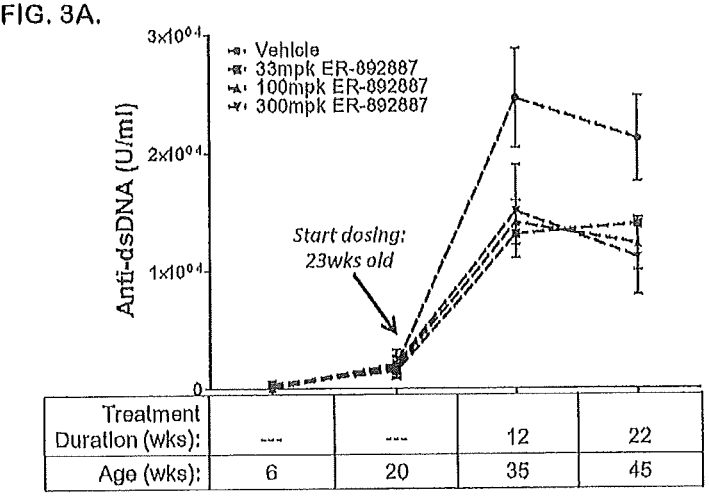
Figure 3B:
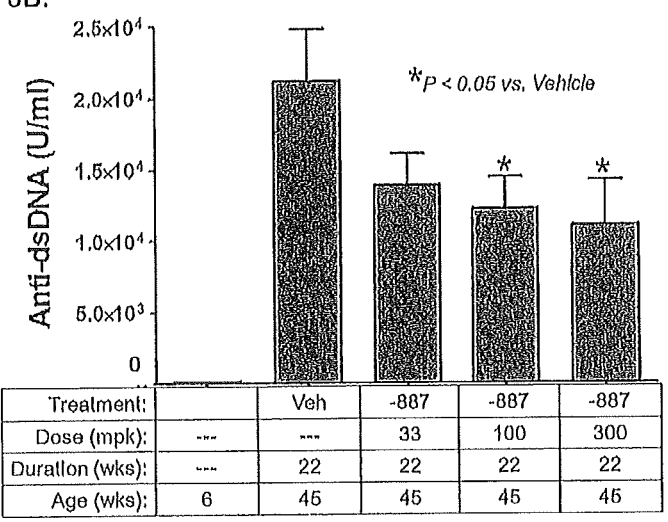
Figure 4A:
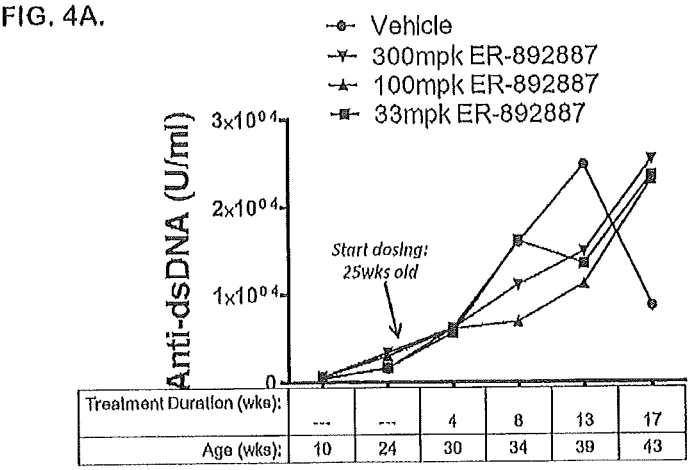
Figure 4B:
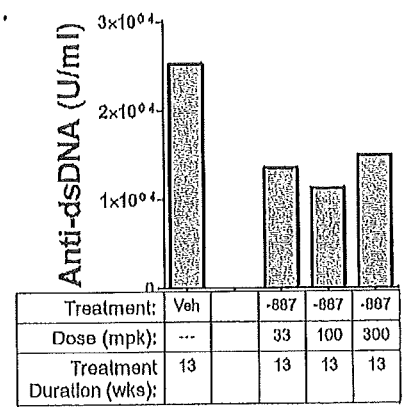
Figure 4D:
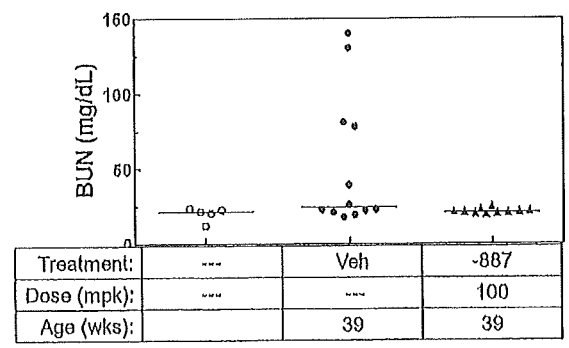
Figure 4E:
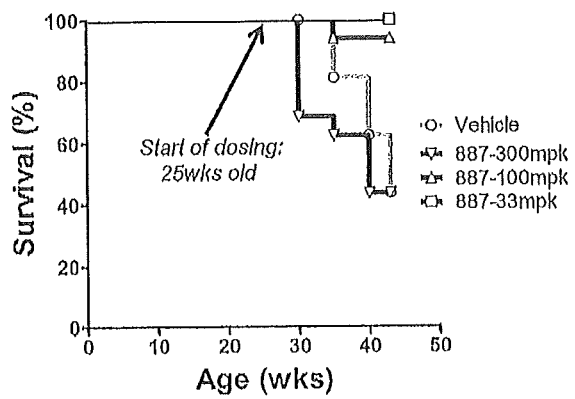
Figure 5B:
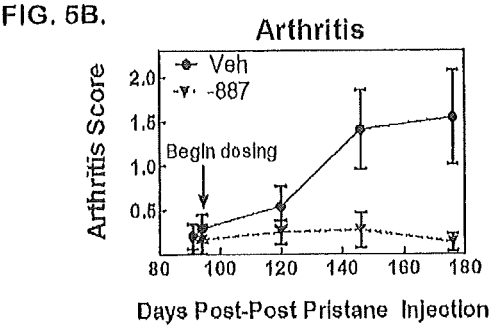
Figure 5C:
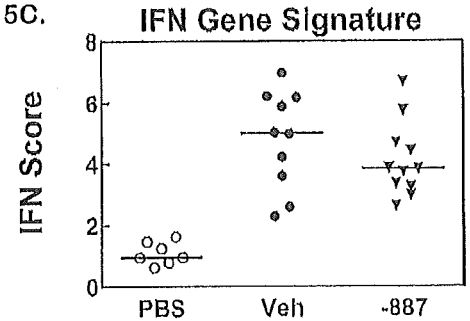
Figure 6A:
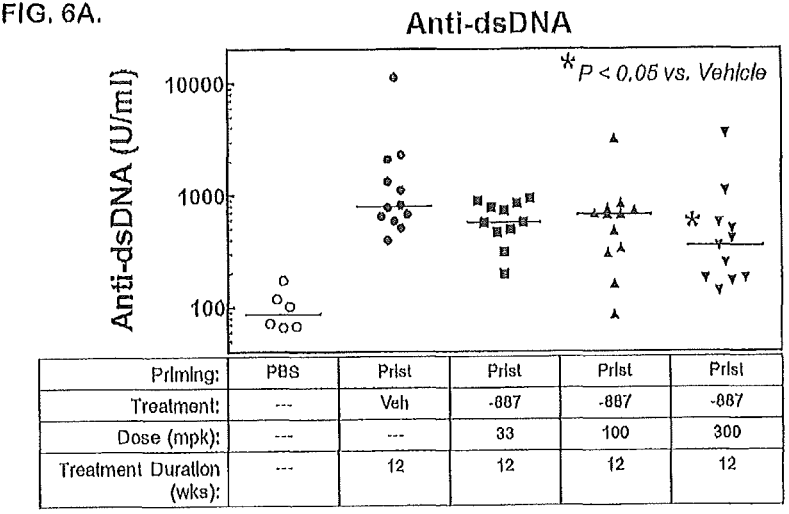
Figure 6B:
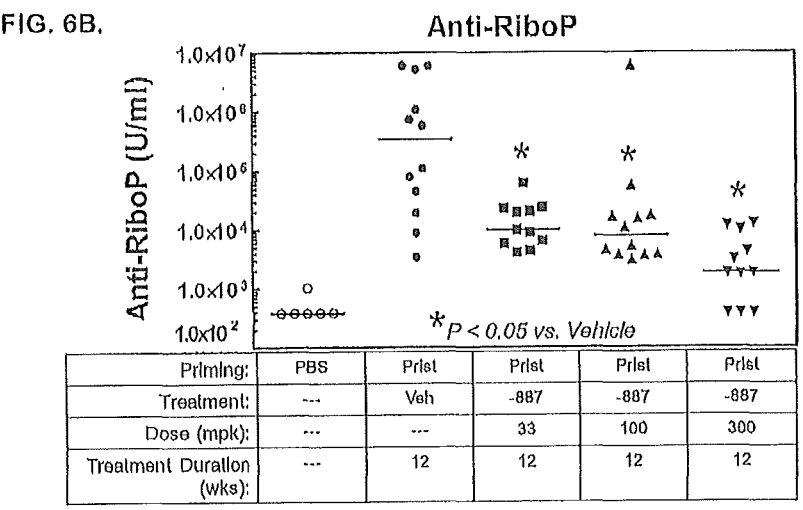
Figure 6C:
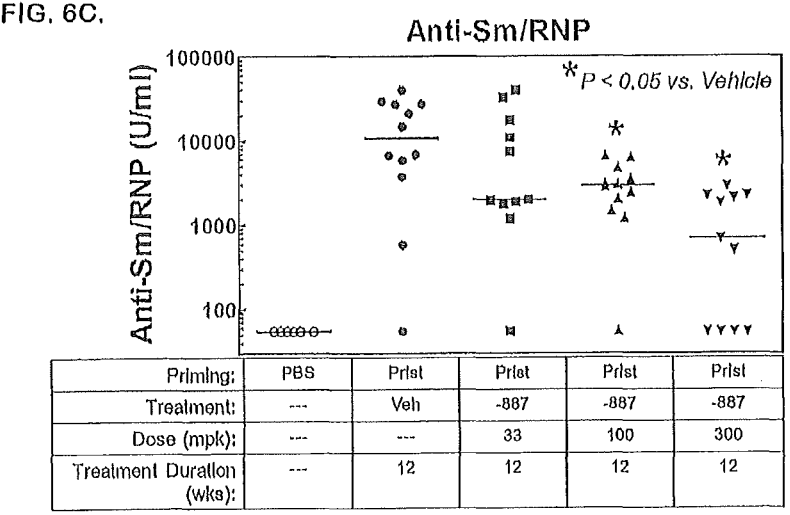
Figures 6D, 6E:
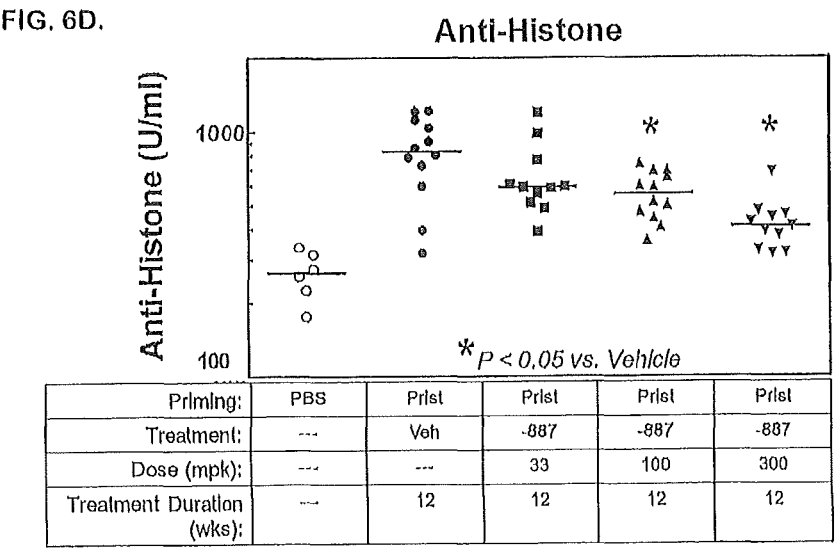
Figure 6F:
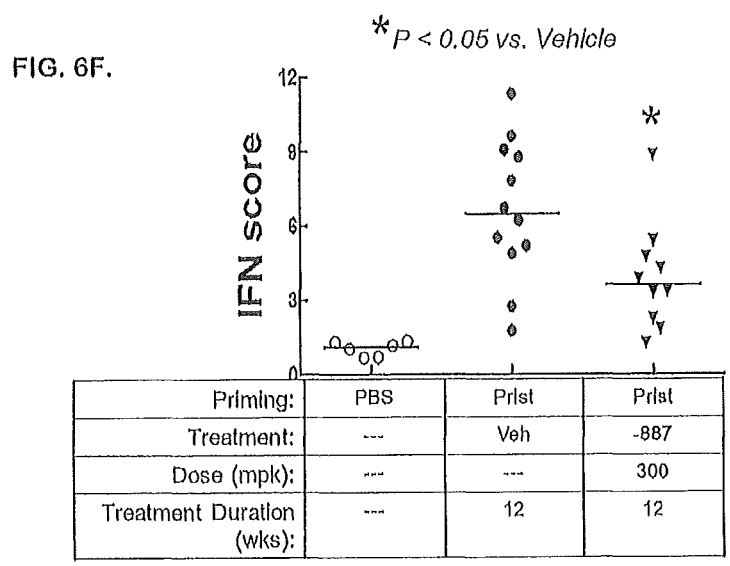
Figure 7A:
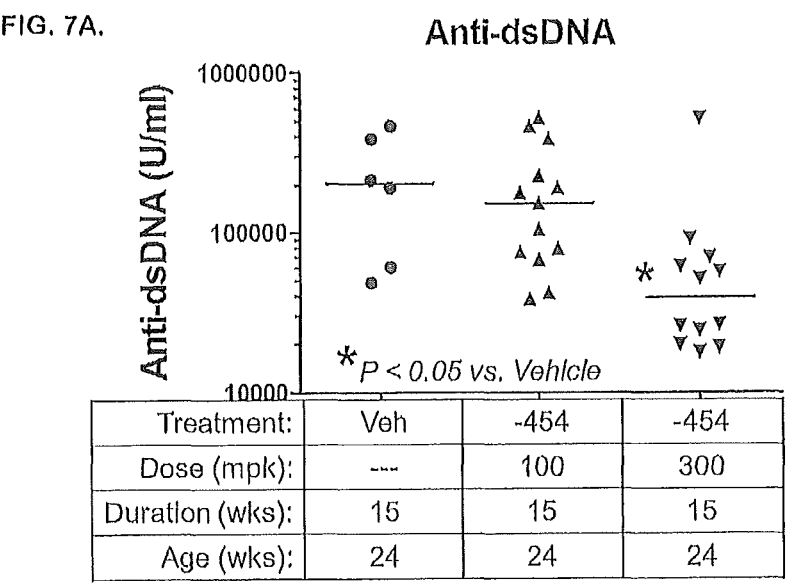
FIG. 7A through FIG. 7D show results of testing compound ER-885454 in the BXSB-Yaa strain lupus disease model. Figure Legend: Nine week old male BXSB-Yaa mice were treated once-a-day orally with Vehicle (Veh; 0.5% methyl-cellulose) alone or 100 mg/kg or 300 mg/kg ER-885454 for 15 weeks total. All mice were sacrificed at 24 weeks of age and final anti-dsDNA (FIG. 7A) and anti-Sm/RNP (FIG. 7B) titers were evaluated by ELISA.
Figure 7B:
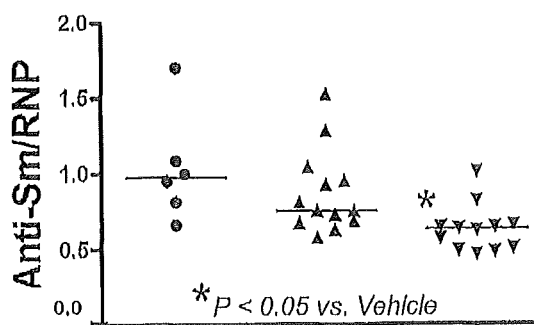
Figures 7C, 7D:
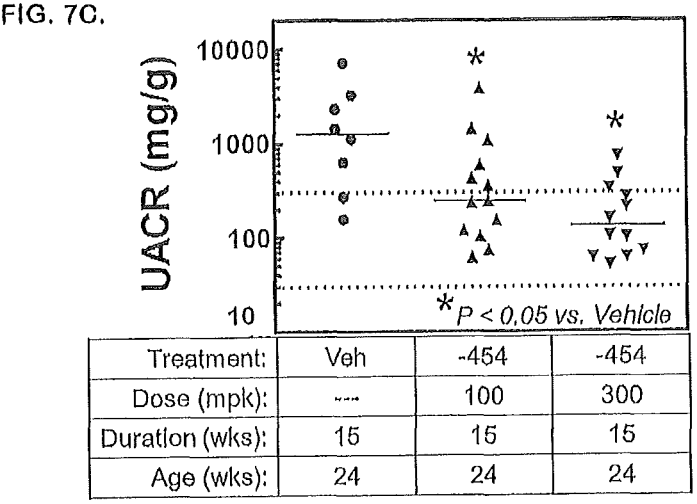
Figure 8A:
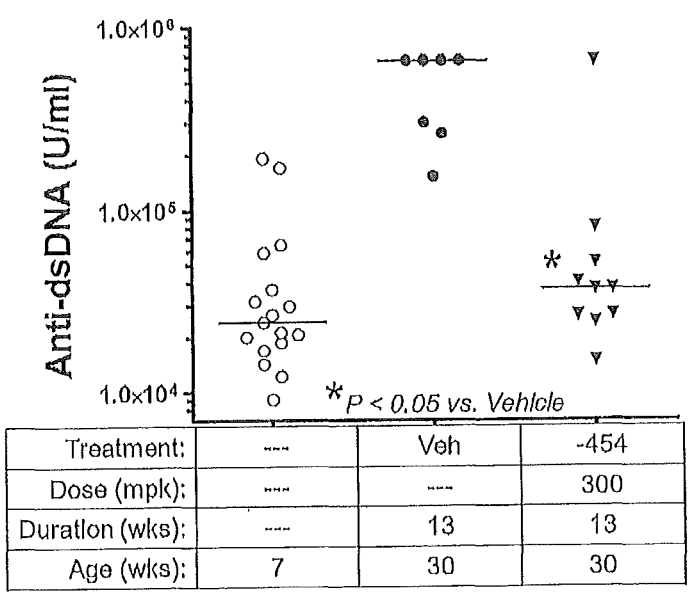
Figure 8B:
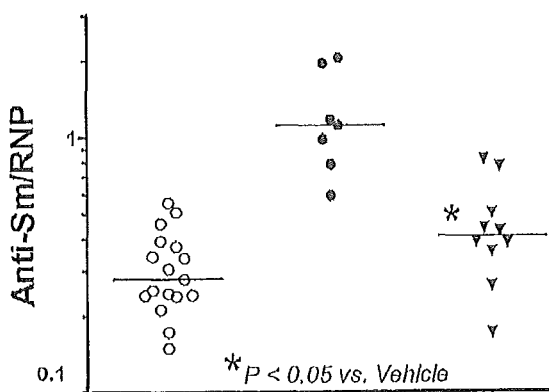
Figure 8C:
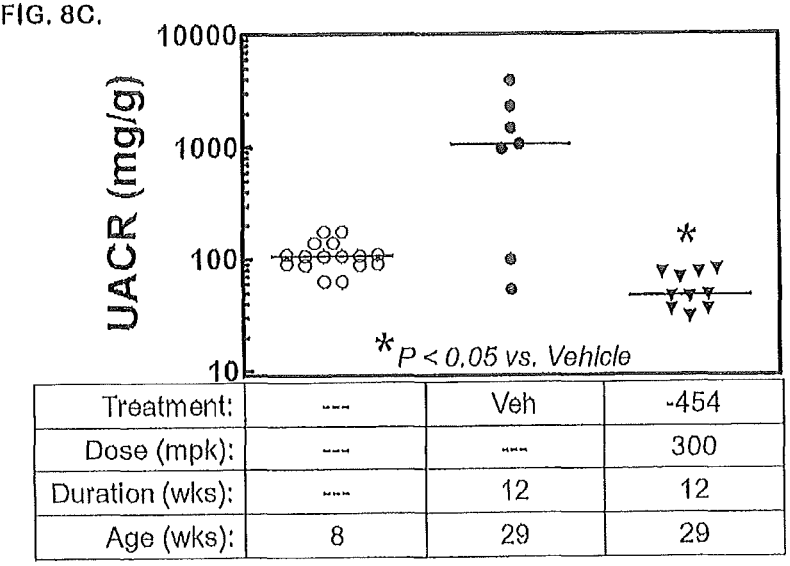
Figure 9A:
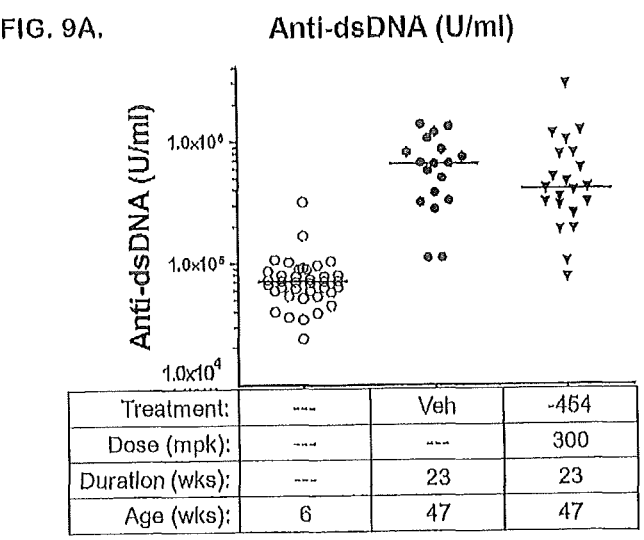
FIG. 9A through FIG. 9C show results of testing compound ER-885454 in the NZBΔNZW strain lupus disease model. Figure Legend: Female NZBWF1/J mice were received at 6 weeks of age, baseline bleeds were performed, and mice were monitored for disease progression by following anti-dsDNA titers. At 24 weeks of age, mice were randomized into groups with equivalent median anti-dsDNA titers and treated with Vehicle (Veh; 0.5% methyl-cellulose) alone or 300 mg/kg ER-885454 once-a-day orally (QD PO). All mice were sacrificed at 47 weeks of age (23 weeks total treatment) and blood plasma anti-dsDNA titers were determined by ELISA (FIG. 9A).
Figures 9B, 9C:
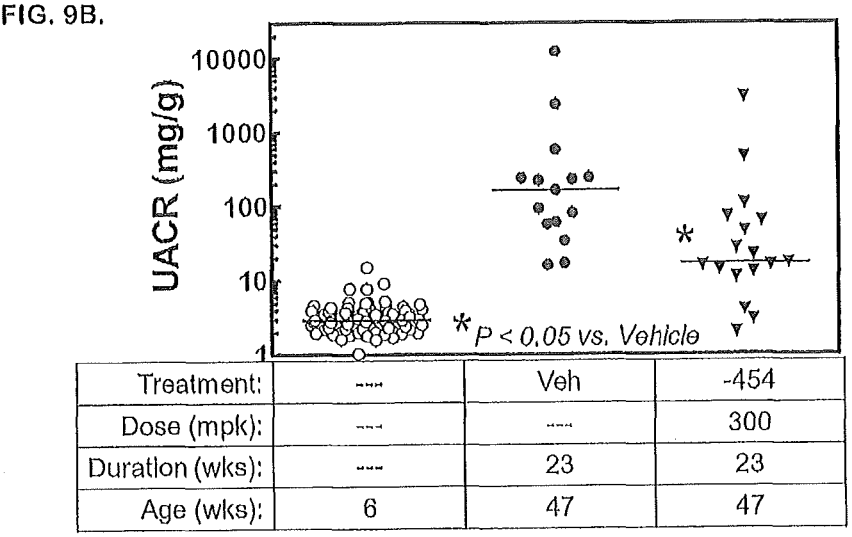

In addition to their role as innate immune receptors capable of detecting exogenous ("non-self") pathogen-associated molecular patterns (PAMPs—i.e., bacterial LPS detection by TLR4), mammalian Toll-like receptors (TLRs) are also capable of recognizing endogenous stimuli (DAMPs) released following host tissue damage or stress. Kono, H. and K. L. Rock, *How dying cells alert the immune system to danger*. Nat Rev Immunol, 2008. 8(4): p. 279-89. In the last decade an appreciation for the link between TLR activation by endogenous ("self") danger-associated molecular patterns (DAMPs) and the etiology of autoimmune disorders has emerged. Specifically, TLR7 can be activated by single-stranded RNA (ssRNA) derived from both mammalian and viral sources, whereas TLR9 can be activated by DNA derived from mammalian, viral, and bacterial sources.

Lupus is characterized by auto-antibodies reactive against double-stranded DNA (dsDNA) itself and associated proteins (histones) as well as against a broad array of RNA-associated proteins such as Ro, La, Smith (Sm), and U1 snRNP. Kirou, K. A., et al., *Activation of the interferon-alpha pathway identifies a subgroup of systemic lupus erythematosus patients with distinct serologic features and active disease*. Arthritis Rheum, 2005. 52(5): p. 1491-503. A second common hallmark of lupus, which was shown to correlate directly with disease severity, is dysregulated expression of type-1 interferons (IFNs), in particular IFNα, and the corresponding elevation of a large panel of IFNα-regulated genes in lupus patients' PBMC (the so called "type-1 IFN gene signature"). Kirou, K. A., et al., supra. A major source of IFN in the blood is a specialized immunocyte called a plasmacytoid dendritic cell (pDC), which constitutively expresses both TLR7 and TLR9.

A causal relationship between these two disease characteristics, auto-antibodies and IFN levels, was postulated when a number of research groups collectively demonstrated that antibody complexes isolated from lupus patients but not from healthy donors are capable of driving IFN production by pDC in a TLR7/9- and RNA/DNA-dependent manner Means, T. K., et al., *Human lupus autoantibody-DNA complexes activate DCs through cooperation of CD32 and TLR9*. J Clin Invest, 2005. 115(2): p. 407-17; Vollmer, J., et al., *Immune stimulation mediated by autoantigen binding sites within small nuclear RNAs involves Toll-like receptors 7 and 8*. J Exp Med, 2005. 202(11): p. 1575-85; Savarese, E., et al., *U1 small nuclear ribonucleoprotein immune complexes induce type I interferon in plasmacytoid dendritic cells through TLR7*. Blood, 2006. 107(8): p. 3229-34. Moreover, IFN stimulates increased TLR7/9 expression on B-cells, thereby enhancing TLR/BCR (B-cell receptor) activation of auto-reactive B-cells to differentiate to antibody-producing plasma cells. Banchereau, J. and V. Pascual, *Type I interferon in systemic lupus erythematosus and other autoimmune diseases*. Immunity, 2006. 25(3): p. 383-92; In this fashion, levels of auto-antibody complexes containing nucleic acid TLR7/9 ligands drive the pro-inflammatory cycle and lupus disease progression. Type-1 IFN alone has been reported to induce lupus-like symptoms in humans. Ho, V., et al., *Severe systemic lupus erythematosus induced by antiviral treatment for hepatitis C*. J. Clin Rheumatol, 2008. 14(3):166-8. Ronnblom L. E., et al. *Possible induction of systemic lupus erythematosus by interferon-alpha treatment in a patient with a malignant carcinoid tumor*. J. Internal Med. 1990. 227:207-10. We believe it is likely that pharmacological antagonism of TLR7/8 will offer therapeutic benefit to lupus patients by disrupting this pro-inflammatory cycle, decreasing IFN levels, and dampening the autoimmune disease process mediated by pDC and B-cells.

Several other lines of evidence suggest a role for TLR7 in human lupus etiology and support the notion that TLR receptors are valid targets for disease intervention. Specific polymorphisms in the 3' UTR of TLR7 have been identified and shown to correlate with both elevated TLR7 expression and enhanced IFN gene signature. Shen, N., et al., *Sex-specific association of X-linked Toll-like receptor 7 (TLR7) with male systemic lupus erythematosus*. Proc Natl Acad Sci USA, 2010. 107(36): p. 15838-43. In addition, lupus standard-of-care (SOC) anti-malarial drugs such as chloroquine disrupt endosomal TLR7/9 signaling and inhibit PBMC and/or pDC IFNα production induced by ssRNA-ribonucleoprotein complexes or lupus patient serum. Moreover, myeloid DC and monocytes produce IL-12p40, TNFα, and IL-6 following self-RNA/TLR8 signaling, suggesting the additional contribution of TLR8-dependent pro-inflammatory cytokines to human lupus etiology in addition to TLR7-driven IFN by pDC. Vollmer, supra; Gorden, K. B., et al., *Synthetic TLR agonists reveal functional differences between human TLR7 and TLR8*. J Immunol, 2005. 174(3): p. 1259-68.

Mouse model evidence also exists for the role of TLR in lupus. Published studies have collectively demonstrated that both single TLR7 or dual TLR7/9 gene deletion or dual TLR7/9 pharmacologic inhibition reduces disease severity in four distinct lupus models. Nickerson, K. M., et al., *TLR9 regulates TLR7-and MyD88-dependent autoantibody production and disease in a murine model of lupus*. J Immunol, 2010. 184(4): p. 1840-8; Fairhurst, A. M., et al., *Yaa autoimmune phenotypes are conferred by overexpression of TLR7*. Eur J Immunol, 2008. 38(7): p. 1971-8; Deane, J. A., et al., *Control of toll-like receptor 7 expression is essential to restrict autoimmunity and dendritic cell proliferation*. Immunity, 2007. 27(5): p. 801-10; Savarese, E., et al., *Requirement of Toll-like receptor 7 for pristane-induced production of autoantibodies and development of murine lupus nephritis*. Arthritis Rheum, 2008. 58(4): p. 1107-15. Highlighting the role of TLR7 as a critical determinant of autoimmunity, transgenic overexpression of TLR7 alone leads to spontaneous anti-RNA auto-reactivity and nephritis in the normally disease-resistant C57BL/6 strain. Deane, supra.

From a safety perspective, there are no reports that TLR7, 8, or 9-single or 7/8- and 7/9-dual gene deficient mice are immune-compromised to the extent that infection by opportunistic pathogens is observed. Likewise, SOC anti-malarials are thought to be largely safe and effective for long-term use in humans to control lupus disease flare at doses predicted to at least partially inhibit TLR7/9 signaling. Lafyatis, R., M. York, and A. Marshak-Rothstein, *Antimalarial agents: closing the gate on Toll-like receptors?* Arthritis Rheum, 2006. 54(10): p. 3068-70; Costedoat-Chalumeau, N., et al., *Low blood concentration of hydroxychloroquine is a marker for and predictor of disease exacerbations in patients with systemic lupus erythematosus*. Arthritis Rheum, 2006. 54(10): p. 3284-90. In fact, save for increased susceptibility to Gram-positive bacterial infections in childhood and to a lesser extent in adulthood, humans with highly compromised TLR and IL-1R signaling pathways (MyD88- or IRAK-4-deficiency) are nonetheless healthy and maintain sufficient host defense mechanisms. Casanova, J. L., L. Abel, and L. Quintana-Murci, *Human TLRs and IL-1Rs in Host Defense: Natural Insights from Evolutionary, Epidemiological, and Clinical Genetics*. Annu Rev Immunol, 2010.

Based on this and other information, we believe that TLR7 in particular is a well-validated target in the context of mouse pre-clinical SLE models. Both genetic and functional human studies support the hypothesis that antagonism of the TLR7 and/or TLR8 pathways will afford therapeutic benefit to lupus patients. Moreover, both mouse TLR gene deletion studies and the long-term use of anti-malarials in humans suggest that pharmacological TLR7, 8 and/or 9 suppression can be undertaken without significantly compromising host defense.

A compound that suppresses TLR7, TLR8, or both TLR7 and TLR8 may therefore be expected to act as a therapeutic or prophylactic agent for SLE or lupus nephritis.

The present inventors have found compounds that suppress TLR 7 and/or 8 and are therefore expected to have a prophylactic or therapeutic effect on SLE or lupus nephritis. Compounds and methods of the disclosure are described herein.

II. Therapeutic Use

Dosage levels of active ingredients in the pharmaceutical compositions of the disclosure may be varied to obtain an amount of the active compound(s) that achieves the desired therapeutic response for a particular patient, composition, and mode of administration. The selected dosage level depends upon the activity of the particular compound, the route of administration, the severity of the condition being treated, and the condition and prior medical history of the patient being treated. Doses are determined for each particular case using standard methods in accordance with factors unique to the patient, including age, weight, general state of health, and other factors that can influence the efficacy of the compound(s) of the disclosure. In general, in the case of oral administration, the THPP compound according to the present disclosure or a pharmaceutically acceptable salt thereof is administered at a dose of approximately 30 µg to 100 µg, a dose of 30 µg to 500 µg, a dose of 30 µg to 10 g, a dose of 100 µg to 5 g, or a dose of 100 µg to 1 g per adult per day. In the case of administration via injection, it is administered at a dose of approximately 30 µg to 1 g, a dose of 100 µg to 500 mg, or a dose of 100 µg to 300 mg per adult per day. In both cases, a dose is administered once or divided over several administrations. Dosage may be simulated, for example, using the Simcyp® program.

It is not intended that the administration of a compound of the disclosure to a mammal, including humans, be limited to a particular mode of administration, dosage, or frequency of dosing. The present disclosure contemplates all modes of administration, including oral, intraperitoneal, intramuscular, intravenous, intraarticular, intralesional, subcutaneous, or any other route sufficient to provide a dose adequate to prevent or treat SLE or lupus nephritis. One or more compounds of the disclosure may be administered to a mammal in a single dose or multiple doses. When multiple doses are administered, the doses may be separated from one another by, for example, several hours, one day, one week, one month, or one year. It is to be understood that, for any particular subject, specific dosage regimes should be adjusted over time according to the individual need and the professional judgment of the person administering or supervising the administration of a pharmaceutical composition that includes a compound of the disclosure.

For clinical applications, a compound of the present disclosure may generally be administered intravenously, subcutaneously, intramuscularly, colonically, nasally, intraperitoneally, rectally, buccally, or orally. Compositions containing at least one compound of the disclosure that is suitable for use in human or veterinary medicine may be presented in forms permitting administration by a suitable route. These compositions may be prepared according to the customary methods, using one or more pharmaceutically acceptable adjuvants or excipients. The adjuvants comprise, inter alia, diluents, sterile aqueous media, and various nontoxic organic solvents. Acceptable carriers or diluents for therapeutic use are well known in the pharmaceutical field, and are described, for example, in Remington: The Science and Practice of Pharmacy (20th ed.), ed. A. R. Gennaro, Lippincott Williams & Wilkins, 2000, Philadelphia, and Encyclopedia of Pharmaceutical Technology, eds. J. Swarbrick and J. C. Boylan, 1988, 1999, Marcel Dekker, New York. The compositions may be presented in the form of tablets, pills, granules, powders, aqueous solutions or suspensions, injectable solutions, elixirs, or syrups, and the compositions may optionally contain one or more agents chosen from the group comprising sweeteners, flavorings, colorings, and stabilizers to obtain pharmaceutically acceptable preparations.

The choice of vehicle and the content of active substance in the vehicle are generally determined in accordance with the solubility and chemical properties of the product, the particular mode of administration, and the provisions to be observed in pharmaceutical practice. For example, excipients such as lactose, sodium citrate, calcium carbonate, and dicalcium phosphate and disintegrating agents such as starch, alginic acids, and certain complex silicates combined with lubricants (e.g., magnesium stearate, sodium lauryl sulfate, and talc) may be used for preparing tablets. To prepare a capsule, it is advantageous to use lactose and high molecular weight polyethylene glycols. When aqueous suspensions are used, they may contain emulsifying agents that facilitate suspension. Diluents such as sucrose, ethanol, polyethylene glycol, propylene glycol, glycerol, chloroform, or mixtures thereof may also be used.

For parenteral administration, emulsions, suspensions, or solutions of the compositions of the disclosure in vegetable oil (e.g., sesame oil, groundnut oil, or olive oil), aqueous-organic solutions (e.g., water and propylene glycol), injectable organic esters (e.g., ethyl oleate), or sterile aqueous solutions of the pharmaceutically acceptable salts are used. The solutions of the salts of the compositions of the disclosure are especially useful for administration by intramuscular or subcutaneous injection. Aqueous solutions that include solutions of the salts in pure distilled water may be used for intravenous administration with the proviso that (i) their pH is adjusted suitably, (ii) they are appropriately buffered and rendered isotonic with a sufficient quantity of glucose or sodium chloride, and (iii) they are sterilized by heating, irradiation, or microfiltration. Suitable compositions containing a compound of the disclosure may be dissolved or suspended in a suitable carrier for use in a nebulizer or a suspension or solution aerosol, or may be absorbed or adsorbed onto a suitable solid carrier for use in a dry powder inhaler. Solid compositions for rectal administration include suppositories formulated in accordance with known methods and containing at least one compound of the disclosure.

Dosage formulations of a compound of the disclosure to be used for therapeutic administration should be sterile. Sterility is readily accomplished by filtration through sterile membranes (e.g., 0.2 micron membranes) or by other conventional methods. Formulations typically are stored in lyophilized form or as an aqueous solution. The pH of the compositions of this disclosure in some embodiments, for example, may be between 3 and 11, may be between 5 and 9, or may be between 7 and 8, inclusive.

While one route of administration is by oral dosage administration, other methods of administration may be used. For example, compositions may be administered subcutaneously, intravenously, intramuscularly, colonically, rectally, nasally, or intraperitoneally in a variety of dosage forms such as suppositories, implanted pellets or small cylinders, aerosols, oral dosage formulations, and topical formulations such as ointments, drops, and dermal patches.

Compounds of embodiments of the disclosure may be incorporated into shaped articles such as implants, including but not limited to valves, stents, tubing, and prostheses, which may employ inert materials such as synthetic polymers or silicones, (e.g., Silastic® compositions, silicone rubber, or other commercially available polymers). Such polymers can include polyvinylpyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, a compound of the disclosure may be coupled to a class of biodegradable polymers useful in achieving controlled release of a drug, for example polylactic acid, polyglycolic acid, copolymers of polylactic and polyglycolic acid, poly-epsilon caprolactone, polyhydroxy butyric acid, polyorthoesters, polyacetals, polydihydropyrans, polycyanoacrylates, and cross linked or amphipathic block copolymers of hydrogels.

A compound of the disclosure may also be administered in the form of liposome delivery systems, such as small unilamellar vesicles, large unilamellar vesicles, and multilamellar vesicles. Liposomes can be formed from a variety of lipids, such as cholesterol, stearylamine, or phosphatidylcholines. A compound of the disclosure may also be delivered using antibodies, antibody fragments, growth factors, hormones, or other targeting moieties to which the compound molecules are coupled (e.g., see Remington: The Science and Practice of Pharmacy, vide supra), including in vivo conjugation to blood components of a compound of an embodiment of the disclosure.

III. Synthesis

General and specific synthesis routes are provided that we found useful for preparation of embodiments of the disclosure. Those skilled in the art may recognize that certain variations or modifications of these procedures could also lead to synthesis of compounds according to the disclosure. In some situations the phrase "such as" is used to enumerate various alternatives for more generic compounds or structures. It will be understood that "such as" should not be construed to be limiting, and that its meaning is in accord with "including, for example, but not limited to."

Certain conditions were common to specific examples presented below. Microwave heating was done using a Biotage® Emrys Liberator or Initiator microwave reactor. Column chromatography was carried out using Biotage® SP4 flash chromatography system. Solvent removal was carried out using either a Biichii rotary evaporator or a Genevac® centrifugal evaporator. NMR spectra were recorded at 400 MHz on a Varian Unity® spectrometer using deuterated solvents. Chemical shifts are reported relative to residual protonated solvent.

Thin layer chromatography was performed on Whatman® glass plates precoated with a 0.25 mm layer of silica gel using various ratios of one or more of the following solvents: ethyl acetate, heptane, dichloromethane or methanol.

Analytical LC/MS was performed on a Waters Acquity™ system using an XBridge™ C18 1.7 µm 2.1×50 mm column. Solvents A and B are Water w/0.1% formic acid and Acetonitrile w/0.1% formic acid, respectively. 5 minute total method time with 5% B to 99% B over 4 minutes with a flow rate of 0.3 ml/min Mass spectral data were acquired on a Waters SQD from 100-2000 amu in electrospray positive mode. These conditions are referred to below as "Condition I."

Alternatively, purity and mass confirmation were carried out on a Waters Autopurification system using an XBridge™ C8 3.5 µm 4.6×50 mm column. Solvents A and B are water w/0.1% formic acid and acetonitrile w/0.1% formic acid, respectively. 6 minute total method time with 10% B to 95% B over 5 minutes with a flow rate of 2.5 ml/min Mass spectral data were acquired on a Micromass ZQ™ from 130-1000 amu in electrospray positive mode. These conditions are referred to below as "Condition II."

Preparative reverse phase LC/MS was carried out on a Waters Autopurification system using an XBridge™ C8 5 µm, 19×100 mm column. Solvents A and B are water w/0.1% formic acid and Acetonitrile w/0.1% formic acid, respectively. 12 minute total method time with 30% B to 95% B over 10 minutes with a flow rate of 20 ml/min Mass spectral data were acquired on a Micromass ZQ™ from 130-1000 amu in electrospray positive mode. These conditions are referred to below as "Condition III."

Preparative HPLC resolution of racemic compounds was carried out using one of the following chiral columns: Chiralpak® IA (5 cm×50 cm or 2 cm×25 cm), Chiralpak® AD (2 cm×25 cm) or Chiralcel® OD (2 cm×25 cm). Enantiomer ratios of purified compounds were determined by HPLC analysis on a 0.45 cm×25 cm column comprised of the same stationary phase (IA, AD or OD).

General methods and experimentals for preparing compounds of the present disclosure are set forth below. In certain cases, a particular compound is described by way of example. However, it will be appreciated that in each case a series of compounds of the present disclosure were prepared in accordance with the schemes and experimentals described below. For those compounds where NMR and/or mass spectrometry data are available, the data is presented immediately following the description of the synthesis of the compound or in Table 11.

The following abbreviations are used herein:
Definitions:
The following abbreviations have the indicated meanings:
HATU: N,N,N',N'-Tetramethyl-O-(7-azabenzotriazol-1-yl)uronium hexafluorophosphate
DIEA: N,N-diisopropylethylamine
DMAP: 4-Dimethylaminopyridine
TEA: triethylamine
DMF: N,N-dimethylformamide
NMP: N-methylpyrrolidine
THF: tetrahydrofuran
DCM: dichloromethane
MTBE: methyl tert-butyl ether
TFA: trifluoroacetic acid
EDC: 1-(3-dimethylaminopropyl)-3-ethylcarbodiimide hydrochloride
NaOH: sodium hydroxide
NaBH4: sodium borohydride
IPA: isopropyl alcohol or isopropanol
EtOH: ethanol
EtOAc: ethyl acetate
TLR: Toll-like receptor
DAMP: Danger-Associated Molecular Pattern
PAMP: Pathogen-Associated Molecular Pattern
IFN: interferon
pDC: plasmacytoid dendritic cell
PBMC: peripheral blood mononuclear cell
qPCR: quantitative polymerase chain reaction
TLDA: Taqman® Low Density Array
PBS: phosphate buffered saline
ssRNA: single-stranded RNA
dsDNA: double-stranded DNA
SOC: standard-of-care
R848: resiquimod
HCQ: hydroxychloroquine
HCl: hydrochloric acid
aq.: aqueous
AcOH: acetic acid
PhNTf$_2$: N-phenyltrifluoromethanesulfonimide
Tf: trifluoromethanesulfonate
MeOH: methanol
ee: enantiomeric excess
HEPES: 4-(2-hydroxyethyl)-1-piperazineethanesulfonic acid
NH$_4$Cl: ammonium chloride Example 1

General Synthetic Methods

Compounds of the disclosure were made according to the general synthetic scheme shown below:

Scheme 1.

$R^1$—CN $\xrightarrow{\text{OK, CH}_3\text{CN}}$ $R^1$—C(NH$_2$)=CH—CN $\xrightarrow{\text{H}_2\text{NNH}_2\cdot\text{H}_2\text{O}, \text{AcOH}}$ I  →  II  →  III (pyrazole with NH$_2$)

IV (ethyl ester with R$^2$) + V (ketone with R$^3$) $\xrightarrow{\text{NaOMe, MeOH}}$ VI (1,3-diketone R$^2$, R$^3$)

III + VI $\xrightarrow{\text{AcOH}}$ VII (pyrazolopyrimidine) $\xrightarrow{\text{reduction}}$ VIII (tetrahydro pyrazolopyrimidine)

VIII $\xrightarrow{\text{Chiral Resolution}}$ VIII

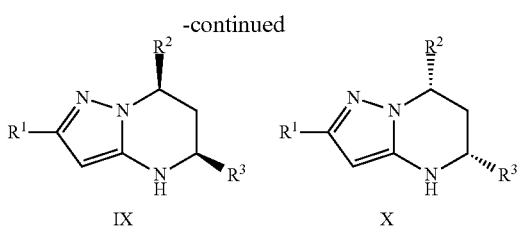

The preparation of several of the examples use the route depicted in Scheme 1. Typically, a commercially available nitrile, such as aromatic, heterocyclic, aliphatic or heteroaliphatic nitrile (I) is subjected to acetonitrile in presence of a strong protic organic base such as potassium t-amylate in a neutral solvent such as toluene at 0° C. or room temperature to provide the cyanoimine (II). The resulting imine is then reacted with hydrazine in the presence of an organic acid such as acetic acid to provide the key intermediate or 3-substituted-5-amino pyrrazole (III). The right half of the these examples is prepared by way of a Claisen condensation using an aromatic or heteroaromatic acylketone (V) with a substituted acetylester such as trifluoro, difluoro or nonsubstituted acetyl ester (IV) to form the diketone (VI).

Condensation of the two intermediates III and VI provides the 2,3-b-pyrazolopyrimidine in the presence of a mild organic acid such as acetic acid. In some cases the 5-substituted-3-amino pyrrazoles (III) are commercially available and are used in this reaction directly. Reduction to form the racemic 5,7-cis tetrahydropyrazolopyrimidine (VIII) is effected using a hydride source or by catalytic hydrogenation. Resolution via chiral, high performance liquid chromatography or using diastereomeric crystallization provides the final desired products IX and X. In many examples the racemic mixture of compound VIII were evaluated biologically without further purification via chiral resolution.

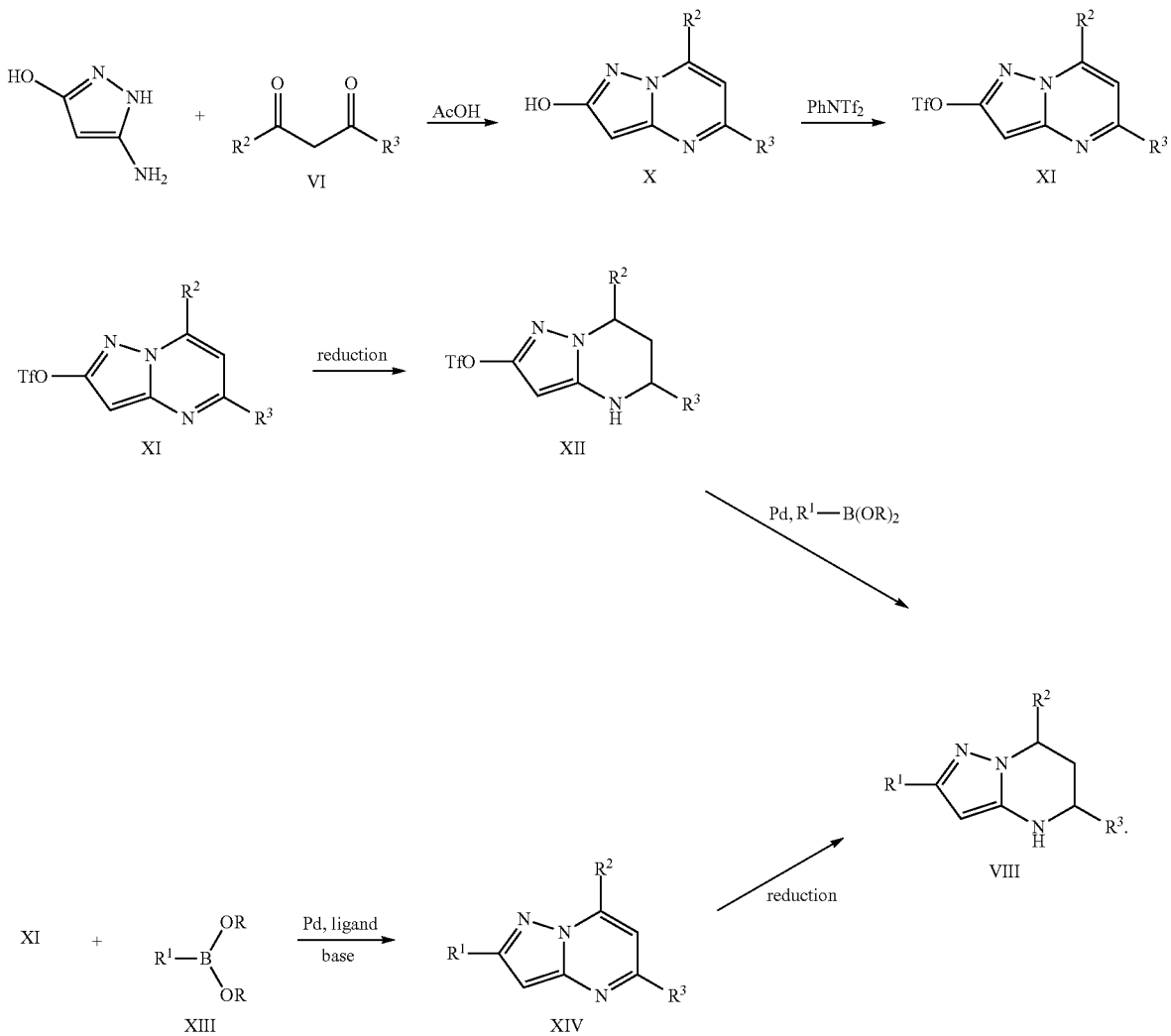

Scheme 2 exemplifies an alternative route to various compounds of the disclosure starting with commercially available 3-hydroxy-5-aminopyrazole condensed with diketone VI to provide 2-hydroxypyrazolopyrimidine X as a key intermediate. Treatment of X with a suitable trifluoromethylsulfonylation reagent provides triflate intermediate XI. Reduction of triflate XI, followed by Suzuki cross-coupling with a variety of boronates, where $R^1$ is an aromatic, heteroaromatic, allylic, heteroallylic or aliphatic gives the racemic final product VIII. Alternatively, triflate XI is subjected to Suzuki cross-coupling first, and the intermediate compound XIV is then reduced to the racemic final product VIII. As in Scheme 1, racemic compound VIII is resolved into its constituent enantiomers by way of chiral chromatography or by diastereomeric crystallization.

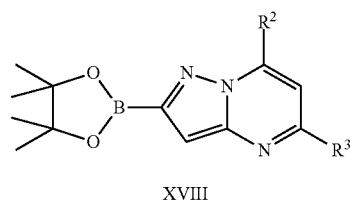

XVIII

Scheme 3.

The route used in Scheme 3 is a modification of Scheme 2 in which a bromide replaces the triflate, i.e. the triflate group in compound XI is replaced by bromide as shown in XVI. 3-bromo-5-aminopyrazole was synthesized according to literature methods (Moy, et al. *J. Med. Chem.* 2010, 53, 1238). The conditions for the Suzuki cross-coupling are essentially the same as those in Scheme 2.

Scheme 4.

The route in Scheme 4 reverses the Suzuki cross-coupling starting materials by the generation of the boronate ester on the key pyrazolopyrimidine followed condensation of a suitable electrophile (XIX, X=OTf, Cl, Br, I) to generate VIII after reduction.

Scheme 5

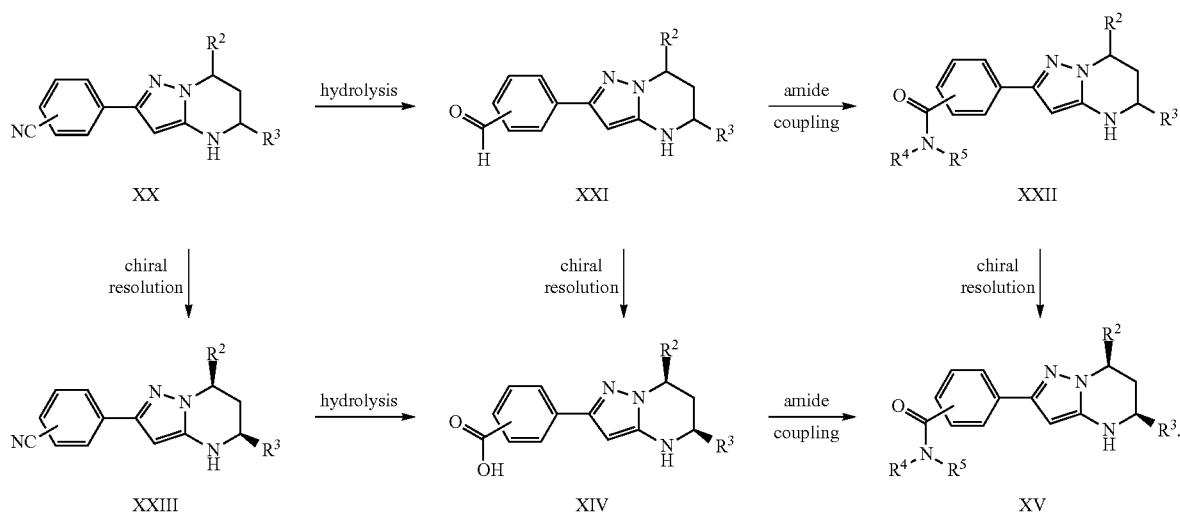

Scheme 5 depicts the final steps in the synthesis of several of the examples of general structure XV presented herein. Accordingly, the common intermediate used is benzonitrile XX, typically substituted at the 3- or 4-position with respect to the pyrazolopyrimidine moiety, which is converted to benzoic acid XXI via acidic or basic hydrolysis. Coupling of XXI with a suitable amine ($R^4R^5NH$) provides the racemic amide XXII, which is resolved into its pure enantiomer XV. Alternatively, the chiral resolution can be carried out either at the stage of the benzonitrile (XX→XXIII) or the benzoic acid (XXI→XXIV) and the enantiopure materials transformed in a similar manner to the final product XV.

Synthetic Examples—Section A

Example 1 (Synthesis of ER-892887)

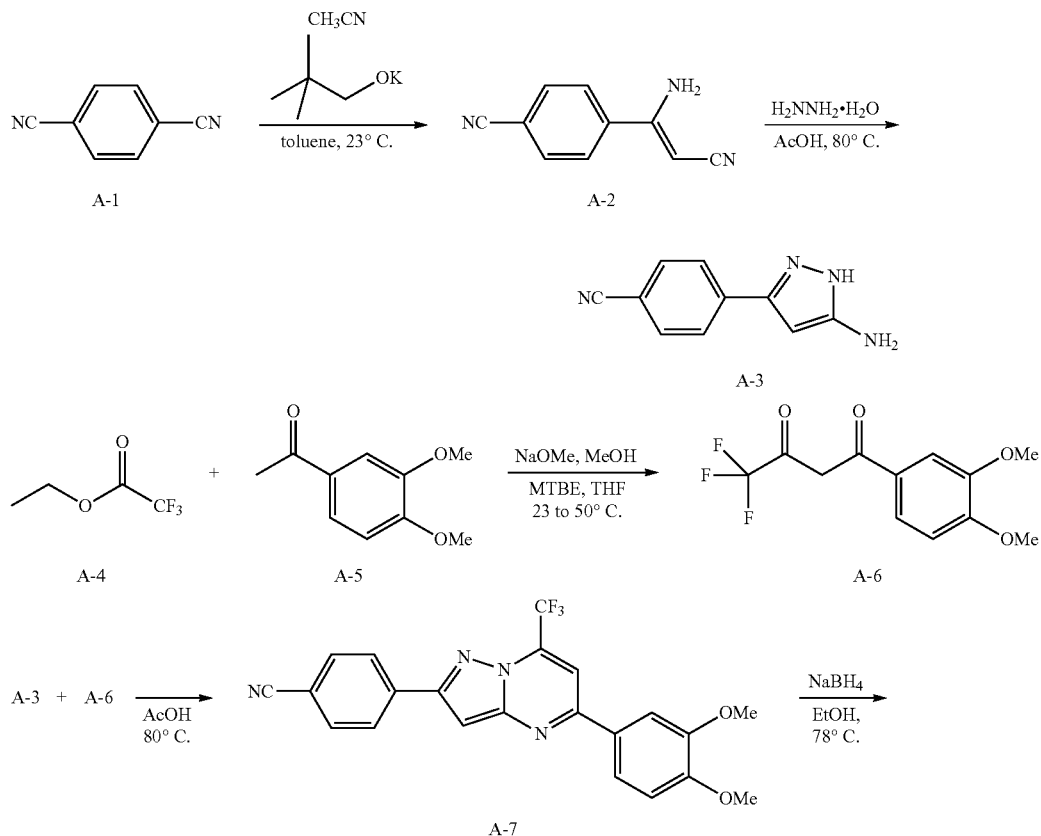

-continued
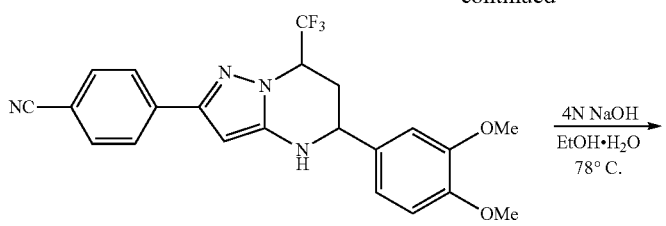
A-8
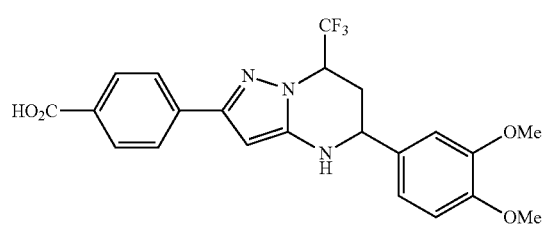
A-9
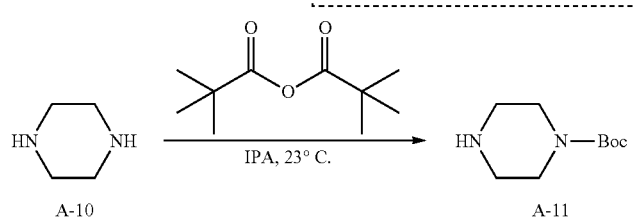
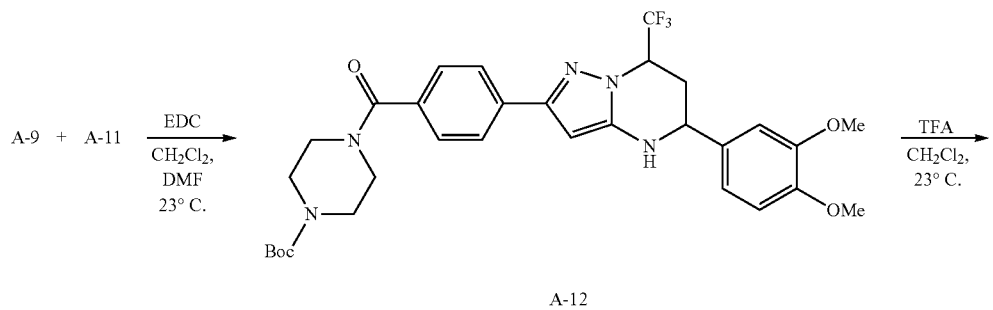
A-12
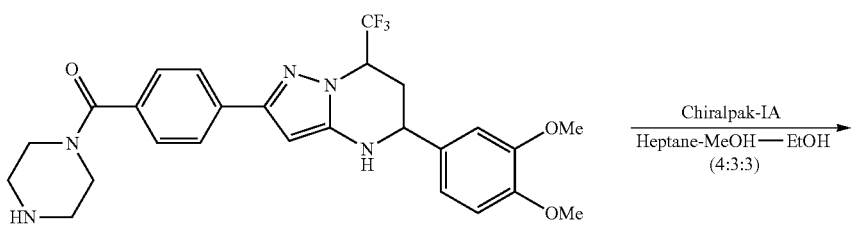
ER-890044
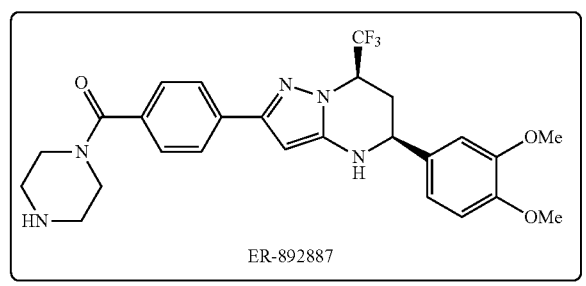
ER-892887
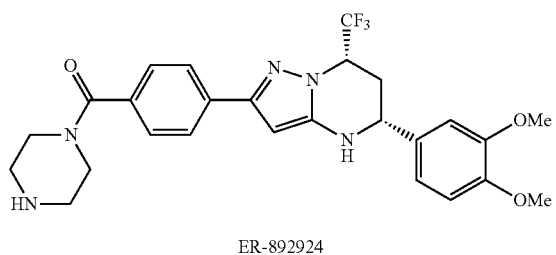
ER-892924

Compound 2

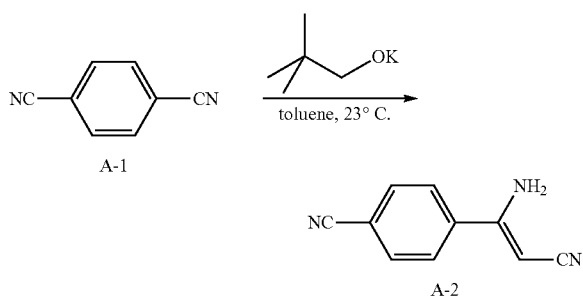

To a 5-L flask charged with terephthalonitrile (300.0 g, 2.34 mol) was added toluene (1.80 L, followed by acetonitrile (245 ml) at room temperature. 24.2 wt % Potassium-t-amylate (1.672 L, 1.338 kg, 2.58 mol) was added while controlling temperature to <30° C. over a 1-hour period.

The mixture (yellow thick paste) was allowed to cool to 20° C. and stirred for 16 hours, after which time water (0.9 L) was added to the vigorously stirred mixture until yellow solids became light tan solids. The mixture was filtered through a glass filter, the resulting solid was rinsed with water (1.8 L) followed by IPA (1.8 L), collected and dried under vacuum at 40° C. for 46 h. 374.1 g of Compound A-2 (2.21 mol, 94% yield) was obtained as light tan powder.

$^1$H NMR (400 MHz, METHANOL-$d_4$) δ ppm 4.26 (s, 1H) 7.72-7.77 (m, 2H) 7.77-7.82 (m, 2H).

MS (M+H$^+$) 170.1.

Compound 6

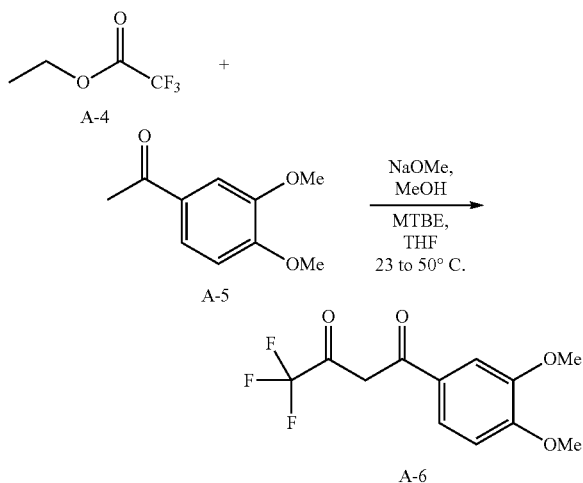

To a 5-L flask was charged with 1-(3,4-dimethoxyphenyl)ethanone (487 g, 2.70 mol) was added THF (487 mL) followed by MTBE (1.46 L). Ethyl trifluoroacetate (516 mL, 4.33 mol) was added followed by 25 wt % solution of sodium methoxide (701 g, 3.24 mol) in methanol at room temperature. The resultant mixture was warmed up to 40° C. and stirred at 40-43° C. for 16 h after which time the reaction mixture was cooled to 10° C. and poured into a pre-cooled (10° C.) mixture of MTBE (2.44 L) and 20 wt % citric acid (1.217 g, 1.279 mol) while maintaining T-internal <20° C.

After 30 min vigorous stirring, the organic layer was separated and sequentially washed with two times with 20 wt % sodium chloride (1.46 L) and then concentrated to approximately $\frac{1}{3}^{rd}$ the volume.

The resultant residue was diluted with MTBE (3.90 L), washed with water (1.95 L) and concentrated to approximately $\frac{1}{3}^{rd}$ the volume upon which time a significant amount of product solids precipitated from the solution. The resultant mixture was azeotroped two times dryness with n-heptane (1.95 L). n-Heptane (877 mL) and MTBE (97 mL) were added and resultant mixture was heated to 50° C., allowed to cool to 15° C. over a 2-h period and then precipitate was filtered. The resulting tan solid was dried under vacuum oven (40° C. for 16 h then 20° C. for 48 h) to provide 714.3 g of Compound A-6 (2.59 mol, 96% yield).

$^1$H NMR (400 MHz, CHLOROFORM-d) δ ppm 3.97 (s, 3H) 3.98 (s, 3H) 6.53 (s, 1H) 6.94 (d, J=8.51 Hz, 1H) 7.48 (d, J=2.10 Hz, 1H) 7.60 (dd, J=8.51, 2.10 Hz, 1H).

MS (M+H$^+$) 277.2.

Compounds A-3 & A-7

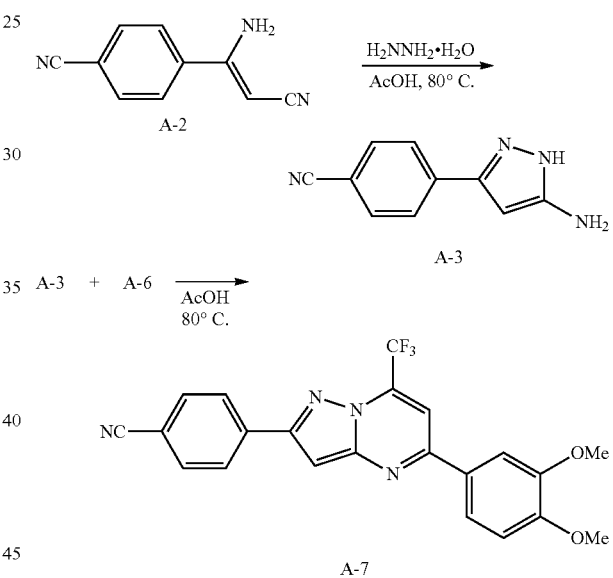

Compound A-2 (250 g, 1.478 mol) was suspended in acetic acid (1.0 L) with stirring at room temperature after which time hydrazine (72.5 mL, 1.478 mol) in water (75 mL) was added with the internal temperature increasing to 42° C. The resultant suspension was heated to 70° C. and maintained at that temperature for 5 min at which time the suspension turned to almost a clear mixture and then became cloudy again to provide compound A-3 in situ.

Toluene (1.50 L) was quickly added to the above mixture (temperature dropped to 48° C.) followed by compound A-6 (408 g, 1.478 mol). The resultant mixture was heated to 80° C. upon which time a significant amount of yellow solids accumulated generating very thick paste. After maintain the reaction at 80° C. for 30 min, the mixture was cooled to 50° C. and iced water (1.50 L) was added with vigorous stirring. The yellow precipitate was collected by filtration and washed with water (3.75 L), water (2.5 L), and IPA (2.50 L). The resultant yellow solid was dried under vacuum (40° C.) for 3 days to provide 464 g of Compound A-7 (1.09 mol, 74% yield).

¹H NMR (400 MHz, METHANOL-d₄) δ ppm 3.90 (s, 4H) 3.95 (s, 4H) 7.10 (d, J=8.54 Hz, 1H) 7.30 (s, 1H) 7.83 (d, J=8.01 Hz, 2H) 7.89 (d, J=2.02 Hz, 1H) 7.92 (s, 1H) 8.23 (d, J=8.66 Hz, 2H).

MS (M+H⁺) 425.4.

Compound 9

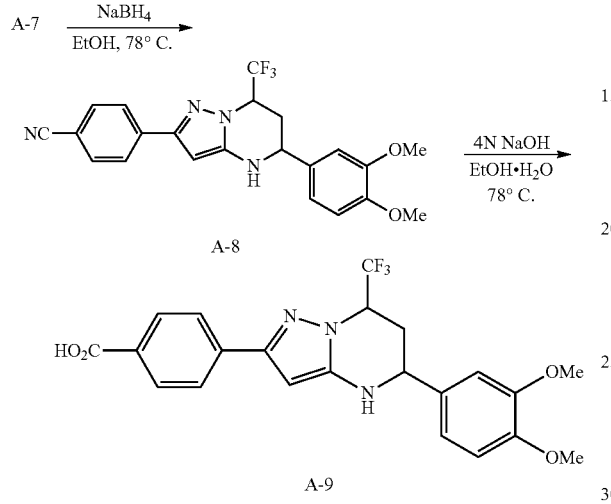

Compound A-7 (326 g, 768.2 mmol) was suspended in ethanol (3.26 L) and water (815 ml) followed by heating to 68-70° C. A sodium borohydride stock solution [previously prepared separately by adding sodium borohydride (96 g, 2.54 mol) to an aqueous solution of 0.1M sodium hydroxide (815 ml, 81.50 mmol) at room temperature followed by stirring for 30 min] was added at room temperature over 1.5 hours upon which the reaction temperature rose to 68-71° C. Upon complete addition the mixture was heated at 68-71° C. for 4 h after which time the mixture was cooled to 40° C. and acetone (564 mL) was added over 30 min (T-internal 40-42° C.) followed by stirring an additional 30 min at 40-42° C. to provide compound A-8 in situ.

¹H NMR (400 MHz, CHLOROFORM-d) δ ppm 2.33-2.44 (m, 1H) 2.51 (d, J=6.09 Hz, 1H) 3.91 (s, 3H) 3.93 (s, 3H) 4.33 (s, 1H) 4.45 (dd, J=11.80, 2.08 Hz, 1H) 4.87-4.97 (m, 1H) 5.81 (s, 1H) 6.87-6.91 (m, 1H) 6.96-7.01 (m, 2H) 7.64-7.68 (m, 2H) 7.85-7.90 (m, 2H).

MS (M+H⁺) 428.9.

Sodium hydroxide (461 g, 11.52 mol) was added to the above mixture after which time the exothermic reaction was heated to 70-73° C. and stirred for 16 hours. After cooling to room temperature, ice water (3.260 L) was added to the mixture to cool it to 10° C. followed by a slow addition of 10% aqueous HCl (4.75 L) while maintaining the temperature to <25° C. with vigorous stirring. Vigorous stirring continued for 30 min. The final reaction mixture was decanted over a glass filter to recover any brown crude product within the solvent.

The solid that remained in the reaction vessel was suspended in water (3.26 L) and stirred vigorously for 30 min and decanted as above. This process was repeated an additional time. The final recovered solids were rinsed with water (3.26 L) followed by IPA (2.61 L) and dried under air/vacuum for 1 h and then under vacuum at 45° C. for 20 h to provide 226.7 g of Compound A-9 (0.507 mol, 66% yield) as a light tan solid.

¹H NMR (400 MHz, DMSO-d₆) δ ppm 3.76 (s, 3H) 3.79 (s, 3H) 5.86 (s, 1H) 6.84 (s, 1H) 6.92-7.04 (m, 2H) 7.08 (d, J=1.50 Hz, 1H) 7.84 (m, J=8.33 Hz, 2H) 7.95 (m, J=8.23 Hz, 2H).

MS (M+H⁺) 448.4.

Compound 12

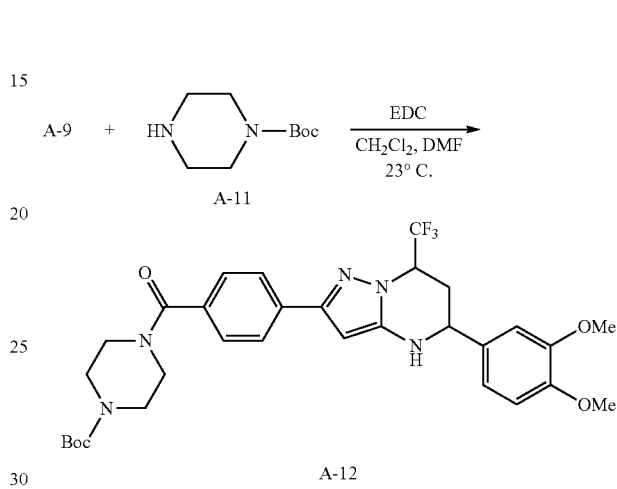

Compound A-9 (333.8 g, 746.1 mmol) was dissolved in DMF (1.335 L) and then diluted with DCM (1.00 L) while stirring at room temperature. Tert-butyl piperazine-1-carboxylate (139 g, 746.1 mmol) was added followed by stirring at room temperature for an additional 20 min EDC (143 g, 746.1 mmol) was added the resultant mixture was stirred for 2 hours at room temperature. n-Heptane (4.01 L) was added to the vigorously stirred mixture followed by water (5.34 L) while maintaining the temperature below 25° C. The resultant biphasic mixture was stirred at room temperature for an additional 30 min after which time the solids were filtered, followed by washing with water (4.0 L) and then n-heptane (2.0 L). The solid was dried under vacuum at 50° C. for 18 h to provide 478.5 g of crude compound A-12.

473 g of crude Compound A-12 was suspended in a solvent mixture of n-heptane (1.0 L) and IPA (1.0 L) followed by heating to 50° C. and stirred at 50° C. for an additional 10 min. The suspension was cooled to 20° C. over a 30-min period followed by stirring for an additional 30 min. The solid was filtered, washed with solvent mixture of IPA (500 mL) and n-heptane (500 mL) and then dried in under vacuum at 50° C. for 5 h. This above suspension and filtration process was repeated one additional time. 403 g of Compound A-12 (0.655 mol, 88% yield?) was obtained as a tan powder.

¹H NMR (400 MHz, METHANOL-d₄) δ ppm 0.94-1.14 (m, 1H) 1.45-1.51 (m, 9H) 1.57-1.75 (m, 1H) 2.17-2.29 (m, 1H) 2.49-2.58 (m, 1H) 3.84 (s, 3H) 3.87 (s, 3H) 4.45 (d, J=11.44 Hz, 1H) 5.03-5.15 (m, 1H) 6.96-7.01 (m, 1H) 7.03-7.08 (m, 1H) 7.11 (d, J=1.79 Hz, 1H) 7.40-7.52 (m, 1H) 7.85 (d, J=8.09 Hz, 2H) 7.99-8.08 (m, 1H).

MS (M+H⁺) 616.3

Compound ER-890044

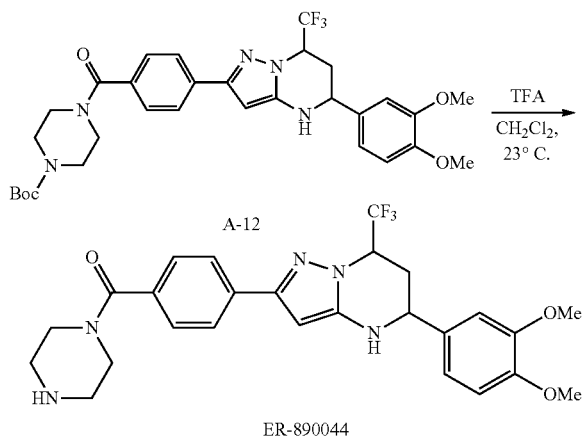

Compound A-12 (340 g, 0.552 mol) was suspended in DCM (510 ml, 7.926 mol) and TFA (510 ml, 6.619 mol) was added to the suspension over 10 min. The mixture was stirred at 23-27° C. for 3 h, after which the mixture was cooled to 15° C. and diluted with water (1700 ml, 9.436 mol) while keeping the internal temperature below 20° C. The mixture was diluted with n-heptane (3.4 L, 23.209 mol) then cooled to 15° C. Sodium hydroxide (2.872 Kg, 7.179 mol) was added over 30 min while controlling T-internal <25° C. The resultant mixture was stirred at 20-25° C. for 20 min then filtered to collect light tan precipitates. The precipitate was first rinsed with water (3.4 L) and then a mixture of n-heptane (1.36 L) and DCM (204 ml). The wet cake was transferred to a tray and dried in vacuum oven at 50° C. overnight to afford 248.8 g (0.483 mol, 87% yield) of ER-890044 as a light tan solid.

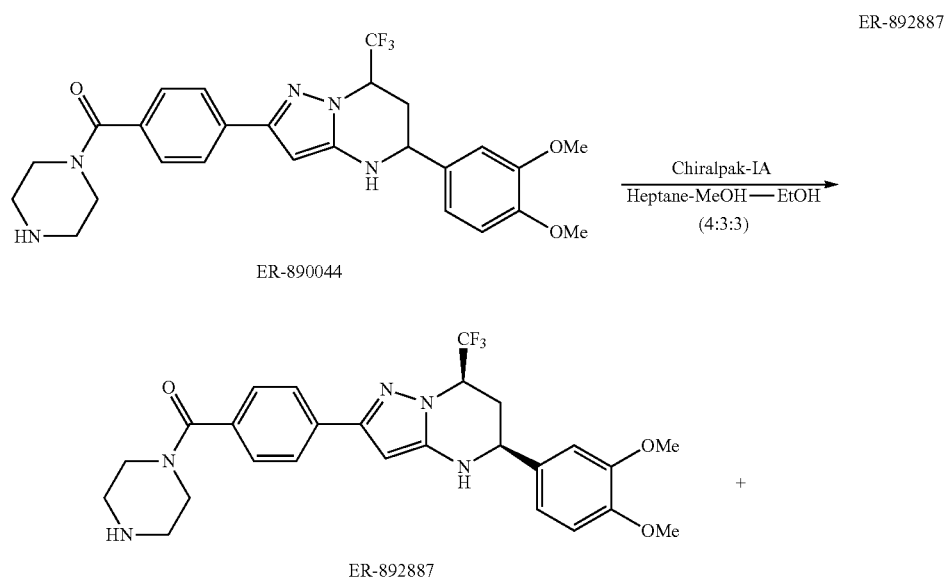

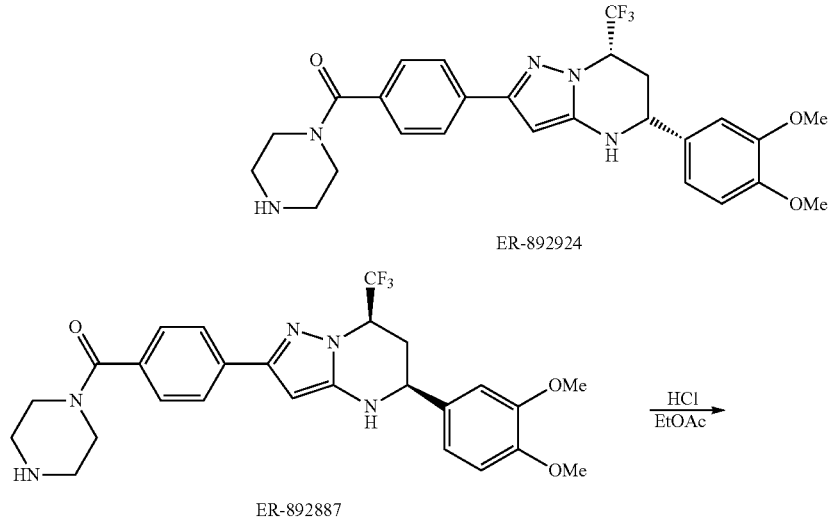

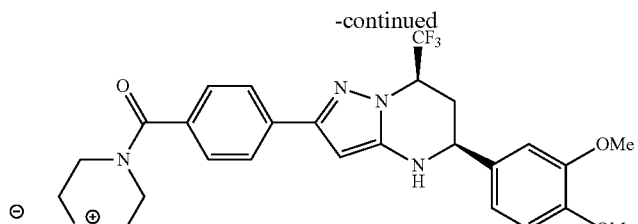

ER-892887-01

ER-890044 (30.3 g, 58.8 mmol) was dissolved in a 1:1 solution of dichloromethane and methanol (120 mL) and the cloudy solution filtered through a medium porosity Buchner funnel. The clear filtrate was directly used for chiral HPLC purification. 4 mL of this solution was loaded onto a 5 cm×50 cm Chiralpak IA column and eluted with a mobile phase comprising of heptane, methanol and ethanol (4:3:3 ratio; modified with 0.06% diethylamine) at a flow rate of 75 mL/min ER-892887 was collected between 18.5 min and 23.2 min, while ER-892924 was collected between 24.2 min and 32 min 30 such injections were carried out and the pooled fractions concentrated under reduced pressure to provide the pure enantiomeric products ER-892887 (10.5 g, 20.3 mmol, >95% ee) and ER-892924 (9.8 g, 19.0 mmol, >95% ee).

To a solution of ER-892887 (8.50 g, 16.5 mmol) in dry ethyl acetate (500 mL), was added 4 M HCl in Dioxane (4.53 mL, 18.1 mmol) drop wise over 10 min A white precipitate was obtained. The resulting suspension was stirred at ambient temperature for 15 min, then filtered under reduced pressure. The collected solid was washed with ethyl acetate (2×100 mL) and ether (2×100 mL) and dried under vacuum to afford 8.29 g of ER-892887 hydrochloride salt (15.0 mmol, 91% yield)) as a white solid.

ER-892930

To a 5 mL screw-cap reaction tube was added compound A-9 4-(7-(difluoromethyl)-5-(3,4-dimethoxyphenyl)-4,5,6, 7-tetrahydropyrazolo[1,5-a]pyrimidin-2-yl)benzoic acid (21.7 mg, 0.049 mmol), 3-Amino-1,2-propanediol (13.2 mg, 0.145 mmol), HATU (1.10 eq, 24.8 mg, 0.065 mmol), NMP (0.500 ml), and HiiniesBase (6.00 ul, 0.044 mmol). The reaction mixture was stirred at 30° C. overnight. The material was purified by LC/MS using HPLC condition III. The fractions containing product were combined and concentrated in vacuo to give compound ER-892930 as an off-white solid (13.3 mg, 53% yield).

ER-894463

To a 5 mL screw-cap reaction tube was added compound A-9 4-(7-(difluoromethyl)-5-(3,4-dimethoxyphenyl)-4,5,6, 7-tetrahydropyrazolo[1,5-a]pyrimidin-2-yl)benzoic acid (30.0 mg, 0.067 mmol), tert-butyl 3-aminopyrrolidine-1-carboxylate (74.9 mg, 0.402 mmol), HATU (50.9 mg, 0.134 mmol), NMP (0.500 ml), and HiiniesBase (6.00 ul, 0.044 mmol). The reaction mixture was stirred at 30° C. overnight. The material was purified by LC/MS using HPLC condition III. The fractions containing product were combined and concentrated in vacuo. The resulting material was then taken up in ethanol (1.0 ml) and 4.0 M HCl in Dioxane (1.0 ml, 4.00 mmol) and the mixture stirred at RT for 1 h. The mixture was then concentrated in vacuo to give compound ER-894463 as a yellow solid (22.1 mg, 60% yield).

ER-895080

To a 5 mL screw-cap reaction tube was added compound A-9 4-(7-(difluoromethyl)-5-(3,4-dimethoxyphenyl)-4,5,6, 7-tetrahydropyrazolo[1,5-a]pyrimidin-2-yl)benzoic acid (20.0 mg, 0.045 mmol), tert-butyl 2,6-diazaspiro[3.4]octane-6-carboxylate (18.98 mg, 0.089 mmol), HATU (18.7 mg, 0.049 mmol), NMP (0.500 ml), and HiiniesBase (6.00 ul, 0.044 mmol). The reaction mixture was stirred at 30° C. overnight. The material was purified by LC/MS using HPLC condition III. The fractions containing product were combined and concentrated in vacuo. The resulting material was then taken up in ethanol (1.0 ml) and 50% trifluoroacetic acid in DCM (1.0 ml, 4.00 mmol) and the mixture stirred at RT for 1 h. The mixture was then concentrated in vacuo to give compound ER-895080 as a yellow solid (2.40 mg, 8% yield).

Example ER-894462-00 was prepared from compound ER-886619 (30.0 mg, 0.067 mmol) and commercially available azetidin-3-ol (29.4 mg, 0.402 mmol) in a manner similar to that of example ER-895080. Purification by LCMS, using HPLC condition III, afforded the desired product (8.1 mg, 24%).

Example ER-894465-00 was prepared from compound ER-886619 (30.0 mg, 0.067 mmol) and commercially available pyrrolidin-3-ol (35.0 mg, 0.402 mmol) in a manner similar to that of example ER-895080. Purification by LCMS, using HPLC condition III, afforded the desired product (18.5 mg, 53%).

Example ER-894464-01 was prepared from compound ER-886619 (30.0 mg, 0.067 mmol) and commercially available tert-butyl pyrrolidin-3-ylcarbamate (74.9 mg, 0.402 mmol) in a manner similar to that of example ER-894463. Purification by LCMS, using HPLC condition III, afforded the desired product (32.6 mg, 88%).

Example ER-895077-01 was prepared from compound ER-886619 (30.0 mg, 0.067 mmol) and commercially available tert-butyl 3-aminoazetidine-1-carboxylate (69.3 mg, 0.402 mmol) in a manner similar to that of example ER-894463. Purification by LCMS, using HPLC condition III, afforded the desired product (8.6 mg, 24%).

Example ER-895078-01 was prepared from compound ER-886619 (30.0 mg, 0.067 mmol) and commercially available tert-butyl azetidin-3-ylcarbamate (69.3 mg, 0.402 mmol) in a manner similar to that of example ER-894463. Purification by LCMS, using HPLC condition III, afforded the desired product (29.7 mg, 82%).

Example ER-895746-01 was prepared from compound ER-886619 (7.8 mg, 0.062 mmol) and commercially available tert-butyl hexahydropyrrolo[3,4-c]pyrrole-2(1H)-carboxylate (37.0 mg, 0.174 mmol) in a manner similar to that of example ER-894463. Purification by LCMS, using HPLC condition III, afforded the desired product (27.5 mg, 77%).

Example ER-895748-01 was prepared from compound ER-886619 (25.0 mg, 0.056 mmol) and commercially available (S)-tert-butyl 3-aminopiperidine-1-carboxylate (35.5 mg, 0.177 mmol) in a manner similar to that of example ER-894463. Purification by LCMS, using HPLC condition III, afforded the desired product (31.3 mg, 99%).

Example ER-895749-01 was prepared from compound ER-886619 (25.0 mg, 0.056 mmol) and commercially available (R)-tert-butyl 3-aminopiperidine-1-carboxylate (36.6 mg, 0.183 mmol) in a manner similar to that of example ER-894463. Purification by LCMS, using HPLC condition III, afforded the desired product (29.5 mg, 93%).

Example ER-895750-01 was prepared from compound ER-886619 (25.0 mg, 0.056 mmol) and commercially available (S)-tert-butyl 3-methylpiperazine-1-carboxylate (31.7 mg, 0.158 mmol) in a manner similar to that of example ER-894463. Purification by LCMS, using HPLC condition III, afforded the desired product (30.6 mg, 97%).

Example ER-895751-01 was prepared from compound ER-886619 (25.0 mg, 0.056 mmol) and commercially available (R)-tert-butyl 3-methylpiperazine-1-carboxylate (43.5 mg, 0.217 mmol) in a manner similar to that of example ER-894463. Purification by LCMS, using HPLC condition III, afforded the desired product (31.2 mg, 98%).

Example ER-895752-01 was prepared from compound ER-886619 (25.0 mg, 0.056 mmol) and commercially available (2S,5R)-tert-butyl 2,5-dimethylpiperazine-1-carboxylate (30.3 mg, 0.141 mmol) in a manner similar to that of example ER-894463. Purification by LCMS, using HPLC condition III, afforded the desired product (30.6 mg, 94%).

Example ER-895753-01 was prepared from compound ER-886619 (25.0 mg, 0.056 mmol) and commercially available (2R,5R)-tert-butyl 2,5-dimethylpiperazine-1-carboxylate (37.6 mg, 0.175 mmol) in a manner similar to that of example ER-894463. Purification by LCMS, using HPLC condition III, afforded the desired product (19.5 mg, 60%).

Example ER-895754-01 was prepared from compound ER-886619 (25.0 mg, 0.056 mmol) and commercially available (1S,4S)-tert-butyl 2,5-diazabicyclo[2.2.1]heptane-2-carboxylate (33.5 mg, 0.169 mmol) in a manner similar to that of example ER-894463. Purification by LCMS, using HPLC condition III, afforded the desired product (26.7 mg, 85%).

Example ER-895083-15 was prepared from compound ER-886619 (24.5 mg, 0.055 mmol) and commercially available tert-butyl (azetidin-3-ylmethyl)(methyl)carbamate (22.4 mg, 0.112 mmol) in a manner similar to that of example ER-895080. Purification by LCMS, using HPLC condition III, afforded the desired product (0.6 mg, 2%).

Example ER-895081-15 was prepared from compound ER-886619 (20.6 mg, 0.046 mmol) and commercially available tert-butyl (6-aminospiro[3.3]heptan-2-yl)carbamate (23.4 mg, 0.103 mmol) in a manner similar to that of example ER-895080. Purification by LCMS, using HPLC condition III, afforded the desired product (13.3 mg, 43%).

Example ER-895082-15 was prepared from compound ER-886619 (23.5 mg, 0.053 mmol) and commercially available tert-butyl 2,7-diazaspiro[4.4]nonane-2-carboxylate (25.1 mg, 0.111 mmol) in a manner similar to that of example ER-895080. Purification by LCMS, using HPLC condition III, afforded the desired product (5.3 mg, 15%).

Example ER-898416 was prepared. 3-(5-(3,4-dimethoxyphenyl)-7-(trifluoromethyl)-4,5,6,7-pyrazolo[1,5-a]pyrimidin-2-yl)benzoic acid was prepared from (3-cyanophenyl)boronic acid (93 mg, 0.631 mmol) and 5-(3,4-dimethoxyphenyl)-7-(trifluoromethyl)-4,5,6,7-tetrahydropyrazolo[1,5-a]pyrimidin-2-yl trifluoromethanesulfonate (100.0 mg, 0.21 mmol) and in a manner similar to that of 5-(3,4-dimethoxyphenyl)-2-(4,4,5,5-tetramethyl-1,3,2-dioxaborolan-2-yl)-7-(trifluoromethyl)pyrazolo[1,5-a]pyrimidine (section G, preparation of ER893393) to yield 3-(5-(3,4-dimethoxyphenyl)-7-(trifluoromethyl)-4,5,6,7-tetrahydropyrazolo[1,5-a]pyrimidin-2-yl)benzonitrile (46 mg, 51% yield). Hydrolysis of material (75 mg, 0.175 mmol) thus prepared in a manner similar to that of compound A-9 afforded the desired compound (42 mg, 54% yield)

Example ER-895811 was prepared in two steps from 3-(5-(3,4-dimethoxyphenyl)-7-(trifluoromethyl)-4,5,6,7-tetrahydropyrazolo[1,5-a]pyrimidin-2-yl)benzoic acid (24 mg, 0.054 mmol) and commercially available (S)-tert-butyl 3-aminopyrrolidine-1-carboxylate (40 mg, 0.215 mmol) in a manner similar to that of example D-6 to afford intermediate (3S)-tert-butyl 3-(3-(5-(3,4-dimethoxyphenyl)-7-(trifluoromethyl)-4,5,6,7-tetrahydropyrazolo[1,5-a]pyrimidin-2-yl)benzamido)pyrrolidine-1-carboxylate (7 mg, 0.011 mmol, 21% yield). Then, this intermediate (6 mg, 0.0097 mmol) was treated with HCl in a manner similar to that of example ER-897560 to afford the desired product ER-895811 (4.4 mg, 82% yield).

Example ER-896386 was prepared in two steps from 3-(5-(3,4-dimethoxyphenyl)-7-(trifluoromethyl)-4,5,6,7-tetrahydropyrazolo[1,5-a]pyrimidin-2-yl)benzoic acid (119 mg, 0.266 mmol) and commercially available tert-butyl hexahydropyrrolo[3,4-c]pyrrole-2(1H)-carboxylate (226 mg, 1.06 mmol) in a manner similar to that of example D-6 to afford intermediate tert-butyl 5-(3-(5-(3,4-dimethoxyphenyl)-7-(trifluoromethyl)-4,5,6,7-tetrahydropyrazolo[1,5-a]pyrimidin-2-yl)benzoyl)hexahydropyrrolo[3,4-c]pyrrole-2(1H)-carboxylate (94 mg, 0.146 mmol, 55% yield). Then, this intermediate was resolved into its constituent enantiomers in a manner similar to that of ER-890044 (Section A) to afford tert-butyl 5-(3-((5S,7R)-5-(3,4-dimethoxyphenyl)-7-(trifluoromethyl)-4,5,6,7-tetrahydropyrazolo[1,5-a]pyrimidin-2-yl)benzoyl)hexahydropyrrolo[3,4-c]pyrrole-2(1H)-carboxylate (33 mg, 0.051 mmol) and tert-butyl 5-(3-((5R,7S)-5-(3,4-dimethoxyphenyl)-7-(trifluoromethyl)-4,5,6,7-tetrahydropyrazolo[1,5-a]pyrimidin-2-yl)benzoyl)hexahydropyrrolo[3,4-c]pyrrole-2(1H)-carboxylate (33 mg, 0.051 mmol). Then, intermediate tert-butyl 5-(3-((5S,7R)-5-(3,4-dimethoxyphenyl)-7-(trifluoromethyl)-4,5,6,7-tetrahydropyrazolo[1,5-a]pyrimidin-2-yl)benzoyl)hexahydropyrrolo[3,4-c]pyrrole-2(1H)-carboxylate (22 mg, 0.034 mmol) was treated with HCl in a manner similar to that of example ER-897560 to afford the desired product ER-896386 (19 mg, 96% yield).

Example ER-896387 was prepared from intermediate tert-butyl 5-(3-((5S,7R)-5-(3,4-dimethoxyphenyl)-7-(trifluoromethyl)-4,5,6,7-tetrahydropyrazolo[1,5-a]pyrimidin-2-yl)benzoyl)hexahydropyrrolo[3,4-c]pyrrole-2(1H)-carboxylate obtained in example ER-896386. Then, this intermediate (16 mg, 0.025 mmol) was treated with HCl in a manner similar to that of example ER-897560 to afford the desired product ER-896387 (14 mg, 99% yield).

Example ER-896388 was prepared in two steps from 3-(5-(3,4-dimethoxyphenyl)-7-(trifluoromethyl)-4,5,6,7-tetrahydropyrazolo[1,5-a]pyrimidin-2-yl)benzoic acid (25 mg, 0.056 mmol) and commercially available tert-butyl piperazine-1-carboxylate (42 mg, 0.224 mmol) in a manner similar to that of example D-6 to afford intermediate tert-butyl 4-(3-(5-(3,4-dimethoxyphenyl)-7-(trifluoromethyl)-4,5,6,7-tetrahydropyrazolo[1,5-a]pyrimidin-2-yl)benzoyl)piperazine-1-carboxylate (18 mg, 0.029 mmol, 52% yield). Then, this intermediate (16 mg, 0.026 mmol) was treated with HCl in a manner similar to that of example ER-897560 to afford the desired product ER-896388 (14 mg, 98% yield).

Example ER-896389 was prepared in two steps from compound 3-(5-(3,4-dimethoxyphenyl)-7-(trifluoromethyl)-4,5,6,7-tetrahydropyrazolo[1,5-a]pyrimidin-2-yl)benzoic acid (25 mg, 0.056 mmol) and commercially available tert-butyl ((3R,5S)-5-methylpiperidin-3-yl)carbamate (48 mg, 0.224 mmol) in a manner similar to that of example D-6 to afford intermediate tert-butyl ((3R,5S)-1-(3-(5-(3,4-dimethoxyphenyl)-7-(trifluoromethyl)-4,5,6,7-tetrahydropyrazolo[1,5-a]pyrimidin-2-yl)benzoyl)-5-methylpiperidin-3-yl)carbamate (22 mg, 0.034 mmol, 61% yield). Then, this intermediate (20 mg, 0.031 mmol) was treated with HCl in a manner similar to that of example ER-897560 to afford the desired product ER-896389 (17.5 mg, 97% yield).

Synthetic Examples—Section B

Example 2 (Preparation of ER-885681)

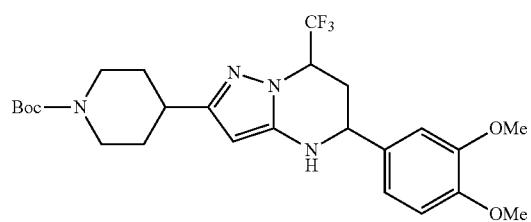

B-1

Compound B-1 was prepared from commercially available tert-butyl 4-cyanopiperidine-1-carboxylate in manner similar to compound A-8 (56 g, 70% yield for the final step).

$^1$H NMR (400 MHz, CHLOROFORM-d) δ ppm 1.44-1.49 (m, 10H) 1.50-1.62 (m, 6H) 1.89 (d, J=12.05 Hz, 2H) 2.31 (dt, J=13.69, 11.51 Hz, 1H) 2.41-2.49 (m, 1H) 2.69-2.88 (m, 3H) 3.89 (s, 3H) 3.91 (s, 3H) 4.06-4.21 (m, 3H) 4.38 (dd, J=11.71, 1.95 Hz, 1H) 4.81 (dt, J=11.29, 5.80 Hz, 1H) 5.28 (s, 1H) 6.84-6.89 (m, 1H) 6.93-6.98 (m, 2H).

MS (M+H$^+$) 511.0.

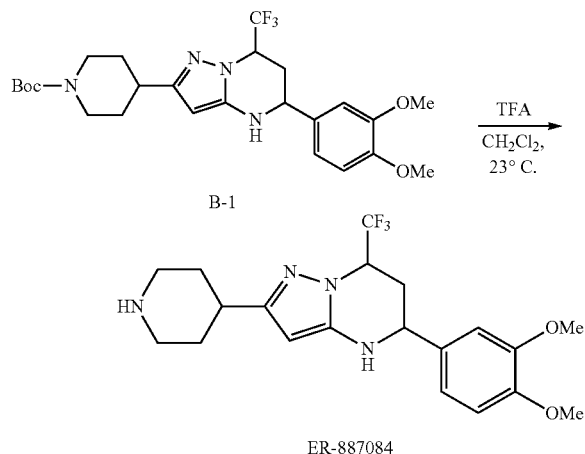

Trifluoroacetic Acid (15 mL) was added to a solution of compound B-1 (7.86 g, 15.4 mmol) in Methylene chloride (15 mL) and the mixture stirred at rt. After 15 min, the reaction mixture was concentrated under reduced pressure, and the residue partitioned between MTBE and sat. NaHCO$_3$. The layers were separated and the aq. solution further extracted with dichloromethane (2×). The combined extracts were washed with brine, dried (Na2SO4) and concentrated under reduced pressure to afford ER-887084 as a white solid (4.28 g. 68%).

$^1$H NMR (400 MHz, METHANOL-d$_4$) δ ppm 1.52-1.64 (m, 3H) 1.84 (br. s., 1H) 2.06-2.17 (m, 1H) 2.40-2.47 (m, 1H) 2.59-2.70 (m, 5H) 3.01-3.09 (m, 3H) 3.79 (s, 3H) 3.82 (s, 3H) 4.33 (dd, J=11.59, 2.25 Hz, 1H) 4.87-4.95 (m, 1H) 5.30 (s, 1H) 6.93 (d, J=8.31 Hz, 1H) 6.96-7.00 (m, 1H) 7.04 (d, J=1.90 Hz, 1H).

MS (M+H$^+$) 411.5.

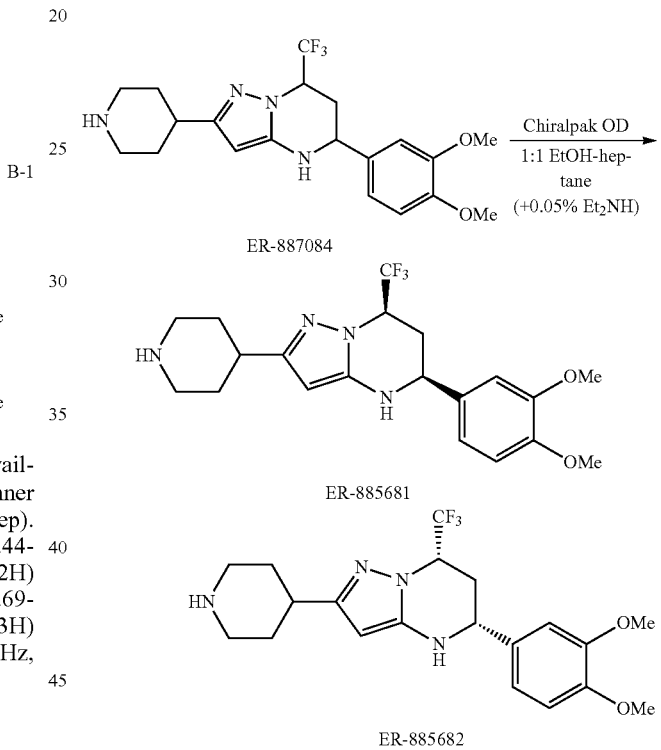

Compounds ER-885681 and ER-885682

Compound ER-887084 (1.19 g, 2.91 mmol) was dissolved in methanol (11 mL) and the solution further diluted with 19 mL of 1:1 ethanol-heptane solution modified with 0.05% diethylamine 1 mL of this solution was loaded onto a 2 cm×25 cm Chiralcel OD column and eluted with a mobile phase comprising of 1:1 heptane-ethanol (containing 0.05% diethylamine) at a flow rate of 15 mL/min Compound ER-885681 was collected between 7.3 min and 9.6 min, while compound ER-885682 was collected between 9.8 min and 14.5 min 33 such injections were carried out and the pooled fractions concentrated under reduced pressure to provide the pure enantiomeric products compound ER-885681 (571 mg, 96% yield, >95% ee) and compound ER-885682 (ER-887275) (574 mg, 96% yield, >95% ee).

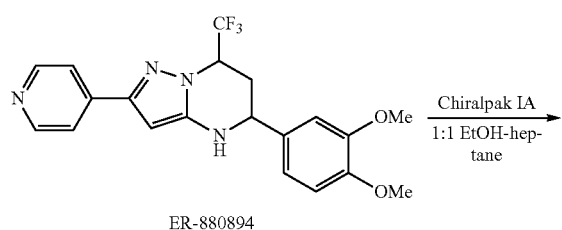

ER-880894

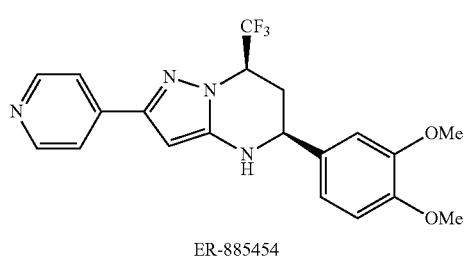

ER-885454

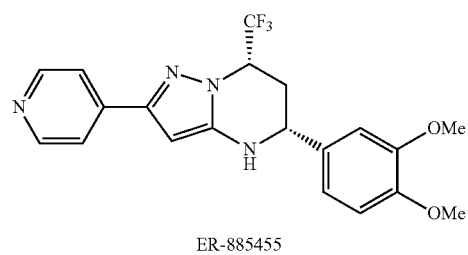

ER-885455

Examples ER-885454 and ER-885455

Compound ER-880894 was prepared from commercially available 4-cyanopyridine (450 g, 4.32 mol) using the general sequence outlined in Scheme I and exemplified by the preparation of compound A-8 (ER-890044) to yield ER-880894 (205 g, mmol 12% overall yield).

$^1$H NMR (400 MHz, CHLOROFORM-d) δ ppm 2.29-2.46 (m, 2H) 2.47-2.60 (m, 2H) 3.91 (s, 3H) 3.93 (s, 3H) 4.36 (s, 1H) 4.45 (d, J=9.96 Hz, 1H) 4.93 (dt, J=11.28, 5.79 Hz, 2H) 5.85 (s, 1H) 6.85-6.93 (m, 1H) 6.93-7.04 (m, 2H) 7.59-7.70 (m, 2H) 8.56-8.66 (m, 2H).

MS (M+H$^+$) 405.2.

Resolution of ER-880894 (200 mg, 0.495 mmol) by chiral HPLC in a manner similar to that of ER-890044 (with the exception that 1:1 ethanol-heptane was used as the mobile phase) gave ER-885454 (96 mg, 48% yield) and ER-885455 (91.2 mg, 46% yield).

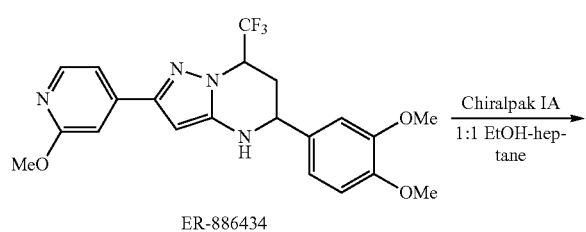

ER-886434

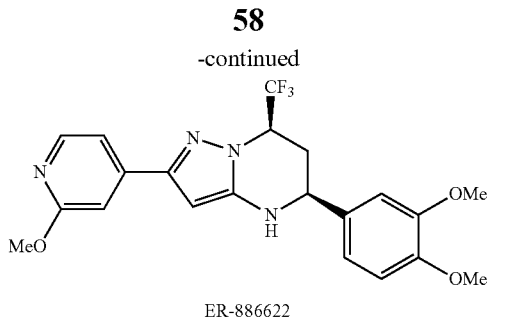

ER-886622

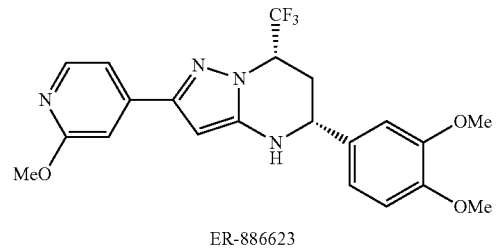

ER-886623

Examples ER-886622 and ER-886623

Example ER-886434 was prepared from commercially available 4-cyano-2-methoxypyridine (mg, mmol) in a manner similar to that of compound ER-880894 to yield ER-886434 (127 mg, 62% yield)

MS (M+H+) 435.6.

Resolution by chiral HPLC in a manner similar to that of ER-880894 gave ER-886622 (21.5 mg, 44% yield, >95% ee) and ER-886623 (20.2 mg, 41% yield, >95% ee).

Synthetic Examples—Section C

Preparation of ER-890035

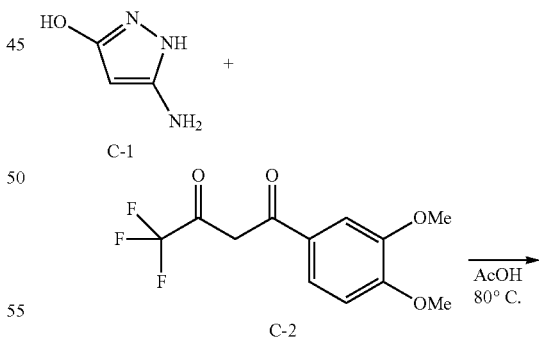

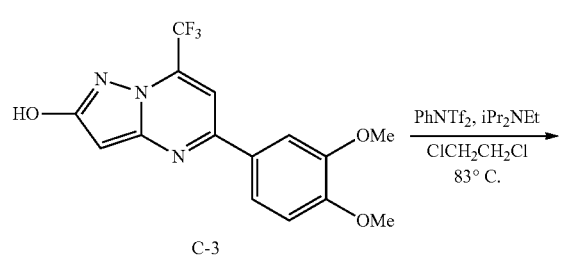

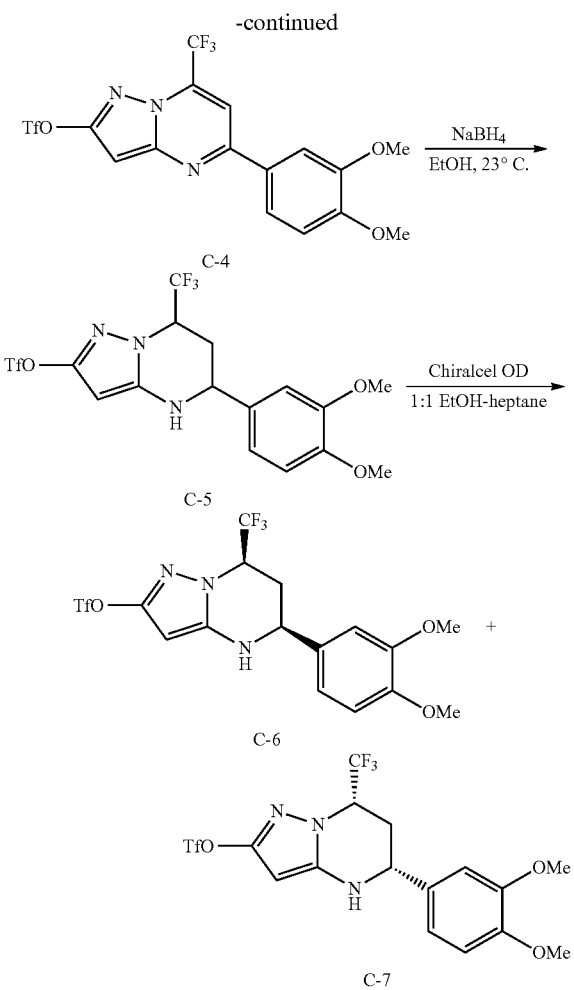

Compound C-3

A solution of compound C-1 (9.91 g, 100 mmol) and compound C-2 (27.6 g, 100 mmol) in acetic acid (60 mL) was heated at 80° C. The clear dark orange reaction mixture turned progressively lighter as a yellow precipitate began to form. Within 30 min, the reaction mixture had turned into a thick yellow slurry. The mixture maintained at 80° C. for another 15 min. The mixture was cooled to rt, and IPA added. The suspension was heated to approximately 75° C., then cooled to room temperature. The yellow precipitate was filtered, and the solids washed with additional IPA, and dried under reduced pressure. Compound C-3 was obtained as a light yellow solid (30.9 g, 91% yield).

$^1$H NMR (400 MHz, METHANOL-d$_4$) d ppm 3.92-3.92 (m, 3H) 3.96 (s, 3H) 7.10 (d, J=8.51 Hz, 1H) 7.67 (s, 1H) 7.75 (dd, J=8.47, 2.21 Hz, 1H) 7.83-7.86 (m, 1H) (major tautomer).

MS (M+H$^+$) 340.5.

Compound C-4

Compound C-3 (9.9 g, 29.2 mmol) was dissolved in N,N-Diisopropylethylamine (25.4 mL) and 1,2-dichloroethane (100 mL) and the mixture stirred at rt. To this solution was added N-phenylbis(trifluoromethanesulphonimide) (20.8 g, 58.2 mmol) and the mixture heated at reflux. After 45 min, the reaction mixture was cooled to rt, and concentrated under reduced pressure to afford an orange brown residue. The residue was purified by silica gel chromatography using gradient elution (10 to 40% EtOAc in Heptane) to afford compound C-4 as a yellow solid (7.10 g, 52% yield). A small amount of the N-sulfonylated regioisomer was formed in the reaction, but not isolated.

$^1$H NMR (400 MHz, DMSO-d$_6$) d ppm 3.87 (s, 3H) 3.90 (s, 3H) 7.15 (d, J=8.65 Hz, 1H) 7.20 (s, 1H) 7.85 (d, J=2.14 Hz, 1H) 8.00 (dd, J=8.55, 2.14 Hz, 1H) 8.35 (s, 1H).
MS (M+H$^+$) 472.3.

Compound C-5

To a solution of compound C-4 (2.24 g, 0.00475 mol) in Ethanol (29.9 mL), was added sodium borohydride (360 mg, 9.50 mol) and the mixture stirred at rt. After 30 min, the reaction mixture was carefully poured into a 1:1 mixture of saturated NH$_4$Cl solution and water. The aqueous solution was extracted with dichloromethane (3×); the combined extracts washed with brine, dried and concentrated under reduced pressure. The crude product was purified by silica gel chromatography using gradient elution (0 to 50% EtOAc in heptane) to afford compound C-5 as a white solid (1.94 g, 86% yield).

$^1$H NMR (400 MHz, METHANOL-d$_4$) δ ppm 2.18 (dt, J=13.35, 11.43 Hz, 1H) 2.47 (ddd, J=13.43, 5.95, 2.59 Hz, 1H) 3.80 (s, 3H) 3.82 (s, 3H) 4.44 (dd, J=11.63, 2.44 Hz, 1H) 4.92-5.03 (m, 1H) 5.32 (s, 1H) 6.94 (d, J=8.28 Hz, 1H) 6.99 (dd, J=8.41, 1.89 Hz, 1H) 7.04 (d, J=1.95 Hz, 1H). MS (M+H$^+$) 472.3.

Compounds C-6 and C-7

Compound C-5 (900 mg, 1.91 mmol) was dissolved in methanol (10 mL) and solution further diluted with ethanol (5 mL) and heptane (5 mL) 1 mL of this solution was loaded onto a 2 cm×25 cm Chiralcel® OD column and eluted with a mobile phase comprising of 1:1 heptane-ethanol at a flow rate of 15 mL/min Compound C-6 (ER-887274) was collected between 6.0 min and 7.7 min, while compound C-7 (ER-887275) was collected between 8.75 min and 11.5 min 17 such injections were carried out and the pooled fractions concentrated under reduced pressure to provide the pure enantiomeric products compound C-6 (ER-887274) (683 mg, 1.44 mmol, >95% ee) and compound C-7 (ER-887275) (671 mg, 1.41 mmol, >95% ee).

Example ER-890035

To a 15 mm×75 mm screw cap tube was added (3-(5-methyl-1,2,4-oxadiazol-3-yl)phenyl)boronic acid (36.1 mg, 0.177 mmol), 0.0750 M of Tetrakis(triphenylphosphine) palladium(0) in 1,4-Dioxane (80.0 uL, 0.006 mmol), 0.150 M 5-(3,4-dimethoxyphenyl)-7-(trifluoromethyl)-4,5,6,7-tetrahydropyrazolo[1,5-a]pyrimidin-2-yl trifluoromethanesulfonate (C-5) in 1,4-dioxane (420.0 uL, 0.0631 mmol), and 2.00 M of sodium carbonate in water (60.0 uL, 120 mmol). The reaction vessel was purged with nitrogen and sealed. The vial was shaken and heated in an aluminum block at 85° C. overnight. To the mixture was added 1.0 mL of saturated aqueous sodium bicarbonate and the mixture was then extracted with ethyl acetate (2×2.0 mL) The combined organic layers were concentrated in vacuo. The remaining residue was dissolved in 500 μL of DMSO. The material was purified by LC/MS on an XTerra C8 19×100 mm column with an acetonitrile:water (formic acid) gradient. The fractions containing product were combined and concentrated in vacuo to give compound ER-890035 as a yellow solid, 2.9 mg (9.5% yield).

Example ER-893972 was prepared from compound C-6 (250 mg, 0.526 mmol) and commercially available (1,4-dimethyl-1H-indazol-5-yl)boronic acid (200 mg, 1.05 mmol) in a manner similar to that of example ER-890035. Purification by silica gel chromatography afforded the desired product (159 mg, 64% yield).

Example ER-892893 was prepared from compound C-6 (250 mg, 0.526 mmol) and commercially available (4-((3-hydroxypropyl)carbamoyl)phenyl)boronic acid (235 mg, 1.05 mmol) in a manner similar to that of example ER-890035. Purification by silica gel chromatography afforded the desired product (166 mg, 63% yield).

Example ER-892892 was prepared from compound C-6 (250 mg, 0.526 mmol) and commercially available (4-carbamoyl-2-fluorophenyl)boronic acid (192 mg, 1.05 mmol) in a manner similar to that of example ER-890035. Purification by silica gel chromatography afforded the desired product (179 mg, 73% yield).

Example ER-892892 was prepared from compound C-6 (250 mg, 0.526 mmol) and commercially available (4-carbamoyl-2-fluorophenyl)boronic acid (192 mg, 1.05 mmol) in a manner similar to that of example ER-890035. Purification by silica gel chromatography afforded the desired product (179 mg, 73% yield). Example ER-894680 was prepared from compound C-6 (250 mg, 0.526 mmol) and commercially available (4-methyl-1H-indazol-5-yl)boronic acid (185 mg, 1.05 mmol in a manner similar to that of example ER-890035. Purification by silica gel chromatography afforded the desired product (90 mg, 37% yield).

Example ER-887734 was prepared from compound C-6 (20 mg, 0.042 mmol) and commercially available (3-acetamidophenyl)boronic acid (22.6 mg, 0.126 mmol) in a manner similar to that of example ER-890035. Purification by LCMS (Rt 7.45 min, condition II) afforded the desired product (9.7 mg, 50% yield).

Example ER-887738 was prepared from compound C-6 (20 mg, 0.042 mmol) and commercially available (3-acetamidophenyl)boronic acid (20.3 mg, 0.126 mmol) in a manner similar to that of example ER-890035. Purification by LCMS (Rt 8.58 min, condition II) afforded the desired product (6.5 mg, 35% yield).

Example ER-892889 was prepared from compound C-6 (200 mg, 0.421 mmol) and commercially available (3-chloro-4-(methylcarbamoyl)phenyl)boronic acid (180 mg, 0.843 mmol in a manner similar to that of example ER-890035. Purification by silica gel chromatography afforded the desired product (88 mg, 42% yield).

Example ER-892890 was prepared from compound C-6 (250 mg, 0.526 mmol) and commercially available (4-carbamoyl-3-chlorophenyl)boronic acid (210 mg, 1.05 mmol in a manner similar to that of example ER-890035. Purification by silica gel chromatography afforded the desired product (138 mg, 55% yield).

Example ER-893961 was prepared from compound C-6 (40 mg, 0.084 mmol) and commercially available (1,6-dimethyl-1H-indazol-5-yl)boronic acid (51 mg, 0.268 mmol in a manner similar to that of example ER-890035. Purification by LCMS afforded the desired product (8.9 mg, 22% yield).

Example ER-893961 was prepared from compound C-6 (40 mg, 0.084 mmol) and commercially available 5-(4,4,5,5-tetramethyl-1,3,2-dioxaborolan-2-yl)-1H-benzo[d]imidazol-2(3H)-one (80.55 mg, 0.309 mmol in a manner similar to that of example ER-890035. Purification by LCMS afforded the desired product (4.3 mg, 11% yield).

Example ER-889871 was prepared from compound C-5 (50.0 mg, 0.105 mmol) and commercially available (4-carbamoylphenyl)boronic acid (2.50 eq) in a manner similar to that of example ER-890035. Purification by LCMS, using HPLC condition III, afforded the desired product (12.8 mg, 27%).

Example ER-889874 was prepared from compound C-5 (50.0 mg, 0.105 mmol) and commercially available (4-(hydroxymethyl)phenyl)boronic acid (2.50 eq) in a manner similar to that of example ER-890035. Purification by LCMS, using HPLC condition III, afforded the desired product (7.8 mg, 17%).

Example ER-890017 was prepared from compound C-5 (30.0 mg, 0.063 mmol) and commercially available (4-carbamoyl-2-fluorophenyl)boronic acid (2.50 eq) in a manner similar to that of example ER-890035. Purification by LCMS, using HPLC condition III, afforded the desired product (13.4 mg, 46%).

Example ER-890019 was prepared from compound C-5 (30.0 mg, 0.063 mmol) and commercially available (4-carbamoyl-3-fluorophenyl)boronic acid (2.50 eq) in a manner similar to that of example ER-890035. Purification by LCMS, using HPLC condition III, afforded the desired product (11.7 mg, 40%).

Example ER-890020 was prepared from compound C-5 (30.0 mg, 0.063 mmol) and commercially available (4-carbamoyl-3-chlorophenyl)boronic acid (2.50 eq) in a manner similar to that of example ER-890035. Purification by LCMS, using HPLC condition III, afforded the desired product (14 mg, 46%).

Example ER-890024 was prepared from compound C-5 (30.0 mg, 0.063 mmol) and commercially available (4-((3-hydroxypropyl)carbamoyl)phenyl)boronic acid (2.50 eq) in a manner similar to that of example ER-890035. Purification by LCMS, using HPLC condition III, afforded the desired product (11.5 mg, 36%).

Example ER-890027 was prepared from compound C-5 (30.0 mg, 0.063 mmol) and commercially available (4-(benzylcarbamoyl)-3-chlorophenyl)boronic acid (2.50 eq) in a manner similar to that of example ER-890035. Purification by LCMS, using HPLC condition III, afforded the desired product (12.3 mg, 34%).

Example ER-890028 was prepared from compound C-5 (30.0 mg, 0.063 mmol) and commercially available (3-chloro-4-(isopropylcarbamoyl)phenyl)boronic acid (2.50 eq) in a manner similar to that of example ER-890035. Purification by LCMS, using HPLC condition III, afforded the desired product (18.1 mg, 55%).

Example ER-890029 was prepared from compound C-5 (30.0 mg, 0.063 mmol) and commercially available (3-chloro-4-(methylcarbamoyl)phenyl)boronic acid (2.50 eq) in a manner similar to that of example ER-890035. Purification by LCMS, using HPLC condition III, afforded the desired product (15.4 mg, 49%).

Example ER-890035 was prepared from compound C-5 (30.0 mg, 0.063 mmol) and commercially available (3-(5-methyl-1,2,4-oxadiazol-3-yl)phenyl)boronic acid (2.50 eq) in a manner similar to that of example ER-890035. Purification by LCMS, using HPLC condition III, afforded the desired product (2.9 mg, 9%).

Example ER-890043 was prepared from compound C-5 (30.0 mg, 0.063 mmol) and commercially available (2-oxo-2,3-dihydro-1H-benzo[d]imidazol-5-yl)boronic acid (2.50 eq) in a manner similar to that of example ER-890035.

Purification by LCMS, using HPLC condition III, afforded the desired product (5.6 mg, 19%).

Example ER-890044 was prepared from compound C-5 (30.0 mg, 0.063 mmol) and commercially available (4-(piperazine-1-carbonyl)phenyl)boronic acid (2.50 eq) in a manner similar to that of example ER-890035. Purification by LCMS, using HPLC condition III, afforded the desired product (13.7 mg, 42%).

Example ER-890050-00 was prepared from compound C-5 (30.0 mg, 0.063 mmol) and commercially available (3-(1H-pyrazol-1-yl)phenyl)boronic acid (2.50 eq) in a manner similar to that of example ER-890035. Purification by LCMS, using HPLC condition III, afforded the desired product (15.4 mg, 52%).

Example ER-891029-00 was prepared from compound C-5 (30.0 mg, 0.063 mmol) and commercially available (6-(methylcarbamoyl)pyridin-3-yl)boronic acid (2.50 eq) in a manner similar to that of example ER-890035. Purification by LCMS, using HPLC condition III, afforded the desired product (9 mg, 31%).

Example ER-891043 was prepared from compound C-5 (30.0 mg, 0.063 mmol) and commercially available (1,7-dimethyl-1H-indazol-5-yl)boronic acid (2.50 eq) in a manner similar to that of example ER-890035. Purification by LCMS, using HPLC condition III, afforded the desired product (18 mg, 61%).

Example ER-891044 was prepared from compound C-5 (30.0 mg, 0.063 mmol) and commercially available (1,4-dimethyl-1H-indazol-5-yl)boronic acid (2.50 eq) in a manner similar to that of example ER-890035. Purification by LCMS, using HPLC condition III, afforded the desired product (14.3 mg, 48%).

Example ER-891047 was prepared from compound C-5 (30.0 mg, 0.063 mmol) and commercially available (1,6-dimethyl-1H-indazol-5-yl)boronic acid (2.50 eq) in a manner similar to that of example ER-890035. Purification by LCMS, using HPLC condition III, afforded the desired product (18.1 mg, 61%).

Example ER-891058 was prepared from compound C-5 (30.0 mg, 0.063 mmol) and commercially available (4-(cyclopropylcarbamoyl)-3-fluorophenyl)boronic acid (2.50 eq) in a manner similar to that of example ER-890035. Purification by LCMS, using HPLC condition III, afforded the desired product (13.8 mg, 43%).

Example ER-892908 was prepared from compound C-5 (30.0 mg, 0.063 mmol) and commercially available (4-(tert-butylcarbamoyl)-3-fluorophenyl)boronic acid (2.50 eq) in a manner similar to that of example ER-890035. Purification by LCMS, using HPLC condition III, afforded the desired product (7 mg, 21%).

Example ER-892931 was prepared from compound C-5 (32.6 mg, 0.069 mmol) and commercially available (1H-indazol-4-yl)boronic acid (2.70 eq) in a manner similar to that of example ER-890035. Purification by LCMS, using HPLC condition III, afforded the desired product (5.5 mg, 18%).

Section C.1 (Compounds Prepared by Cross-Coupling from Bromide)

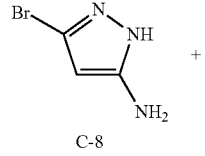

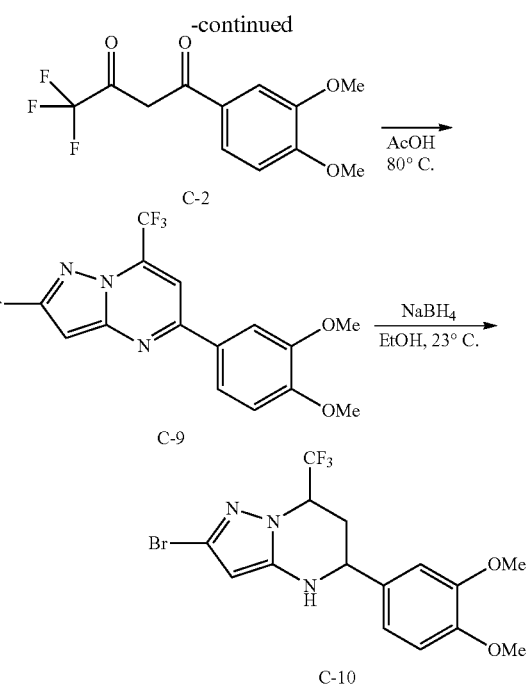

Compound C-9

A mixture of 3-amino-5-bromopyrazole C-8 (3.24 g, 20 mmol) and diketone C-2 (5.52 g, 20 mmol) in Acetic acid (20 mL) was heated to 80° C. After 1 h, the reaction mixture was cooled to rt, and diluted with IPA. A yellow ppt formed in the mixture, which was collected by filtration. Upon standing, additional ppt was formed in the mother liquor. The combined crops were collected and dried under vacuum to afford 3.89 g of compound C-9 as a yellow solid (9.67 mmol, 48% yield).

$^1$H NMR (400 MHz, CHLOROFORM-d) δ ppm 3.99 (s, 3H) 4.05 (s, 3H) 6.85 (s, 1H) 7.00 (d, J=8.47 Hz, 1H) 7.57 (s, 1H) 7.62 (dd, J=8.45, 2.16 Hz, 1H) 7.80 (d, J=2.14 Hz, 1H)

MS (M+H$^+$) 402.2

Compound C-10

Compound C-9 (1.1 g, 2.74 mmol) was suspended in ethanol (5 mL) and sodium borohydride (155 mg, 4.1 mmol) added. The mixture was stirred at rt for 1.5 h. At this time additional Sodium borohydride (155 mg) was added and the mixture stirred at rt for another 2 h. Acetic acid (1.56 mL) was added to quench the reaction and the resulting aq solution poured into sat. NaHCO3 solution. The precipitated white solid was collected by filtration, washed with water, and dried under reduced pressure to afford 667 mg of compound C-10 as an off-white solid (1.64 g, 60% yield).

$^1$H NMR (400 MHz, CHLOROFORM-d) δ ppm 2.34-2.37 (m, 1H) 2.49 (m, 1H) 3.86 (s, 1H) 3.91 (s, 3H) 3.92 (s, 3H) 4.40 (dd, J=11.75, 2.44 Hz, 1H) 4.82 (dt, J=11.32, 5.73 Hz, 1H) 5.51 (s, 1H) 6.80-6.91 (m, 2H) 6.93-7.00 (m, 1H)

MS (M+H$^+$) 406.4

Example ER-889925 was prepared from compound C-10 (37.0 mg, 0.091 mmol) and commercially available isoquinolin-5-ylboronic acid (2.50 eq) in a manner similar to that of example ER-890035. Purification by LCMS, using HPLC condition III, afforded the desired product (9.9 mg, 24%).

Synthetic Examples—Section D
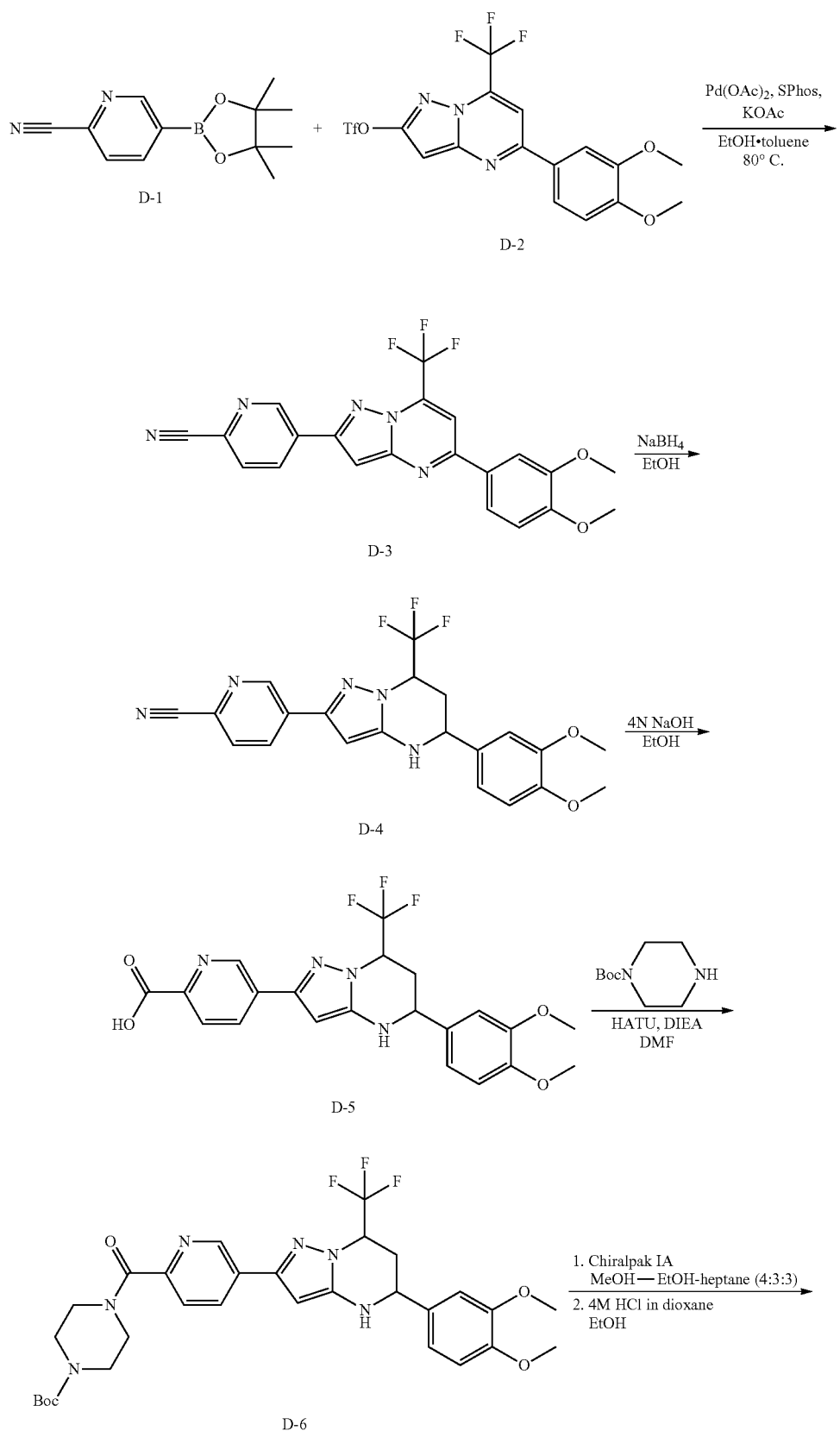

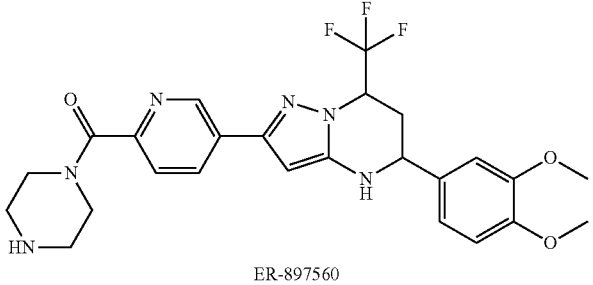

ER-897560

5-(5-3,4-dimethoxyphenyl)-7-(trifluoromethyl)pyrazolo[1,5-a]pyrimidin-2-yl)picolinonitrile (D-3)

To a vial was added 5-(4,4,5,5-tetramethyl-1,3,2-dioxaborolan-2-yl)picolinonitrile (1.95 g, 8.48 mmol), dicyclohexyl(2′,6′-dimethoxy-[1,1′-biphenyl]-2-yl)phosphine (0.261 g, 0.636 mmol), 5-(3,4-dimethoxyphenyl)-7-(trifluoromethyl)pyrazolo[1,5-a]pyrimidin-2-yl trifluoromethanesulfonate (2.00 g, 4.24 mmol), potassium acetate (0.833 g, 8.49 mmol) and palladium(II) acetate (0.095 g, 0.424 mmol). After flushing vial and contents with nitrogen, a degassed solution of 1:1 toluene/ethanol (20 mL) was added, vial was sealed and heated to 80° C. for 2 days. Ethyl acetate was added to the resulting light yellow precipitate was collected by filtration and dried under high vacuum (1.13 g, 63%). This material was used in the next step without further purification.

$^1$H NMR (400 MHz CDCl$_3$) δ ppm 4.00 (3H), 4.06 (3H), 7.02 (2H), 7.21 (1H), 7.66 (2H), 7.84 (2H), 8.5 (1H), 9.33 (1H).

MS (M+H$^+$) 426.0.

5-(5-(3,4-dimethoxyphenyl)-7-(trifluoromethyl)-4,5,6,7-tetrahydropyrazolo[1,5-a]pyrimidin-2-yl)picolinonitrile (D-4)

To a mixture of 5-(5-3,4-dimethoxyphenyl)-7-(trifluoromethyl)pyrazolo[1,5-a]pyrimidin-2-yl)picolinonitrile (1.03 g, 2.43 mmol) in ethanol (23.0 mL) was added sodium borohydride (0.276 g, 7.29 mmol); reaction mixture was heated to reflux for 2 h after which the reaction mixture was allowed to cool to room temperature and stir overnight. Acetic acid (1.40 mL) followed by 1.0 N hydrochloric acid solution (48.6 mL) was added and the mixture was concentrated using rotary evaporation. Dichloromethane was added to the residue and filtered. Concentration of the filtrate by rotary evaporation afforded crude product as a light brown foam (0.694 g, 66%). This material was used in the next step without further purification.

$^1$H NMR (400 MHz DMSO-d6) δ ppm 2.13 (1H), 2.46 (1H), 3.77 (6H), 4.48 (1H), 5.36 (1H), 5.97 (1H), 6.98 (3H), 7.08 (1H), 8.08 (1H), 8.28 (1H), 9.05 (1H).

MS (M+H$^+$) 430.0.

5-(5-(3,4-dimethoxyphenyl)-7-(trifluoromethyl)-4,5,6,7-tetrahydropyrazolo[1,5-a]pyrimidin-2-yl)picolinic acid (D-5)

To a suspension of 5-(5-(3,4-dimethoxyphenyl)-7-(trifluoromethyl)-4,5,6,7-tetrahydropyrazolo[1,5-a]pyrimidin-2-yl)picolinonitrile (0.694 g, 1.62 mmol) was added 4.00 M sodium hydroxide solution in water (2.02 mL) The resulting mixture was heated at reflux for 3 h. 1.0 N hydrochloric acid solution (11.3 mL) was added and the light brown precipitate was filtered, rinsed with copious amounts of water, dried under air/vacuum for 30 min, and then under high vacuum 48 h to give a light brown solid (0.535 g, 74%). This material was used in the next step without further purification.

$^1$H NMR (400 MHz DMSO-d6) δ ppm 2.13 (1H), 2.46 (1H), 3.76 (3H), 3.79 (3H), 4.48 (1H), 5.35 (1H), 6.00 (1H), 6.99 (3H), 7.08 (1H), 8.11 (1H), 8.32 (1H), 9.04 (1H).

MS (M+H$^+$) 449.01

Tert-butyl 4-(5-(5-(3,4-dimethoxyphenyl)-7-(trifluoromethyl)-4,5,6,7-tetrahydropyrazolo[1,5-a]pyrimidin-2-yl)picolinoyl)piperazine-1-carboxylate (D-6)

To a solution of 5-(5-(3,4-dimethoxyphenyl)-7-(trifluoromethyl)-4,5,6,7-tetrahydropyrazolo[1,5-a]pyrimidin-2-yl) picolinic acid (458 mg, 1.02 mmol) in DMF (4.0 mL) was added N,N-diisopropylethylamine (535 µl, 3.06 mmol) and HATU (427 mg, 1.12 mmol). After stirring 1 h at rt, tert-butyl piperazine-1-carboxylate (209 mg, 1.12 mmol) was added and the reaction was stirred overnight at room temperature. Water was added and the resulting light brown precipitate was collected by filtration (0.5385 g). Purification by column chromatography (15% to 100% ethyl acetate/heptane afforded tert-butyl 4-(5-(5-(3,4-dimethoxyphenyl)-7-(trifluoromethyl)-4,5,6,7-tetrahydropyrazolo[1,5-a]pyrimidin-2-yl)picolinoyl)piperazine-1-carboxylate (332 mg, 54%) as a light yellow solid.

$^1$H NMR (400 MHz CD3OD) δ ppm 1.46 (9H), 2.2 (1H), 2.5 (1H), 3.50 (8H), 3.73 (1H), 3.82 (6H), 4.45 (1H), 5.08 (1H), 5.91 (1H), 7.02 (3H), 7.62 (1H), 8.23 (1H), 8.92 (1H).

MS (M+H$^+$) 617.2.

(5-(5-(3,4-Dimethoxyphenyl)-7-(trifluoromethyl)-4,5,6,7-tetrahydropyrazolo[1,5-a]pyrimidin-2-yl)pyridin-2-yl)(piperazin-1-yl)methanone (ER-897560)

Compound D-6 (66 mg, 0.107 mmol) was resolved into its constituent enantiomers in a manner similar to that of ER-890044 (Section A) to afford tert-butyl 4-(5-((5S,7R)-5-(3,4-dimethoxyphenyl)-7-(trifluoromethyl)-4,5,6,7-tetrahydropyrazolo[1,5-a]pyrimidin-2-yl)picolinoyl)piperazine-1-carboxylate (9.2 mg, 14% yield) and tert-butyl 4-(5-((5R,7S)-5-(3,4-dimethoxyphenyl)-7-(trifluoromethyl)-4,5,6,7-tetrahydropyrazolo[1,5-a]pyrimidin-2-yl)picolinoyl) piperazine-1-carboxylate (9.2 mg, 14% yield).

To a solution of tert-butyl 4-(5-((5S,7R)-5-(3,4-dimethoxyphenyl)-7-(trifluoromethyl)-4,5,6,7-tetrahydropyrazolo[1,5-a]pyrimidin-2-yl)picolinoyl)piperazine-1-carboxylate (90.0 mg, 0.146 mmol) in ethanol (4 mL) was added 4.0 M HCl in 1,4-dioxane (1.84 mL) The reaction was heated to 40° C. for 1 h. The reaction mixture was concentrated by rotary evaporation and azeotroped with toluene to give ER-897560 as a pale yellow solid (91 mg, 106% yield).

Example ER-897097 was prepared from compound C-9 (500 mg, 1.243 mmol) and commercially available tert-butyl 4-(4,4,5,5-tetramethyl-1,3,2-dioxaborolan-2-yl)-5,6-dihydropyridine-1(2H)-carboxylate (461 mg, 1.492 mmol) in a manner similar to that of example D-4. Purification by silica gel chromatography afforded the Boc-protected ER-897097 (460 mg, 73% yield). Deprotection of this Boc-protected product (100 mg, 0.197 mmol) was carried in a manner similar to that of ER-887084 (Section B) to afford ER-897097 (80 mg, 99% yield). (LC-MS: Rt 1.49 min, $(M+1)^+$ 409.08 under condition II)

Example ER-897269

Compound ER-897097 (94 mg, 0.229 mmol) was resolved into its constituent enantiomers in a manner similar to that of ER-890044 (Section A) to afford one of the isomers ER-897269 (15 mg, 16% yield, >95% ee).

Example ER-897105 was prepared from compound C-9 (500 mg, 1.243 mmol) and commercially available tert-butyl 4-(4-(4,4,5,5-tetramethyl-1,3,2-dioxaborolan-2-yl)-1H-pyrazol-1-yl)piperidine-1-carboxylate (563 mg, 1.492 mmol) in a manner similar to that of example D-4. Purification by silica gel chromatography afforded the Boc-protected ER-897105 (312 mg, 44% yield). Deprotection of this Boc-protected product (100 mg, 0.173 mmol) was carried in a manner similar to that of ER-887084 (Section B) to afford ER-897105 (71 mg, 86% yield).

LC-MS: Rt 1.48 min, $(M+1)^+$ 477.09 under condition II.

Examples ER-897214 and ER-897215

Compound ER-897105 (50 mg, 0.105 mmol) was resolved into its constituent enantiomers in a manner similar to that of ER-890044 (Section A) to afford ER-897214 (19 mg, 39% yield, >95% ee) and ER-897215 (19 mg, 39% yield, >95% ee).

Example ER-897381 was prepared from compound C-4 (500 mg, 1.061 mmol) and commercially available tert-butyl 4-(5-(4,4,5,5-tetramethyl-1,3,2-dioxaborolan-2-yl)pyrimidin-2-yl)piperazine-1-carboxylate (621 mg, 1.591 mmol) in a manner similar to that of example D-4. Purification by silica gel chromatography afforded the Boc-protected ER-897381 (311 mg, 50% yield). Deprotection of this Boc-protected product (100 mg, 0.17 mmol) was carried in a manner similar to that of ER-887084 (Section B) to afford ER-897381 (75 mg, 90% yield). LC-MS: Rt 1.52 min, $(M+1)^+$ 489.21 under condition II).

Example ER-897714 and ER-897715

Compound ER-897381 (71 mg, 0.134 mmol) was resolved into its constituent enantiomers in a manner similar to that of ER-890044 (Section A) to afford ER-897714 (27 mg, 38% yield, >95% ee) and ER-897716 (30 mg, 42% yield, >95% ee).

Example ER-897405 was prepared from compound C-4 (500 mg, 1.061 mmol) and commercially available tert-butyl 4-(5-(4,4,5,5-tetramethyl-1,3,2-dioxaborolan-2-yl)pyridin-2-yl)piperazine-1-carboxylate (619 mg, 1.591 mmol) in a manner similar to that of example D-4. Purification by silica gel chromatography afforded the Boc-protected ER-897405 (311 mg, 65% yield). Deprotection of this Boc-protected product (100 mg, 0.17 mmol) was carried in a manner similar to that of ER-887084 (Section B) to afford ER-897405 (72 mg, 87% yield). LC-MS: Rt 1.45 min, $(M+1)^+$ 489.04 under condition II.

Example ER-897716 and ER-897717

Compound ER-897405 (70 mg, 0.143 mmol) was resolved into its constituent enantiomers in a manner similar to that of ER-890044 (Section A) to afford ER-897716 (23 mg, 33% yield) and ER-897717 (23 mg, 33% yield).

Example ER-897765 was prepared from compound C-4 (438 mg, 0.93 mmol) and commercially available tert-butyl (1-(5-(4,4,5,5-tetramethyl-1,3,2-dioxaborolan-2-yl)pyridin-2-yl)piperidin-4-yl)carbamate (250 mg, 0.62 mmol) in a manner similar to that of example D-4. Purification by silica gel chromatography afforded the Boc-protected ER-897765 (161 mg, 43% yield). Deprotection of this Boc-protected product (161 mg, 0.267 mmol) was carried in a manner similar to that of ER-887084 (Section B) to afford ER-897765 (131 mg, 98% yield).

Example ER-895809 was prepared in two steps from compound D-5 (19 mg, 0.042 mmol) and commercially available (S)-tert-butyl 3-aminopyrrolidine-1-carboxylate (32 mg, 0.169 mmol) in a manner similar to that of example D-6 to afford intermediate (3S)-tert-butyl 3-(5-(5-(3,4-dimethoxyphenyl)-7-(trifluoromethyl)-4,5,6,7-tetrahydropyrazolo[1,5-a]pyrimidin-2-yl)picolinamido)pyrrolidine-1-carboxylate (19 mg, 0.031 mmol, 72% yield). Then, this intermediate (17 mg, 0.028 mmol) was treated with HCl in a manner similar to that of example ER-897560 to afford the desired product ER-895809 (16 mg, 98% yield).

Example ER-895810 was prepared in two steps from compound D-5 (19 mg, 0.042 mmol) and commercially available (R)-tert-butyl 3-aminopyrrolidine-1-carboxylate (32 mg, 0.169 mmol) in a manner similar to that of example D-6 to afford intermediate (3R)-tert-butyl 3-(5-(5-(3,4-dimethoxyphenyl)-7-(trifluoromethyl)-4,5,6,7-tetrahydropyrazolo[1,5-a]pyrimidin-2-yl)picolinamido)pyrrolidine-1-carboxylate (24 mg, 0.039 mmol, 92% yield). Then, this intermediate (22 mg, 0.036 mmol) was treated with HCl in a manner similar to that of example ER-897560 to afford the desired product ER-895810 (21 mg, 100% yield). Exact mass calculated: 516.21. Observed: 517.5.

Example ER-896133 was prepared in two steps from compound D-5 (15 mg, 0.033 mmol) and commercially available tert-butyl piperazine-1-carboxylate (25 mg, 0.134 mmol) in a manner similar to that of example D-6 to afford intermediate tert-butyl 4-(5-(5-(3,4-dimethoxyphenyl)-7-(trifluoromethyl)-4,5,6,7-tetrahydropyrazolo[1,5-a]pyrimidin-2-yl)picolinoyl)piperazine-1-carboxylate (6 mg, 0.009 mmol, 29% yield). Then, this intermediate (6 mg, 0.009 mmol) was treated with HCl in a manner similar to that of example ER-897560 to afford the desired product ER-896133 (5.3 mg, 92% yield).

Example ER-896134 was prepared in two steps from compound D-5 (15 mg, 0.033 mmol) and commercially available tert-butyl 4-aminopiperidine-1-carboxylate (27 mg, 0.134 mmol) in a manner similar to that of example D-6 to afford intermediate tert-butyl 4-(5-(5-(3,4-dimethoxyphenyl)-7-(trifluoromethyl)-4,5,6,7-tetrahydropyrazolo[1,5-a]pyrimidin-2-yl)picolinamido)piperidine-1-carboxylate (7 mg, 0.011 mmol, 33% yield). Then, this intermediate (7 mg, 0.011 mmol) was treated with HCl in a manner similar to that of example ER-897560 to afford the desired product ER-896134 (5.8 mg, 87% yield).

Example ER-896135 was prepared in two steps from compound D-5 (15 mg, 0.033 mmol) and commercially available (S)-tert-butyl 3-aminopiperidine-1-carboxylate (27 mg, 0.134 mmol) in a manner similar to that of example D-6 to afford intermediate (3S)-tert-butyl 3-(5-(5-(3,4-dimethoxyphenyl)-7-(trifluoromethyl)-4,5,6,7-tetrahydropyrazolo[1,5-a]pyrimidin-2-yl)picolinamido)piperidine-1-carboxylate (7 mg, 0.011 mmol, 33% yield). Then, this intermediate (7 mg, 0.011 mmol) was treated with HCl in a manner similar to that of example ER-897560 to afford the desired product ER-896135 (6.5 mg, 97% yield).

Example ER-896136 was prepared in two steps from compound D-5 (15 mg, 0.033 mmol) and commercially available (R)-tert-butyl 3-aminopiperidine-1-carboxylate (27 mg, 0.134 mmol) in a manner similar to that of example D-6 to afford intermediate (3R)-tert-butyl 3-(5-(5-(3,4-dimethoxyphenyl)-7-(trifluoromethyl)-4,5,6,7-tetrahydropyrazolo[1,5-a]pyrimidin-2-yl)picolinamido)piperidine-1-carboxylate (7 mg, 0.011 mmol, 33% yield). Then, this intermediate (7 mg, 0.011 mmol) was treated with HCl in a manner similar to that of example ER-897560 to afford the desired product ER-896136 (6.1 mg, 91% yield).

Example ER-896137 was prepared from compound D-5 (15 mg, 0.033 mmol) and commercially available propan-2-amine (8 mg, 0.134 mmol) in a manner similar to that of example D-6 to afford the desired product ER-896137 (5 mg, 31% yield).

4-(5-(3,4-dimethoxyphenyl)-7-(trifluoromethyl)-4,5,6,7-tetrahydropyrazolo[1,5-a]pyrimidin-2-yl)picolinic acid was prepared in a manner similar to that of example D-5 (101 mg, 29% yield).

Example ER-897034 was prepared in two steps from 4-(5-(3,4-dimethoxyphenyl)-7-(trifluoromethyl)-4,5,6,7-tetrahydropyrazolo[1,5-a]pyrimidin-2-yl)picolinic acid (25 mg, 0.056 mmol) and commercially available tert-butyl piperazine-1-carboxylate (31 mg, 0.167 mmol) in a manner similar to that of example D-6 to afford intermediate tert-butyl 4-(4-(5-(3,4-dimethoxyphenyl)-7-(trifluoromethyl)-4,5,6,7-tetrahydropyrazolo[1,5-a]pyrimidin-2-yl)picolinoyl)piperazine-1-carboxylate (15 mg, 0.024 mmol, 44% yield). Then, this intermediate (13 mg, 0.021 mmol) was treated with HCl in a manner similar to that of example ER-897560 to afford the desired product ER-897034 (12.2 mg, 98% yield).

Example ER-897036 was prepared in two steps from 4-(5-(3,4-dimethoxyphenyl)-7-(trifluoromethyl)-4,5,6,7-tetrahydropyrazolo[1,5-a]pyrimidin-2-yl)picolinic acid (25 mg, 0.056 mmol) and commercially available (S)-tert-butyl 3-aminopiperidine-1-carboxylate (33 mg, 0.167 mmol) in a manner similar to that of example D-6 to afford intermediate (3S)-tert-butyl 3-(4-(5-(3,4-dimethoxyphenyl)-7-(trifluoromethyl)-4,5,6,7-tetrahydropyrazolo[1,5-a]pyrimidin-2-yl)picolinamido)piperidine-1-carboxylate (15 mg, 0.024 mmol, 43% yield). Then, this intermediate (13 mg, 0.021 mmol) was treated with HCl in a manner similar to that of example ER-897560 to afford the desired product ER-897036 (12 mg, 96% yield).

Example ER-897037 was prepared in two steps from 4-(5-(3,4-dimethoxyphenyl)-7-(trifluoromethyl)-4,5,6,7-tetrahydropyrazolo[1,5-a]pyrimidin-2-yl)picolinic acid (25 mg, 0.056 mmol) and commercially available tert-butyl 4-aminopiperidine-1-carboxylate (33 mg, 0.167 mmol) in a manner similar to that of example D-6 to afford intermediate tert-butyl 4-(4-(5-(3,4-dimethoxyphenyl)-7-(trifluoromethyl)-4,5,6,7-tetrahydropyrazolo[1,5-a]pyrimidin-2-yl)picolinamido)piperidine-1-carboxylate (14 mg, 0.022 mmol, 40% yield). Then, this intermediate (13 mg, 0.021 mmol) was treated with HCl in a manner similar to that of example ER-897560 to afford the desired product ER-897037 (11 mg, 90% yield).

Synthetic Examples—Section F

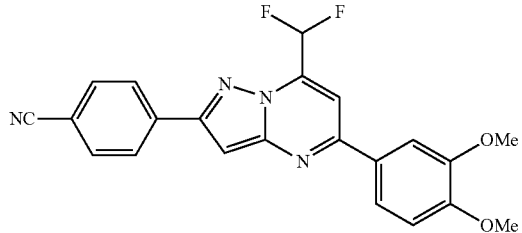

F-1

4-(5-amino-1H-pyrazol-3-yl)benzonitrile (compound A-2; 5.31 g, 31.4 mmol) and commercially available 1-(3,4-dimethoxyphenyl)-4,4-difluorobutane-1,3-dione (8.1 g, 31.4 mmol) in a manner similar to that of compound A-7 afforded compound F-1 (9.84 g, 77% yield). MS (M+H$^+$) 407.3.

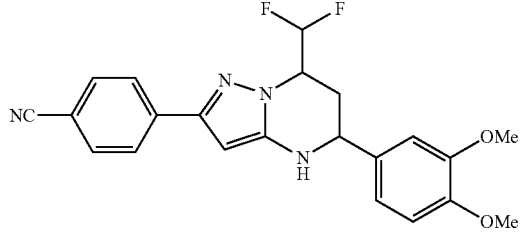

F-2

Compound F-2 (9.8 g, 99% yield) was obtained by NaBH$_4$ reduction of F-1 (9.8 g, 24.1 mmol) in a manner similar to that of compound A-8.
$^1$H NMR (400 MHz, METHANOL-d$_4$) δ ppm 2.17-2.39 (m, 2H) 3.83-3.85 (m, 3H) 3.85-3.88 (m, 3H) 4.47 (dd, J=10.87, 2.29 Hz, 1H) 4.66-4.81 (m, 1H) 5.86 (s, 1H) 6.60 (t, J=55.00 Hz, 1H) 6.97 (d, J=7.97 Hz, 1H) 7.01-7.07 (m, 1H) 7.10 (s, 1H) 7.66-7.76 (m, 2H) 7.91 (d, J=8.13 Hz, 2H). MS (M+H$^+$) 411.7.

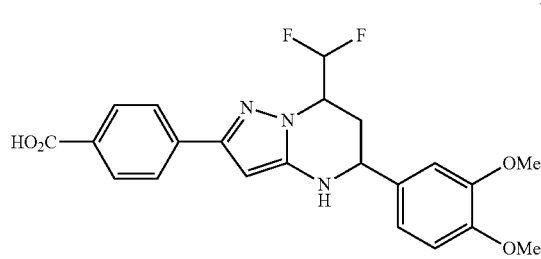

F-3

Compound F-3 (9.4 g, 100% yield) was obtained by hydrolysis of F-1 (8.94 g, 21.8 mmol) using aq. NaOH in a manner similar to that of compound A-9.
$^1$H NMR (400 MHz, METHANOL-d$_4$) δ ppm 2.21-2.37 (m, 2H) 3.80-3.82 (m, 4H) 3.84 (s, 3H) 4.46 (dd, J=10.83, 2.56 Hz, 1H) 6.60 (t, J=55.00 Hz, 1H) 6.95 (d, J=8.28 Hz, 1H) 7.00-7.04 (m, 1H) 7.08 (d, J=1.91 Hz, 1H) 7.81 (m, J=8.35 Hz, 2H) 8.00 (m, J=8.39 Hz, 2H). MS (M+H$^+$) 431.4.

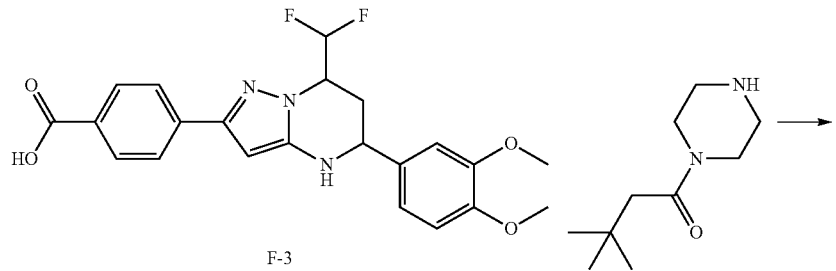

F-3

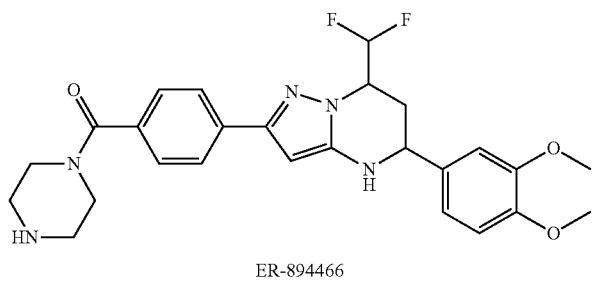

ER-894466

To a 5 mL screw-cap reaction tube was added compound F-3 4-(7-(difluoromethyl)-5-(3,4-dimethoxyphenyl)-4,5,6,7-tetrahydropyrazolo[1,5-a]pyrimidin-2-yl)benzoic acid (1.99 g, 4.64 mmol), tert-butyl piperazine-1-carboxylate (1.05 g, 5.61 mmol), HATU (2.14 g, 5.62 mmol), DMF (10.0 ml), and Hünig's Base (0.815 ml, 4.67 mmol). The reaction mixture was stirred at 30° C. overnight. The mixture was diluted with ethyl acetate, washed with water, washed with 0.1N aqueous hydrochloric acid, washed with aqueous sodium bicarbonate, washed with brine, dried over anhydrous magnesium sulfate, filtered, and concentrated in vacuo to give a brown solid. The material was purified by flash chromatography with a heptane:ethyl acetate gradient 0-90%. The fractions containing product were combined and concentrated in vacuo to give an off-white solid. The resultant solid was then taken up in ETHANOL (10.0 ml) and 4.0 M HCl in Dioxane (10.0 ml, 40.00 mmol) and the mixture stirred at RT for 1 h. The mixture was then concentrated in vacuo to give compound ER-894466 as a yellow solid (1.91 g, 77% yield).

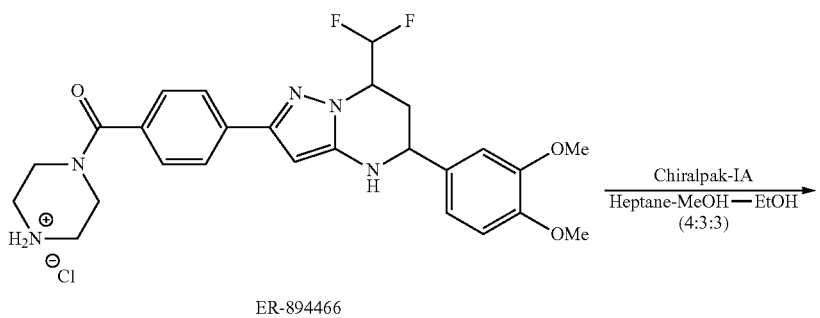

ER-894466

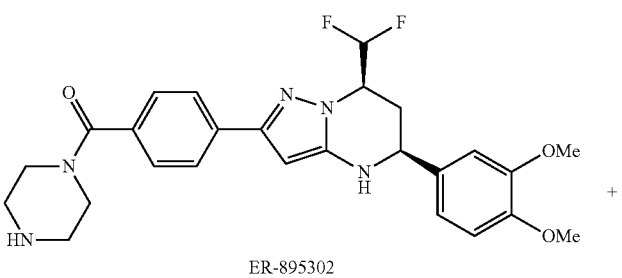

ER-895302

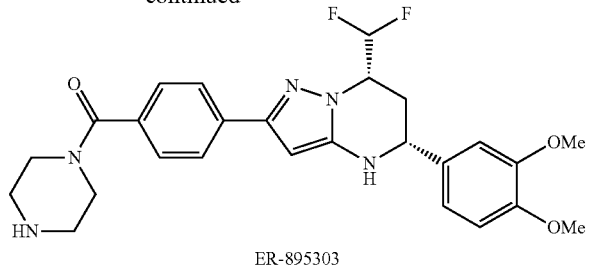
ER-895303

Chiral resolution of ER-894466 (1.91 g, 3.59 mmol) by HPLC in a manner similar to ER-890044 provided ER-895302 (538 mg, 56% yield, >95% ee) and ER-895303 (671 mg, 70% yield, >95% ee).

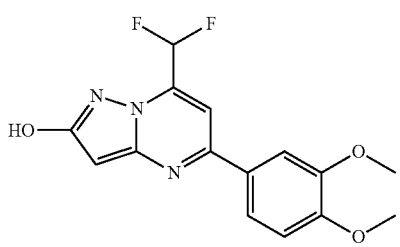
F-4

5-amino-1H-pyrazol-3-ol (9.91 g, 100 mmol) and 1-(3,4-dimethoxyphenyl)-4,4-difluorobutane-1,3-dione (25.8 g, 100 mmol) in a manner similar to that of compound A-14, gave compound F-4 7-(difluoromethyl)-5-(3,4-dimethoxyphenyl)pyrazolo[1,5-a]pyrimidin-2-ol (30.6 g, 95 mmol, 95% yield).

$^1$H NMR (400 MHz, METHANOL-$d_4$) δ ppm 3.87-3.90 (m, 3H) 3.90-3.93 (m, 3H) 5.94 (s, 1H) 7.06 (d, J=8.39 Hz, 1H) 7.29 (t, J=53.00 Hz, 1H) 7.47 (s, 1H) 7.67 (dd, J=8.43, 1.45 Hz, 1H) 7.77 (d, J=1.75 Hz, 1H). MS (M+H$^+$) 323.3.

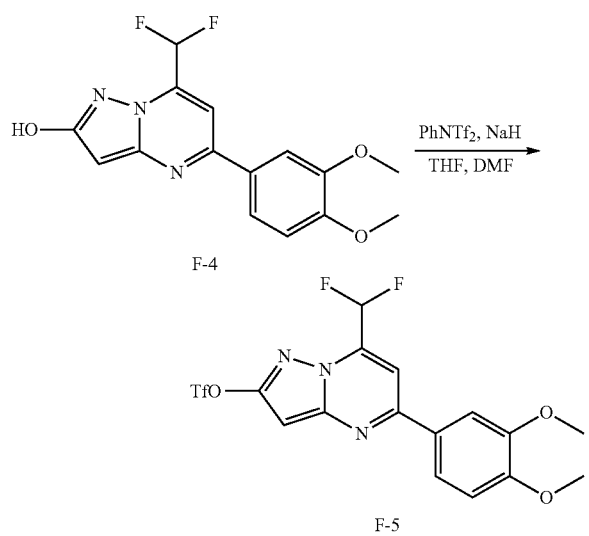

To a suspension of compound F-4 7-(difluoromethyl)-5-(3,4-dimethoxyphenyl)pyrazolo[1,5-a]pyrimidin-2-ol (3.21 g, 9.99 mmol) in DMF (5.00 ml) and THF (25.0 ml) at 0° C. was added sodium hydride (0.480 g, 11.99 mmol) in small portions. The mixture was stirred at 0° C. for 30 min 1,1,1-Trifluoro-N-phenyl-N-(trifluoromethyl)sulfonyl methanesulfonamide (4.28 g, 11.99 mmol) was added in small portions and the mixture allowed to attain rt. After 1 h, the reaction mixture was poured into 0.1 N HCl solution giving rise to a white ppt, which was filtered and washed with water. The crude product was suspended in IPA, heated to ~70° C. and cooled to rt. The white ppt obtained was washed with additional IPA, and dried under reduced pressure to afford compound F-5 7-(difluoromethyl)-5-(3,4-dimethoxyphenyl)pyrazolo[1,5-a]pyrimidin-2-yl trifluoromethanesulfonate as a white solid (2.85 g, 6.29 mmol, 62.9% yield)

$^1$H NMR (400 MHz, METHANOL-$d_4$) δ ppm 3.89 (s, 3H) 3.92 (s, 3H) 6.70 (s, 1H) 7.07 (d, J=8.50 Hz, 1H) 7.17-7.27 (m, 2H) 7.29-7.38 (m, 1H) 7.78 (dd, J=8.51, 2.14 Hz, 1H) 7.82-7.89 (m, 2H). MS (M+H$^+$) 454.4.

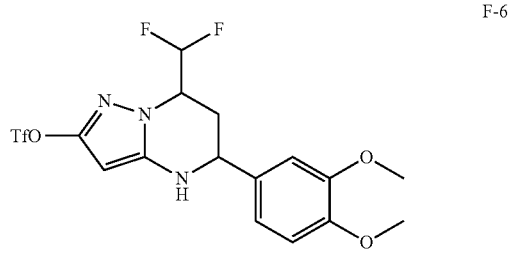 [SMILES: COc1ccc(C2CC(C(F)F)n3nc(OS(=O)(=O)C(F)(F)F)cc3N2)cc1OC]
F-6

Compound F-6 (27.2 g, 77% yield) was obtained by NaBH4 reduction of compound F-5 (35.0 g, 77.2 mmol) in a manner similar to that of compound A-16.

$^1$H NMR (400 MHz, METHANOL-$d_4$) δ ppm 2.14-2.32 (m, 2H) 3.79 (s, 3H) 3.81 (s, 3H) 4.44 (dd, J=11.06, 2.67 Hz, 1H) 4.53-4.66 (m, 1H) 5.28 (s, 1H) 6.40 (t, J=2.49 Hz, 1H) 6.91-6.94 (m, 1H) 6.96-7.00 (m, 1H) 7.03 (d, J=1.94 Hz, 1H). MS (M+H$^+$) 458.1.

Example ER-895088-01 was prepared from compound ER-895305 (25.0 mg, 0.058 mmol) and commercially available (S)-tert-butyl 3-methylpiperazine-1-carboxylate (35.2 mg, 0.177 mmol) in a manner similar to that of example ER-894463. Purification by LCMS, using HPLC condition III, afforded the desired product (9.3 mg, 29%).

Example ER-895116 was prepared from compound ER-895305 (25.0 mg, 0.058 mmol) and commercially available (R)-tert-butyl pyrrolidin-3-ylcarbamate (36.5 mg, 0.196 mmol) in a manner similar to that of example ER-894463. Purification by LCMS, using HPLC condition III, afforded the desired product (16 mg, 52%).

Example ER-895089 was prepared from compound ER-895305 (25.0 mg, 0.058 mmol) and commercially available (S)-tert-butyl pyrrolidin-3-ylcarbamate (36.7 mg, 0.197 mmol) in a manner similar to that of example ER-894463. Purification by LCMS, using HPLC condition III, afforded the desired product (7.1 mg, 23%).

Example ER-895090 was prepared from compound ER-895305 (25.0 mg, 0.058 mmol) and commercially available (1S,4S)-tert-butyl 2,5-diazabicyclo[2.2.1]heptane-2-carboxylate (38.6 mg, 0.196 mmol) in a manner similar to that of example ER-894463. Purification by LCMS, using HPLC condition III, afforded the desired product (18.1 mg, 57%).

Example ER-895115 was prepared from compound ER-895305 (25.6 mg, 0.060 mmol) and commercially available (S)-tert-butyl 3-aminopyrrolidine-1-carboxylate (31.5 mg, 0.169 mmol) in a manner similar to that of example ER-894463. Purification by LCMS, using HPLC condition III, afforded the desired product (3.5 mg, 11%).

Example ER-895745 was prepared from compound ER-895305 (26.2 mg, 0.061 mmol) and commercially available tert-butyl hexahydropyrrolo[3,4-c]pyrrole-2(1H)-carboxylate (32.9 mg, 0.155 mmol) in a manner similar to that of example ER-894463. Purification by LCMS, using HPLC condition III, afforded the desired product (18.1 mg, 53%).

Example ER-895091-01 was prepared from compound 4-(7-(difluoromethyl)-5-(3,4-dimethoxyphenyl)-4,5,6,7-tetrahydropyrazolo[1,5-a]pyrimidin-2-yl)-2-fluorobenzoic acid (25.0 mg, 0.056 mmol) and commercially available tert-butyl piperazine-1-carboxylate (21.0 mg, 0.113 mmol) in a manner similar to that of example ER-894463. Purification by LCMS, using HPLC condition III, afforded the desired product (2.5 mg, 8%).

Example ER-895092 was prepared from compound 4-(7-(difluoromethyl)-5-(3,4-dimethoxyphenyl)-4,5,6,7-tetrahydropyrazolo[1,5-a]pyrimidin-2-yl)-2-fluorobenzoic acid (25.0 mg, 0.056 mmol) and commercially available tert-butyl 4-aminopiperidine-1-carboxylate (22.0 mg, 0.110 mmol) in a manner similar to that of example ER-894463. Purification by LCMS, using HPLC condition III, afforded the desired product (5.2 mg, 16%).

Example ER-895093 was prepared from compound 4-(7-(difluoromethyl)-5-(3,4-dimethoxyphenyl)-4,5,6,7-tetrahydropyrazolo[1,5-a]pyrimidin-2-yl)-2-fluorobenzoic acid (25.0 mg, 0.056 mmol) and commercially available (S)-tert-butyl 3-aminopiperidine-1-carboxylate (22.0 mg, 0.110 mmol) in a manner similar to that of example ER-894463. Purification by LCMS, using HPLC condition III, afforded the desired product (10.3 mg, 32%).

Example ER-895094 was prepared from compound 4-(7-(difluoromethyl)-5-(3,4-dimethoxyphenyl)-4,5,6,7-tetrahydropyrazolo[1,5-a]pyrimidin-2-yl)-2-fluorobenzoic acid (25.0 mg, 0.056 mmol) and commercially available (R)-tert-butyl 3-aminopiperidine-1-carboxylate (22.0 mg, 0.110 mmol) in a manner similar to that of example ER-894463. Purification by LCMS, using HPLC condition III, afforded the desired product (7.4 mg, 23%).

Example ER-895096 was prepared from compound 4-(7-(difluoromethyl)-5-(3,4-dimethoxyphenyl)-4,5,6,7-tetrahydropyrazolo[1,5-a]pyrimidin-2-yl)-2-fluorobenzoic acid (25.0 mg, 0.056 mmol) and commercially available (2S,5R)-tert-butyl 2,5-dimethylpiperazine-1-carboxylate (24.0 mg, 0.113 mmol) in a manner similar to that of example ER-894463. Purification by LCMS, using HPLC condition III, afforded the desired product (13.9 mg, 43%).

Example ER-895097 was prepared from compound 4-(7-(difluoromethyl)-5-(3,4-dimethoxyphenyl)-4,5,6,7-tetrahydropyrazolo[1,5-a]pyrimidin-2-yl)-2-fluorobenzoic acid (25.0 mg, 0.056 mmol) and commercially available (R)-tert-butyl 3-aminopyrrolidine-1-carboxylate (21.0 mg, 0.113 mmol) in a manner similar to that of example ER-894463. Purification by LCMS, using HPLC condition III, afforded the desired product (17.3 mg, 56%).

Example ER-895098 was prepared from compound 4-(7-(difluoromethyl)-5-(3,4-dimethoxyphenyl)-4,5,6,7-tetrahydropyrazolo[1,5-a]pyrimidin-2-yl)-2-fluorobenzoic acid (25.0 mg, 0.056 mmol) and commercially available (S)-tert-butyl 3-aminopyrrolidine-1-carboxylate (21.0 mg, 0.113 mmol) in a manner similar to that of example ER-894463. Purification by LCMS, using HPLC condition III, afforded the desired product (18.5 mg, 60%).

Example ER-895101 was prepared from compound 4-(7-(difluoromethyl)-5-(3,4-dimethoxyphenyl)-4,5,6,7-tetrahydropyrazolo[1,5-a]pyrimidin-2-yl)-2-fluorobenzoic acid (25.0 mg, 0.056 mmol) and commercially available (1S,4S)-tert-butyl 2,5-diazabicyclo[2.2.1]heptane-2-carboxylate (22.0 mg, 0.112 mmol) in a manner similar to that of example ER-894463. Purification by LCMS, using HPLC condition III, afforded the desired product (9 mg, 28%).

Example ER-895099 was prepared from compound 4-(7-(difluoromethyl)-5-(3,4-dimethoxyphenyl)-4,5,6,7-tetrahydropyrazolo[1,5-a]pyrimidin-2-yl)-2-fluorobenzoic acid (25.0 mg, 0.056 mmol) and commercially available tert-butyl 3-aminoazetidine-1-carboxylate (19.0 mg, 0.110 mmol) in a manner similar to that of example ER-895080. Purification by LCMS, using HPLC condition III, afforded the desired product (14.1 mg, 41%).

Example ER-895102 was prepared from compound 4-(7-(difluoromethyl)-5-(3,4-dimethoxyphenyl)-4,5,6,7-tetrahydropyrazolo[1,5-a]pyrimidin-2-yl)-3-fluorobenzoic acid (25.0 mg, 0.056 mmol) and commercially available tert-butyl piperazine-1-carboxylate (21.0 mg, 0.113 mmol) in a manner similar to that of example ER-894463. Purification by LCMS, using HPLC condition III, afforded the desired product (17.2 mg, 56%).

Example ER-895104 was prepared from compound 4-(7-(difluoromethyl)-5-(3,4-dimethoxyphenyl)-4,5,6,7-tetrahydropyrazolo[1,5-a]pyrimidin-2-yl)-3-fluorobenzoic acid (25.0 mg, 0.056 mmol) and commercially available (S)-tert-butyl 3-aminopiperidine-1-carboxylate (22.0 mg, 0.110 mmol) in a manner similar to that of example ER-894463. Purification by LCMS, using HPLC condition III, afforded the desired product (17.1 mg, 54%).

Example ER-89510 was prepared from compound 4-(7-(difluoromethyl)-5-(3,4-dimethoxyphenyl)-4,5,6,7-tetrahydropyrazolo[1,5-a]pyrimidin-2-yl)-3-fluorobenzoic acid (25.0 mg, 0.056 mmol) and commercially available (R)-tert-butyl 3-aminopiperidine-1-carboxylate (22.0 mg, 0.110 mmol) in a manner similar to that of example ER-894463. Purification by LCMS, using HPLC condition III, afforded the desired product (15.8 mg, 50%).

Example ER-895106 was prepared from compound 4-(7-(difluoromethyl)-5-(3,4-dimethoxyphenyl)-4,5,6,7-tetrahydropyrazolo[1,5-a]pyrimidin-2-yl)-3-fluorobenzoic acid (25.0 mg, 0.056 mmol) and commercially available (S)-tert-butyl 3-methylpiperazine-1-carboxylate (22.0 mg, 0.110 mmol) in a manner similar to that of example ER-894463. Purification by LCMS, using HPLC condition III, afforded the desired product (14.9 mg, 47%).

Example ER-895107 was prepared from compound 4-(7-(difluoromethyl)-5-(3,4-dimethoxyphenyl)-4,5,6,7-tetrahydropyrazolo[1,5-a]pyrimidin-2-yl)-3-fluorobenzoic acid (25.0 mg, 0.056 mmol) and commercially available (2S,5R)-tert-butyl 2,5-dimethylpiperazine-1-carboxylate (24.0 mg, 0.112 mmol) in a manner similar to that of example ER-894463. Purification by LCMS, using HPLC condition III, afforded the desired product (14.2 mg, 44%).

Example ER-895109 was prepared from compound 4-(7-(difluoromethyl)-5-(3,4-dimethoxyphenyl)-4,5,6,7-tetrahydropyrazolo[1,5-a]pyrimidin-2-yl)-3-fluorobenzoic acid (25.0 mg, 0.056 mmol) and commercially available (S)-tert-butyl 3-aminopyrrolidine-1-carboxylate (21.0 mg, 0.113 mmol) in a manner similar to that of example ER-894463. Purification by LCMS, using HPLC condition III, afforded the desired product (17.7 mg, 57%).

Example ER-895112 was prepared from compound 4-(7-(difluoromethyl)-5-(3,4-dimethoxyphenyl)-4,5,6,7-tetrahydropyrazolo[1,5-a]pyrimidin-2-yl)-3-fluorobenzoic acid (25.0 mg, 0.056 mmol) and commercially available (1S,4S)-tert-butyl 2,5-diazabicyclo[2.2.1]heptane-2-carboxylate (22.0 mg, 0.111 mmol) in a manner similar to that of example ER-894463. Purification by LCMS, using HPLC condition III, afforded the desired product (14.4 mg, 46%).

Example ER-895111 was prepared from compound 4-(7-(difluoromethyl)-5-(3,4-dimethoxyphenyl)-4,5,6,7-tetrahydropyrazolo[1,5-a]pyrimidin-2-yl)-3-fluorobenzoic acid (25.0 mg, 0.056 mmol) and commercially available tert-butyl 2,6-diazaspiro[3.3]heptane-2-carboxylate (22.0 mg, 0.111 mmol) in a manner similar to that of example ER-895080. Purification by LCMS, using HPLC condition III, afforded the desired product (22.7 mg, 63%).

Example ER-895731 was prepared from compound 3-(7-(difluoromethyl)-5-(3,4-dimethoxyphenyl)-4,5,6,7-tetrahydropyrazolo[1,5-a]pyrimidin-2-yl)benzoic acid (25.0 mg, 0.058 mmol) and commercially available tert-butyl piperazine-1-carboxylate (32.8 mg, 0.176 mmol) in a manner similar to that of example ER-894463. Purification by LCMS, using HPLC condition III, afforded the desired product (22.1 mg, 70%).

Example ER-895732 was prepared from compound 3-(7-(difluoromethyl)-5-(3,4-dimethoxyphenyl)-4,5,6,7-tetrahydropyrazolo[1,5-a]pyrimidin-2-yl)benzoic acid (25.0 mg, 0.058 mmol) and commercially available tert-butyl 4-aminopiperidine-1-carboxylate (31.0 mg, 0.155 mmol) in a manner similar to that of example ER-894463. Purification by LCMS, using HPLC condition III, afforded the desired product (22 mg, 70%).

Example ER-895733 was prepared from compound 3-(7-(difluoromethyl)-5-(3,4-dimethoxyphenyl)-4,5,6,7-tetrahydropyrazolo[1,5-a]pyrimidin-2-yl)benzoic acid (25.0 mg, 0.058 mmol) and commercially available (S)-tert-butyl 3-aminopiperidine-1-carboxylate (34.0 mg, 0.170 mmol) in a manner similar to that of example ER-894463. Purification by LCMS, using HPLC condition III, afforded the desired product (26.5 mg, 85%).

Example ER-895734 was prepared from compound 3-(7-(difluoromethyl)-5-(3,4-dimethoxyphenyl)-4,5,6,7-tetrahydropyrazolo[1,5-a]pyrimidin-2-yl)benzoic acid (25.0 mg, 0.058 mmol) and commercially available (R)-tert-butyl 3-aminopiperidine-1-carboxylate (36.3 mg, 0.181 mmol) in a manner similar to that of example ER-894463. Purification by LCMS, using HPLC condition III, afforded the desired product (23.4 mg, 75%).

Example ER-895739 was prepared from compound 3-(7-(difluoromethyl)-5-(3,4-dimethoxyphenyl)-4,5,6,7-tetrahydropyrazolo[1,5-a]pyrimidin-2-yl)benzoic acid (25.0 mg, 0.058 mmol) and commercially available (S)-tert-butyl 3-aminopyrrolidine-1-carboxylate (37.7 mg, 0.202 mmol) in a manner similar to that of example ER-894463. Purification by LCMS, using HPLC condition III, afforded the desired product (22.9 mg, 73%).

Example ER-895740 was prepared from compound 3-(7-(difluoromethyl)-5-(3,4-dimethoxyphenyl)-4,5,6,7-tetrahydropyrazolo[1,5-a]pyrimidin-2-yl)benzoic acid (25.0 mg, 0.058 mmol) and commercially available (R)-tert-butyl 3-aminopyrrolidine-1-carboxylate (34.8 mg, 0.187 mmol) in a manner similar to that of example ER-894463. Purification by LCMS, using HPLC condition III, afforded the desired product (23.1 mg, 73%).

Example ER-895744 was prepared from compound 3-(7-(difluoromethyl)-5-(3,4-dimethoxyphenyl)-4,5,6,7-tetrahydropyrazolo[1,5-a]pyrimidin-2-yl)benzoic acid (25.0 mg, 0.058 mmol) and commercially available tert-butyl hexahydropyrrolo[3,4-c]pyrrole-2(1H)-carboxylate (26.9 mg, 0.127 mmol) in a manner similar to that of example ER-894463. Purification by LCMS, using HPLC condition III, afforded the desired product (26.5 mg, 82%).

Example ER-895741 was prepared from compound 3-(7-(difluoromethyl)-5-(3,4-dimethoxyphenyl)-4,5,6,7-tetrahydropyrazolo[1,5-a]pyrimidin-2-yl)benzoic acid (25.0 mg, 0.058 mmol) and commercially available tert-butyl 3-aminoazetidine-1-carboxylate (30.1 mg, 0.175 mmol) in a manner similar to that of example ER-895080. Purification by LCMS, using HPLC condition III, afforded the desired product (5.5 mg, 16%).

Example ER-895718 was prepared from compound 4-(7-(difluoromethyl)-5-(3,4-dimethoxyphenyl)-4,5,6,7-tetrahydropyrazolo[1,5-a]pyrimidin-2-yl)-3-methylbenzoic acid (25.0 mg, 0.056 mmol) and commercially available tert-butyl 4-aminopiperidine-1-carboxylate (45.4 mg, 0.227 mmol) in a manner similar to that of example ER-894463. Purification by LCMS, using HPLC condition III, afforded the desired product (21.4 mg, 68%).

Example ER-895719 was prepared from compound 4-(7-(difluoromethyl)-5-(3,4-dimethoxyphenyl)-4,5,6,7-tetrahydropyrazolo[1,5-a]pyrimidin-2-yl)-3-methylbenzoic acid (25.0 mg, 0.056 mmol) and commercially available (S)-tert-butyl 3-aminopiperidine-1-carboxylate (29.8 mg, 0.149 mmol) in a manner similar to that of example ER-894463. Purification by LCMS, using HPLC condition III, afforded the desired product (21.6 mg, 69%).

Example ER-895720 was prepared from compound 4-(7-(difluoromethyl)-5-(3,4-dimethoxyphenyl)-4,5,6,7-tetrahydropyrazolo[1,5-a]pyrimidin-2-yl)-3-methylbenzoic acid (25.0 mg, 0.056 mmol) and commercially available (R)-tert-butyl 3-aminopiperidine-1-carboxylate (28.6 mg, 0.143 mmol) in a manner similar to that of example ER-894463. Purification by LCMS, using HPLC condition III, afforded the desired product (21.7 mg, 69%).

Example ER-895721 was prepared from compound 4-(7-(difluoromethyl)-5-(3,4-dimethoxyphenyl)-4,5,6,7-tetrahydropyrazolo[1,5-a]pyrimidin-2-yl)-3-methylbenzoic acid (25.0 mg, 0.056 mmol) and commercially available (S)-tert-butyl 3-methylpiperazine-1-carboxylate (31.1 mg, 0.155 mmol) in a manner similar to that of example ER-894463. Purification by LCMS, using HPLC condition III, afforded the desired product (20.2 mg, 64%).

Example ER-895722 was prepared from compound 4-(7-(difluoromethyl)-5-(3,4-dimethoxyphenyl)-4,5,6,7-tetrahydropyrazolo[1,5-a]pyrimidin-2-yl)-3-methylbenzoic acid (25.0 mg, 0.056 mmol) and commercially available (R)-tert-butyl 3-methylpiperazine-1-carboxylate (41.2 mg, 0.206 mmol) in a manner similar to that of example ER-894463. Purification by LCMS, using HPLC condition III, afforded the desired product (21 mg, 67%).

Example ER-895723 was prepared from compound 4-(7-(difluoromethyl)-5-(3,4-dimethoxyphenyl)-4,5,6,7-tetrahydropyrazolo[1,5-a]pyrimidin-2-yl)-3-methylbenzoic acid (25.0 mg, 0.056 mmol) and commercially available (2S,5R)-tert-butyl 2,5-dimethylpiperazine-1-carboxylate (34.1 mg, 0.159 mmol) in a manner similar to that of example ER-894463. Purification by LCMS, using HPLC condition III, afforded the desired product (20.5 mg, 64%).

Example ER-895725 was prepared from compound 4-(7-(difluoromethyl)-5-(3,4-dimethoxyphenyl)-4,5,6,7-tetrahydropyrazolo[1,5-a]pyrimidin-2-yl)-3-methylbenzoic acid (25.0 mg, 0.056 mmol) and commercially available (S)-tert-butyl 3-aminopyrrolidine-1-carboxylate (43.7 mg, 0.235 mmol) in a manner similar to that of example ER-894463. Purification by LCMS, using HPLC condition III, afforded the desired product (19.8 mg, 65%).

Example ER-895726—was prepared from compound 4-(7-(difluoromethyl)-5-(3,4-dimethoxyphenyl)-4,5,6,7-tetrahydropyrazolo[1,5-a]pyrimidin-2-yl)-3-methylbenzoic acid (25.0 mg, 0.056 mmol) and commercially available (R)-tert-butyl 3-aminopyrrolidine-1-carboxylate (31.0 mg, 0.167 mmol) in a manner similar to that of example ER-894463. Purification by LCMS, using HPLC condition III, afforded the desired product (20.6 mg, 67%).

Example ER-895729 was prepared from compound 4-(7-(difluoromethyl)-5-(3,4-dimethoxyphenyl)-4,5,6,7-tetrahydropyrazolo[1,5-a]pyrimidin-2-yl)-3-methylbenzoic acid (25.0 mg, 0.056 mmol) and commercially available (1S,4S)-tert-butyl 2,5-diazabicyclo[2.2.1]heptane-2-carboxylate (29.9 mg, 0.151 mmol) in a manner similar to that of example ER-894463. Purification by LCMS, using HPLC condition III, afforded the desired product (19.6 mg, 62%).

Example ER-895730 was prepared from compound 4-(7-(difluoromethyl)-5-(3,4-dimethoxyphenyl)-4,5,6,7-tetrahydropyrazolo[1,5-a]pyrimidin-2-yl)-3-methylbenzoic acid (25.0 mg, 0.056 mmol) and commercially available tert-butyl hexahydropyrrolo[3,4-c]pyrrole-2(1H)-carboxylate (28.9 mg, 0.136 mmol) in a manner similar to that of example ER-894463. Purification by LCMS, using HPLC condition III, afforded the desired product (23.9 mg, 74%).

Example ER-895755 was prepared from compound 4-(7-(difluoromethyl)-5-(3,4-dimethoxyphenyl)-4,5,6,7-tetrahydropyrazolo[1,5-a]pyrimidin-2-yl)-3-methylbenzoic acid (25.5 mg, 0.058 mmol) and commercially available tert-butyl piperazine-1-carboxylate (27.9 mg, 0.150 mmol) in a manner similar to that of example ER-894463. Purification by LCMS, using HPLC condition III, afforded the desired product (28.3 mg, 89%).

Example ER-895727 was prepared from compound 4-(7-(difluoromethyl)-5-(3,4-dimethoxyphenyl)-4,5,6,7-tetrahydropyrazolo[1,5-a]pyrimidin-2-yl)-3-methylbenzoic acid (25.0 mg, 0.056 mmol) and commercially available tert-butyl 3-aminoazetidine-1-carboxylate (37.0 mg, 0.215 mmol) in a manner similar to that of example ER-895080. Purification by LCMS, using HPLC condition III, afforded the desired product (22.3 mg, 65%).

Example ER-896059 was prepared from compound ER-895435 (10.0 mg, 0.023 mmol) and commercially available tert-butyl 4-aminopiperidine-1-carboxylate (17.8 mg, 0.089 mmol) in a manner similar to that of example ER-894463. Purification by LCMS, using HPLC condition III, afforded the desired product (11.2 mg, 87%).

Example ER-896060 was prepared from compound ER-895435 (25.0 mg, 0.056 mmol) and commercially available (S)-tert-butyl 3-aminopiperidine-1-carboxylate (19.3 mg, 0.096 mmol) in a manner similar to that of example ER-894463. Purification by LCMS, using HPLC condition III, afforded the desired product (12.3 mg, 95%).

Example ER-896061 was prepared from compound ER-895435 (25.0 mg, 0.056 mmol) and commercially available (R)-tert-butyl 3-aminopiperidine-1-carboxylate (16.9 mg, 0.084 mmol) in a manner similar to that of example ER-894463. Purification by LCMS, using HPLC condition III, afforded the desired product (12.2 mg, 94%).

Example ER-896062 was prepared from compound ER-895435 (25.0 mg, 0.056 mmol) and commercially available (S)-tert-butyl 3-methylpiperazine-1-carboxylate (23.9 mg, 0.119 mmol) in a manner similar to that of example ER-894463. Purification by LCMS, using HPLC condition III, afforded the desired product (10.7 mg, 83%).

Example ER-896063 was prepared from compound ER-895435 (25.0 mg, 0.056 mmol) and commercially available (R)-tert-butyl 3-methylpiperazine-1-carboxylate (20.5 mg, 0.102 mmol) in a manner similar to that of example ER-894463. Purification by LCMS, using HPLC condition III, afforded the desired product (10.9 mg, 84%).

Example ER-896064 was prepared from compound ER-895435 (25.0 mg, 0.056 mmol) and commercially available (2S,5R)-tert-butyl 2,5-dimethylpiperazine-1-carboxylate (17.2 mg, 0.080 mmol) in a manner similar to that of example ER-894463. Purification by LCMS, using HPLC condition III, afforded the desired product (10.3 mg, 78%).

Example ER-896067 was prepared from compound ER-895435 (25.0 mg, 0.056 mmol) and commercially available (1S,4S)-tert-butyl 2,5-diazabicyclo[2.2.1]heptane-2-carboxylate (15.2 mg, 0.077 mmol) in a manner similar to that of example ER-894463. Purification by LCMS, using HPLC condition III, afforded the desired product (9.9 mg, 77%).

Example ER-896068 was prepared from compound ER-895435 (25.0 mg, 0.056 mmol) and commercially available tert-butyl hexahydropyrrolo[3,4-c]pyrrole-2(1H)-carboxylate (17.3 mg, 0.081 mmol) in a manner similar to that of example ER-894463. Purification by LCMS, using HPLC condition III, afforded the desired product (12.3 mg, 93%).

Example ER-896071 was prepared from compound ER-895435 (25.9 mg, 0.060 mmol) and commercially available tert-butyl 3-(aminomethyl)azetidine-1-carboxylate (30.4 mg, 0.163 mmol) in a manner similar to that of example ER-895080. Purification by LCMS, using HPLC condition III, afforded the desired product (18.6 mg, 51%).

Synthetic Examples—Section G

Preparation of ER-893993

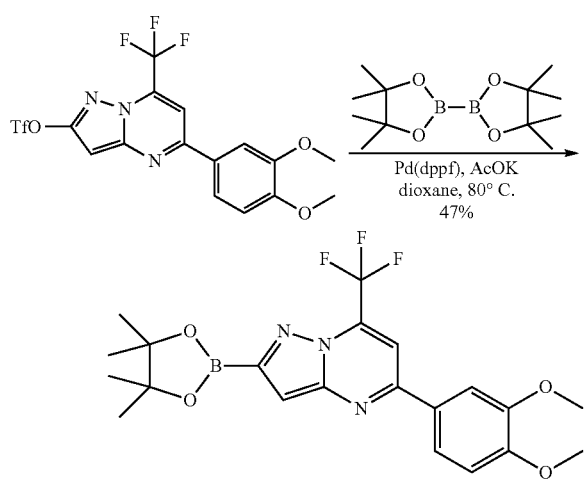

A 500 mL flask was charged with 4,4,4',4',5,5,5',5'-octamethyl-2,2'-bi(1,3,2-dioxaborolane) (10.78 g, 42 mmol), 5-(3,4-dimethoxyphenyl)-7-(trifluoromethyl)pyrazolo[1,5-a]pyrimidin-2-yl trifluoromethanesulfonate (10.0 g, 21 mmol), Potassium acetate (10.41 g, 106 mmol), and 1,4-dioxane (100 ml). The reaction mixture was degassed with nitrogen for 15 minutes. 1,1'-Bis(diphenylphosphino)ferrocene-palladium(II) dichloride dichloromethane complex (4.33 g, 5.3 mmol) was added and the mixture was sealed and stirred for 3 hours at 80° C. The reaction mixture was cooled at room temperature and was partitioned between EtOAc (1000 mL) and sat. NaHCO3 solution (200 mL) Phases were separated and the aqueous was back extract 2× with EtOAc (200 mL) The combined organic layers were washed with brine (200 mL) The organic layer was dried with anhydrous sodium sulfate, filtered and concentrated. Crude material was dissolved in EtOAc (500 mL), Heptane (500 mL) was added and the black solid impurity was removed by filtration. The filtrate containing the desired product was concentrated under reduced pressure, was suspended in 150 mL of IPA, was heated at 70° C. for 30 minutes and then cooled at room temperature. The green precipitate was filtered off, rinsed with IPA and dried on vacuum pump. 5-(3,4-dimethoxyphenyl)-2-(4,4,5,5-tetramethyl-1,3,2-dioxaborolan-2-yl)-7-(trifluoromethyl)pyrazolo[1,5-a]pyrimidine (4.50 g, 10.02 mmol, 47.2% yield)

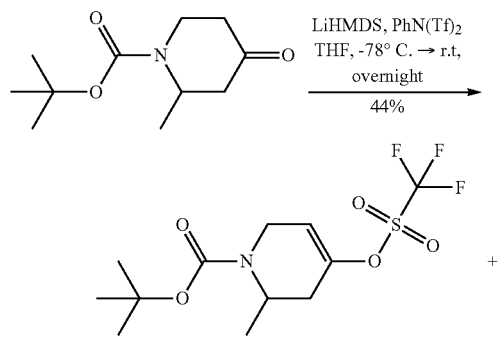

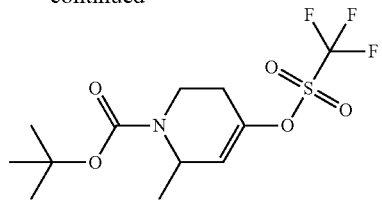

In a 25 mL flask and under an atmosphere of nitrogen, to a solution of tert-butyl 2-methyl-4-oxopiperidine-1-carboxylate (558 mg, 2.6 mmol) and 1,1,1-Trifluoro-N-phenyl-N-(trifluoromethyl)sulfonyl methanesulfonamide (1869 mg, 5.2 mmol) in anhydrous THF (5 mL) at −78° C. was added 1.0M LiHMDS in THF (5.23 mL, 5.2 mmol). The mixture was stirred overnight while slowly being allowed to warm at room temperature. The reaction was quenched with saturated NaHCO3. Then the mixture was extracted 3× with MTBE. The combined organic layers were dried with sodium sulfate, filtered and concentrated. A mixture of regioisomers (tert-butyl 6-methyl-4-(((trifluoromethyl)sulfonyl)oxy)-5,6-dihydropyridine-1(2H)-carboxylate and tert-butyl 2-methyl-4-(((trifluoromethyl)sulfonyl)oxy)-5,6-dihydropyridine-1(2H)-carboxylate) was obtained as a pale yellow oil (397 mg, 44% yield).

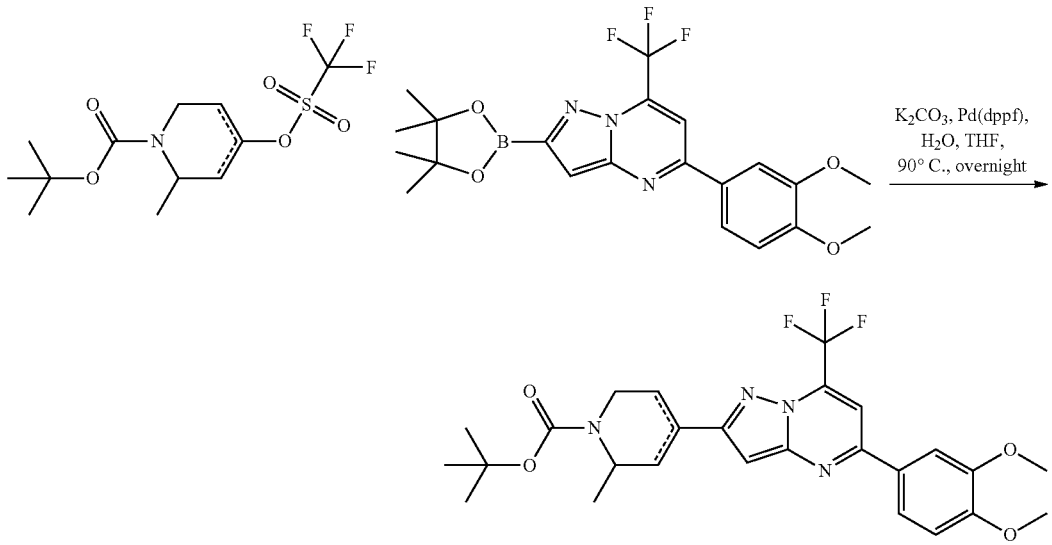

A 5-10 mL microwave vial was charged with 5-(3,4-dimethoxyphenyl)-2-(4,4,5,5-tetramethyl-1,3,2-dioxaborolan-2-yl)-7-(trifluoromethyl)pyrazolo[1,5-a]pyrimidine (650 mg, 1.45 mmol), tert-butyl 2-methyl-4-(((trifluoromethyl)sulfonyl)oxy)-5,6-dihydropyridine-1(2H)-carboxylate (mixture with tert-butyl 6-methyl-4-(((trifluoromethyl)sulfonyl)oxy)-5,6-dihydropyridine-1(2H)-carboxylate, total is 396 mg, 1.15 mmol), Potassium carbonate (792 mg, 5.7 mmol), Water (2.0 ml) and THF (4.5 ml). The reaction mixture was degassed with nitrogen for 15 minutes. 1,1'-Bis(diphenylphosphino)ferrocene-palladium(II) dichloride dichloromethane complex (234 mg, 0.29 mmol) was added and the mixture was sealed and stirred overnight at 90° C. The reaction mixture was cooled at room temperature and concentrated. The crude product was purified on silica-gel (Column Interchim 40 g, 30 µM) eluting with 12-100% EtOAc/Heptane. A mixture of regioisomers (tert-butyl 4-(5-(3,4-dimethoxyphenyl)-7-(trifluoromethyl)pyrazolo[1,5-a]pyrimidin-2-yl)-2-methyl-5,6-dihydropyridine-1(2H)-carboxylate and tert-butyl 4-(5-(3,4-dimethoxyphenyl)-7-

(trifluoromethyl)pyrazolo[1,5-a]pyrimidin-2-yl)-6-methyl-5,6-dihydropyridine-1(2H)-carboxylate) was obtained as a yellow solid (142 mg, 24% yield).

Synthesis of ER-896993

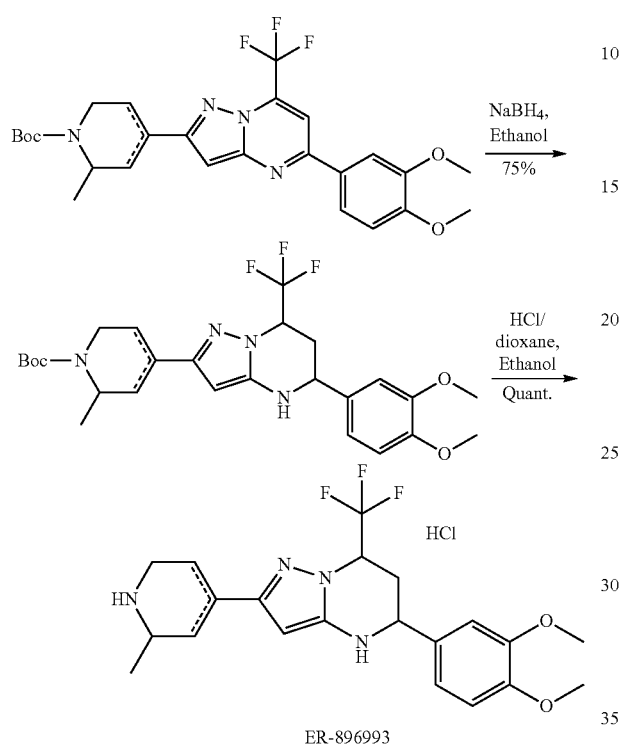

ER-896993

Sodium tetrahydroborate (10.94 mg, 0.29 mmol) was slowly added to a suspension of tert-butyl 4-(5-(3,4-dimethoxyphenyl)-7-(trifluoromethyl)pyrazolo[1,5-a]pyrimidin-2-yl)-2-methyl-5,6-dihydropyridine-1(2H)-carboxylate (Mixture with regioisomer tert-butyl 4-(5-(3,4-dimethoxyphenyl)-7-(trifluoromethyl)pyrazolo[1,5-a]pyrimidin-2-yl)-6-methyl-5,6-dihydropyridine-1(2H)-carboxylate, total is 50 mg, 0.096 mmol) in Ethanol (1.0 ml) at room temperature. The mixture was heated to 80° C. for 60 minutes. Ethyl acetate was added. The mixture was sequentially washed with an aqueous saturated solution of NH₄Cl and then brine. The organic layer was dried with anhydrous sodium sulfate, was filtered and was concentrated. The crude product was purified on silica-gel (Column Interchim 25 g, 30 µM) eluting with 12-100% EtOAc/Heptane. A mixture of regioisomers (tert-butyl 4-(5-(3,4-dimethoxyphenyl)-7-(trifluoromethyl)-4,5,6,7-tetrahydropyrazolo[1,5-a]pyrimidin-2-yl)-2-methyl-5,6-dihydropyridine-1(2H)-carboxylate and tert-butyl 4-(5-(3,4-dimethoxyphenyl)-7-(trifluoromethyl)-4,5,6,7-tetrahydropyrazolo[1,5-a]pyrimidin-2-yl)-6-methyl-5,6-dihydropyridine-1(2H)-carboxylate) was obtained as a white solid (38 mg, 75% yield).

Tert-butyl 4-(5-(3,4-dimethoxyphenyl)-7-(trifluoromethyl)-4,5,6,7-tetrahydropyrazolo[1,5-a]pyrimidin-2-yl)-2-methyl-5,6-dihydropyridine-1(2H)-carboxylate (Mixture with regioisomer tert-butyl 4-(5-(3,4-dimethoxyphenyl)-7-(trifluoromethyl)-4,5,6,7-tetrahydropyrazolo[1,5-a]pyrimidin-2-yl)-6-methyl-5,6-dihydropyridine-1(2H)-carboxylate, total is 34 mg, 0.065 mmol) was dissolved in Ethanol (0.5 ml) and 4.00M HCl in Dioxane (0.5 ml) and the mixture was stirred at 40° C. for 1 hour. 1 mL of toluene was added. The reaction mixture was concentrated.

The product was dried on vacuum pump to afford 29 mg of the final product as HCl salt (mixture of regioisomers 5-(3,4-dimethoxyphenyl)-2-(6-methyl-1,2,3,6-tetrahydropyridin-4-yl)-7-(trifluoromethyl)-4,5,6,7-tetrahydropyrazolo[1,5-a]pyrimidine hydrochloride and 5-(3,4-dimethoxyphenyl)-2-(2-methyl-1,2,3,6-tetrahydropyridin-4-yl)-7-(trifluoromethyl)-4,5,6,7-tetrahydropyrazolo[1,5-a]pyrimidine hydrochloride) (ER-896993).

Synthesis of ER-896994

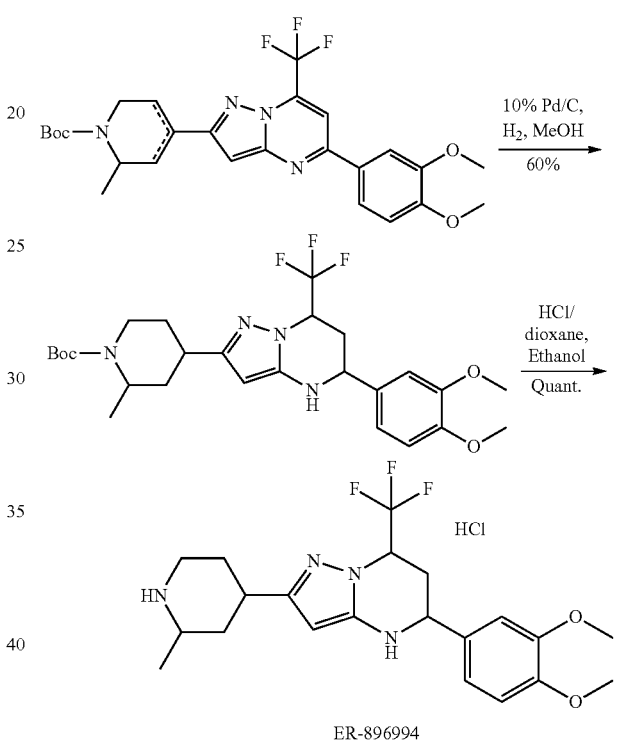

ER-896994

Tert-butyl 4-(5-(3,4-dimethoxyphenyl)-7-(trifluoromethyl)pyrazolo [1,5-a]pyrimidin-2-yl)-2-methyl-5,6-dihydropyridine-1(2H)-carboxylate (Mixture with regioisomer tert-butyl 4-(5-(3,4-dimethoxyphenyl)-7-(trifluoromethyl) pyrazolo[1,5-a]pyrimidin-2-yl)-6-methyl-5,6-dihydropyridine-1(2H)-carboxylate, total is 60 mg, 0.116 mmol) was dissolved in Methanol (2.5 ml). The solution was treated with Hydrogen for 2.5 hrs at room temperature using H-Cube (Full H2, 1 mL/min, small size (30 mm) 10% Palladium on Carbon CatCart). 1 mL Toluene was added. Solvent was concentrated. The crude product was purified on silica-gel (Column Interchim 25 g, 30 µM) eluting with 12-100% EtOAc/Heptane to afford tert-butyl 4-(5-(3,4-dimethoxyphenyl)-7-(trifluoromethyl)-4,5,6,7-tetrahydropyrazolo[1,5-a]pyrimidin-2-yl)-2-methylpiperidine-1-carboxylate (36 mg, 0.069 mmol, 59% yield) as a white solid.

Tert-butyl 4-(5-(3,4-dimethoxyphenyl)-7-(trifluoromethyl)-4,5,6,7-tetrahydropyrazolo[1,5-a]pyrimidin-2-yl)-2-methylpiperidine-1-carboxylate (29 mg, 0.055 mmol) was dissolved in Ethanol (0.5 ml) and 4.00M HCl in Dioxane (0.5 ml) and the mixture was stirred at 40° C. for 1 hour. 1 mL of toluene was added. The reaction mixture was concentrated. The product was dried on vacuum pump to afford 25 mg of the final product as HCl salt (5-(3,4-dimethoxyphenyl)-2-(2-methylpiperidin-4-yl)-7-(trifluoromethyl)-4,5,6,7-tetrahydropyrazolo[1,5-a]pyrimidine hydrochloride, ER-896994).

Example ER-897090

Example ER-897090 was prepared from 5-(3,4-dimethoxyphenyl)-2-(4,4,5,5-tetramethyl-1,3,2-dioxaborolan-2-yl)-7-(trifluoromethyl)pyrazolo[1,5-a]pyrimidine (507 mg, 1.129 mmol) and tert-butyl 4-(((trifluoromethyl)sulfonyl)oxy)-2,3,6,7-tetrahydro-1H-azepine-1-carboxylate (300 mg, 0.869 mmol) prepared from commercially available tert-butyl 4-oxoazepane-1-carboxylate in a manner similar to that of ER-896993 (Section G) except the deprotection step was carried out in a manner similar to that of ER-887084 (Section B) to afford ER-897090 (96 mg, 26% yield). LC-MS: Rt 1.49 min, (M+1)$^+$423.06 under condition II.

Compound ER-897090 (94 mg, 0.224 mmol) was resolved into its constituent enantiomers in a manner similar to that of ER-890044 (Section A) to afford one of the isomer ER-897212. (17 mg, 18% yield).

Example ER-897130 was prepared from 5-(3,4-dimethoxyphenyl)-2-(4,4,5,5-tetramethyl-1,3,2-dioxaborolan-2-yl)-7-(trifluoromethyl)pyrazolo[1,5-a]pyrimidine (493 mg, 1.097 mmol) and tert-butyl 3-(((trifluoromethyl)sulfonyl)oxy)-2,5-dihydro-1H-pyrrole-1-carboxylate (174 mg, 0.548 mmol) prepared from commercially available tert-butyl 3-oxopyrrolidine-1-carboxylate in a manner similar to that of ER-896993 (Section G) except the deprotection step was carried out in a manner similar to that of ER-887084 (Section B) to afford ER-897130 (68 mg, 31% yield).

Example ER-897142 was prepared from 5-(3,4-dimethoxyphenyl)-2-(4,4,5,5-tetramethyl-1,3,2-dioxaborolan-2-yl)-7-(trifluoromethyl)pyrazolo[1,5-a]pyrimidine (489 mg, 1.089 mmol) and 4-((tert-butoxycarbonyl)amino)cyclohex-1-en-1-yl trifluoromethanesulfonate (188 mg, 0.544 mmol) prepared from commercially available tert-butyl (4-oxocyclohexyl)carbamate in a manner similar to that of ER-896993 (Section G) except the deprotection step was carried out in a manner similar to that of ER-887084 (Section B) to afford ER-897142 (111 mg, 48% yield). (LC-MS: Rt 1.57 min, (M+1)$^+$423.06 under condition II)

Example ER-897364 and ER-897365

Compound ER-897090 (100 mg, 0.237 mmol) was resolved into its constituent enantiomers in a manner similar to that of ER-890044 (Section A) to afford ER-897364 (4 mg, 4% yield, >95% ee). and ER-897365 (6.4 mg, 6% yield, >95% ee).

Example ER-897547

Preparation of tert-butyl 3-methyl-4-oxopiperidine-1-carboxylate

A solution of 1-benzyl-3-methylpiperidin-4-one (1.63 g, 8.018 mmol) and di-tert-butyl dicarbonate (1.925 g, 8.82 mmol) in 50 ml of Methanol was hydrogenated using H-Cube (Controlled H2 at 50 bar, flow rate 1.0 ml/min) with Pd—C cartridge. The reaction mixture was recirculated for 12 hours. After washing the H-Cube thoroughly with Methanol, the solvent was evaporated and the resulting oil was purified by silica gel chromatography to afford the title compound (1.5 g, 88%).

Example ER-897547 was prepared from 5-(3,4-dimethoxyphenyl)-2-(4,4,5,5-tetramethyl-1,3,2-dioxaborolan-2-yl)-7-(trifluoromethyl)pyrazolo[1,5-a]pyrimidine (488 mg, 1.086 mmol) and tert-butyl 5-methyl-4-(((trifluoromethyl)sulfonyl)oxy)-5,6-dihydropyridine-1(2H)-carboxylate (250 mg, 0.724 mmol) prepared from tert-butyl 3-methyl-4-oxopiperidine-1-carboxylate in a manner similar to that of ER-896993 (Section G) except the deprotection step was carried out in a manner similar to that of ER-887084 (Section B) to afford ER-897547 (68 mg, 31% yield).

Example ER-897597 was prepared from 5-(3,4-dimethoxyphenyl)-2-(4,4,5,5-tetramethyl-1,3,2-dioxaborolan-2-yl)-7-(trifluoromethyl)pyrazolo[1,5-a]pyrimidine (475 mg, 1.058 mmol) and commercially available tert-butyl 4-(4-bromophenyl)piperidine-1-carboxylate (240 mg, 0.705 mmol) in a manner similar to that of ER-896993 (Section G) except the deprotection step was carried out in a manner similar to that of ER-887084 (Section B) to afford ER-897597 (32 mg, 9% yield). LC-MS: Rt 1.72 min, (M+1)$^+$486.95 under condition II.

Example ER-897814 and ER-897815

Compound ER-897597 (20 mg, 0.041 mmol) was resolved into its constituent enantiomers in a manner similar to that of ER-890044 (Section A) to afford ER-897814 (7 mg, 35% yield, >95% ee). and ER-897815 (3 mg, 15% yield, >95% ee).

Example ER-897728

Preparation of benzyl 9-oxo-3-azaspiro[5.5]undec-7-ene-3-carboxylate

Benzyl 4-formylpiperidine-1-carboxylate (5.17 g, 20.907 mmol) and p-Toluenesulfonic acid monohydrate (0.398 g, 2.091 mmol) were stirred in Benzene (30.0 ml, 334.136 mmol) at 70° C. But-3-en-2-one (3.76 ml, 41.813 mmol) was added and the reaction mixture was refluxed o/n while removing water with dean-stark trap. After cooling the reaction mixture to rt, sat. NaHCO3 soln. was added and the organic layer was dried over Na2SO4 and evaporated. The resulting oil was purified by Biotage (SiO2, 250 g, EtOAc/Hep 10% to 50%) to afford the title compound (3.58 g, 11.96 mmol, 57.2% yield).

Preparation of tert-butyl 9-oxo-3-azaspiro[5.5]undecane-3-carboxylate

A solution of benzyl 9-oxo-3-azaspiro[5.5]undec-7-ene-3-carboxylate (1.26 g, 4.209 mmol), di-tert-butyl dicarbonate (1.01 g, 4.63 mmol) and TEA (1.47 ml, 10.522 mmol) in 50 ml of Methanol was hydrogenated using H-Cube (Full H2, flow rate 1.0 ml/min) with Pd—C cartridge. The reaction mixture was recirculated for 5 hours. After washing the H-Cube thoroughly with Methanol, the solvent was evaporated and the resulting oil was purified by silica gel chromatography to afford the title compound (681 mg, 61%).

Example ER-897728 was prepared from 5-(3,4-dimethoxyphenyl)-2-(4,4,5,5-tetramethyl-1,3,2-dioxaborolan-2-yl)-7-(trifluoromethyl)pyrazolo[1,5-a]pyrimidine (489 mg, 1.089 mmol) and tert-butyl 9-(((trifluoromethyl)sulfonyl)oxy)-3-azaspiro[5.5]undec-8-ene-3-carboxylate (290 mg, 0.726 mmol) prepared from tert-butyl 9-oxo-3-azaspiro[5.5]undecane-3-carboxylate in a manner similar to that of ER-896993 (Section G) except the deprotection step was carried out in a manner similar to that of ER-887084

(Section B) to afford ER-897728 (91 mg, 26% yield). LC-MS: Rt 1.67 min, (M+1)⁺477.13 under condition II.

Example ER-897851

Compound ER-897728 (85 mg, 0.178 mmol) was resolved into its constituent enantiomers in a manner similar to that of ER-890044 (Section A) to afford one of the isomer ER-897851. (28 mg, 33% yield).

Example ER-890978 was prepared from compound G2 (600 mg, 1.34 mmol) and commercially available 4-bromo-2-chloropyridine in a manner similar to that of example ER-896993 to afford 2-(2-chloropyridin-4-yl)-5-(3,4-dimethoxyphenyl)-7-(trifluoromethyl)pyrazolo[1,5-a]pyrimidine (311 mg, 54% yield), followed by NaBH₄ reduction (carried out on 300 mg of this material). Purification by silica gel chromatography afforded the desired product (277 mg, 92% yield).

Synthetic Examples

Section H

Preparation 1:
1-methyl-2-(propan-2-ylidene)hydrazine

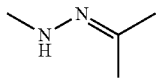

Acetone (100 mL) was treated dropwise (syringe pump) over 45 minutes with N-Methylhydrazine (20 mL), and the reaction solution was stirred at room temperature for 45 minutes. The reaction solution was then heated at 55° C. for an additional 15 minutes, cooled to room temperature, dried over sodium sulfate, filtered and concentrated via rotavap at 40° C. or less. The crude product was then purified by distillation at 110-122° C. to afford the title compound as a colorless oil (14.2 g, 43.9%).
¹HNMR (400 MHz, DMSO-d6) δ: 1.58 (s, 3H), 1.72, (s, 3H), 2.63, (s, 3H), 5.21, (br s, 1H).

Preparation 2:
3-(ethoxymethylene)pentane-2,4-dione

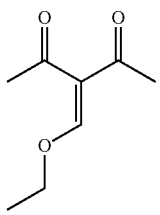

A solution of Acetylacetone (40 mL), Ethyl orthoformate (95.4 mL) and Acetic anhydride (54.2 mL) was heated to reflux (150° C.) for 1 hour. The reaction solution was cooled to room temperature and was directly subjected to flash column chromatography (E. Merck Silica Gel (~120 g); Eluent: 100% EtOAc followed by 5% EtOH in EtOAc). Concentration of the fractions containing the pure product using a rotavap at 40° C. afforded the title compound as a dark red viscous oil (10.4 g, 17.0%).
¹HNMR (400 MHz, CDCl₃) δ: 1.36, (t, 3H), 2.28, (s, 3H), 2.35, (s, 3H), 4.22, (q, 2H), 7.67, s, 1H).

Preparation 3: 3-((1-methyl-2-(propan-2-ylidene)hydrazinyl)methylene)pentane-2,4-dione

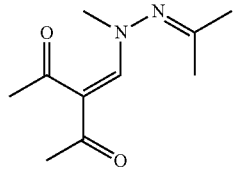

3-(ethoxymethylene)pentane-2,4-dione (Preparation 2, 8.6 g) was dissolved in Ether (30 mL) and cooled to 0° C. The reaction solution was then slowly treated with 1-methyl-2-(propan-2-ylidene)hydrazine (Preparation 1, 4.8 g) dropwise over 5 minutes, and then warmed and stirred at room temperature overnight. The reaction solution was purified directly by flash column chromatography (Biotage Quad 25; Eluent: 20% EtOH in EtOAc) to afford the title compound as a light red solid. (9.1 g, 84.0%).
¹HNMR (400 MHz, DMSO-d6) δ: 1.82, (s, 3H), 1.89, (s, 3H), 2.05, (s, 6H), 3.07, (s, 3H), 7.40, (s, 1H).

Preparation 4:
1-(1,3-dimethyl-1H-pyrazol-4-yl)ethanone

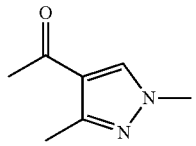

3-((1-methyl-2-(propan-2-ylidene)hydrazinyl)methylene)pentane-2,4-dione (Preparation 3, 9.1 g) was dissolved in Ethanol (20 mL) and treated with 1M Hydrogen chloride in Water (20 mL) the reaction solution was stirred at room temperature for 15 minutes. The reaction solution was then concentrated under vacuum with a rotavap to approximately 20 mL total volume. The reaction solution was then treated with saturated aqueous sodium bicarbonate (45 mL), and extracted with methylene chloride (4×50 mL) The combined organic extracts were dried over sodium sulfate, filtered and concentrated in vacuo afford the title compound as a light orange solid. (6.2 g, 97%).
¹HNMR (400 MHz, CDCl₃) δ: 2.37, (s, 3H), 2.45, (s, 3H), 3.84, (s, 3H), 7.75, (s, 1H)

Preparation 5: 1-(1,3-dimethyl-1H-pyrazol-4-yl)-4,4,4-trifluoro-3-hydroxybut-2-en-1-one

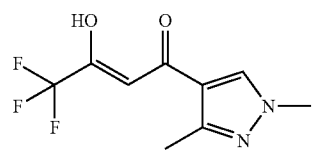 [SMILES: Cc1nn(C)cc1C(=O)/C=C(\O)C(F)(F)F]

1-(1,3-dimethyl-1H-pyrazol-4-yl)ethanone (Preparation 4, 4.46 g) was dissolved in Methanol (21 mL) and 25% Sodium methoxide in Methanol (11.07 mL) was added. The mixture was stirred for 5 minutes, and Acetic acid, trifluoro-, ethyl ester (7.701 mL) was added. The mixture was heated to reflux at 75° C. and was stirred for 19 hours. The reaction solution was purified directly by flash column chromatography (Biotage Quad 25; Eluent: 100% EtOAc followed by 5% EtOH in EtOAc and then 20% EtOH in EtOAc) affording the title compound (tautomer) as a light red foamy solid (7.0 g, 92.3%).

$^1$HNMR (400 MHz, CDCl$_3$) δ: 2.33 (s, 3H), 3.76, (s, 3H), 6.10, (s, 1H), 7.84, (s, 1H)

Preparation 6: 3-bromo-1H-pyrazol-5-amine

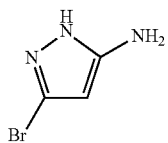

To a solution of 3,4,5-Tribromopyrazole (60 g) in Acetic acid (900 mL) at 10° C. was added Nitric acid (21 mL) (90%, fuming) Acetic anhydride (300 mL) was then added over 20 minutes. The reaction solution was warmed to room temperature and stirred for 3 hours. The reaction mixture was then poured over ice resulting in a white precipitate. The precipitate was filtered off and washed with water (200 mL) The filtered precipitate was then dissolved in Toluene (750 mL), washed with water (200 mL) and brine (100 mL), dried over sodium sulfate, and filtered. To the toluene solution was then added 1H-Pyrazole, 3,5-dimethyl-(20 g), and the solution was heated at reflux for 20 minutes. The reaction solution was cooled and concentrated in vacuo. The crude product was triturated with heptane and the resulting precipitate which contained mostly product by TLC was filtered and dried in vacuo. The crude title compound was carried on without further purification. (71.7 mg, 67.6%).

This intermediate, 3,4-dibromo-5-nitro-1H-pyrazole (69 g) was reduced by refluxing with Stannous chloride, dihydrate (135 g) in Ethyl acetate (600 mL) and Ethanol (300 mL) at 110° C. for 45 minutes. The yellow homogenous reaction solution was cooled to room temperature and slowly poured over a vigorously stirring solution of sodium bicarbonate (33 g) in water (200 mL) and ethyl acetate (800 mL) To the resultant slurry was added Celite (30 g), and this slurry was filtered through a bed of Celite. The filter cake was washed with additional ethyl acetate (600 mL) The organic solution was then washed with brine (200 mL), dried over sodium sulfate, filtered, and concentrated in vacuo to give the crude product as an orange oil. The crude product was then purified by flash column chromatography (Biotage, Quad 25; Eluent: 6% EtOH in methylene chloride). This afforded the title compound as a light beige solid (13.2 g, 32%). $^1$HNMR (400 MHz, DMSO-d6) δ: 5.20, (m, 3H), 11.60, (br s, 1H).

Preparation 7: 2-bromo-5-(1-ethyl-3-methyl-1H-pyrazol-4-yl)-7-(trifluoromethyl)pyrazolo[1,5-a]pyrimidine

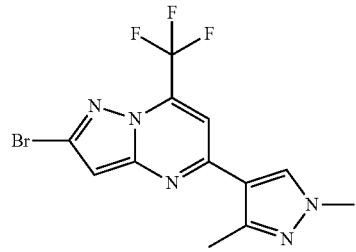 [SMILES: Cc1nn(C)cc1-c1cc(C(F)(F)F)n2nc(Br)cc2n1]

1-(1,3-dimethyl-1H-pyrazol-4-yl)-4,4,4-trifluoro-3-hydroxybut-2-en-1-one (Preparation 5, 1.7 g) and 3-bromo-1H-pyrazol-5-amine (Preparation 6, 1.18 g) in Acetic acid (52.61 mL) was heated at 120° C. in a sealed tube overnight. The reaction solution was cooled to room temperature, and poured into ice water (500 mL) resulting in a white precipitate. The precipitate was filtered and washed with copious amounts of water. The precipitate was then collected and dried in vacuo to afford the title compound as a white powder (1.9 g, 73.1%). $^1$HNMR (400 MHz, DMSO-d6) δ: 2.47 (s, 3H), 3.79, (s, 3H), 6.95, (s, 1H), 7.73, (s, 1H), 8.67, (s, 1H).

Preparation 8: 2-bromo-5-(1,3-dimethyl-1H-pyrazol-4-yl)-7-(trifluoromethyl)-4,5,6,7-tetrahydropyrazolo[1,5-a]pyrimidine

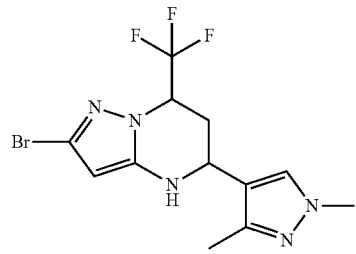 [SMILES: Cc1nn(C)cc1C1CC(C(F)(F)F)n2nc(Br)cc2N1]

Sodium tetrahydroborate (472 mg) was slowly added to a suspension of 2-bromo-5-(1-ethyl-3-methyl-1H-pyrazol-4-yl)-7-(trifluoromethyl)pyrazolo[1,5-a]pyrimidine (Preparation 7, 1.8 g) in Ethanol (20 mL) The reaction mixture was stirred at room temperature for 3 hours. The reaction solution was then very slowly added to ice cooled 1N HCl until a pH=2.0 was achieved to quench any remaining sodium tetrahydroborate. The solution was then concentrated under high vacuum to remove the majority of ethanol. Saturated sodium bicarbonate aqueous solution was then slowly added to the acidic solution until a neutral pH (7.0) was achieved and a white precipitate forms. The precipitate was filtered off and washed with water (200 mL) and ether (20 mL) The white precipitate was collected and dried in vacuo to afford the title compound as a white powder (1.36 g, 74.7%). $^1$HNMR (400 MHz, DMSO-d6) δ: 2.00, (m, 1H), 2.09, (s, 3H), 2.30, (m, 1H), 3.67, (s, 3H), 4.34, (m, 1H), 5.15, (m, 1H), 5.31, (s, 1H), 6.69, (s, 1H), 7.63, (s, 1H).

Preparation 9: (5S,7R)-2-bromo-5-(1,3-dimethyl-1H-pyrazol-4-yl)-7-(trifluoromethyl)-4,5,6,7-tetrahydropyrazolo[1,5-a]pyrimidine

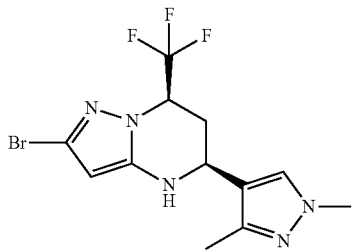 [SMILES: Cc1nn(C)cc1[C@@H]1C[C@H](C(F)(F)F)n2nc(Br)cc2N1]

The racemic 2-bromo-5-(1,3-dimethyl-1H-pyrazol-4-yl)-7-(trifluoromethyl)-4,5,6,7-tetrahydropyrazolo[1,5-a]pyrimidine (1.5 g, 4.1 mmol, Preparation 8) was dissolved in methanol (35 mL) and the cloudy solution was gently warmed providing a clear solution. The solution was then filtered through a medium porosity Buchner funnel. The clear filtrate was directly used for chiral HPLC purification. 1 mL of this solution was loaded onto a 2.1 cm×25 cm Chiralcel OD column and eluted with a mobile phase comprising of isopropyl alcohol and methanol (1:1 ratio) at a flow rate of 15 mL/min. The two (R and S) enantiomers were collected separately. 27 such injections were carried out and the pooled fractions of pure (R and S) enantiomers were concentrated under reduced pressure. The title compound was isolated as a white powder (0.71 g, 1.95 mmols, >95% ee).

Preparation 10: (5R,7S)-2-bromo-5-(1,3-dimethyl-1H-pyrazol-4-yl)-7-(trifluoromethyl)-4,5,6,7-tetrahydropyrazolo[1,5-a]pyrimidine

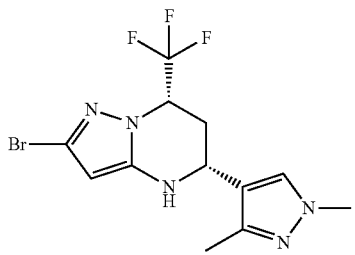 [SMILES: Cc1nn(C)cc1[C@H]1C[C@@H](C(F)(F)F)n2nc(Br)cc2N1]

The racemic 2-bromo-5-(1,3-dimethyl-1H-pyrazol-4-yl)-7-(trifluoromethyl)-4,5,6,7-tetrahydropyrazolo[1,5-a]pyrimidine (1.5 g, 4.1 mmol, Preparation 8) was dissolved in methanol (35 mL) and the cloudy solution was gently warmed providing a clear solution. The solution was then filtered through a medium porosity Buchner funnel. The clear filtrate was directly used for chiral HPLC purification. 1 mL of this solution was loaded onto a 2.1 cm×25 cm Chiralcel OD column and eluted with a mobile phase comprising of isopropyl alcohol and methanol (1:1 ratio) at a flow rate of 15 mL/min. The two (R and S) enantiomers were collected separately. 27 such injections were carried out and the pooled fractions of pure (R and S) enantiomers were concentrated under reduced pressure. The title compound was isolated as a white powder (0.71 g, 1.95 mmols, >95% ee).

Example ER-889996

To a 5 mL screw-cap vial was added 4-(Piperazine-1-carbonyl)phenylboronic acid, pinacol ester (51.0 mg, 0.161 mmol), Tetrakis(triphenylphosphine)palladium(0) in 1,4-Dioxane (0.075M, 90 uL), a solution of 2-bromo-5-(1,3-dimethyl-1H-pyrazol-4-yl)-7-(trifluoromethyl)-4,5,6,7-tetrahydropyrazolo[1,5-a]pyrimidine (25.0 mg, 0.069 mmol, Preparation 8) in 1,4-Dioxane (450 uL) and 2M Sodium carbonate in Water (70 uL). The reactor vessel was purged with nitrogen and sealed. The vial was shaken and heated in an aluminum block at 85° C. for 40 h. To the mixture was added 1.0 mL of saturated aqueous sodium bicarbonate and the mixture was then extracted with ethyl acetate (2×2.0 mL) The combined organic layers were concentrated in vacuo. The remaining residue was purified by LC/MS according to method. This afforded the title compound as a white powder (7.8 mg, 24.0%).

Example ER-889862 was prepared from 2-bromo-5-(1,3-dimethyl-1H-pyrazol-4-yl)-7-(trifluoromethyl)-4,5,6,7-tetrahydropyrazolo[1,5-a]pyrimidine (40.1 mg, 0.11 mmol, Preparation 8) and commercially available Isoquinolin-5-yl boronic acid (2.5 eq) in a manner similar to that of example ER-889996. Purification by LCMS, using HPLC condition III, afforded the title compound as a white powder (7.5 mg, 17%).

Example ER-890007 was prepared from 2-bromo-5-(1,3-dimethyl-1H-pyrazol-4-yl)-7-(trifluoromethyl)-4,5,6,7-tetrahydropyrazolo[1,5-a]pyrimidine (25.0 mg, 0.069 mmol, Preparation 8) and commercially available 8-Methylquinolin-5-yl boronic acid (2.5 eq) in a manner similar to that of example ER-889996. Purification by LCMS, using HPLC condition III, afforded the title compound as a white powder (12.2 mg, 42%).

Example ER-892900 was prepared from 2-bromo-5-(1,3-dimethyl-1H-pyrazol-4-yl)-7-(trifluoromethyl)-4,5,6,7-tetrahydropyrazolo[1,5-a]pyrimidine (23.0 mg, 0.063 mmol, Preparation 8) and commercially available 1,4-Dimethyl-1H-indazol-5-yl boronic acid (2.5 eq) in a manner similar to that of example ER-889996. Purification by LCMS, using HPLC condition III, afforded the title compound as a white powder (7.7 mg, 28%).

Example ER-890066 was prepared from 2-bromo-5-(1,3-dimethyl-1H-pyrazol-4-yl)-7-(trifluoromethyl)-4,5,6,7-tetrahydropyrazolo[1,5-a]pyrimidine (25.0 mg, 0.069 mmol, Preparation 8) and commercially available 2-Methyl-2H-indazol-5-yl boronic acid (2.5 eq) in a manner similar to that of example ER-889996. Purification by LCMS, using HPLC condition III, afforded the title compound as a white powder (0.2 mg, 1%).

Example ER-889550

A sealed tube was charged with 2-bromo-5-(1-ethyl-3-methyl-1H-pyrazol-4-yl)-7-(trifluoromethyl)pyrazolo[1,5-a]pyrimidine (40 mg, 0.11 mmols, Preparation 7), 4-(N-Ethylaminocarbonyl)phenylboronic acid (73.2 mg, 0.38 mmols), Potassium carbonate (76.8 mg, 0.56 mmols), Water (0.559 mL), and Tetrahydrofuran (0.838 mL) The reaction mixture was stirred while being degassed with nitrogen for 15 minutes. [1,1'-Bis(diphenylphosphino)ferrocene]dichloropalladium(II), complex with dichloromethane (1:1) (22.7 mg, 0.03 mmols) was added and the reaction mixture was sealed and heated at 95° C. for 16 hours. The crude reaction mixture was cooled to room temperature and then purified directly by flash column chromatography (Biotage Quad 25; Eluent: 100% EtOAc). This afforded 4-(5-(1,3-dimethyl- 1H-pyrazol-4-yl)-7-(trifluoromethyl)pyrazolo[1,5-a]pyrimidin-2-yl)-N-ethylbenzamide as a light yellow solid (41.1 mg, 86.4%).

Sodium tetrahydroborate (6.62 mg) was added to a suspension of 4-(5-(1,3-dimethyl-1H-pyrazol-4-yl)-7-(trifluoromethyl)pyrazolo[1,5-a]pyrimidin-2-yl)-N-ethylbenzamide (30 mg, 0.07 mmols) in ethanol (1 mL) and the mixture stirred at room temperature for 3 hours. The reaction solution was concentrated under a stream of nitrogen. 1N HCl was then very slowly added until the borohydride was fully consumed (~2 mL) resulting in a brown precipitate. The aqueous solution was decanted off and slowly neutralized with saturated sodium bicarbonate until pH=7.0 was reached. The neutralized solution was then extracted with EtOAc (2×5 mL) The organic extracts were combined and washed with brine (2 mL), dried over sodium sulfate, filtered and concentrated in vacuo. This afforded the title compound as a white powder (18.8 mg, 62.1%).

Example ER-893888

A sealed tube was charged with 2-bromo-5-(1,3-dimethyl-1H-pyrazol-4-yl)-7-(trifluoromethyl)-4,5,6,7-tetrahydropyrazolo[1,5-a]pyrimidine (30 mg, 0.08 mmols, Preparation 8), 4-(Ureido)phenylboronic acid, pinacol ester (73.8 mg, 0.28 mmols), Potassium carbonate (56.9 mg, 0.41 mmols), Water (0.414 mL), and Tetrahydrofuran (0.621 mL) The reaction mixture was stirred while being degassed with nitrogen for 15 minutes. [1,1'-Bis(diphenylphosphino)ferrocene]dichloropalladium(II), complex with dichloromethane (1:1) (16.8 mg, 0.02 mmols) was added and the reaction mixture was sealed and heated at 95° C. for 16 hours. The crude reaction mixture was cooled to room temperature and then purified directly by flash column chromatography (Biotage Quad 25; Eluent: 10% EtOH in EtOAc). This afforded the title compound as a light yellow powder (31.1 mg, 90.0%).

Example ER-894595 was prepared from (5S,7R)-2-bromo-5-(1,3-dimethyl-1H-pyrazol-4-yl)-7-(trifluoromethyl)-4,5,6,7-tetrahydropyrazolo[1,5-a]pyrimidine (150.0 mg, 0.41 mmol, Preparation 9) and commercially available 4-(Ureido)phenylboronic acid, pinacol ester (368.8 mg, 1.4 mmols) in a manner similar to that of example ER-893888. Purification by flash column chromatography (Biotage Quad 25; Eluent: 10% EtOH in EtOAc) afforded the title compound as a light yellow powder (141.6 mg, 82.0%).

Example ER-894596 was prepared from (5R,7S)-2-bromo-5-(1,3-dimethyl-1H-pyrazol-4-yl)-7-(trifluoromethyl)-4,5,6,7-tetrahydropyrazolo[1,5-a]pyrimidine (150.0 mg, 0.41 mmol, Preparation 10) and commercially available 4-(Ureido)phenylboronic acid, pinacol ester (368.8 mg, 1.4 mmols) in a manner similar to that of example ER-893888. Purification by flash column chromatography (Biotage Quad 25; Eluent: 10% EtOH in EtOAc) afforded the title compound as a light yellow powder (144.6 mg, 83.7%).

Example ER-893986 was prepared from (5S,7R)-2-bromo-5-(1,3-dimethyl-1H-pyrazol-4-yl)-7-(trifluoromethyl)-4,5,6,7-tetrahydropyrazolo[1,5-a]pyrimidine (50.0 mg, 0.14 mmol, Preparation 9) and commercially available 1,4-Dimethyl-1H-indazole-5-boronic acid (89.1 mg, 0.47 mmols) in a manner similar to that of example ER-893888. Purification by flash column chromatography (Biotage Quad 25; Eluent: 10% EtOH in EtOAc) afforded the title compound as a light yellow powder (42.7 mg, 72.4%).

Example ER-893987 was prepared from (5R,7S)-2-bromo-5-(1,3-dimethyl-1H-pyrazol-4-yl)-7-(trifluoromethyl)-4,5,6,7-tetrahydropyrazolo[1,5-a]pyrimidine (150.0 mg, 0.41 mmol, Preparation 10) and commercially available 1,4-Dimethyl-1H-indazole-5-boronic acid (267.3 mg, 1.41 mmols) in a manner similar to that of example ER-893888. Purification by flash column chromatography (Biotage Quad 25; Eluent: 10% EtOH in EtOAc) afforded the title compound as a light yellow powder (155.7 mg, 88.0%).

Example ER-893990 was prepared from (5S,7R)-2-bromo-5-(1,3-dimethyl-1H-pyrazol-4-yl)-7-(trifluoromethyl)-4,5,6,7-tetrahydropyrazolo[1,5-a]pyrimidine (40.0 mg, 0.11 mmol, Preparation 9) and commercially available 2-Methylindazole-5-boronic acid pinacol ester (96.8 mg, 0.38 mmols) in a manner similar to that of example ER-893888. Purification by flash column chromatography (Biotage Quad 25; Eluent: 10% EtOH in EtOAc) afforded the title compound as a light yellow powder (36.9 mg, 80.9%).

Example ER-893991 was prepared from (5R,7S)-2-bromo-5-(1,3-dimethyl-1H-pyrazol-4-yl)-7-(trifluoromethyl)-4,5,6,7-tetrahydropyrazolo[1,5-a]pyrimidine (30.0 mg, 0.082 mmol, Preparation 10) and commercially available 2-Methylindazole-5-boronic acid pinacol ester (72.6 mg, 0.28 mmols) in a manner similar to that of example ER-893888. Purification by flash column chromatography (Biotage Quad 25; Eluent: 10% EtOH in EtOAc) afforded the title compound as a light yellow powder (22.0 mg, 64.3%).

Synthetic Examples—Section J

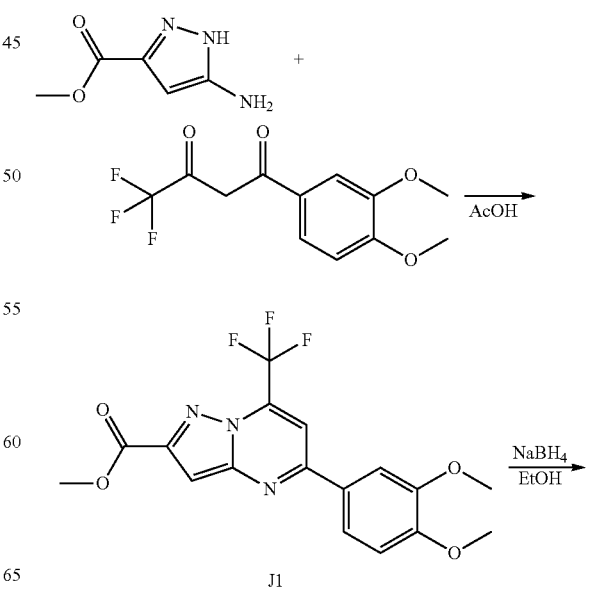

J1

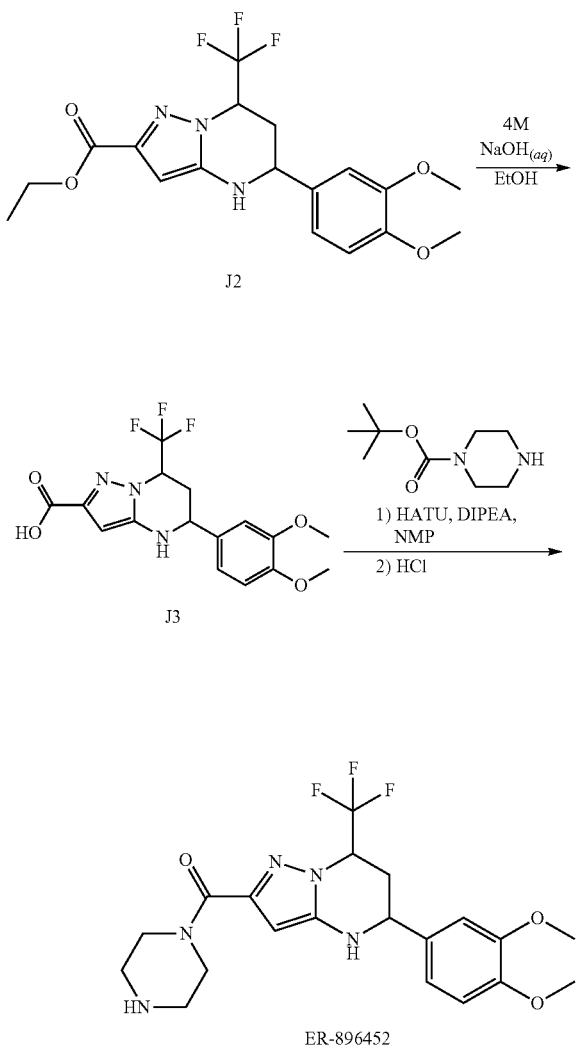

stirred for 5 minutes. The precipitate was collected by filtration, washed with water and air dried. The material was purified by flash chromatography using a 25 g silica column with a heptane:ethyl acetate gradient to give J2 as a white solid, 507 mg (48% yield).

To a suspension of ethyl 5-(3,4-dimethoxyphenyl)-7-(trifluoromethyl)-4,5,6,7-tetrahydropyrazolo[1,5-a]pyrimidine-2-carboxylate (503 mg, 1.26 mmol) in ethanol (5.0 mL, 85.633 mmol) was added 4.00 M sodium Hydroxide in water (1.574 mL, 6.298 mmol). The mixture was heated at 50° C. for 1 hour. The mixture was cooled at room temperature and was acidified with 1.00 M HCl in Water (12.60 mL, 12.595 mmol), water was added and the precipitate collected by filtration, washed with water and dried under vacuum to give J3 as a white solid, 422 mg (95% yield).

A 5 mL microwave vial was charged with 5-(3,4-dimethoxyphenyl)-7-(trifluoromethyl)-4,5,6,7-tetrahydropyrazolo[1,5-a]pyrimidine-2-carboxylic acid (50 mg, 0.135 mmol), tert-butyl piperazine-1-carboxylate (75 mg, 0.404 mmol), HATU (205 mg, 0.539 mmol), N,N-diisopropylethylamine (0.059 mL, 0.337 mmol) and DMF (1.0 mL, 12.915 mmol). The vial was capped and the mixture was stirred for 6 hours at 40° C. The mixture was diluted with Ethyl acetate (5 mL), washed 2× with water (2 mL), washed with 0.1N aqueous HCl (2 mL), washed with saturated aqueous sodium bicarbonate (2 mL), washed with brine (2 mL), dried with sodium sulfate, filtered and concentrated. Compound was purified by chromatography on Biotage SP4 (Column Interchim 25 g, 30 µM) using 12-100% EtOAc/Heptane as eluent to afford intermediate tert-butyl 4-(5-(3,4-dimethoxyphenyl)-7-(trifluoromethyl)-4,5,6,7-tetrahydropyrazolo[1,5-a] pyrimidine-2-carbonyl)piperazine-1-carboxylate (38 mg, 0.070 mmol, 52.3% yield).

The intermediate tert-butyl 4-(5-(3,4-dimethoxyphenyl)-7-(trifluoromethyl)-4,5,6,7-tetrahydropyrazolo[1,5-a]pyrimidine-2-carbonyl)piperazine-1-carboxylate (36 mg, 0.067 mmol) was dissolved in ethanol (0.5 mL, 8.563 mmol) and 4.00M HCl in Dioxane (0.5 mL, 2.00 mmol) and the mixture was stirred at 40° C. for 1 hour. The reaction mixture was concentrated and the product was dried on vacuum pump to afford ER-896452 as the HCl salt (31.0 mg, 0.065 mmol, 98% yield).

A suspension of methyl 5-amino-1H-pyrazole-3-carboxylate (1.00 g, 7.086 mmol) and 1-(3,4-dimethoxyphenyl)-4,4,4-trifluorobutane-1,3-dione (2.153 g, 7.794 mmol) in ACETIC ACID (10 ml, 174.682 mmol) was heated to reflux (at 100° C.) for 5 hours. The mixture was cooled at room temperature, water was added and the precipitate collected by filtration, washed with water and dried under vacuum to give J1 as a green solid, 2.33 g (86% yield).

Sodium borohydride (0.446 g, 11.802 mmol) was slowly added to a suspension of methyl 5-(3,4-dimethoxyphenyl)-7-(trifluoromethyl)pyrazolo[1,5-a]pyrimidine-2-carboxylate (1.00 g, 2.623 mmol) in ETHANOL (25 ml, 428.167 mmol) at room temperature. The mixture was heated to reflux (80° C.) for 60 minutes and reaction was monitored by UPLC/MS. The mixture was cooled at room temperature. The excess sodium borohydride was decomposed with ACETIC ACID (1.501 ml, 26.226 mmol). The reaction was poured into 1.00 M HCl in Water (52.5 ml, 52.451 mmol) and was

ER-896453

Example ER-896453 was prepared in two steps from acid J3 (50 mg, 0.135 mmol) and commercially available (S)-tert-butyl 3-aminopiperidine-1-carboxylate (81 mg, 0.404 mmol) in a manner similar to that of example ER-896452 to afford intermediate (3S)-tert-butyl 3-(5-(3,4-dimethoxyphenyl)-7-(trifluoromethyl)-4,5,6,7-tetrahydropyrazolo[1,5-a] pyrimidine-2-carboxamido)piperidine-1-carboxylate (67 mg, 0.121 mmol, 90% yield). This intermediate (49 mg, 0.089 mmol) was treated with HCl in a manner similar to that of example ER-896452 to afford the desired product ER-896453 (42 mg, 97% yield).

Determination of Absolute configuration of ER-885454 and its correlation to ER-892887

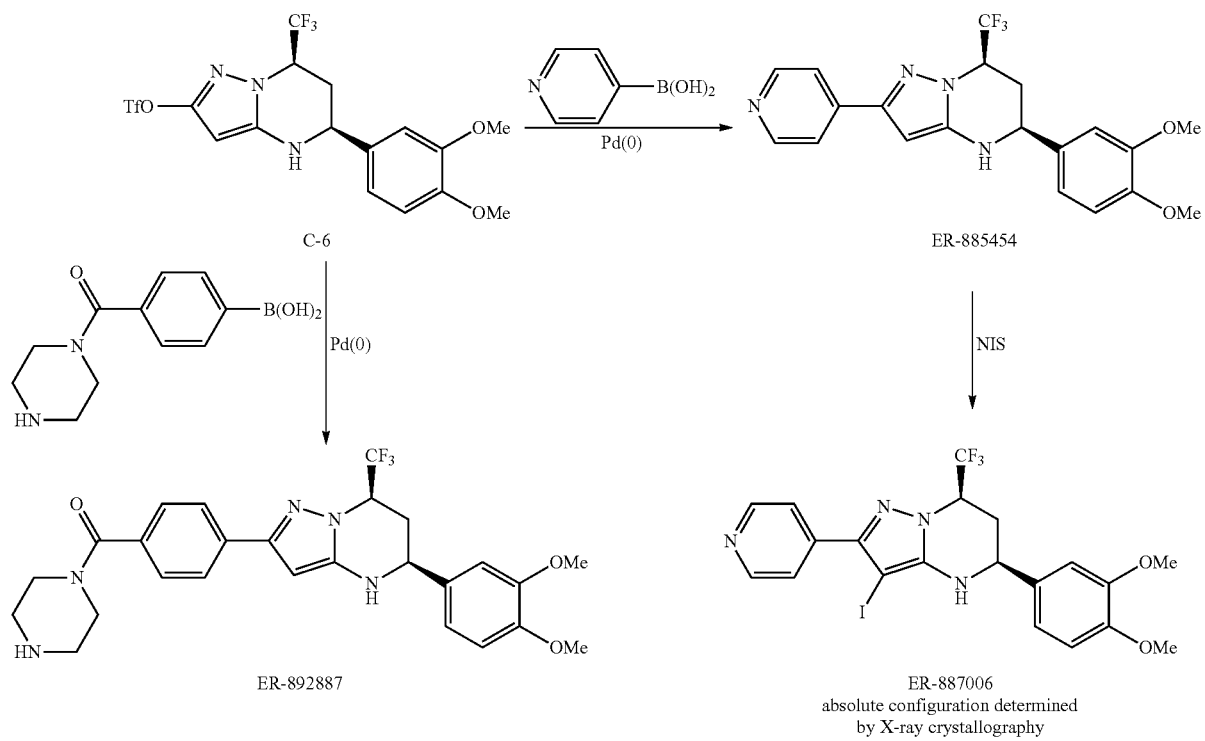

Figure 10:
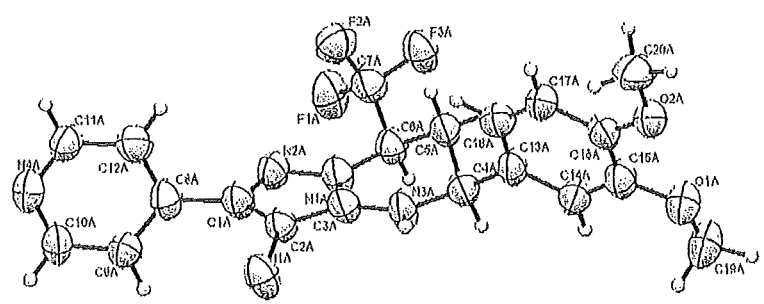
FIG. 10 shows an ORTEP representation of the X-ray structure of compound ER-887006.
Figure 12A:
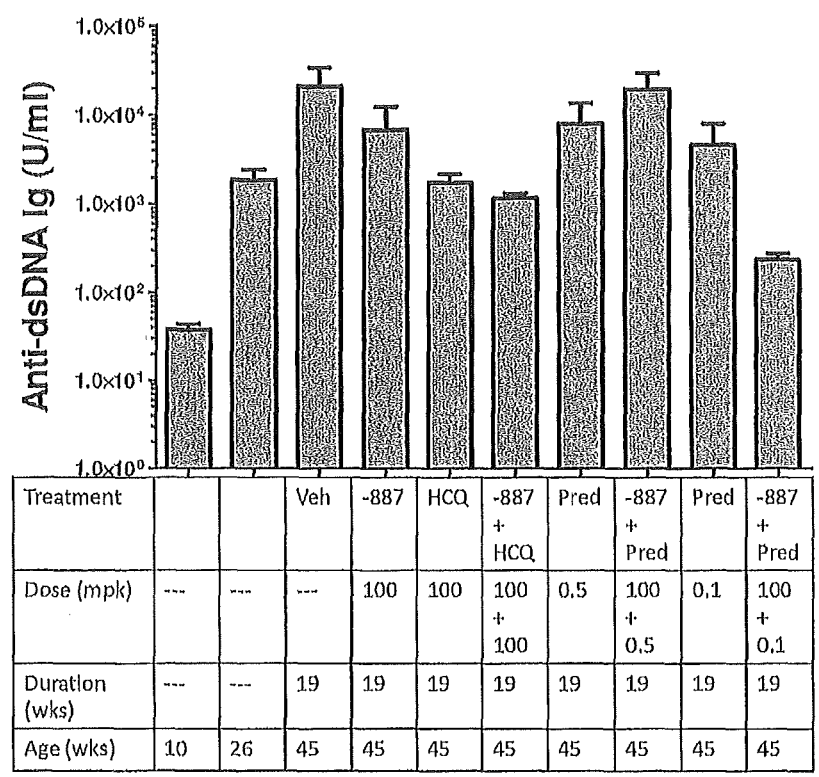
FIG. 12A through FIG. 12F show the effect of ER-892887 and two commonly used human lupus treatments in the NZBΔNZW strain lupus disease model. Figure Legend: Female NZBWF1/J mice were received at 4 weeks of age, baseline bleeds were performed at 10 and 26 weeks, and mice were monitored for disease progression by following anti-dsDNA titers and proteinuria. At 26 weeks of age, mice were randomized into groups with equivalent median anti-dsDNA titers and treated with Vehicle (Veh; 0.5% methyl-cellulose) alone or 100 mg/kg ER-892887, 100 mg/kg hydroxychloroquine, 0.1 mg/kg prednisolone or 0.5 mg/kg prednisolone, alone or in the combinations indicated, once-a-day orally (QD PO). All mice were sacrificed at 45 weeks of age (19 weeks of drug treatment) and blood plasma anti-dsDNA titers were determined by ELISA.
Figure 12B:
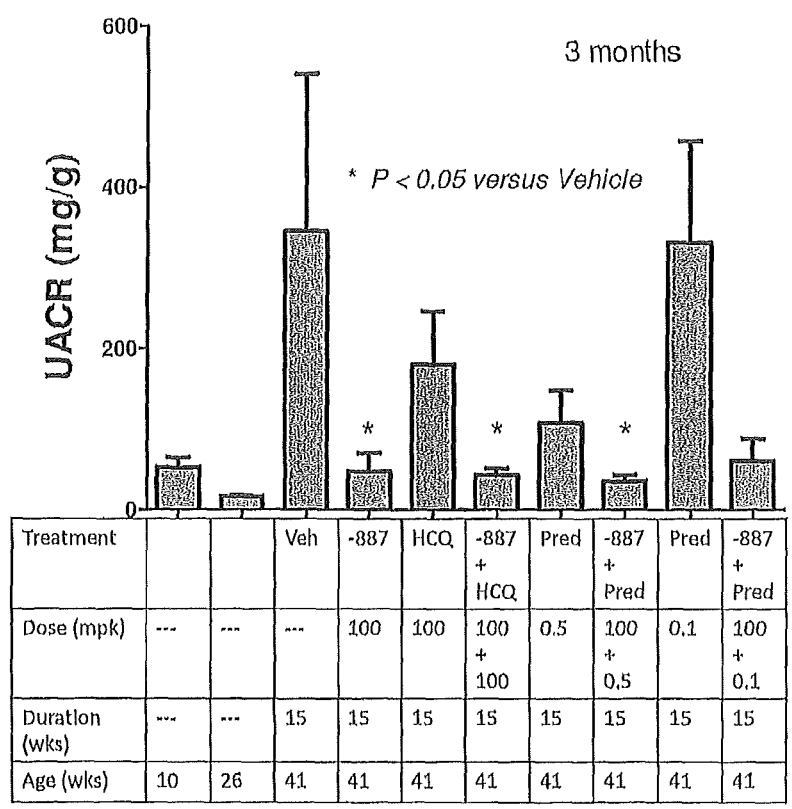
Figure 12C:
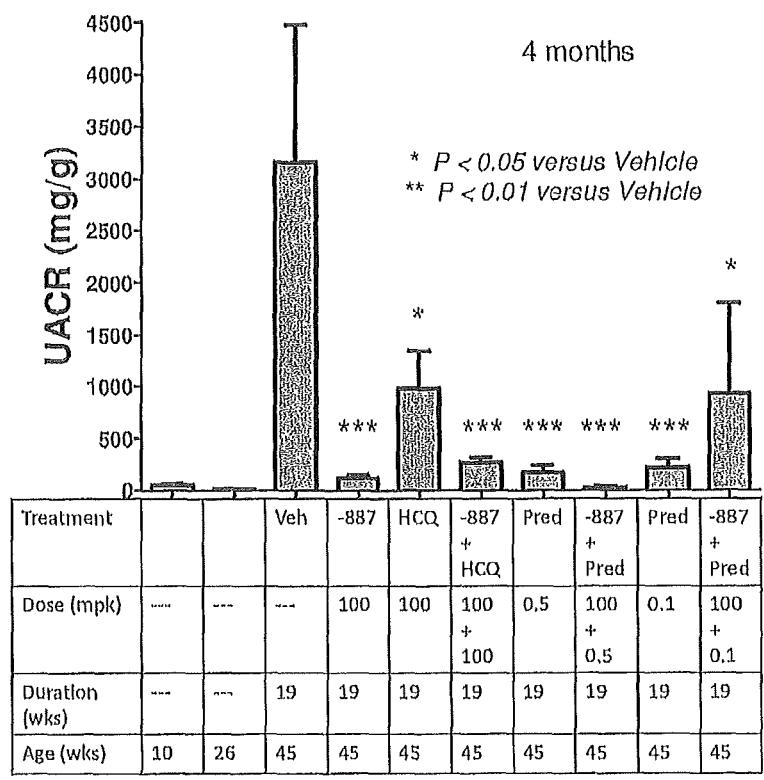
Figure 12D:
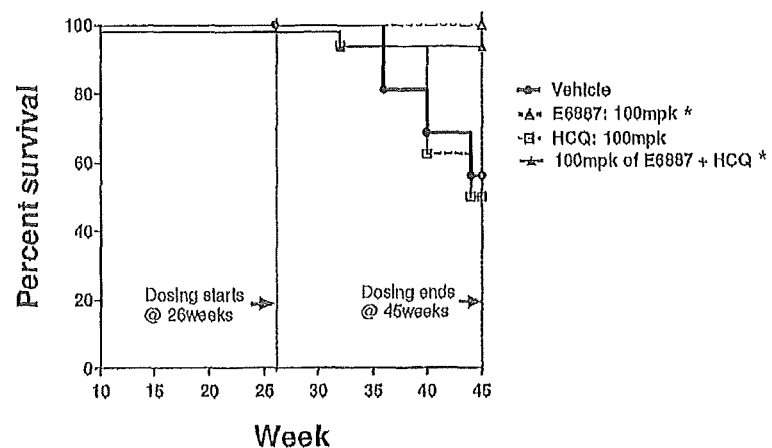
Figure 12E:
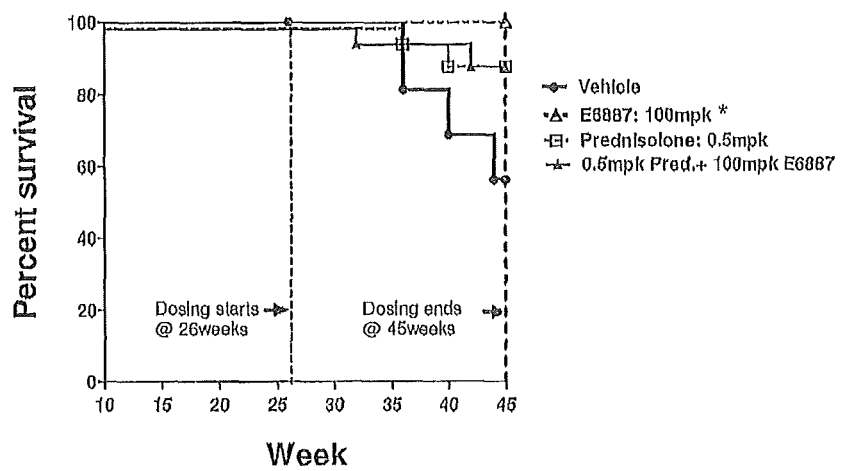
Figure 12F:
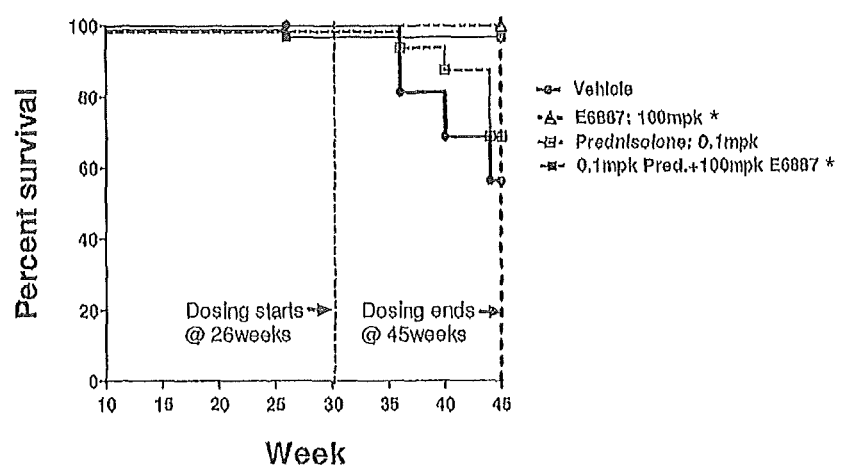
Figure 13A:
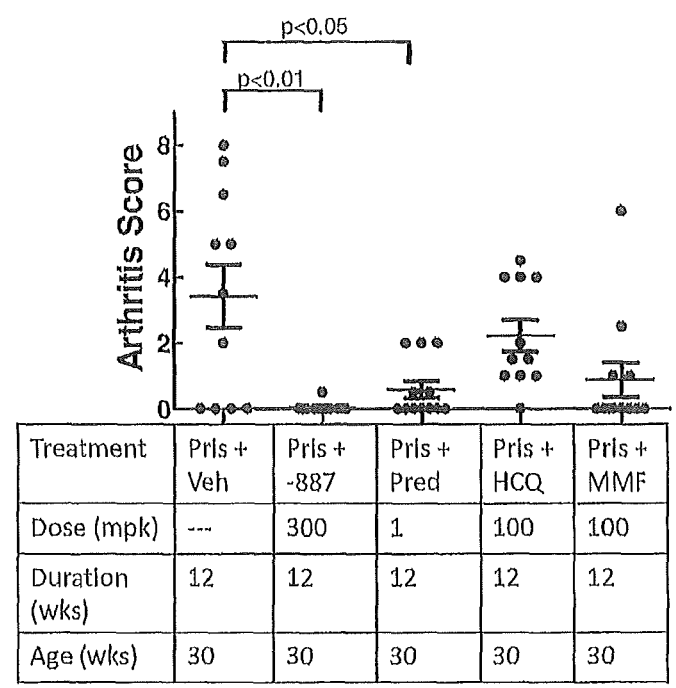
Figure 13B:
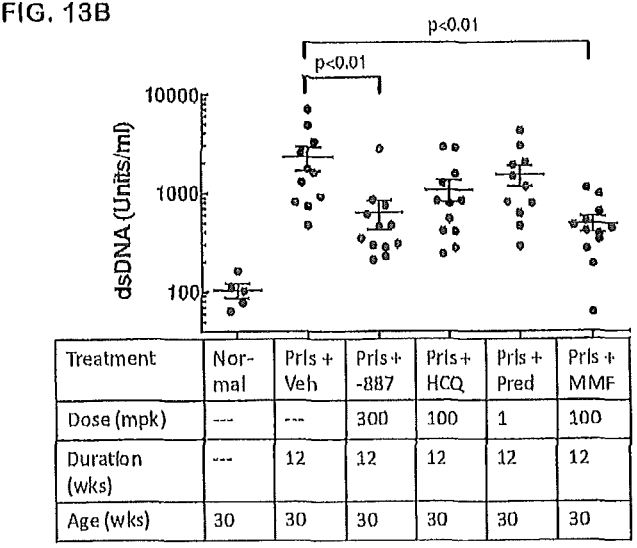
Figure 13B:
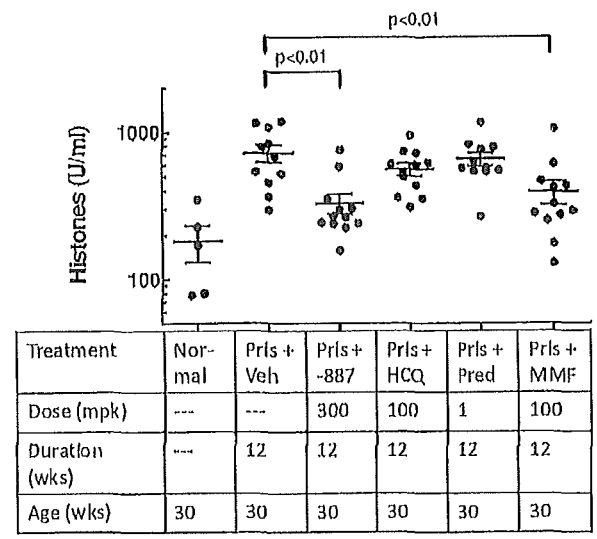
Figure 13B:
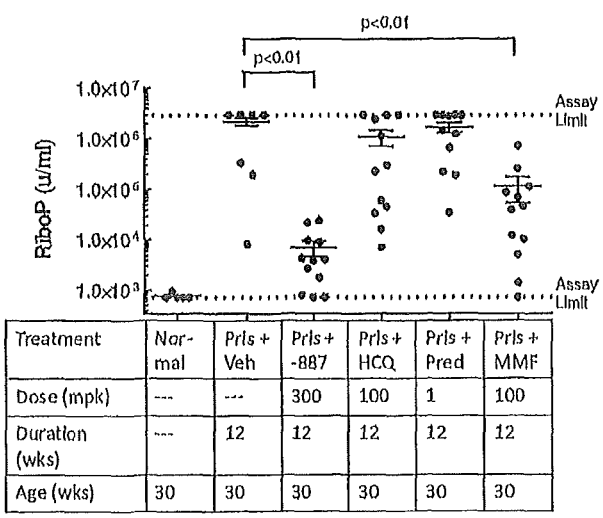
Figure 13B:
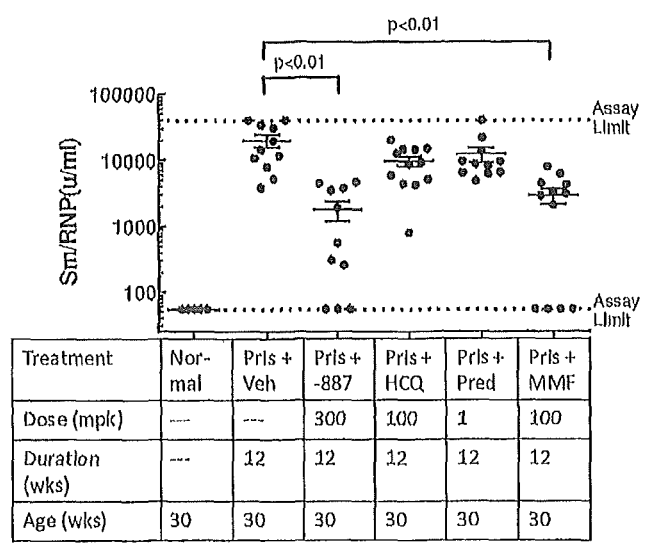
Figures 13D, 13E:
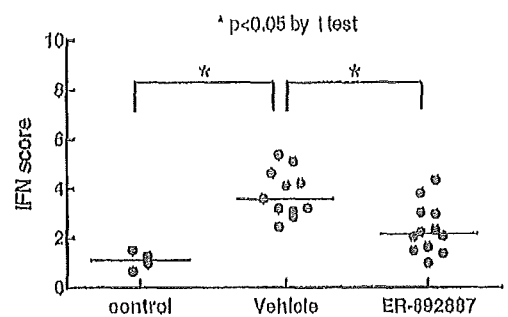
Figure 14A:
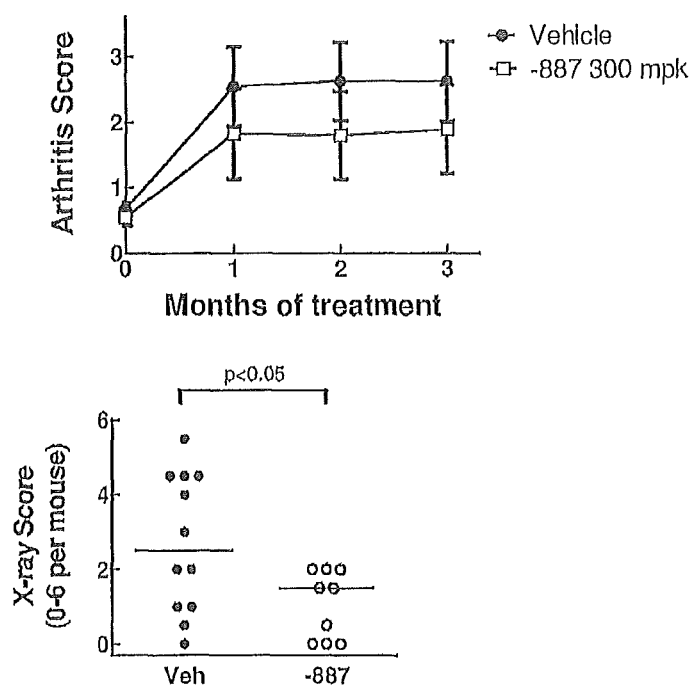
FIG. 14A, FIG. 14B, and FIG. 14C present the effect of compound ER-892887 on arthritis and autoantibodies in the Pristane: DBA/1 strain lupus disease model. Figure Legend: Female DBA/1 mice at 10 weeks of age were given an intraperitoneal injection of 0.5 ml pristane or PBS. At 22 weeks of age, mice were randomized into groups with equivalent median anti-dsDNA titers and treated with Vehicle (Veh; 0.5% methyl-cellulose) alone or 300 mg/kg ER-892887 once-a-day orally (QD PO). Arthritis symptoms (swelling and inflammation) were recorded monthly by blinded observers. All mice were sacrificed at 34 weeks of age (12 weeks of treatment) and blood plasma autoantibody titers were determined by ELISA. Prior to termination paws were x-rayed and scored for bone damage and erosions by two blinded analysts.
Figure 14B:
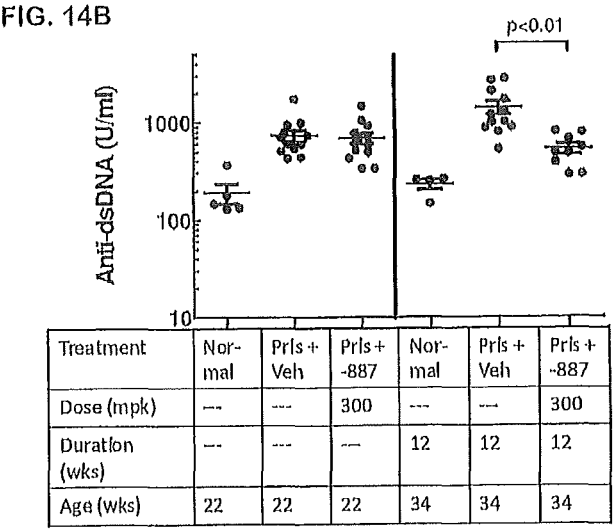
Figure 14B:
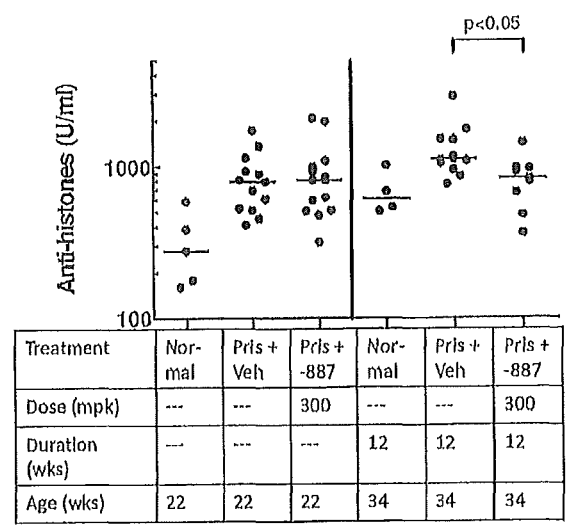
Figure 14C:
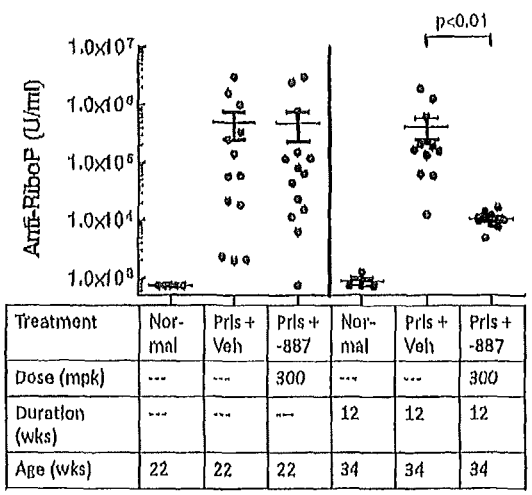
Figure 14C:
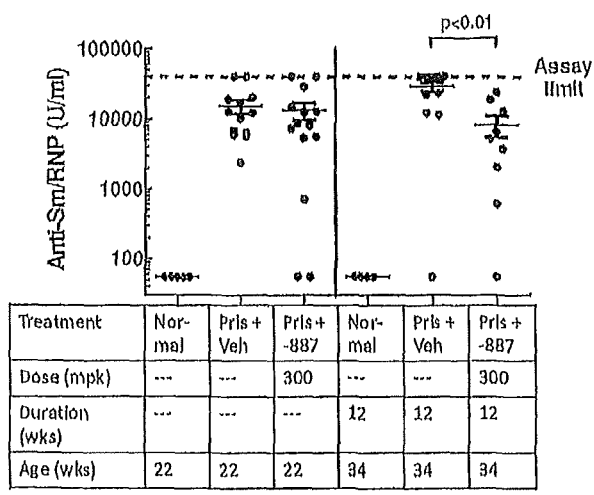

The absolute configuration of ER-885454 was established by converting it to the 3-iodo derivative ER-887006 as shown above. The structure of ER-887006 was determined by single crystal X-ray diffraction. Results are shown in FIG. 10. Since this transformation does not affect the chiral centers in the molecule, the absolute configuration of ER-885454 is as shown. Moreover, the absolute configuration of ER-892887 was established via its correlation to compound C-6, which in turn was correlated to ER-885454.

General Screening Assay and Pharmacology Strategy.

To identify potent and selective TLR7/8 compounds, analogs were initially screened across a cell-based panel of human TLR4, TLR7, and TLR9 reporter lines (see Materials and Methods for more details). A subset of compounds that were potent and selective for TLR7 were also tested for TLR8 activity (see Table 2 below) and for TLR7/8 potency in the primary human PBMC assay (see Materials and Methods for more details). Certain compounds were advanced into the short-term in vivo (STIV) assay to determine dose-dependent activity and duration-of-action against mouse TLR7 (see Materials and Methods for more details). Select compounds were then evaluated for impact in one or more of the following mouse lupus disease models: BXSB-Yaa, NZBΔNZW, and Pristane:DBA/1.

Many compounds reported as embodiments herein demonstrate nanomolar potency against both human and mouse TLR7 and human TLR8 when these receptors, expressed on either cell lines or primary cells, are stimulated by synthetic, small molecule (CLO97, R848) or nucleic-acid (RNA) ligands. Conversely, most compounds reported as embodiments herein are inactive against the TLR9 pathway.

Current lupus SOC drugs include anti-malarials such as chloroquine and hydroxychloroquine (HCQ) which have been shown to inhibit TLR7/9 signaling in vitro. This may at least partially explain their effectiveness in controlling lupus flare. Embodiments of the disclosure, however, have been shown to offer significantly more potent inhibition. For example, compound ER-892887 (shown and discussed above) was found to be approximately 100-fold more potent against the RNA-Ig TLR7/8 stimulus versus HCQ (ER-892887 IC$_{50}$=0.015 uM, HCQ IC$_{50}$~1.5 uM). This suggests that ER-892887 would offer much more effective TLR7/8 pathway inhibition versus current lupus treatments. This is demonstrated by results shown in Table 1 below.

TABLE 1

Potency and selectivity of compound ER-892887 as compared to hydroxychloroquine (Plaquenil ®).

| Cell Format: | Ligand: | Receptor(s): | Analyte: | ER-892887 IC50 (uM) | HCQ[2] IC50 (uM) |
|---|---|---|---|---|---|
| HEK-293 | LPS | Human TLR4 | NFkB-luciferase | >10 | N.D. |
| HEK-293 | CLO97 | Human TLR7 | NFkB-luciferase | 0.010 | N.D. |
| HEK-293 | CLO97 | Mouse TLR7 | NFkB-luciferase | 0.276 | N.D. |
| HEK-293 | CLO97 | Human TLR8 | NFkB-luciferase | 0.080 | N.D. |
| HEK-293 | CpG-ODN | Human TLR9 | NFkB-luciferase | >10 | N.D. |
| Hu PBMC | [1]RNA-Ig | Human TLR7/8 | IL-6 | 0.015 | 1-2 |
| Hu PBMC | [1]RNA-Ig | Human TLR7/8 | TNFα | 0.013 | N.D. |

TABLE 1-continued

Potency and selectivity of compound ER-892887 as compared to hydroxychloroquine (Plaquenil ®).

| Cell Format: | Ligand: | Receptor(s): | Analyte: | ER-892887 IC50 (uM) | HCQ[2] IC50 (uM) |
|---|---|---|---|---|---|
| Hu PBMC | [1]RNA-Ig | Human TLR7/8 | IP-10 | 0.045 | N.D. |
| Hu PBMC | R848 | Human TLR7/8 | IL-6 | 0.016 | N.D. |
| Mu Spleen | R848 | Mouse TLR7 | IL-6 | 0.070 | N.D. |
| Hu PBMC | Pam3CSK4 | Human TLR1/2 | IL-6 | >10 | N.D. |
| Hu PBMC | LPS | Human TLR4 | IL-6 | >10 | >10 |
| Hu PBMC | CpG-ODN | Human TLR9 | IL-6 | >10 | 0.15-0.30 |

TABLE KEY:
[1]RNA-Ig = ssRNA derived from U1snRNA stem loop IV sequence in complex with antibody (see Materials and Methods for more details)
[2]HCQ = Hydroxychloroquine

TABLE 2

Potency of select compounds against human TLR8 in the HEK-293 assay format (see Materials and Methods for more details).

| ER-number | HEK/TLR8 IC50 (µM) |
|---|---|
| ER-885454-00 | 0.28 |
| ER-885484-00 | >10 |
| ER-885690-00 | 1.49 |
| ER-886434-00 | 0.30 |
| ER-886622-00 | 0.07 |
| ER-887534-00 | 0.41 |
| ER-887734-00 | 0.14 |
| ER-887738-00 | >10 |
| ER-892887-00 | 0.08 |
| ER-892889-00 | 0.15 |
| ER-892890-00 | 1.47 |
| ER-892892-00 | 0.14 |
| ER-892900-00 | 0.33 |
| ER-892924-00 | 0.22 |
| ER-893888-00 | 0.46 |
| ER-893961-00 | 0.16 |
| ER-893969-00 | 0.25 |
| ER-893972-00 | 0.30 |
| ER-893987-00 | 0.22 |
| ER-894595-00 | 0.32 |
| ER-894596-00 | 0.54 |

Short-Term In Vivo (STIV) Assay:

To assess compound potency in vivo against mouse TLR7, a short-term in vivo (STIV) assay was utilized. Briefly, mice were orally dosed with compounds and at various time points afterwards were injected subcutaneously with agonist R848 to stimulate TLR7. The plasma IL-6 level following R848 stimulation was then measured by ELISA to assess compound potency and duration-of-action Importantly, cytokine production following in vitro or in vivo stimulation with R848 was shown to be completely TLR7-dependent utilizing TLR7-deficient mice. Therefore, the activity of compounds in the STIV assay can be confidently attributed to their modulation of the TLR7 pathway. A single oral dose of ER-892887 at 300 mg/kg suppresses the R848/TLR7/IL-6 pathway in vivo by 80-90% for at least 24 hours (see FIG. 1). A summary of STIV assay potency for a panel of compounds appears in Table 3 below.

TABLE 3

Short-term in vivo (STIV) assay data summary for select compounds.
Short-term In Vivo (STIV) Assay Data Summary

| Time Point: | Dose (mg/kg) | % Suppression vs. Vehicle | | | | | | | | |
|---|---|---|---|---|---|---|---|---|---|---|
| | | ER-892887 | ER-892893 | ER-889549 | ER-892889 | ER-892890 | ER-889904 | ER-893972 | ER-892892 | ER-885681 | ER-893971 |
| 3 hr | 11 | | | | | | | | | | |
| | 33 | | | | | | | | | 90 | |
| | 100 | | 30 | 93 | 98 | 64 | 98 | 83 | 96 | 98 | 99 |
| | 300 | | | | | | | | | 99 | |
| 6 hr | 11 | | | | | | | | | | |
| | 33 | 83 | 23 | 43 | 48 | 68 | 77 | 83 | 86 | 42 | 99 |
| | 100 | 100 | 0 | 84 | 99 | 84 | 100 | 96 | 94 | 81 | 99 |
| | 300 | | | | | | | | | 96 | |
| 13 hr | 11 | 27 | | | | | | | | | |
| | 33 | 12 | | | | 18 | | 78 | | 0 | 10 |

TABLE 3-continued

Short-term in vivo (STIV) assay data summary for select compounds.
Short-term In Vivo (STIV) Assay Data Summary

|   | Dose | | | | | | | | |
|---|---|---|---|---|---|---|---|---|---|
|   | 100 | 49 | | | 6 | 92 | | 7 | 99 |
|   | 300 | 90 | | | | | | 50 | |
| 19 hr | 11 | | | | | | | | |
|   | 33 | | 7 | 53 | | | 49 | | |
|   | 100 | | 0 | 0 | 45 | 24 | 52 | | |
|   | 300 | | | | | | | | |
| 24 hr | 11 | | | | | | | | |
|   | 33 | 0 | | | | | | | |
|   | 100 | 12 | | | | | | | |
|   | 300 | 86 | | | | | | | |

| Time Point: | Dose (mg/kg) | % Suppression vs. Vehicle | | | | | | | | |
|---|---|---|---|---|---|---|---|---|---|---|
|   |   | ER-895676 | ER-895678 | ER-895498 | ER-895496 | ER-895302 | ER-895303 | ER-894680 | ER-885454 | ER-894595 |
| 3 hr | 11 | | | | | | | | | |
|   | 33 | | | | | | | | | |
|   | 100 | | | | | | | | | |
|   | 300 | | | | | | | 98 | | |
| 6 hr | 11 | | | | | | | | | |
|   | 33 | 0 | 0 | 35 | 71 | 93 | 92 | 98 | | 0 |
|   | 100 | | | | | 99 | | 98 | | 57 |
|   | 300 | | | | | 99 | | | | |
| 13 hr | 11 | | | | | | | | | |
|   | 33 | 0 | 0 | 34 | 33 | 14 | 0 | 4 | | 0 |
|   | 100 | 28 | 28 | 56 | 43 | 16 | 18 | 95 | | 0 |
|   | 300 | 0 | 8 | 81 | 96 | 91 | 90 | | | |
| 19 hr | 11 | | | | | | | | | |
|   | 33 | | | | | | | | | |
|   | 100 | | | | | | | | 56 | |
|   | 300 | | | | | | | | 100 | |
| 24 hr | 11 | | | | | | | | | |
|   | 33 | | 0 | 25 | 35 | 30 | | | | |
|   | 100 | 0 | 0 | 39 | 13 | 0 | 0 | | | |
|   | 300 | 27 | 3 | 70 | 45 | 37 | 60 | | | |

Mouse Lupus Disease Models.

Three distinct lupus disease models (BXSB-Yaa, NZBΔNZW, and Pristane) were chosen for compound POC evaluation because (1) the BXSB-Yaa and NZB/W strains develop spontaneous disease with polygenic etiology, demonstrating many hallmarks of human lupus such as DNA- and RNA-associated autoreactivity, proteinuria, and immune-complex mediated nephritis, and (2) positive TLR7 and/or TLR9 target validation results have been reported for all three disease models.

Key findings for ER-892887 in the SLE disease models are as follows (see FIG. 1, FIG. 2A-FIG. 2D, FIG. 3A-FIG. 3E, FIG. 4A-FIG. 4F, FIG. 5A-FIG. 5D, FIG. 6A-FIG. 6G, FIG. 12A-FIG. 12F, FIG. 13A-FIG. 13E, and FIG. 14A-FIG. 14C):

1) ER-892887 significantly reduced anti-dsDNA titers in the TLR7-driven BXSB-Yaa model, corresponding to a trend towards reduced proteinuria and complete prevention of Grade 3/4 nephritis onset.
2) ER-892887 reduced anti-dsDNA titers in the NZB/W model. Lower doses (33-100 mg/kg) of ER-892887 afforded survival benefit in this model, corresponding to reduced proteinuria and histological signs of glomerulonephritis. ER-892887 delayed the development of proteinuria in the NZB/W model more effectively than two drugs commonly used in the treatment of human lupus, and was efficacious in combination with hydroxychloroquine and prednisolone.
3) ER-892887 suppressed various auto-antibodies in the Pristane model, with particularly robust impact on RNA-related reactivity such as anti-RiboP titers. These changes corresponded to a reduction of whole blood interferon-driven gene expression and TN gene signature score by ER-892887 in this model. ER-892887 reduced arthritis severity in the pristane model, and suppressed the interferon gene signature score significantly, while three commonly used lupus treatments did not. ER-892887 also suppressed autoantibodies better than hydroxychloroquine or prednisolone at the doses tested.

Key findings for ER-885454 in the SLE disease models are as follows (see FIG. 7A-FIG. 7D, FIG. 8A-FIG. 8D, and FIG. 9A-FIG. 9C):

1) ER-885454 significantly reduced anti-dsDNA and anti-Sm/nRNP titers in the TLR7-driven BXSB-Yaa model, corresponding to significantly reduced proteinuria and complete prevention of Grade 3/4 nephritis onset.
2) ER-885454 reduced anti-dsDNA, proteinuria, and histological signs of glomerulonephritis in the NZB/W model.

Summary of Findings:

These data show a moderating effect of the compounds described on processes involved in important aspects of human lupus. Immune complexes containing nucleic acids can drive type 1 interferon production by dendritic cells, and the "interferon signature", reflecting presence of interferon and subsequent expression of interferon regulated genes, is associated with disease severity. ER-892887 blocks cytokine responses to RNA-Ig complexes in vitro, and suppressed the upregulation of interferon-driven genes in the pristane model. Both ER-892887 and ER-885454 limited the production of several autoantibody specificities, and suppressed kidney disease as manifested by proteinuria and histologic changes. Treatment with ER-892887 significantly enhanced survival in long-term dosing studies in the spontaneous NZB/W model. The results indicate that these compounds have the potential to control lupus symptoms and progression in human patients.

Pharmacology Materials & Methods

In vitro pharmacology: HEK-293 cells (ATCC) were engineered to stably express a NF-kappaB transcription factor inducible E-selectin (ELAM-1) luciferase reporter derived from the plasmid pGL3 (Promega) containing base pairs −2241 bp to −254 bp from the promoter of the human E-selectin gene (Accession No. NM_000450). These cells were then subsequently engineered to stably and individually express human TLR4, TLR7 or TLR9 full-length ORF cDNAs. Human TLR4 cDNA (Accession No. NM_138554) was cloned into pcDNA 3.0 expression vector (Invitrogen). TLR4 transfected cells were also engineered to express human MD-2 co-receptor [MD-2 cDNA (Accession No. NM_015364) was cloned into the pEF-BOS vector] and were supplemented with 10 nM soluble CD14 (R&D Systems) in the media to optimize LPS responsiveness. Human TLR9 cDNA (Accession No. NM_017442) was cloned into the pBluescript II KS vector (Agilent). Human TLR7 cDNA (Accession No. NM_016562) was obtained from OriGene. HEK-293 cells stably expressing human TLR8 (Accession No. NM_138636) or mouse TLR7 (Accession No. NM_133211) were purchased from InvivoGen and were then stably transfected with pNiFty2(NF-kappaB)-luciferase reporter plasmid (InvivoGen). Each cell type was plated in Dulbecco's modified Eagle's medium (DMEM) containing 10% fetal bovine serum (FBS) at a density of $2.22 \times 10^5$ cells/ml into a 384-well plate and incubated for 2 days at 37° C., 5% $CO_2$. Varying concentrations of antagonist compounds were then added. Cells were then incubated for another 30 minutes before adding the appropriate TLR agonist as follows (final concentrations indicated): lipopolysaccharide (LPS; Sigma) at 10 ng/ml for TLR4, CLO97 (InvivoGen) at 3 ug/ml for human TLR7 and TLR8 and mouse TLR7, and CpG-2006-2A [sequence: TCGTCGT-TAAGTCGTTAAGTCGTT (SEQ ID NO: 1) with phosphorothioate backbone, synthesized by Sigma-Aldrich] at 0.6 uM for TLR9. The cells were then incubated overnight, and NF-kappaB dependent luciferase reporter activation was quantified by measuring luminescence with SteadyGlo® (Promega) or Steadylite™ (Perkin Elmer) reagent as per the manufacturer's suggested protocol.

Human PBMC Cell-Based Assay.

Human peripheral blood mononuclear cells (PBMC) were isolated from freshly-drawn heparinized (10 USP units/ml, Hospira, Lakeforest, Ill.) healthy donor whole blood by density gradient (Histopaque® 1077, Sigma, Inc., St. Louis, Mo.). Briefly, 25 ml blood was diluted with 15 ml PBS (without $Ca^{2+}$, $Mg^{2+}$) in a 50 ml conical tube, and 12 ml Histopaque was underlaid using a spinal needle. Tubes were centrifuged for 45 minutes at 1200 rpm (350×g), and PBMC were collected from the buffy coat. Cells were then washed twice in PBS, and red blood cells were lysed by suspension in 5 ml ammonium chloride solution (1× Red Blood Cell Lysis Buffer, eBioscience) for 5 minutes at room temperature. After a final wash in PBS, PBMC were resuspended at a final concentration of $2 \times 10^6$/ml in RPMI-1640 media with L-glutamine (Invitrogen) and supplemented with 25 mM HEPES (Mediatech, Inc, Manassas Va.), 10% fetal bovine serum (HyClone, Logan, Utah), and Penicillin-Streptomycin-Glutamine (Mediatech) and plated at 100 ul/well ($2 \times 10^5$ cells/well) in tissue culture treated 96-well plates (Falcon). Antagonist compounds solubilized and serial diluted in 100% DMSO were added in triplicate to cells to yield a final concentration of 0.1% DMSO (v/v). Hydroxychloroquine (Acros Organics) solubilized and serial diluted in PBS was added in triplicate to cells. PBMC were incubated with antagonist compounds or HCQ for 30 minutes at 37° C., 5% $CO_2$ before adding various TLR agonist reagents in 100 ul complete media per well as follows (final concentrations indicated): R848 (Resiquimod; GLSynthesis, Worcester, Mass.) at 1 uM for TLR7 and TLR8, Pam3CSK4 (InvivoGen) at 50 ng/ml for TLR1/2, LPS (Sigma) at 10 ng/ml for TLR4, and CpG-2216 (InvivoGen) at 5 ug/ml for TLR9. To prepare a TLR7/8 agonist that mimics RNA-containing auto-antibody immune complexes in lupus patients, a 26-mer RNA with a sequence derived from human U1 snRNA stem loop IV [(sequence: GGGGGACUGCGU-UCGCGCUUUCCC (SEQ ID NO: 2) with phosphorothioate backbone] was synthesized (Dharmacon, Inc., Lafayette, Colo.), which has been shown previously to be a potent TLR7 and TLR8 agonist. This RNA molecule was diluted to 2.5 μM in serum-free RPMI, and mouse anti-human single stranded DNA monoclonal antibody (MAB3034, Millipore, Inc., Billerica, Mass.), which also cross-reacts with RNA, was added at a 1:25 dilution or at 1 ug/ml. The resulting "RNA-Ig" stimulus was incubated at room temperature for 15-30 minutes before adding to cells. PBMC were incubated with the various TLR agonists for 20 hours at 37° C., 5% $CO_2$. Cell culture supernatants were collected, and levels of various human cytokines were assessed as indicated by standard ELISA procedure according to the manufacturer's recommended protocol (BD Biosciences, Inc., San Diego, Calif.).

Mouse Spleen Cell-Based Assay.

Spleens were harvested from female BALB/c mice (Jackson Labs, Bar Harbor, Me.) euthanized by $CO_2$. A single cell suspension was obtained by passing spleens through a 40 μm nylon cell strainer. Cells were washed twice with 50 ml PBS (Mediatech, Inc., Manassas, Va.) and red blood cells were lysed in 5 ml RBC Lysis buffer (eBioscience, Inc., San Diego, Calif.) for 5 minutes at room temperature. Cells were washed twice more in PBS and finally resuspended in supplemented RPMI-1640 at $2.5 \times 10^6$ cells/ml. Cells were plated at 100 μl/well ($2.5 \times 10^5$ cells/well) in 96-well tissue culture treated plates (Falcon). Serial dilutions of compounds solubilized in 100% DMSO were added in triplicate to cells to yield a final concentration of 0.1% DMSO. Cells were incubated with compound for 30 minutes at 37° C., 5% $CO_2$ before adding 100 μl/well of 740 nM R848 (Resiquimod; GLSynthesis, Worcester, Mass.) in complete media for a final concentration of 370 nM R848. Cells were incubated for 20 hours at 37° C., 5% $CO_2$. Culture supernatants were collected, and levels of IL-6 were assessed by standard ELISA procedure according to the manufacturer's recommended protocol (BD Biosciences, Inc., San Diego, Calif.).

In Vivo Pharmacology:

Short-Term In Vivo (STIV) Assay.

Six to eight week old female BALB/c mice (Jackson Labs, Bar Harbor, Me.) were dosed by oral gavage in 200 ul volume with antagonist compounds formulated in 0.5% aqueous methyl-cellulose (Sigma, St. Louis, Mo.). At various time points afterwards, mice were injected subcutaneously (s.c.) in 100 ul volume with 15 ug R848 (Resiquimod; GLSynthesis, Worcester, Mass.) to stimulate TLR7. Blood plasma was collected by cardiac puncture, and levels of IL-6 at 1.5 hours after TLR7 stimulation were then assessed by standard ELISA procedure according to the manufacturer's recommended protocol (R&D Systems).

Mouse Lupus Disease Model Strains.

Male BXSB-Yaa and female NZBWF1/J mice were purchased from Jackson Labs (Bar Harbor, Me.), both of which manifest with spontaneous lupus disease. Female DBA/1 mice were purchased from Harlan Laboratories (Indianapolis, Ind.) and at the indicated ages given an intraperitoneal injection of 0.5 ml pristane (2,6,10,14-Tetramethylpentadecane; Sigma, St. Louis, Mo.) to chemically induce lupus disease or of 0.5 ml PBS to generate age-matched, non-diseased control mice. Mice were dosed daily by oral administration of compound or drug in 0.5% methylcellulose, for the time period indicated.

Assessment of Auto-Antibody Titers by ELISA.

Anti-dsDNA, -Sm/nRNP, -RiboP, and Histone titers were evaluated by standard ELISA approach. Briefly, 96-well EIA/RIA ELISA plates (Corning) were coated with 100 ul of diluted antigen in PBS for 90 minutes at room temperature as follows (final concentrations indicated): 10 U/ml Sm/nRNP complex (Immunovision), 10 ug/ml calf thymus dsDNA (Sigma), 5 U/ml RiboP (Immunovision), and 5 ug/ml Histone (Immunovision). Plates were washed with PBS/0.05% Tween20 (washing buffer) and blocked overnight with PBS/1% BSA (blocking buffer) at 4 C. Plates were washed, mouse plasma samples diluted in blocking buffer (ranging from 1:25-1:10,000 depending on the model and the antigen) were added to wells in 100 ul volume per well, and plates were incubated for 90 minutes at room temperature. Plates were then washed, 100 ul anti-mouse-IgG-HRPO (Southern Biotech) diluted 1:50,000 in PBS/1% BSA/0.05% Tween was added to each well, and plates were incubated for 90 minutes at room temperature. Plates were washed, and 100 ul of a 1:1 mix of substrate components from the OptEIA TMB substrate kit (BD Biosciences) was added to the wells. Plates were incubated at room temperature, and after sufficient color development the reaction was stopped by adding 100 ul of 0.18M sulfuric acid solution. Plates were read by spectrophotometry at 450 nm.

Assessment of Proteinuria.

Urine was collected manually from individual mice or by housing 1-2 mice per metabolic cage for 18 hours, and the Urinary Albumin Creatinine Ratio (UACR) was determined for each animal as an indirect measure of kidney function (UACR calculated as the ratio of mg of albumin/g of creatinine per dL of urine). Albumin levels in the urine samples were determined using a custom sandwich ELISA protocol using an anti-mouse albumin antibody set (Bethyl Labs), which included a coating antibody and a secondary antibody tagged with an HRP conjugate for detection. Creatinine levels were determined using a commercial creatinine assay kit (Cayman).

Histological Assessment of Nephritis.

Kidneys were collected from individual mice, fixed in 10% formalin for 24 hours, embedded in paraffin, and H&E stained sections were generated for histopathology assessment in a blinded fashion. Features of Nephritis Disease Scores are as follows: Grade 0—normal limits; Grade 1—ribbon-like capillary wall thickening; Grade 2—hypercellularity, segmentation, crescent formation; Grade 3—see Grade 2, increased severity and extent (% glomeruli affected) of glomerular lesions; Grade 4—sclerosis; severe glomerular disease (non-functional organ).

Statistics:

Differences in UACR, cytokine or antibody titer between drug-treated and vehicle-treated groups were calculated using values from all individual animals in the group. They were tested by one-way ANOVA with Dunn's post-test to compare each experimental group to vehicle. P values are stated in the figures, or by convention a single asterisk indicates $p<0.05$, two asterisks indicates $p<0.01$ and three asterisks indicates $p<0.001$. Sets of mortality curves were compared by Mantel-Cox, and where significance was found, pairs of curves were tested for difference using Wilcoxon analysis.

Assessment of Interferon Gene Expression in Whole Blood.

The expression of IFN-regulated genes in whole blood was measured by qPCR. Briefly, mice were euthanized, blood was collected via the vena cava, and 100 ul was preserved in tubes containing RNAlater (Ambion, Austin Tex.). Total RNA was isolated using the Mouse RiboPure Blood RNA Isolation Kit (Ambion). RNA concentrations were determined using a NanoDrop ND-1000 spectrophotometer (Thermo Scientific, Waltham Mass.). First strand cDNA was synthesized from 100 ng total RNA using High Capacity RNA-to-cDNA Master Mix (Applied Biosystems, Foster City Calif.). After reverse transcription, cDNA was diluted with nuclease-free water and mixed with Gene Expression Master Mix (Applied Biosystems). The mixture was then applied to a custom TaqMan® Low Density Array (TLDA) manufactured by Applied Biosystems, and qPCR was performed on the ABI 7900HT Fast Real-time PCR System (Applied Biosystems). Raw data was collected using RQ Manager 1.2.1 (Applied Biosystems) and analyzed using GeneData Analyst 2.2 software (GeneData).

The TLDA panel contained as many as 45 target genes and 3 housekeeping genes for normalization (see Table 4 below). The housekeeping gene Hprtl was chosen for normalization based on coefficient-of-variation. Relative quantities were determined for the target genes and used to calculate a fold change for each diseased mouse relative to the non-diseased control group receiving intraperitoneal PBS injection only. A standard Student's t-test was performed to determine which target genes were significantly increased between the non-diseased group (PBS treated) and the vehicle-treated diseased group (pristane treated), thereby representing the disease-regulated gene set. An "IFN score" was subsequently calculated for each mouse as the median fold change of all disease-regulated genes identified in the t-test.

TABLE 4

| Gene symbol | Taqman ID | Gene name |
|---|---|---|
| 18S | Hs99999901_s1 | Eukaryotic 18S rRNA |
| Bst2 | Mm01609165_g1 | bone marrow stromal cell antigen 2 |
| C1qa | Mm00432142_m1 | Complement component 1q |
| C3 | Mm00437858_m1 | complement component 3 |
| C3ar1 | Mm02620006_s1 | complement component 3a receptor 1 |
| Ccl2 | Mm00441243_g1 | chemokine (C-C motif) ligand 2 |
| Ccr2 | Mm00438270_m1 | chemokine (C-C motif) receptor 2 |
| Cd300e | Mm00468131_m1 | CD300e antigen |
| CMPK2 | Mm00469582_m1 | cytidine monophosphate (UMP-CMP) kinase 2 |
| CD38 | Mm01220906_m1 | CD38 antigen |
| Cxcl10 | Mm00445235_m1 | chemokine (C—X—C motif) ligand 10 |
| DDX60 | Mm00460708_m1 | DEAD (Asp-Glu-Ala-Asp) box polypeptide 60 |
| Elane | Mm00469310_m1 | elastase, neutrophil expressed |
| Epsti1 | Mm00712734_m1 | epithelial stromal interaction 1 (breast) |
| Fcgr1 | Mm00438874_m1 | Fc receptor, IgG, high affinity I |
| Fpr1 | Mm00442803_s1 | formyl peptide receptor 1 |
| Gapdh | Mm99999915_g1 | glyceraldehyde-3-phosphate dehydrogenase |
| HERC6 | Mm01341950_m1 | hect domain and RLD 6 |
| Hprt | Mm00446968_m1 | hypoxanthine guanine phosphoribosyl transferase |
| Ifi202b | Mm00839397_m1 | interferon activated gene 202B |
| Ifi204 | Mm00492602_m1 | interferon activated gene 204 |
| IFI27 | Mm01329883_gH | interferon, alpha-inducible protein 27 like 2A |

TABLE 4-continued

| Gene symbol | Taqman ID | Gene name |
|---|---|---|
| Ifi35 | Mm00510329_m1 | interferon-induced protein 35 |
| Ifi44 | Mm00505670_m1 | interferon-induced protein 44 |
| IFIH1 | Mm00459183_m1 | erferon induced with helicase C domain 1 |
| Ifit1 | Mm00515153_m1 | interferon-induced protein with tetratricopeptide repeats 1 |
| IFIT2 | Mm00492606_m1 | interferon-induced protein with tetratricopeptide repeats 2 |
| IFIT3 | Mm01704846_s1 | interferon-induced protein with tetratricopeptide repeats 3 |
| Irf7 | Mm00516788_m1 | interferon regulatory factor 7 |
| Isg15 | Mm01705338_s1 | ISG15 ubiquitin-like modifier |
| Isg20 | Mm00469585_m1 | interferon-stimulated protein |
| Ly6e | Mm01200460_g1 | lymphocyte antigen 6 complex, locus E |
| Mmp8 | Mm00439509_m1 | matrix metallopeptidase 8 |
| Mmp9 | Mm00442991_m1 | matrix metallopeptidase 9 |
| Mpo | Mm00447886_m1 | myeloperoxidase |
| Ms4a6c | Mm00459296_m1 | membrane-spanning 4-domains, subfamily A, member 6C |
| Mx1 | Mm00487796_m1 | myxovirus (influenza virus) resistance 1 |
| Oas3 | Mm00460944_m1 | 2-5 oligoadenylate synthetase 3 |
| Oasl2 | Mm00496187_m1 | 2-5 oligoadenylate synthetase-like 2 |
| Ppia | Mm02342430_g1 | peptidylprolyl isomerase A (cyclophilin A) |
| Rsad2 | Mm00491265_m1 | radical S-adenosyl methionine domain containing 2 |
| SIGLEC1 | Mm00488332_m1 | sialic acid binding Ig-like lectin 1, sialoadhesin |
| Stat1 | Mm00439531_ml | signal transducer and activator of transcription 1 |
| Tlr7 | Mm00446590_m1 | toll-like receptor 7 |
| Tlr9 | Mm00446193_m1 | toll-like receptor 9 |
| Tnf | Mm00443258_m1 | tumor necrosis factor |
| Tnfsf13b | Mm00446347_m1 | tumor necrosis factor (ligand) superfamily, member 13b |
| Treml4 | Mm00553947_m1 | triggering receptor expressed on myeloid cells-like 4 |
| Usp18 | Mm00449455_m1 | ubiquitin specific peptidase 18 |
| Xaf1 | Mm01248390_m1 | XIAP associated factor 1 |

We claim:

1. A method for antagonizing TLR7, comprising administering a pharmaceutically effective amount of a compound of formula (I)

(I)

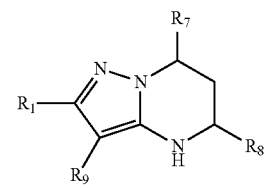

or a pharmaceutically acceptable salt thereof, or a stereoisomer thereof or mixture of stereoisomers thereof, wherein $R_1$ is optionally substituted piperidinyl, optionally substituted pyridyl, optionally substituted pyrrolyl, optionally substituted pyrrodinyl, 1,4-dimethylthiazolyl, 2-ethyl-4-methylthiazolyl, 2-isopropylthiazol-5-yl, thiazolyl, 3-ethylthiazol-5-yl, 1-methylsulfonylpiperidin-4-yl, or $R_1$ is —C(O)Z, where Z is piperazinyl, (S)-2-(3-ethylpiperazin-1-yl), optionally substituted pyrrolopyrrolyl, piperidin-3-ylamino, or, $R_1$ is where $R_{13}$ is H, methylpyrazolyl, methylimidazolyl, benzyl, 3-hydroxybutyl, 3-(dimethylamino)-2,2-dimethylpropyl, ethylamide, methylpyridyl, methylsulfonyl, (1-methylimidazol-2-yl)methyl, (1,5-dimethylimidazol-4-yl)methyl, (1-methylpyrrol-2-yl)methyl, or

SEQUENCE LISTING

<160> NUMBER OF SEQ ID NOS: 2

<210> SEQ ID NO 1
<211> LENGTH: 24
<212> TYPE: DNA
<213> ORGANISM: Artificial Sequence
<220> FEATURE:
<223> OTHER INFORMATION: synthetic construct

<400> SEQUENCE: 1
tcgtcgttaa gtcgttaagt cgtt 24

<210> SEQ ID NO 2
<211> LENGTH: 24
<212> TYPE: RNA
<213> ORGANISM: Artificial Sequence
<220> FEATURE:
<223> OTHER INFORMATION: synthetic construct

<400> SEQUENCE: 2
gggggacugc guucgcgcuu uccc 24 where R₁₃ is C(O)W, where W is N(CH₃)₂, piperidinyl, piperazinyl, or morpholinyl, or,
R₁ is
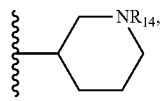
where R₁₄ is C(O)CH₃, H, or (1-methylpyrrol-2-yl)methyl, or,
R₁ is
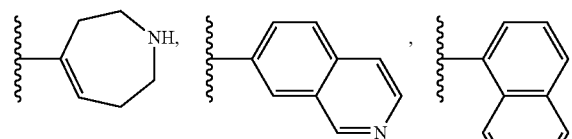
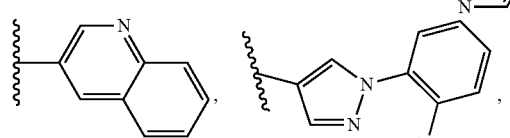
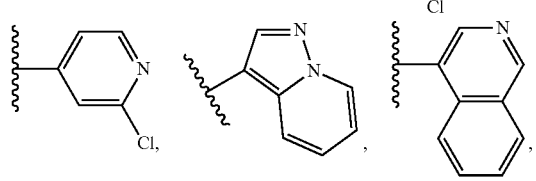
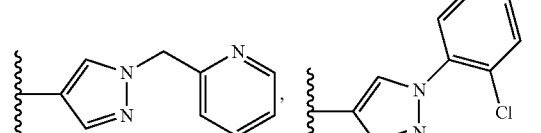
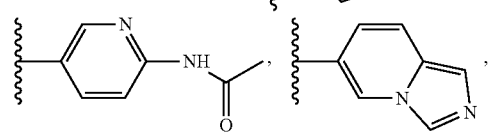
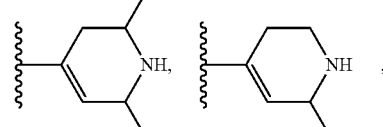
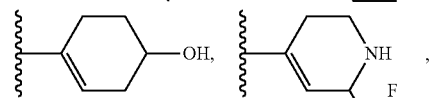
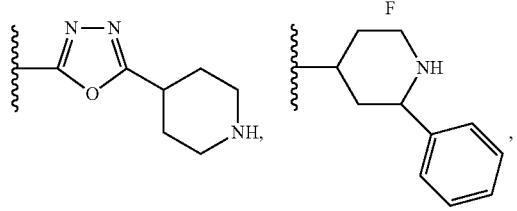
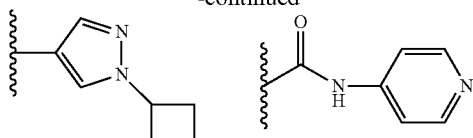
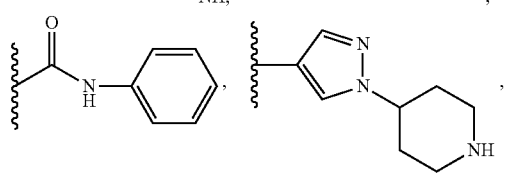
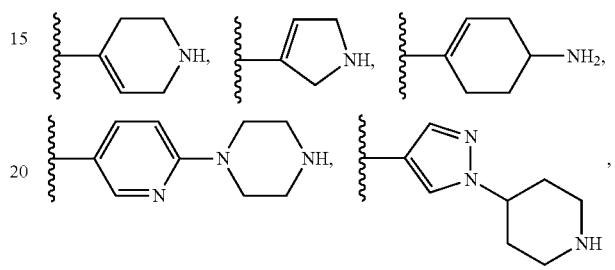
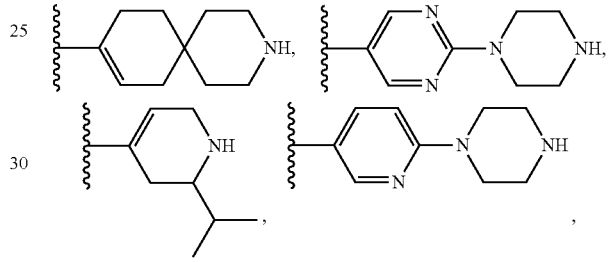
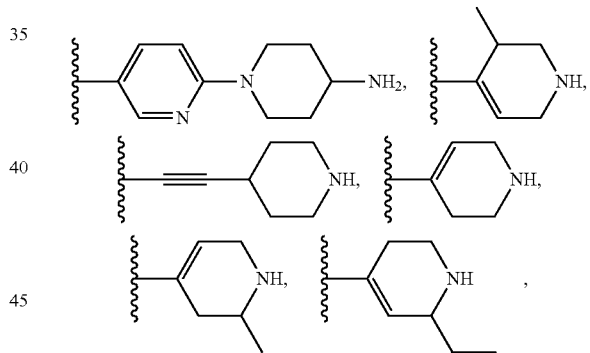
or
R₁ is
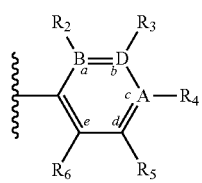
where A, B, and D may all be carbon, or where two of A, B, and D are carbon and the other is nitrogen, or where one of A, B, and D is carbon and the remaining two are nitrogen; and when A is nitrogen R₄ is absent, when B is nitrogen R₂ is absent, and when D is nitrogen R₃ is absent; and wherein R₂ is H, —CH₃, or F, or, with R₃ and the atoms at positions a and b, forms an optionally substituted pyridine or a pyrazole; and wherein R₃ is H, F, Cl, —CN, —CH₃, —OCH₃, —OH, —NH₂, methylsulfonyl,

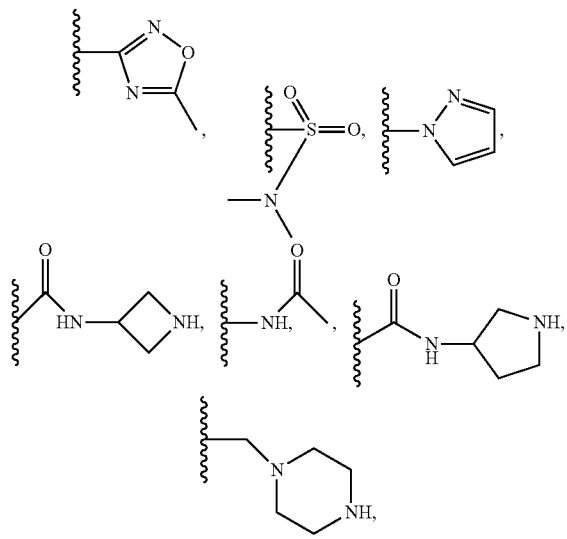

or, with R₄ and the atoms at b and c, forms an optionally substituted benzene, optionally substituted imidazole, optionally substituted pyrazole, optionally substituted pyrazolidine, optionally substituted imidazolidine, optionally substituted isothiazole,

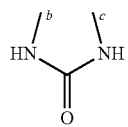

or, with R₂ and the atoms at a and b, forms an optionally substituted pyridine or optionally substituted pyrazole; and wherein R₄ is F, —CN, —OCH₃, —OEt, H, Cl, Br, —NH—C(O)—CH—(CH₃)₂, —N(CH₃)₂, —CH₃, —CH₂OH,

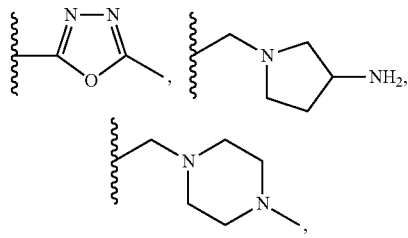

optionally substituted piperazinyl, 4-hydroxypiperizin-1-yl, optionally substituted piperidinyl not attached to a phenyl group through a nitrogen, or, with R₃ and the atoms at b and c, forms an optionally substituted pyrazole ring or

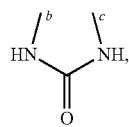

or, with R₅ and the atoms at c and d, forms an optionally substituted pyrazole ring or an optionally substituted pyrrole ring, or, R₄ is -(q)-C(O)X, where q is a bond, is —NH—, or is —CH₂—, and where X is —NR₁₁R₁₂, where R₁₁ and R₁₂ are both H, both —CH₂CH₃, or both —CH₃, or where one of R₁₁ and R₁₂ is H and the other is 1,1-dimethylethyl, cyclobutyl, cyclopropyl, lower alkyl, methyl alcohol, propyl alcohol, cyclobutylmethyl; 2,3-dihydroxypropyl, benzyl, azetidinyl, pyrrolidinyl, piperidinyl, methylazetidinyl, —CH₂—NH—CH₃, pyrazolyl, piperazinyl, alcohol, —OCH₃, or

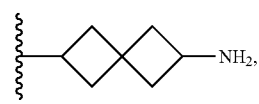 [SMILES: *C1CC2(C1)CC(N)C2]

or where X is optionally substituted pyrrolidinyl attached through a nitrogen to the carbonyl group of R₄, optionally substituted piperidinyl not attached through a nitrogen to the carbonyl group of R₄, optionally substituted pyrrolidinyl attached through a nitrogen to the carbonyl group of R₄, optionally substituted piperazinyl attached through a nitrogen to the carbonyl group of R₄, or optionally substituted morpholinyl attached through a nitrogen to the carbonyl group of R₄,

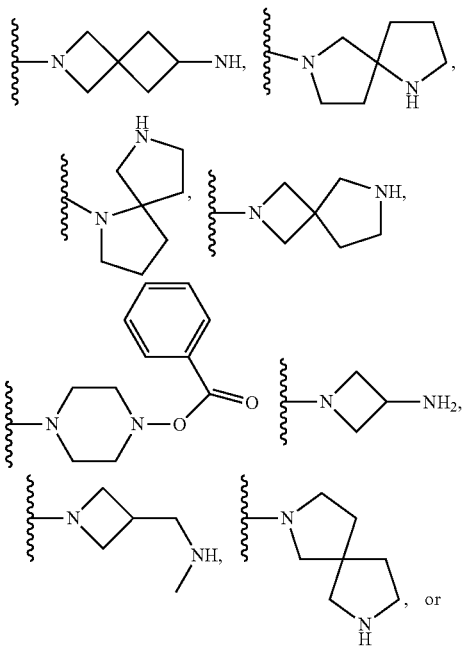

and wherein
R$_5$ is H, F, Cl, —CH$_3$, —OCH$_3$, pyrrolyl, —CH$_2$OH, —NH$_2$, —OH, or, with R$_4$ and the atoms at c and d, forms an optionally substituted benzene, an optionally substituted pyrazole, or an optionally substituted pyrrole, or, with R$_6$ and the atoms at d and e, forms an optionally substituted pyridine, or R$_5$ is C(O)Y, where Y is —NH$_2$, —N(CH$_3$)$_2$, optionally substituted piperazinyl, optionally substituted piperidinyl, and wherein
R$_6$ is H, F, —CH$_3$, —CF$_3$, or, with R$_5$ and the atoms at c and d, forms an optionally substituted benzene or an optionally substituted pyrazole; and wherein
R$_7$ is —CF$_3$ or —CHF$_2$; and wherein
R$_8$ is and wherein
R$_9$ is Br, Cl, F, I, or H;
with the following provisos:
  when R$_4$ is F: R$_2$ is not —CH$_3$ or F; R$_3$ is not —CH$_3$, —CN, F, Cl, or —OCH$_3$; R$_5$ is not —CH$_3$, F, Cl, or —OCH$_3$; and R$_6$ is not —CH$_3$ or F;
  when R$_4$ is Cl: R$_2$ is not F; R$_3$ is not F or —CN; R$_5$ is not F, —CN, or —C(O)N(CH$_3$)$_2$; R$_6$ is not —CF$_3$ or F; D is not nitrogen; and either R$_5$ is —C(O)NH$_2$ or one of R$_2$, R$_3$, R$_5$, and R$_6$ is —CH$_3$;
  when R$_4$ is —CH$_3$: R$_3$ is not F; R$_5$ is not F; and R$_5$ and R$_6$ do not form a pyrimidine together with the atoms at d and e;
  when R$_4$ is —OCH$_3$: R$_2$ is not F; R$_3$ is not Cl or —OCH$_3$, R$_5$ is not Cl or —OCH$_3$; and R$_6$ is not F or —CF$_3$;
  when R$_4$ is —CN: R$_2$ is not F; R$_3$ is not Cl, F, or —OCH$_3$, R$_5$ is not Cl, F, or —OCH$_3$; and R$_6$ is not F;
  when R$_4$ is —OCH$_2$CH$_3$: R$_3$ is not Cl or F; R$_5$ is not Cl or F; and R$_6$ is not —CF$_3$;
  when R$_4$ is R$_3$ is not H or F; and R$_5$ is not H or F;
  when R$_4$ is at least one of R$_2$, R$_3$, R$_5$, and R$_6$ is not H;
  when R$_4$ is R$_3$ is not F; and R$_5$ is not F;
  when R$_2$ is F: R$_3$ is not —OCH$_3$ or F; R$_5$ is not —CN; and at least one of R$_3$, R$_4$, R$_5$, and R$_6$ is not H;
  when R$_2$ is Cl: R$_3$ is not F;
  when R$_2$ is —CH$_3$: R$_3$ is not Cl; at least one of R$_3$, R$_4$, R$_5$, and R$_6$ is not —CH$_3$; and R$_4$ and R$_5$ do not form a pyrazolyl with the atoms at c and d;
  when R$_3$ is —OCH$_3$: R$_2$ is not F; and R$_6$ is not F;
  when R$_3$ is F: R$_2$ is not —OCH$_3$; and X is not when R$_3$ is Cl: R$_5$ is not Cl; R$_{11}$ is not benzyl; and R$_{12}$ is not benzyl;
  when R$_5$ is Cl, R$_6$ is not —CH$_3$; R$_{11}$ is not benzyl; and R$_{12}$ is not benzyl;
  when R$_5$ is F or —OCH$_3$: R$_6$ is not F;
  when R$_6$ is F: at least one of R$_2$, R$_3$, R$_4$, and R$_5$ is not H;
  when R$_3$ and R$_5$ are H: R$_{11}$ is not cyclopropyl; and R$_{12}$ is not cyclopropyl;
  when R$_9$ is Cl, R$_1$ is not an amide group;
  when B is nitrogen and A and D are carbon: R$_4$ may not be —CN or

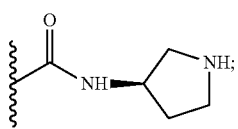 [SMILES: *C(=O)N[C@@H]1CCNC1]

when R$_7$ is —CHF$_2$ and R$_4$ is

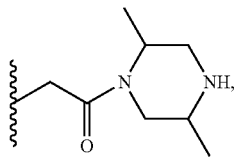

then R$_4$ does not have the absolute stereochemistry

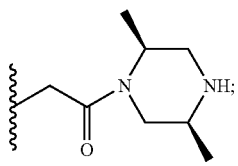

and
wherein, when R$_8$ is

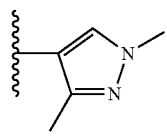 [SMILES: *c1cn(C)nc1C]

then the following provisos are in effect:
  when R$_4$ is F: at least one of R$_2$, R$_3$, R$_5$, and R$_6$ is not H; R$_3$ is not C(O)N(CH$_3$)$_2$; and R$_5$ is not C(O)N(CH$_3$)$_2$;
  when R$_4$ is Cl: at least one of R$_2$, R$_3$, R$_5$, and R$_6$ is not H;
  when R$_3$ is F: R$_4$ is not C(O)NHCH$_2$CH$_2$CH$_2$CH$_3$, C(O)N(CH$_3$)$_2$, C(O)NHCH$_2$CH$_2$CH$_3$, or C(O)NHC(CH$_3$)$_3$;
  R$_4$ is not C(O)NHCH$_2$CH$_2$OH, C(O)NHCH(CH$_3$)$_2$, —CN, or

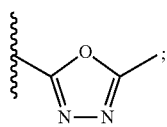 [SMILES: *c1nnc(C)o1]

R$_1$ is not

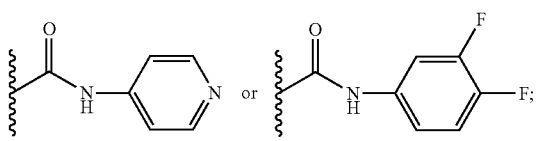 [SMILES: *C(=O)Nc1ccncc1 ; *C(=O)Nc1ccc(F)c(F)c1]

R$_5$ is not

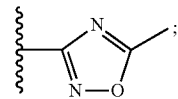

R$_3$ is not

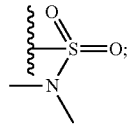

when R$_2$ is F: R$_5$ is not —C(O)NH$_2$;
when R$_2$ is —CH$_3$, R$_4$ and R$_5$ do not form a pyrazole with atoms at c and d; and
when B is nitrogen, R$_3$ and R$_4$ do not form an optionally substituted imidazole with the atoms at b and c; and
wherein, when R$_8$ is

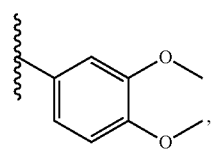

then the following provisos are in effect:
  R$_4$ is not —CH$_3$, —C(O)NHCH$_2$CH$_2$OH, —NHC(O)CH(CH$_3$)$_2$, or

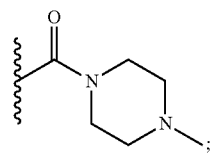

when R$_4$ is C(O)NHCH$_3$, at least one of R$_2$, R$_3$, R$_5$, and R$_6$ is not H;
when R$_4$ is —OCH$_3$: R$_3$ is not F or —CH$_3$; and R$_5$ is not F or —CH$_3$;
when R$_4$ is

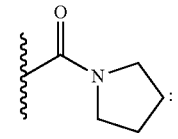 [SMILES: *C(=O)N1CCCC1]

R$_3$ is not Cl; and R$_5$ is not Cl;
when R$_4$ is —C(O)NHCH(CH$_3$)$_2$ or —C(O)N(CH$_2$CH$_3$)$_2$: at least one of R$_3$ and R$_5$ is not H;
R$_5$ is not —C(O)NH$_2$; and
R$_6$ is not —CF$_3$.

2. The method of claim 1, wherein said compound is administered as a pharmaceutically acceptable salt.

3. The method of claim 2, wherein the administration of said pharmaceutically acceptable salt of 4-((5 S,7R)-5-(3,4- dimethoxyphenyl)-7-(trifluoromethyl)-4,5,6,7-tetrahydropyrazolo[1,5-a]pyrimidin-2-yl)phenyl)(piperazin-1-yl)methanone antagonizes TLR8.

4. The method of claim 1, wherein the administration of a pharmaceutically effective amount of a compound of formula (I) or pharmaceutically acceptable salt thereof antagonizes TLR8.

5. A method for antagonizing TLR7, comprising administering a pharmaceutically effective amount of 4-((5S,7R)-5-(3,4-dimethoxyphenyl)-7-(trifluoromethyl)-4,5,6,7-tetrahydropyrazolo[1,5-a]pyrimidin-2-yl)phenyl)(piperazin-1-yl)methanone, or a pharmaceutically acceptable salt thereof.

6. The method of claim 5, wherein the administration of a pharmaceutically effective amount of 4-((5S,7R)-5-(3,4-dimethoxyphenyl)-7-(trifluoromethyl)-4,5,6,7-tetrahydropyrazolo[1,5-a]pyrimidin-2-yl)phenyl)(piperazin-1-yl)methanone, or a pharmaceutically acceptable salt thereof antagonizes TLR8.

7. A method for antagonizing TLR7, comprising administering a pharmaceutically effective amount of a compound of formula (IV)

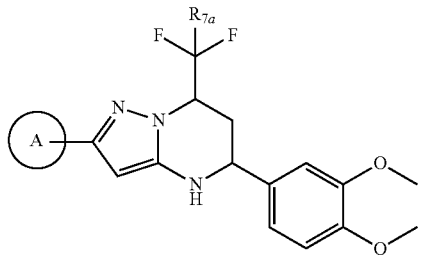

Formula (IV)

or a pharmaceutically acceptable salt thereof, or a stereoisomer thereof or mixture of stereoisomers thereof, wherein: $R_{7a}$ is H or F; and wherein
Ring A is:

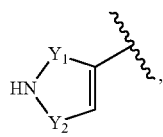

wherein $Y_1$ and $Y_2$ are independently selected from the group consisting of —$CH_2$— and —$CH_2CH_2$—, and wherein each of $Y_1$ and $Y_2$ is optionally substituted by $C_{1-3}$ alkyl;

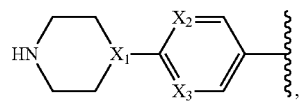

wherein $X_1$, $X_2$, and $X_3$ are independently selected from the group consisting of —CH— and N;

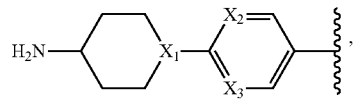

wherein $X_1$, $X_2$, and $X_3$ are independently selected from the group consisting of —CH— and N;

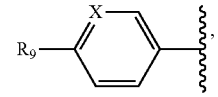

wherein X is N or —CH— optionally substituted by —$CH_3$, F, or Cl, and
wherein $R_9$ is —C(O)Z, wherein Z is 2, 3-dihydroxypropylamine; a five to seven member cyclic diamine that is optionally bridged or optionally substituted at a carbon atom with a lower alkyl; a seven to ten member bicyclodiamine; a seven to eleven member spirodiamine; —NH substituted with a four to seven member cyclic amine optionally substituted with —$NH_2$; —OH; —$CH_2NHR$, wherein R is H or lower alkyl; —NH substituted with a seven to eleven member spiroalkane optionally substituted with —$NH_2$; or
$R_9$ is $CH_3NHC(O)$—, and a carbon atom on the aryl ring to which $R_9$ is attached is substituted with one of —$CH_3$, F, or Cl; $R_9$ is $(CH_3)_2CHNHC(O)$—, and a carbon atom on the aryl ring to which $R_9$ is attached is substituted with one of —$CH_3$, F, or Cl; or $R_9$ is $(CH_3)_3CNHC(O)$— and a carbon atom on the aryl ring to which $R_9$ is attached is substituted with one of —$CH_3$, F, or Cl; or
$R_9$ is

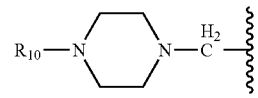

wherein the piperazine is optionally bridged or substituted with lower alkyl and $R_{10}$ is H or —$CH_3$; or
$R_9$ is

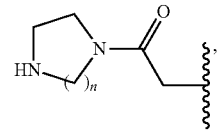

wherein n is 1-3 and the cyclic diamine is optionally bridged or substituted with lower alkyl; or
$R_9$ is

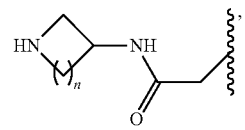

wherein n is 1-4; or
$R_9$ is —$NHC(O)NH_2$, —$CH_2C(O)NH$— wherein the nitrogen is substituted with a four to seven member cyclic amine; —$CH_2$—C(O)— wherein the carbonyl is substituted with a seven to ten member bicyclodiamine; and a four to seven member cyclic amine substituted with —CH₂C(O)NH₂; or

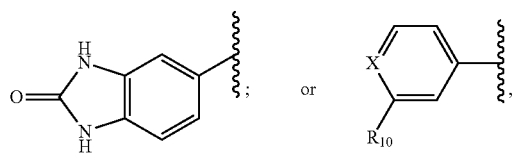

wherein X is N or —CH— wherein the C is optionally substituted by —CH₃, F, or Cl, and wherein $R_{10}$ is —C(O)NH— wherein the nitrogen is substituted by a four to seven member cyclic amine; —C(O)— substituted by a seven to ten member bicyclodiamine; —C(O)— substituted by a seven to eleven member spirodiamine; pyrazole; [1,2,4]oxadiazole optionally substituted by —CH₃ on a carbon atom of the oxadiazole; —NHC(O)CH₃; —CH₂— substituted by a piperazine; —CH₂— substituted by a piperazine including a methyl substituent; —C(O)— substituted by a five to seven member cyclic diamine; —C(O)NHCH₂— wherein the —CH₂— is substituted by azetidine; or —C(O)— substituted with a five to seven member cyclic amine wherein the amine includes an —NH₂ substituent; or cyanophenyl; isoquinoline; cyclohexene substituted with —NH₂ at the 4' position; 1,4-dimethylindazole-5-yl; 1,6-dimethylindazole-5-yl; cyclohexene substituted with spiropiperidine at the 4' position; 1-piperidinopyrazole; or o-methoxypyridine.

8. The method of claim 7, wherein the administration of a pharmaceutically effective amount of a compound of formula (IV) or a pharmaceutically acceptable salt thereof antagonizes TLR8.

9. A method for antagonizing TLR8, comprising administering a pharmaceutically effective amount of a compound of formula (I)

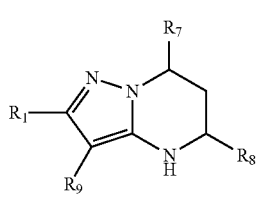

or a pharmaceutically acceptable salt thereof, or a stereoisomer thereof or mixture of stereoisomers thereof, wherein $R_1$ is optionally substituted piperidinyl, optionally substituted pyridyl, optionally substituted pyrrolyl, optionally substituted pyrrodinyl, 1,4-dimethylthiazolyl, 2-ethyl-4-methylthiazolyl, 2-isopropylthiazol-5-yl, thiazolyl, 3-ethylthiazol-5-yl, 1-methylsulfonylpiperidin-4-yl, or $R_1$ is —C(O)Z, where Z is piperazinyl, (S)-2-(3-ethylpiperazin-1-yl), optionally substituted pyrrolopyrrolyl, piperidin-3-ylamino, or, $R_1$ is

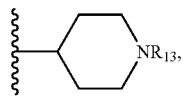

where $R_{13}$ is H, methylpyrazolyl, methylimidazolyl, benzyl, 3-hydroxybutyl, 3-(dimethylamino)-2,2-dimethylpropyl, ethylamide, methylpyridyl, methylsulfonyl, (1-methylimidazol-2-yl)methyl, (1,5-dimethylimidazol-4-yl)methyl, (1-methylpyrrol-2-yl)methyl, or where $R_{13}$ is C(O)W, where W is —N(CH₃)₂, piperidinyl, piperazinyl, or morpholinyl, or, $R_1$ is

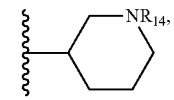

where $R_{14}$ is —C(O)CH₃, H, or (1-methylpyrrol-2-yl)methyl, or, $R_1$ is

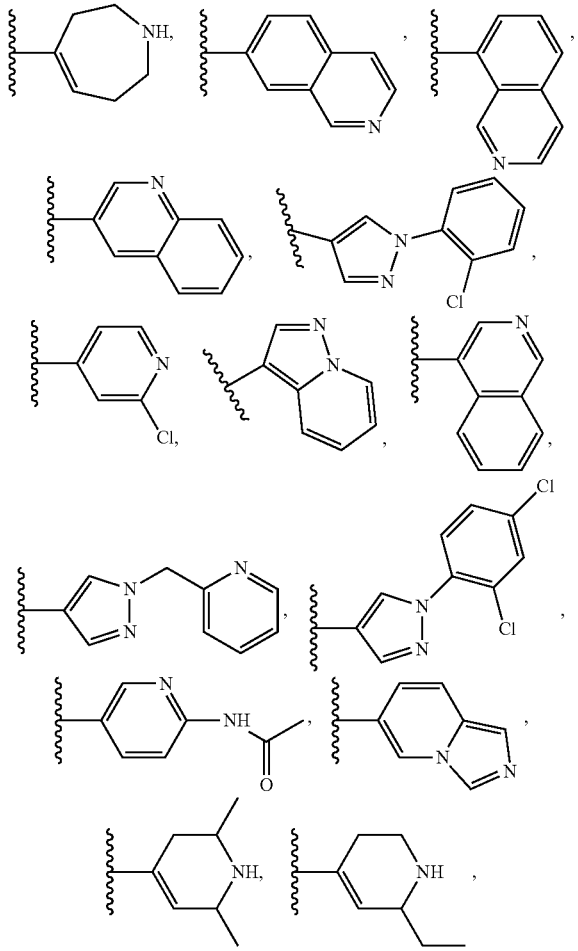

-continued

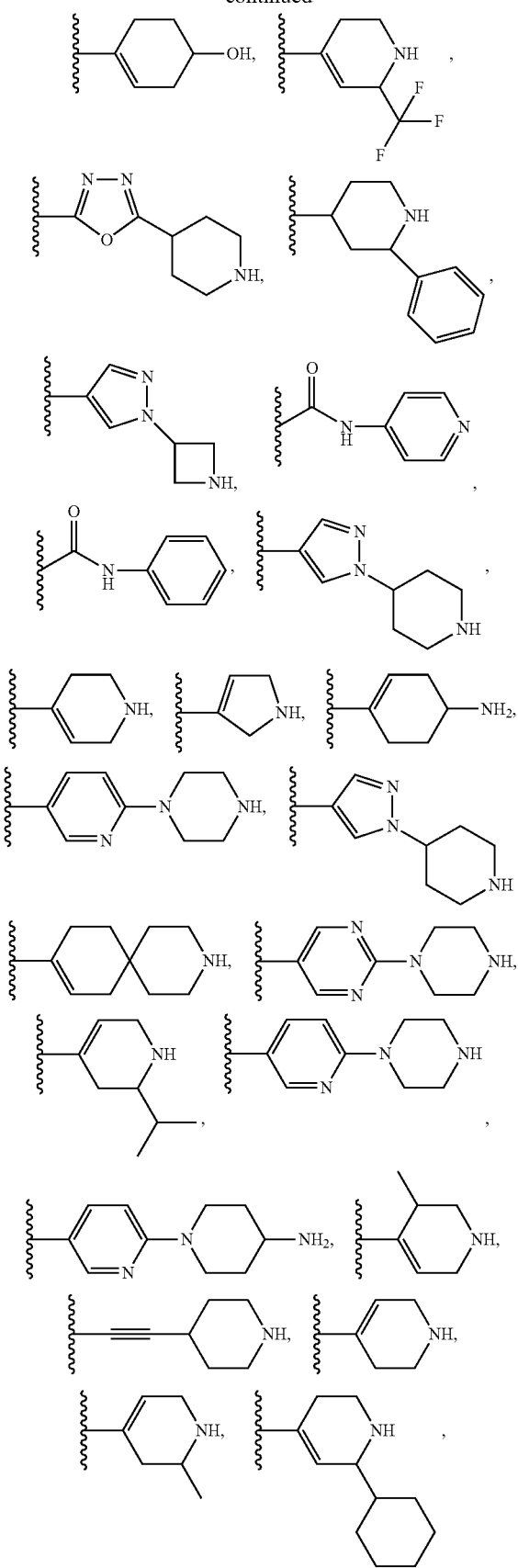

or

R₁ is

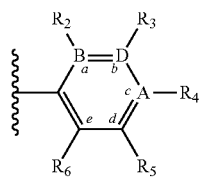

where A, B, and D may all be carbon, or where two of A, B, and D are carbon and the other is nitrogen, or where one of A, B, and D is carbon and the remaining two are nitrogen; and when A is nitrogen $R_4$ is absent, when B is nitrogen $R_2$ is absent, and when D is nitrogen $R_3$ is absent; and wherein $R_2$ is H, —CH₃, or F, or, with $R_3$ and the atoms at positions a and b, forms an optionally substituted pyridine or a pyrazole; and wherein $R_3$ is H, F, Cl, —CN, —CH₃, —OCH₃, —OH, —NH₂, methylsulfonyl,

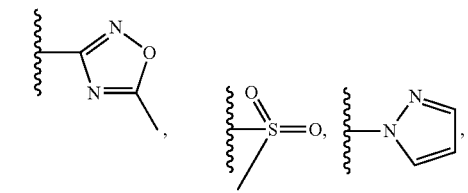

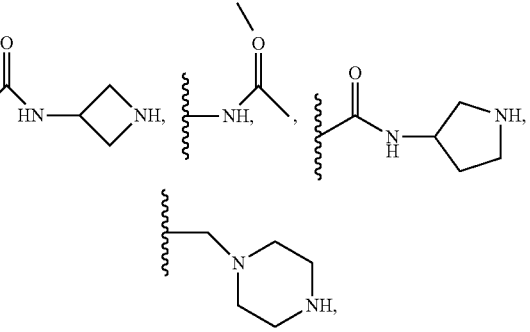

or, with $R_4$ and the atoms at b and c, forms an optionally substituted benzene, optionally substituted imidazole, optionally substituted pyrazole, optionally substituted pyrazolidine, optionally substituted imidazolidine, optionally substituted isothiazole,

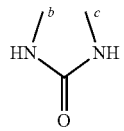

or, with $R_2$ and the atoms at a and b, forms an optionally substituted pyridine or optionally substituted pyrazole; and wherein $R_4$ is F, —CN, —OCH₃, —OEt, H, Cl, Br, —NH—C(O)—CH—(CH₃)₂, —N(CH₃)₂, —CH₃, —CH₂OH,

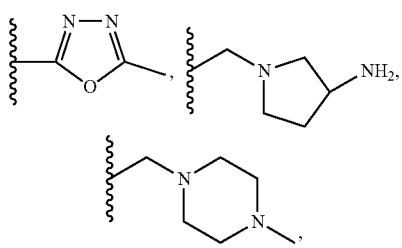

optionally substituted piperazinyl, 4-hydroxypiperizin-1-yl, optionally substituted piperidinyl not attached to a phenyl group through a nitrogen, or, with $R_3$ and the atoms at b and c, forms an optionally substituted pyrazole ring or

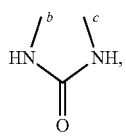

or, with $R_5$ and the atoms at c and d, forms an optionally substituted pyrazole ring or an optionally substituted pyrrole ring, or, $R_4$ is -(q)-C(O)X, where q is a bond, is —NH—, or is —CH$_2$—, and where X is —NR$_{11}$R$_{12}$, where $R_{11}$ and $R_{12}$ are both H, both —CH$_2$CH$_3$, or both —CH$_3$, or where one of $R_{11}$ and $R_{12}$ is H and the other is 1,1-dimethylethyl, cyclobutyl, cyclopropyl, lower alkyl, methyl alcohol, propyl alcohol, cyclobutylmethyl; 2,3-dihydroxypropyl, benzyl, azetidinyl, pyrrolidinyl, piperidinyl, methylazetidinyl, —CH$_2$—NH—CH$_3$, pyrazolyl, piperazinyl, alcohol, —OCH$_3$, or

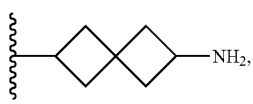 [SMILES: *C1CC2(C1)CC(N)C2]

or where X is optionally substituted pyrrolidinyl attached through a nitrogen to the carbonyl group of $R_4$, optionally substituted piperidinyl not attached through a nitrogen to the carbonyl group of $R_4$, optionally substituted pyrrolidinyl attached through a nitrogen to the carbonyl group of $R_4$, optionally substituted piperazinyl attached through a nitrogen to the carbonyl group of $R_4$, or optionally substituted morpholinyl attached through a nitrogen to the carbonyl group of $R_4$,

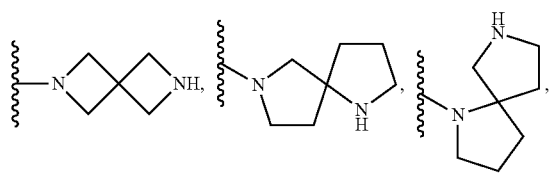

-continued

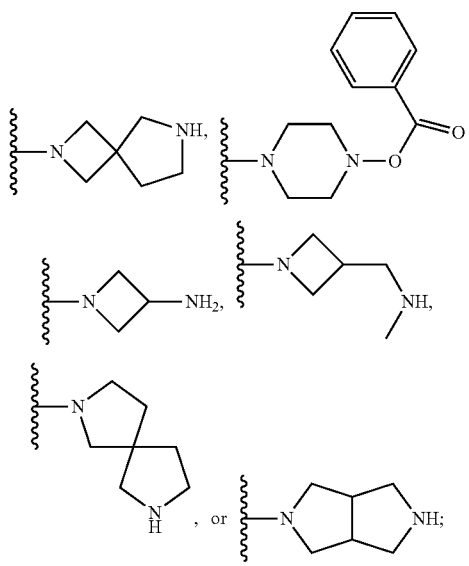

and wherein $R_5$ is H, F, Cl, —CH$_3$, —OCH$_3$, pyrrolyl, —CH$_2$OH, —NH$_2$, —OH,

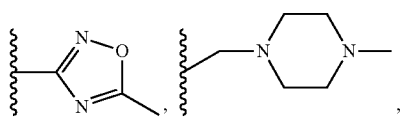

or, with $R_4$ and the atoms at c and d, forms an optionally substituted benzene, an optionally substituted pyrazole, or an optionally substituted pyrrole, or, with $R_6$ and the atoms at d and e, forms an optionally substituted pyridine, or $R_5$ is C(O)Y, where Y is —NH$_2$, —N(CH$_3$)$_2$, optionally substituted piperazinyl, optionally substituted piperidinyl,

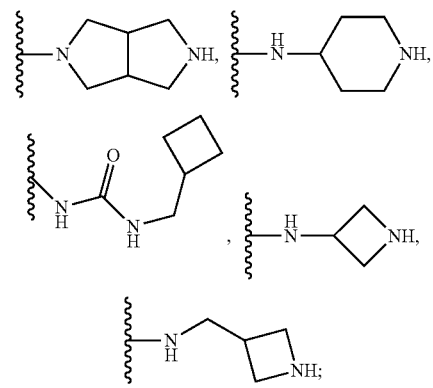

and wherein $R_6$ is H, F, —CH$_3$, —CF$_3$, or, with $R_5$ and the atoms at c and d, forms an optionally substituted benzene or an optionally substituted pyrazole; and wherein $R_7$ is —$CF_3$ or —$CHF_2$; and wherein
$R_8$ is

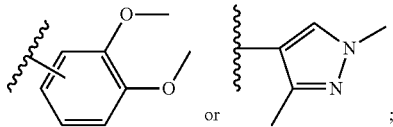

and wherein
$R_9$ is Br, Cl, F, I, or H;
with the following provisos:
when $R_4$ is F: $R_2$ is not —$CH_3$ or F; $R_3$ is not —$CH_3$, —CN, F, Cl, or —$OCH_3$; $R_5$ is not —$CH_3$, F, Cl, or —$OCH_3$; and $R_6$ is not —$CH_3$ or F;
when $R_4$ is Cl: $R_2$ is not F; $R_3$ is not F or —CN; $R_5$ is not F, —CN, or —$C(O)N(CH_3)_2$; $R_6$ is not —$CF_3$ or F; D is not nitrogen; and either $R_5$ is —$C(O)NH_2$ or one of $R_2$, $R_3$, $R_5$, and $R_6$ is —$CH_3$;
when $R_4$ is —$CH_3$: $R_3$ is not F; $R_5$ is not F; and $R_5$ and $R_6$ do not form a pyrimidine together with the atoms at d and e;
when $R_4$ is —$OCH_3$: $R_2$ is not F; $R_3$ is not Cl or —$OCH_3$, $R_5$ is not Cl or —$OCH_3$; and $R_6$ is not F or —$CF_3$;
when $R_4$ is —CN: $R_2$ is not F; $R_3$ is not Cl, F, or —$OCH_3$, $R_5$ is not Cl, F, or —$OCH_3$; and $R_6$ is not F;
when $R_4$ is —$OCH_2CH_3$: $R_3$ is not Cl or F; $R_5$ is not Cl or F; and $R_6$ is not —$CF_3$;
when $R_4$ is

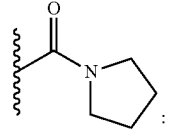

$R_3$ is not H or F; and $R_5$ is not H or F;
when $R_4$ is

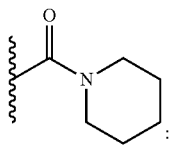 [SMILES: *C(=O)N1CCCCC1]

at least one of $R_2$, $R_3$, $R_5$, and $R_6$ is not H;
when $R_4$ is

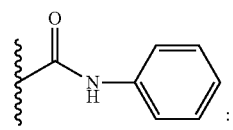 [SMILES: *C(=O)Nc1ccccc1]

$R_3$ is not F; and $R_5$ is not F;
when $R_2$ is F: $R_3$ is not —$OCH_3$ or F; $R_5$ is not —CN; and at least one of $R_3$, $R_4$, $R_5$, and $R_6$ is not H;
when $R_2$ is Cl: $R_3$ is not F;
when $R_2$ is —$CH_3$: $R_3$ is not Cl; at least one of $R_3$, $R_4$, $R_5$, and $R_6$ is not —$CH_3$; and $R_4$ and $R_5$ do not form a pyrazolyl with the atoms at c and d;

when $R_3$ is —$OCH_3$: $R_2$ is not F; and $R_6$ is not F;
when $R_3$ is F: $R_2$ is not —$OCH_3$; and X is not

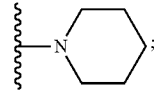

when $R_3$ is Cl: $R_5$ is not Cl; $R_{11}$ is not benzyl; and $R_{12}$ is not benzyl;
when $R_5$ is Cl, $R_6$ is not —$CH_3$; $R_{11}$ is not benzyl; and $R_{12}$ is not benzyl;
when $R_5$ is F or —$OCH_3$: $R_6$ is not F;
when $R_6$ is F: at least one of $R_2$, $R_3$, $R_4$, and $R_5$ is not H;
when $R_3$ and $R_5$ are H: $R_{11}$ is not cyclopropyl; and $R_{12}$ is not cyclopropyl;
when $R_9$ is Cl, $R_1$ is not an amide group;
when B is nitrogen and A and D are carbon: $R_4$ may not be —CN or

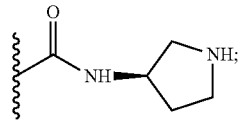 [SMILES: *C(=O)N[C@@H]1CCNC1]

when $R_7$ is —$CHF_2$ and $R_4$ is

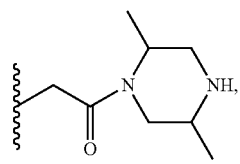 [SMILES: *CC(=O)N1CC(C)NCC1C]

then $R_4$ does not have the absolute stereochemistry

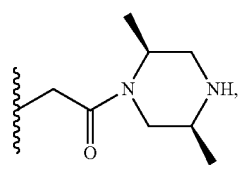 [SMILES: *CC(=O)N1C[C@H](C)NC[C@@H]1C]

and
wherein, when $R_8$ is

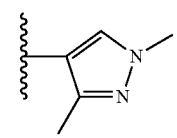 [SMILES: *c1cn(C)nc1C]

then the following provisos are in effect:
when $R_4$ is F: at least one of $R_2$, $R_3$, $R_5$, and $R_6$ is not H; $R_3$ is not $C(O)N(CH_3)_2$; and $R_5$ is not $C(O)N(CH_3)_2$;
when $R_4$ is Cl: at least one of $R_2$, $R_3$, $R_5$, and $R_6$ is not H;
when $R_3$ is F: $R_4$ is not $C(O)NHCH_2CH_2CH_2CH_3$, $C(O)N(CH_3)_2$, $C(O)NHCH_2CH_2CH_3$, or $C(O)NHC(CH_3)_3$;
$R_4$ is not $C(O)NHCH_2CH_2CH_2OH$, $C(O)NHCH(CH_3)_2$, —CN, or $R_1$ is not

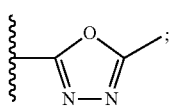 [SMILES: *c1nnc(C)o1]

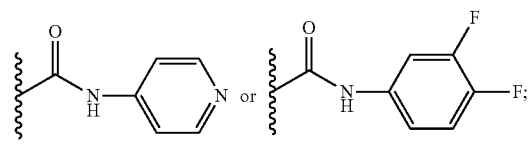

$R_5$ is not

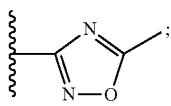 [SMILES: *c1noc(C)n1]

$R_3$ is not

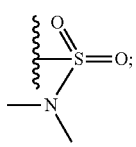 [SMILES: *S(=O)(=O)N(C)C]

when $R_2$ is F: $R_5$ is not —C(O)NH$_2$;

when $R_2$ is —CH$_3$, $R_4$ and $R_5$ do not form a pyrazole with atoms at c and d; and when B is nitrogen, $R_3$ and $R_4$ do not form an optionally substituted imidazole with the atoms at b and c; and wherein, when $R_8$ is

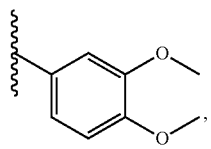 [SMILES: *c1ccc(OC)c(OC)c1]

then the following provisos are in effect:

$R_4$ is not —CH$_3$, —C(O)NHCH$_2$CH$_2$OH, —NHC(O)CH(CH$_3$)$_2$, or

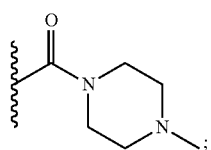

when $R_4$ is C(O)NHCH$_3$, at least one of $R_2$, $R_3$, $R_5$, and $R_6$ is not H;

when $R_4$ is —OCH$_3$: $R_3$ is not F or —CH$_3$; and $R_5$ is not F or —CH$_3$;

when $R_4$ is

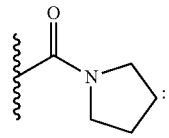 [SMILES: *C(=O)N1CCCC1]

$R_3$ is not Cl; and $R_5$ is not Cl;

when $R_4$ is —C(O)NHCH(CH$_3$)$_2$ or —C(O)N(CH$_2$CH$_3$)$_2$: at least one of $R_3$ and $R_5$ is not H;

$R_5$ is not —C(O)NH$_2$; and $R_6$ is not —CF$_3$.

10. The method of claim 9, wherein said compound is administered as a pharmaceutically acceptable salt.

11. A method for antagonizing TLR8, comprising administering a pharmaceutically effective amount of 4-((5S,7R)-5-(3,4-dimethoxyphenyl)-7-(trifluoromethyl)-4,5,6,7-tetrahydropyrazolo[1,5-a]pyrimidin-2-yl)phenyl)(piperazin-1-yl)methanone, or a pharmaceutically acceptable salt thereof.

12. A method for antagonizing TLR8, comprising administering a pharmaceutically effective amount of a compound of formula (IV)

Formula (IV)

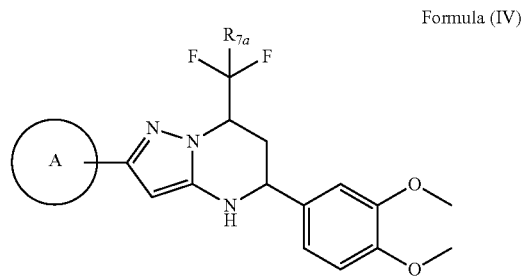

or a pharmaceutically acceptable salt thereof, or a stereoisomer thereof or mixture of stereoisomers thereof, wherein: $R_{7a}$ is H or F; and wherein Ring A is:

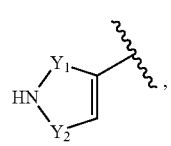

wherein $Y_1$ and $Y_2$ are independently selected from the group consisting of —CH$_2$— and —CH$_2$CH$_2$—, and wherein each of $Y_1$ and $Y_2$ is optionally substituted by $C_{1-3}$ alkyl;

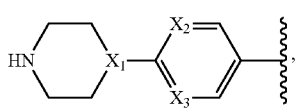

wherein $X_1$, $X_2$, and $X_3$ are independently selected from the group consisting of —CH— and N;

131

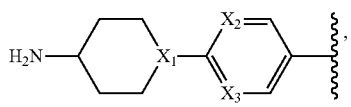

wherein $X_1$, $X_2$, and $X_3$ are independently selected from the group consisting of —CH— and N;

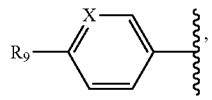

wherein X is N or —CH— optionally substituted by —CH$_3$, F, or Cl, and wherein $R_9$ is —C(O)Z, wherein Z is 2, 3-dihydroxypropylamine; a five to seven member cyclic diamine that is optionally bridged or optionally substituted at a carbon atom with a lower alkyl; a seven to ten member bicyclodiamine; a seven to eleven member spirodiamine; —NH substituted with a four to seven member cyclic amine optionally substituted with —NH$_2$; —OH; —CH$_2$NHR, wherein R is H or lower alkyl; —NH substituted with a seven to eleven member spiroalkane optionally substituted with —NH$_2$; or $R_9$ is CH$_3$NHC(O)—, and a carbon atom on the aryl ring to which $R_9$ is attached is substituted with one of —CH$_3$, F, or Cl; $R_9$ is (CH$_3$)$_2$CHNHC(O)—, and a carbon atom on the aryl ring to which $R_9$ is attached is substituted with one of —CH$_3$, F, or Cl; or $R_9$ is (CH$_3$)$_3$CNHC(O)— and a carbon atom on the aryl ring to which $R_9$ is attached is substituted with one of —CH$_3$, F, or Cl; or $R_9$ is

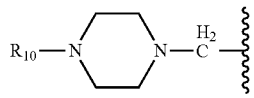

wherein the piperazine is optionally bridged or substituted with lower alkyl and $R_{10}$ is H or —CH$_3$; or $R_9$ is

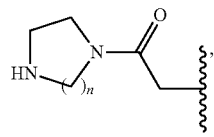

132 wherein n is 1-3 and the cyclic diamine is optionally bridged or substituted with lower alkyl; or $R_9$ is

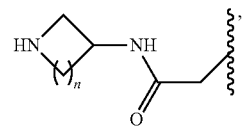

wherein n is 1-4; or $R_9$ is —NHC(O)NH$_2$, —CH$_2$C(O)NH— wherein the nitrogen is substituted with a four to seven member cyclic amine; —CH$_2$—C(O)— wherein the carbonyl is substituted with a seven to ten member bicyclodiamine; and a four to seven member cyclic amine substituted with —CH$_2$C(O)NH$_2$; or

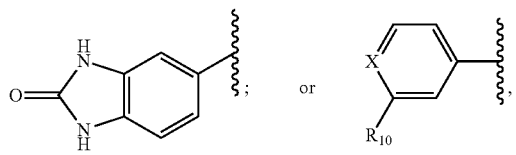

wherein X is N or —CH— wherein the C is optionally substituted by —CH$_3$, F, or Cl, and wherein $R_{10}$ is —C(O)NH— wherein the nitrogen is substituted by a four to seven member cyclic amine; —C(O)— substituted by a seven to ten member bicyclodiamine; —C(O)— substituted by a seven to eleven member spirodiamine; pyrazole; [1,2,4]oxadiazole optionally substituted by —CH$_3$ on a carbon atom of the oxadiazole; —NHC(O)CH$_3$; —CH$_2$— substituted by a piperazine; —CH$_2$— substituted by a piperazine including a methyl substituent; —C(O)— substituted by a five to seven member cyclic diamine; —C(O)NHCH$_2$— wherein the —CH$_2$— is substituted by azetidine; or —C(O)— substituted with a five to seven member cyclic amine wherein the amine includes an —NH$_2$ substituent; or cyanophenyl; isoquinoline; cyclohexene substituted with —NH$_2$ at the 4' position; 1,4-dimethylindazole-5-yl; 1,6-dimethylindazole-5-yl; cyclohexene substituted with spiropiperidine at the 4' position; 1-piperidinopyrazole; or o-methoxypyridine.

* * * * *